US007906325B2

(12) United States Patent
Bryan et al.

(10) Patent No.: US 7,906,325 B2
(45) Date of Patent: Mar. 15, 2011

(54) **MODIFICATION OF FATTY ACID BIOSYNTHESIS USING RECOMBINANT DIACYLGLYCEROL ACYLTRANSFERASE SEQUENCES FROM RYEGRASS (*LOLIUM*) AND FESCUE (*FESTUCA*)**

(75) Inventors: Gregory Thomas Bryan, Manawatu (NZ); Margaret Fiona Burling, Palmerston North (NZ); Nicholas John Roberts, Palmerston North (NZ); Alana Jean Trollope, Palmerston North (NZ); Derek Ross Woodfield, Palmerston North (NZ)

(73) Assignees: Agriculture Victoria Services Pty Ltd, Attwood, Victoria (AU); AgResearch Limited, Hamilton (NZ)

( * ) Notice: Subject to any disclaimer, the term of this patent is extended or adjusted under 35 U.S.C. 154(b) by 1055 days.

(21) Appl. No.: 10/556,950

(22) PCT Filed: May 14, 2004
(Under 37 CFR 1.47)

(86) PCT No.: PCT/AU2004/000635
§ 371 (c)(1),
(2), (4) Date: Nov. 14, 2005

(87) PCT Pub. No.: WO2004/101793
PCT Pub. Date: Nov. 25, 2004

(65) Prior Publication Data

US 2007/0118927 A1 May 24, 2007

(30) Foreign Application Priority Data

May 16, 2003 (AU) ................................ 2003902413

(51) Int. Cl.
*C12N 15/11* (2006.01)
*C12N 15/63* (2006.01)

(52) U.S. Cl. ..................... 435/320.1; 536/24.3; 536/23.2

(58) Field of Classification Search ........................ None
See application file for complete search history.

(56) References Cited

U.S. PATENT DOCUMENTS 7,214,786 B2 * 5/2007 Kovalic et al. ............... 536/23.6

FOREIGN PATENT DOCUMENTS

WO 00/32756 6/2000
WO 00/36114 6/2000
WO 01/16308 3/2001

OTHER PUBLICATIONS

Fescue. From Wikipedia, the free encyclopedia; printout of Jul. 30, 2008, pp. 1-3.*

*Lolium perenne*. From Wikipedia, the free encyclopedia; printout of Jul. 30, 2008, pp. 1-2.*

Score printout of SEQ ID No. 9762 from US patent 7,214,786 printout dated Sep. 23, 2009.*

GenBank Accession No. BU974328 (Oct. 2002).*

Farese R V et al. "Triglyceride Synthesis: Insights from the Cloning of Diacylglycerol Acyltransferase", 2000, pp. 229-234, vol. 11, No. 3, Current Opinion in Lipidology, London, GB.

Lu Chaofu et al. "Expression pattern of diacylglycerol acyltransferase-1, an enzyme involved in triacylglycerol biosynthesis, in *Arabidopsis thaliana*" May 1, 2003, pp. 31-41, vol. 52 No. 1, Plant Molecular Biology, Springer, Dordrecht, NL.

Bouvier-Nave et al., Expression in yeast and tobacco of plant cDNAs encoding acyl CoA:diacylglycerol acyltransferase, European Journal of Biochemistry, 2000, p. 85-96, vol. 267.

* cited by examiner

*Primary Examiner* — Rebecca E. Prouty
(74) *Attorney, Agent, or Firm* — Larson & Anderson, LLC

(57) ABSTRACT

The present invention relates to nucleic acids or nucleic acid fragments encoding amino acid sequences for fatty acid biosynthesis enzymes in plants, and the use thereof for the modification of, for example, fatty acid biosynthesis in plants. In particular, the present invention relates to nucleic acids or nucleic acid fragments encoding amino acid sequences of diacylglycerol acyltransferase enzymes.

12 Claims, 17 Drawing Sheets

```
                            1                                                    50
      O. sativa (D43212)    ~~~~~~~~~~ ~~~~~~~~~~ ~~~~~~~~~~ ~~~~~~~~~~ ~~~~~~~~~~
     L. perenne (deduced)   ~~~~~~~~~~ ~~~~~~~~~~ ~~~~~~~~~~ ~~~~~~~~~~ ~~~~~~~~~~
   P. frutescens (Q9FV16)   --MAILDSPE ILDTTSSSAD NGAAHHTTLR RRQSARSVPP LLDSDSNSLE
    A. thaliana (CAB45373)  ~~~~~~~~MA ILDSAGVTTV TENGGGEFVD LDRLRRRKSR SDSSNGLLLS
        B. napus (Q9M4V2)   ~~~~~~~~ME ILDSGGVTMP TENGG...AD LDTLRHRKPR SDSSNGLL..
 M. truncatula (AL381190)   ~~~~~~~~~~ ~~~~~~~~~~ ~~~~~~~~~~ ~~~~~~~~~~ ~~~~~~~~~~
         G. max (AW349274)  ~~~~~~~~~~ ~~~~~~~~~~ ~~~~~~~~~~ ~~~~~~~~~~ ~~~~~~~~~~
      N. tabacum (Q9SEG9)   MVIMELPESV EMTTTTTTSG IENLNSDLNH SVRRRRGSNG FEAASAINSS
      O. sativa (deduced)   ~~~~~~~~~~ ~~~~~~~~~~ ~~~~~~~~~~ ~~~~~~~~~~ ~~~~~~~~~~

                            51                                                  100
      O. sativa (D43212)    ~~~~~~~~~~ ~~~~~~~~~~ ~~~~~~~~~~ ~~~~~~~~~~ ~~~~~~~~~~
     L. perenne (deduced)   ~~~~~~~~~~ ~~~~~~~~~~ ~~~~~~~~~~ ~~~~~~~~~~ ~~~~~~~~~~
   P. frutescens (Q9FV16)   AESAINDSEN VRNDANLIEN LRGGAVESEN EKQESYGKEE GAKVKENGET
    A. thaliana (CAB45373)  GSDNNSPSDD VGAPADVRDR IDSVVNDDAQ GTANLAGDNN GGGDNNGGGR
        B. napus (Q9M4V2)   .PDSVTVSD. ....ADVRDR VDSAV.EDTQ GKANLAGENE .......IRE
 M. truncatula (AL381190)   ~~~~~~~~~~ ~~~~~~~~~~ ~~~~~~~~~~ ~~~~~~~~~~ ~~~~~~~~~~
         G. max (AW349274)  ~~~~~~~~~~ ~~~~~~~~~~ ~~~~~~~~~~ ~~~~~~~~~~ ~~~~~~~~~~
      N. tabacum (Q9SEG9)   DANMSEDRRD VCGSGAGLET VNERSKSVGE SSDVIRKEDD RNDNVANGEE
      O. sativa (deduced)   ~~~~~~~~~~ ~MAPPPSLAP DRGGGEPDDA LRLRARAAAA AGDAPAPQQQ

                            101                                                 150
      O. sativa (D43212)    ~~~~~~~~~~ ~~~~~~~~~~ ~~~~~~~~~~ ~~~~~~~~~~ ~~~~~~~~~~
     L. perenne (deduced)   ~~~~~~~~~~ ~~~~~~~~~~ ~~~~~~~~~~ ~~~~~~~~~~ ~~~~~~~~~~
   P. frutescens (Q9FV16)   SNGNGTDVMA VKFTFRPAAP AHRKNKESPL SSDAIFKQSH AGLFNLCIVV
    A. thaliana (CAB45373)  GGGEGRGNAD ATFTYRPSVP AHRRARESPL SSDAIFKQSH AGLFNLCVVV
        B. napus (Q9M4V2)   SGGEAGGNVD VRYTYRPSVP AHRRVRESPL SSDAIFKQSH AGLFNLCVVV
 M. truncatula (AL381190)   ~~~~~~~~~~ ~~~~~~~~~~ ~~~~~~~~~~ ~~~~~~~~~~ ~~~~~~~~~~
         G. max (AW349274)  ~~~~~~~~~~ ~~~~~~~~~~ ~~~~~~~~~~ ~~~~~~~~~~ ~~~~~~~~~~
      N. tabacum (Q9SEG9)   SKSTETTTTP FKFAYRASAP AHRRIKESPL SSDAIFKQSH AGLFNLCVVV
      O. sativa (deduced)   QEQRHQEQQQ QLLWYRASAP AHRRVRESPL SSDAIFRQSH AGLLNLCIVV

                            151                                                 200
      O. sativa (D43212)    ~~~~~~~~~~ ~~~~~~~~~~ ~~~~~~~~~~ ~~~~~~~~~~ ~~~~~~~~~~
     L. perenne (deduced)   ~~~~~~~~~~ ~~~~~~~~~~ ~~~~~~~~~~ ~~~~~~~~~~ ~~~~~~~~~~
   P. frutescens (Q9FV16)   LVAVNSRLII ENLMKYGWLI KSGFWFSSTS LRDWPLLMCC LSLPVFALAS
    A. thaliana (CAB45373)  LIAVNSRLII ENLMKYGWLI RTDFWFSSRS LRDWPLFMCC ISLSIFPLAA
        B. napus (Q9M4V2)   LVAVNSRLII ENLMKYGWLI RTDFWFSSTS LRDWPLFMCC LSLSIFPLAA
 M. truncatula (AL381190)   ~~~~~~~~~~ ~~~~~~~~~~ ~~~~~~~~~~ ~~~~~~~~~~ ~~~~~~~~~~
         G. max (AW349274)  ~~~~~~~~~~ ~~~~~~~~~~ ~~~~~~~~~~ ~~~~~~~~~~ ~~~~~~~~~~
      N. tabacum (Q9SEG9)   LIAVNSRLII ENLMKYGLLI RAGFWFSSKS LRDWPLLMCC LSLQILPLAA
      O. sativa (deduced)   LVAVNSRLII ENLMKYGLLI RAGFWFSGTS LADWPLLMCC LTLPTFPLAA

                            201                                                 250
      O. sativa (D43212)    ~~~~~~~~~~ ~~~~~~~~~~ ~~~~~~~~~~ ~~~~~~~~~~ ~~~~~~~~~~
     L. perenne (deduced)   ~~~~~~~~~~ ~~~~~~~~~~ ~~~~~~~~~~ ~~~~~~~~~~ ~~~~~~~~~~
   P. frutescens (Q9FV16)   FLVEKLVKLN YIPEWVAVFL HVTITTVEIL FPVVVILRCD SAVLSGVTLM
    A. thaliana (CAB45373)  FTVEKLVLQK YISEPVVIFL HIIITMTEVL YPVYVTLRCD SAFLSGVTLM
        B. napus (Q9M4V2)   FTVEKLVLQK CISEPVVIIL HIIITMTEVL YPVYVTLRCD SAFLSGVTLM
 M. truncatula (AL381190)   ~~~~~~~~~~ ~~~~~~~~~~ ~~~~~~~~~~ ~~~~~~~~~~ ~~~~~~~~~~
         G. max (AW349274)  ~~~~~~~~~~ ~~~~~~~~~~ ~~~~~~~~~~ ~~~~~~~~~~ ~~~~~~~~~~
      N. tabacum (Q9SEG9)   FLVEKLAQQR HLTERAVVTL HITITTAAIL YPVLVILGCD SAFLFGVILM
      O. sativa (deduced)   LMVEKLAQRK LI...VVILL HIVITTSVLV YPVVVILKCD SAVLSGFVLM

                            251                                                 300
      O. sativa (D43212)    ~~~~~~~~~~ ~~~~~~~~~~ ~~~~~~~~~~ ~~~~~~~~~~ ~~~~~~~~~~
     L. perenne (deduced)   ~~~~~~~~~~ ~~~~~~~~~~ ~~~~~~~~~~ ~~~~~~~~~~ ~~~~~~~~~~
   P. frutescens (Q9FV16)   LFACTVWLKL VSYAHTNYDL RVLAKSLDKW EAMSRYWNLD YAYDVSFKSL
    A. thaliana (CAB45373)  LLTCIVWLKL VSYAHTSYDI RSLANAADK. ..A....NPE VSYYVSLKSL
        B. napus (Q9M4V2)   LLTCIVWLKL VSYAHTNYDI RTLANSSDK. ..A....NPE VSYYVSLKSL
 M. truncatula (AL381190)   ~~~~~~~~~~ ~~~~~~~~~~ ~~~~~~~~~~ ~~~~~~~~~~ ~~~~~~~~~~
         G. max (AW349274)  ~~~~~~~~~~ ~~~~~~~~~~ ~~~~~~~~~~ ~~~~~~~~~~ ~~~~~~~~~~
      N. tabacum (Q9SEG9)   LVACIVWMKL VSYAHTNHDM RQLAKSTDKD ETS....DGD FSYDVSFKSL
      O. sativa (deduced)   FLASIIWLKL VSFAHTNYDI RMLSKSIEK. .......DPE NIKWPTFKRL
```

FIGURE 1

```
                              301                                                  350
      O. sativa (D43212)      ~~~~~~~~~~ ~~~~~~~~~~ ~~~~~~~~~~ ~~~~~~~~~~ ~~~~~~~~~~
     L. perenne (deduced)     ~~~~~~~~~~ ~~~~~~~~~~ ~~~~~~~~~~ ~~~~~~~~~~ ~~~~~~~~~~
   P. frutescens (Q9FV16)     AYFMVAPTLC YQPSYPRTAC IRKGWVVRQL IKLVIFTGLM GFIIEQYINP
    A. thaliana (CAB45373)    AYFMVAPTLC YQPSYPRSAC IRKGWVARQF AKLVIFTGFM GFIIEQYINP
        B. napus (Q9M4V2)     AYFMLAPTLC YQPSYPRSPC IRKGWVARQF AKLIIFTGFM GFIIEQYINP
M. truncatula (AL381190)      ~~~~~~~~~~ ~~~~~~~~~~ ~~~~~~~~~~ ~~~~~~~~~~ ~~~~~~~~~~
         G. max (AW349274)    ~~~~~~~~~~ ~~~~~~~~~~ ~~~~~~~~~~ ~~~~~~~~~~ ~~~~~~~~~~
      N. tabacum (Q9SEG9)     AYFMVAPTLC YQLSYPHTPC IRKGWVARQF IKLVIFTGLM GFIIEQYINP
      O. sativa (deduced)     SYFMLAPTLC YQGASLHD.. .....FSWYF IYIAVCILNM SFIF.QYINP

                              351                                                  400
      O. sativa (D43212)      ~~~~~~~~~~ ~~~~~~~~~~ ~~~~~~~~~~ ~~~~~~~~~~ ~~~~~~~~~~
     L. perenne (deduced)     ~~~~~~~~~~ ~~~~~~~~~~ ~~~~~~~~~~ ~~~~~~~~~~ ~~~~~~~~~~
   P. frutescens (Q9FV16)     IVQNSQHPLK GNLLYAIERV LKLSVPNLYV WLCMFYCFFH LWLNILAELL
    A. thaliana (CAB45373)    IVRNSKHPLK GDLLYAIERV LKLSVPNLYV WLCMFYCFFH LWLNILAELL
        B. napus (Q9M4V2)     IVRNSKHPLK GDLLYGVERV LKLSVPNLYV WLCMFYCFFH LWLNILAELL
M. truncatula (AL381190)      ~~~~~~~~~~ ~~~~~~~~~~ ~~~~~~~~~~ ~~~~~~~~~~ ~~~~~~~~~~
         G. max (AW349274)    ~~~~~~~~~~ ~~~~~~~~~~ ~~~~~~~~~~ ~~~~~~~~~~ ~~~NILAELL
      N. tabacum (Q9SEG9)     IVQNSQHPLK GNLLYAIERV LKLSVPNLYV WLCMFYCFFH LWLNILAELL
      O. sativa (deduced)     IVKNSKHPLK GNFLNAIERV LKLSVPTLYV WLCMFYCFFH LWLNILAELL

                              401                                                  450
      O. sativa (D43212)      ~~~~~~~~~~ ~~~~~~~~~~ ~~~~~~~~~~ ~~VRHIYFPC MRNGISKEVA
     L. perenne (deduced)     ~~~~~~~~~~ ~~~~~~~~~~ ~~~~~~~~~~ ~~~~~~~~~~ ~~~~~~~~~~
   P. frutescens (Q9FV16)     CFGDREFYKD WWNARTVEEY WRMWNMPVHK WMVRHIYCPC LQNGIPKIVA
    A. thaliana (CAB45373)    CFGDREFYKD WWNAKSVGDY WRMWNMPVHK WMVRHIYFPC LRSKIPKTLA
        B. napus (Q9M4V2)     CFGDREFYKD WWNAKSVGDY WRMWNMPVHK WMVRHVYFPC LRRNIPKVPA
M. truncatula (AL381190)      ~~~~~~~~~~ ~~~~~~~~~~ ~~~~~~~~~~ ~~~~~~~~~~ ~~~~~PKGAA
         G. max (AW349274)    RFGDREFYKD WWNAKTVEDY WRMWNMPVHK WMIRHLYFPC LRHGLPKAAA
      N. tabacum (Q9SEG9)     CFGDREFYKD WWNAKTIDEY WRMWNMPVHK WMVRHIYFPC LRNGIPKGVA
      O. sativa (deduced)     CFGDREFYKD WWNAKTVEEY WRMWNMPVHK WVIRHIYFPC IRNGFSKGVA

                              451                                                  500
      O. sativa (D43212)      .LISFLVSAV LHELCVAVPC RILKFWAFLG IMLQIPLIVL TA~~~~~~~~
     L. perenne (deduced)     ~~~~~~VSAV LHELCVAVPC RI~~~~~~~~ ~~~~~~~~~~ ~~~~~~~~~~
   P. frutescens (Q9FV16)     VLIAFLVSAI FHELCVAVPC QIFKFWAFSG IMLQVPLVIV TNYLQEKFKN
    A. thaliana (CAB45373)    IIIAFLVSAV FHELCIAVPC RLFKLWAFLG IMFQVPLVFI TNYLQERF.G
        B. napus (Q9M4V2)     IILAFLVSAV FHELCIAVPC RLFKLWAFLG IMFQVPLVFI TNYLQERF.G
M. truncatula (AL381190)      VLIAFMVSAL FHELCIAVPC HIFKLWAFSG IMFQVPLVLI TNYLQNKFSN
         G. max (AW349274)    LLIXXLVSAL FHELCIAVPC HIFKLWAFGG IMFQVPLVLI TNYLQNKFRN
      N. tabacum (Q9SEG9)     ILIAFLVSAV FHELCIAVPC RLFKWWAFMG IMFQVPLVIL TNFLQNKFQS
      O. sativa (deduced)     ILISFLVSAA FHELCVAVPC HIFKFWAFIG IMFQIPLVFL TKYLQDKFNN

                              501                                     538
      O. sativa (D43212)      ~~~~~~~~~~ ~~~~~~~~~~ ~~~~~~~~~~ ~~~~~~~~
     L. perenne (deduced)     ~~~~~~~~~~ ~~~~~~~~~~ ~~~~~~~~~~ ~~~~~~~~
   P. frutescens (Q9FV16)     SMVGNMMFWC FFCIFGQPMC VLLYYHDLMN RKASAR~~
    A. thaliana (CAB45373)    STVGNMIFWF IFCIFGQPMC VLLYYHDLMN RKGSMS~~
        B. napus (Q9M4V2)     SMVGNMIFWF TFCIFGQPMC VLLYYHDLMN RKGKMS~~
M. truncatula (AL381190)      SMVGNMFFWF TFCILGQPMC VLLYYHDLMN RNSKLD~~
         G. max (AW349274)    SMVGNMIFWF IFSILGQPMC VLLYYHDLMN RKGKLD~~
      N. tabacum (Q9SEG9)     SMVGNMMFWC FFCILGQPMC VLLYYHDVMN RKSSAR~~
      O. sativa (deduced)     TMVGNMIFWF FFSILGQPMC VLLYYHDVMN RQQAQTNR
```

FIGURE 1 (cont.)

```
TACTGGAGAATGTGGAATATGGTATGCTTCTCTTTTCTCTACCATGTTACTTTCTTGCAA
Y--W--R--M--W--N--M--V--C--F--S--F--L--Y--H--V--T--F--L--Q--
-T--G--E--C--G--I--W--Y--A--S--L--F--S--T--M--L--L--S--C--N-
--L--E--N--V--E--Y--G--M--L--L--F--S--L--P--C--Y--F--L--A--T

CCTTCTGGCAATTAGAGACCATATTTCTCCATAAGCTTGCTTGCATTTTTTTCCAAGGAG
P--S--G--N--*--R--P--Y--F--S--I--S--L--L--A--F--F--S--K--E--
-L--L--A--I--R--D--H--I--S--P--*--A--C--L--H--F--F--P--R--S-
--F--W--Q--L--E--T--I--F--L--H--K--L--A--C--I--F--F--Q--G--V

TTACAATGTTAGAATGTTTATCTTATTCAAAGAAACAGCATGAGAATATGACAAACTCAA
L--Q--C--*--N--V--Y--L--I--Q--R--N--S--M--R--I--*--Q--T--Q--
-Y--N--V--R--M--F--I--L--F--K--E--T--A--*--E--Y--D--K--L--K-
--T--M--L--E--C--L--S--Y--S--K--K--Q--H--E--N--M--T--N--S--N

ATGAAACTGTTTGACAAGAACAGCACATTTTCTATGATTAAACTTTACCAAATTTCAGTA
M--K--L--F--D--K--N--S--T--F--S--M--I--K--L--Y--Q--I--S--V--
-*--N--C--L--T--R--T--A--H--F--L--*--L--N--F--T--K--F--Q--*-
--E--T--V--*--Q--E--Q--H--I--F--Y--D--*--T--L--P--N--F--S--R

GGTGAAGGAGTGGCAAATACCTCGAATTTTATTGATTTATGTTATATTGCTTGCTGTTTC
G--E--G--V--A--N--T--S--N--F--I--D--L--C--Y--I--A--C--C--F--
-V--K--E--W--Q--I--P--R--I--L--L--I--Y--V--I--L--L--A--V--S-
--*--R--S--G--K--Y--L--E--F--Y--*--F--M--L--Y--C--L--L--F--L

TCCACTAATTTGTTTATTTGTTTTTAACTATTTTTTATTTATGTCTGCATTCACAGCCTG
S--T--N--L--F--I--C--F--*--L--F--F--I--Y--V--C--I--H--S--L--
-P--L--I--C--L--F--V--F--N--Y--F--L--F--M--S--A--F--T--A--C-
--H--*--F--V--Y--L--F--L--T--I--F--Y--L--C--L--H--S--Q--P--V

TGCATAAATGGGTTGTTCGCCATATATATTTTCCCCCCAGGCGCAGTGGTATATCAAAGG
C--I--N--G--L--F--A--I--Y--I--F--P--P--G--A--V--V--Y--Q--R--
-A--*--M--G--C--S--P--Y--I--F--S--P--Q--A--Q--W--Y--I--K--G-
--H--K--W--V--V--R--H--I--Y--F--F--P--R--R--S--G--I--S--K--V

TAAACTGCTAGCTGTTAGACTACTAAGCTCTTCATGCTTTGGACATAGTTTAAGCTGGGT
*--T--A--S--C--*--T--T--K--L--F--M--L--W--T--*--F--K--L--G--
-K--L--L--A--V--R--L--L--S--S--S--C--F--G--H--S--L--S--W--V-
--N--C--*--L--L--D--Y--*--A--L--H--A--L--D--I--V--*--A--G--S

CCTTTGTGCTGTTTTTCTTGCAGGAAGTTGCTGTCTTTGTATCATTTTTTGTATCTGCCG
P--L--C--C--F--S--C--R--K--L--L--S--L--Y--H--F--L--Y--L--P--
-L--C--A--V--F--L--A--G--S--C--C--L--C--I--I--F--C--I--C--R-
--F--V--L--F--F--L--Q--E--V--A--V--F--V--S--F--F--V--S--A--V

TGCTCCATGAGGTAAAACATGCCCCTTTCTTTCGCAGGCACTTCATATATCCACACCAGT
C--S--M--R--*--N--M--P--L--S--F--A--G--T--S--Y--I--H--T--S--
-A--P--*--G--K--T--C--P--F--L--S--Q--A--L--H--I--S--T--P--V-
--L--H--E--V--K--H--A--P--F--F--R--R--H--F--I--Y--P--H--Q--L

TATTTAGCTCTCTTTTCCGCTCTTTTGATCCAAGTTGGTTCTGAGCTTATAATAATAAAA
Y--L--A--L--F--S--A--L--L--I--Q--V--G--S--E--L--I--I--I--K--
-I--*--L--S--F--P--L--F--*--S--K--L--V--L--S--L--*--*--*--N-
--F--S--S--L--F--R--S--F--D--P--S--W--F--*--A--Y--N--N--K--M
```

FIGURE 5

```
TGTTGCAGTTGTGTGGTTACGTCATTTTTTAATGTTGTTAAATAAAAAGTTGCTAGTTGG
C--C--S--C--V--V--T--S--F--F--N--V--V--K--*--K--V--A--S--W--
-V--A--V--V--W--L--R--H--F--L--M--L--L--N--K--K--L--L--V--G-
--L--Q--L--C--G--Y--V--I--F--*--C--C--*--I--K--S--C--*--L--A

CCTGTTTTGATTAACTCATGATGCCTTATCTTAATTAATGTACACCAGTTATGTGTTGCT
P--V--L--I--N--S--*--C--L--I--L--I--N--V--H--Q--L--C--V--A--
-L--F--*--L--T--H--D--A--L--S--*--L--M--Y--T--S--Y--V--L--L-
--C--F--D--*--L--M--M--P--Y--L--N--*--C--T--P--V--M--C--C--C

GTCCCCTGCCGAATTGTCAAGTTCTGGGCATTCTTAGGGATCATGCTGCAGGTATGTCAA
V--P--C--R--I--V--K--F--W--A--F--L--G--I--M--L--Q--V--C--Q--
-S--P--A--E--L--S--S--S--G--H--S--*--G--S--C--C--R--Y--V--K-
--P--L--P--N--C--Q--V--L--G--I--L--R--D--H--A--A--G--M--S--K

AAATTACTGCTGAATGGATGATGTGCCATCTCATTCACTTCATTGATTAGTATGTTGCTA
K--L--L--L--N--G--*--C--A--I--S--F--T--S--L--I--S--M--L--L--
-N--Y--C--*--M--D--D--V--P--S--H--S--L--H--*--L--V--C--C--Y-
--I--T--A--E--W--M--M--C--H--L--I--H--F--I--D--*--Y--V--A--T

CTTTCTAAGTAAAAATGTGTCTGCTTTTGAGGATCATCTTGCATTTTGTATATATGTGGA
L--S--K--*--K--C--V--C--F--*--G--S--S--C--I--L--Y--I--C--G--
-F--L--S--K--N--V--S--A--F--E--D--H--L--A--F--C--I--Y--V--E-
--F--*--V--K--M--C--L--L--L--R--I--I--L--H--F--V--Y--M--W--K

AATTTATTTGTAAGCAGGATGGATGGGCCCATCCTGTTATACCATCTGAGACAATGAACT
N--L--F--V--S--R--M--D--G--P--I--L--L--Y--H--L--R--Q--*--T--
-I--Y--L--*--A--G--W--M--G--P--S--C--Y--T--I--*--D--N--E--L-
--F--I--C--K--Q--D--G--W--A--H--P--V--I--P--S--E--T--M--N--F

TTGCTTATTCCATATCCTTTCCTCCCTTGTTACCAGATCCCTCTTATCATATTGACATCA
L--L--I--P--Y--P--F--L--P--C--Y--Q--I--P--L--I--I--L--T--S--
-C--L--F--H--I--L--S--S--L--V--T--R--S--L--L--S--Y--*--H--H-
--A--Y--S--I--S--F--P--P--L--L--P--D--P--S--Y--H--I--D--I--I

TACCTGAAGAGCAAATTCAGAGATACAATGGTTAGCCATCTTTACCATGTTTGTACTAAA
Y--L--K--S--K--F--R--D--T--M--V--S--H--L--Y--H--V--C--T--K--
-T--*--R--A--N--S--E--I--Q--W--L--A--I--F--T--M--F--V--L--K-
--P--E--E--Q--I--Q--R--Y--N--G--*--P--S--L--P--C--L--Y--*--K

AGGATATATACTTTGATGTTAGACCAGTTCTAATTTGTGCCACCTTCAACAGGCCGGCAA
R--I--Y--T--L--M--L--D--Q--F--*--F--V--P--P--S--T--G--R--Q--
-G--Y--I--L--*--C--*--T--S--S--N--L--C--H--L--Q--Q--A--G--N-
--D--I--Y--F--D--V--R--P--V--L--I--C--A--T--F--N--R--P--A--T

CATGATATTCTGGTTCTTTTTCTGCATCTACGGACAGCCTATGTGCGTTCTCCTGTACTA
H--D--I--L--V--L--F--L--H--L--R--T--A--Y--V--R--S--P--V--L--
-M--I--F--W--F--F--F--C--I--Y--G--Q--P--M--C--V--L--L--Y--Y-
--*--Y--S--G--S--F--S--A--S--T--D--S--L--C--A--F--S--C--T--T

CCATGATGTGATGAATAGGATTGGGAAGACGGGATAGAAGAACACATATCGCTCTTCCTG
P--*--C--D--E--*--D--W--E--D--G--I--E--E--H--I--S--L--F--L--
-H--D--V--M--N--R--I--G--K--T--G--*--K--N--T--Y--R--S--S--C-
--M--M--*--*--I--G--L--G--R--R--D--R--R--T--H--I--A--L--P--V
```

FIGURE 5 (cont.)

```
TTTATGGCAAAAGGATGTTACGACATGGAGCTGCATAATTTCCAACACTGGCATACATCC
F--M--A--K--G--C--Y--D--M--E--L--H--N--F--Q--H--W--H--T--S--
-L--W--Q--K--D--V--T--T--W--S--C--I--I--S--N--T--G--I--H--P-
--Y--G--K--R--M--L--R--H--G--A--A--*--F--P--T--L--A--Y--I--L

TTCCAGTCTTTCTTGGAAAATACAGTGCATAATTTTACCATGTTTTGTGGCGGGTGGTTG
F--Q--S--F--L--E--N--T--V--H--N--F--T--M--F--C--G--G--W--L--
-S--S--L--S--W--K--I--Q--C--I--I--L--P--C--F--V--A--G--G--C-
--P--V--F--L--G--K--Y--S--A--*--F--Y--H--V--L--W--R--V--V--A

CAGGCTTGTGACTGTACATAAGCTTCAGTCTATGATATAGAATCCTGCCTAATTGCTGGC
Q--A--C--D--C--T--*--A--S--V--Y--D--I--E--S--C--L--I--A--G--
-R--L--V--T--V--H--K--L--Q--S--M--I--*--N--P--A--*--L--L--A-
--G--L--*--L--Y--I--S--F--S--L--*--Y--R--I--L--P--N--C--W--R

GTGGCGGTGATAATTTTTTGTAGAGATGGAAGCTTTATTATCCCTGGCCTGTGCGTTACA
V--A--V--I--I--F--C--R--D--G--S--F--I--I--P--G--L--C--V--T--
-W--R--*--*--F--F--V--E--M--E--A--L--L--S--L--A--C--A--L--H-
--G--G--D--N--F--L--*--R--W--K--L--Y--Y--P--W--P--V--R--Y--I

TATGCATACGGCCTTAATTATTTTACCGTGTATCACAAATTGTTAGGAAGCGTCCCCGTG
Y--A--Y--G--L--N--Y--F--T--V--Y--H--K--L--L--G--S--V--P--V--
-M--H--T--A--L--I--I--L--P--C--I--T--N--C--*--E--A--S--P--C-
--C--I--R--P--*--L--F--Y--R--V--S--Q--I--V--R--K--R--P--R--A

CCCTTAGGGTAATTTGTTAATAAAAAATAATTACATTTGTTTCTCTTGAATAGAAGAGGC
P--L--G--*--F--V--N--K--K--*--L--H--L--F--L--L--N--R--R--G--
-P--*--G--N--L--L--I--K--N--N--Y--I--C--F--S--*--I--E--E--A-
--L--R--V--I--C--*--*--K--I--I--T--F--V--S--L--E--*--K--R--Q

AACTGATGATGTAGTATTTTTTGTTTTTGTTTTGTACAGATGTATCTAGACACAAATACA
N--*--*--C--S--I--F--C--F--C--F--V--Q--M--Y--L--D--T--N--T--
-T--D--D--V--V--F--F--V--F--V--L--Y--R--C--I--*--T--Q--I--H-
--L--M--M--*--Y--F--L--F--L--F--C--T--D--V--S--R--H--K--Y--M

TGTATCTAGAAAAAGTTCAGACTATTAATATTGTTGCCGTAAGGTGATTGTGGGGCAATC
C--I--*--K--K--F--R--L--L--I--L--L--P--*--G--D--C--G--A--I--
-V--S--R--K--S--S--D--Y--*--Y--C--C--R--K--V--I--V--G--Q--S-
--Y--L--E--K--V--Q--T--I--N--I--V--A--V--R--*--L--W--G--N--L

TAAGATAAGGTACTATTCAATCTTTTTTCTCGAAAAGAGACGATGTACATGGAGTATTTA
*--D--K--V--L--F--N--L--F--S--R--K--E--T--M--Y--M--E--Y--L--
-K--I--R--Y--Y--S--I--F--F--L--E--K--R--R--C--T--W--S--I--Y-
--R--*--G--T--I--Q--S--F--F--S--K--R--D--D--V--H--G--V--F--I

TTT
F--
-X-
--X
```

FIGURE 5 (cont.)

```
                                   1                                                    50
           o._sativa_(d43212)      ~~~~~~~~~~ ~~~~~~~~~~ ~~~~~~~~~~ ~~~~~~~~~~ ~~~~~~~~~~
ryegrass_exon10-15_frame1_1        ~~~~~~~~~~ ~~~~~~~~~~ ~~~~~~~~~~ ~~~~~~~~~~ ~~~~~~~~~~
           o._sativa_(deduced)     ~~~~~~~~~~ ~~~~~~~~~~ ~~~~~~~~~~ ~~~~~~~~~~ ~~~~~~~~~~
        a._thaliana_(cab45373)     ~~~MAILDSA GVTTVTENGG GEFVDLDRLR RRKSRSDSSN GLLLSGSDNN
            b._napus_(q9m4v2)      ~~~MEILDSG GVTMPTENGG ...ADLDTLR HRKPRSDSSN GLL...PDSV
     m._truncatula_(al381190)      ~~~~~~~~~~ ~~~~~~~~~~ ~~~~~~~~~~ ~~~~~~~~~~ ~~~~~~~~~~
            g._max_(aw349274)      ~~~~~~~~~~ ~~~~~~~~~~ ~~~~~~~~~~ ~~~~~~~~~~ ~~~~~~~~~~
             n._tabaccum-dgat      MVIMELPESV EMTTTTTTSG IENLNSDLNH SVRRRRGSNG FEAASAINSS
        p._frutescens_(q9fv16)     ~~~MAILDSP EILDTTSSSA DNGAAHHTTL RRRQSARSVP PLLDSDSNSL

                                   51                                                  100
           o._sativa_(d43212)      ~~~~~~~~~~ ~~~~~~~~~~ ~~~~~~~~~~ ~~~~~~~~~~ ~~~~~~~~~~
ryegrass_exon10-15_frame1_1        ~~~~~~~~~~ ~~~~~~~~~~ ~~~~~~~~~~ ~~~~~~~~~~ ~~~~~~~~~~
           o._sativa_(deduced)     ~~~~~~~~~~ ~~MAPPPSLA PDRGGGEPDD ALRLRARAAA AAGDAPAPQQ
        a._thaliana_(cab45373)     SPSDDVGAPA DVR......D RIDSVVNDDA QGTANLAGDN NGGGDNNGGG
            b._napus_(q9m4v2)      TVSD.....A DVR......D RVDSAV.EDT QGKANLAGEN E.......IR
     m._truncatula_(al381190)      ~~~~~~~~~~ ~~~~~~~~~~ ~~~~~~~~~~ ~~~~~~~~~~ ~~~~~~~~~~
            g._max_(aw349274)      ~~~~~~~~~~ ~~~~~~~~~~ ~~~~~~~~~~ ~~~~~~~~~~ ~~~~~~~~~~
             n._tabaccum-dgat      DANMS.EDRR DVCGSGAGLE TVNERSKSVG ESSDVIRKED DRNDNVANGE
        p._frutescens_(q9fv16)     EAESAINDSE NVRNDANLIE NLRGGAVESE NEKQESYGKE EGAKVKENGE

                                   101                                                 150
           o._sativa_(d43212)      ~~~~~~~~~~ ~~~~~~~~~~ ~~~~~~~~~~ ~~~~~~~~~~ ~~~~~~~~~~
ryegrass_exon10-15_frame1_1        ~~~~~~~~~~ ~~~~~~~~~~ ~~~~~~~~~~ ~~~~~~~~~~ ~~~~~~~~~~
           o._sativa_(deduced)     QQEQRHQEQQ QQLLWYRASA PAHRRVRESP LSSDAIFRQS HAGLLNLCIV
        a._thaliana_(cab45373)     RGGGEGRGNA DATFTYRPSV PAHRRARESP LSSDAIFKQS HAGLFNLCVV
            b._napus_(q9m4v2)      ESGGEAGGNV DVRYTYRPSV PAHRRVRESP LSSDAIFKQS HAGLFNLCVV
     m._truncatula_(al381190)      ~~~~~~~~~~ ~~~~~~~~~~ ~~~~~~~~~~ ~~~~~~~~~~ ~~~~~~~~~~
            g._max_(aw349274)      ~~~~~~~~~~ ~~~~~~~~~~ ~~~~~~~~~~ ~~~~~~~~~~ ~~~~~~~~~~
             n._tabaccum-dgat      ESKSTETTTT PFKFAYRASA PAHRRIKESP LSSDAIFKQS HAGLFNLCVV
        p._frutescens_(q9fv16)     TSNGNGTDVM AVKFTFRPAA PAHRKNKESP LSSDAIFKQS HAGLFNLCIV

                                   151                                                 200
           o._sativa_(d43212)      ~~~~~~~~~~ ~~~~~~~~~~ ~~~~~~~~~~ ~~~~~~~~~~ ~~~~~~~~~~
ryegrass_exon10-15_frame1_1        ~~~~~~~~~~ ~~~~~~~~~~ ~~~~~~~~~~ ~~~~~~~~~~ ~~~~~~~~~~
           o._sativa_(deduced)     VLVAVNSRLI IENLMKYGLL IRAGFWFSGT SLADWPLLMC CLTLPTFPLA
        a._thaliana_(cab45373)     VLIAVNSRLI IENLMKYGWL IRTDFWFSSR SLRDWPLFMC CISLSIFPLA
            b._napus_(q9m4v2)      VLVAVNSRLI IENLMKYGWL IRTDFWFSST SLRDWPLFMC CLSLSIFPLA
     m._truncatula_(al381190)      ~~~~~~~~~~ ~~~~~~~~~~ ~~~~~~~~~~ ~~~~~~~~~~ ~~~~~~~~~~
            g._max_(aw349274)      ~~~~~~~~~~ ~~~~~~~~~~ ~~~~~~~~~~ ~~~~~~~~~~ ~~~~~~~~~~
             n._tabaccum-dgat      VLIAVNSRLI IENLMKYGLL IRAGFWFSSK SLRDWPLLMC CLSLQILPLA
        p._frutescens_(q9fv16)     VLVAVNSRLI IENLMKYGWL IKSGFWFSST SLRDWPLLMC CLSLPVFALA

                                   201                                                 250
           o._sativa_(d43212)      ~~~~~~~~~~ ~~~~~~~~~~ ~~~~~~~~~~ ~~~~~~~~~~ ~~~~~~~~~~
ryegrass_exon10-15_frame1_1        ~~~~~~~~~~ ~~~~~~~~~~ ~~~~~~~~~~ ~~~~~~~~~~ ~~~~~~~~~~
           o._sativa_(deduced)     ALMVEKLAQR KLI...VVIL LHIVITTSVL VYPVVVILKC DSAVLSGFVL
        a._thaliana_(cab45373)     AFTVEKLVLQ KYISEPVVIF LHIIITMTEV LYPVYVTLRC DSAFLSGVTL
            b._napus_(q9m4v2)      AFTVEKLVLQ KCISEPVVII LHIIITMTEV LYPVYVTLRC DSAFLSGVTL
     m._truncatula_(al381190)      ~~~~~~~~~~ ~~~~~~~~~~ ~~~~~~~~~~ ~~~~~~~~~~ ~~~~~~~~~~
            g._max_(aw349274)      ~~~~~~~~~~ ~~~~~~~~~~ ~~~~~~~~~~ ~~~~~~~~~~ ~~~~~~~~~~
             n._tabaccum-dgat      AFLVEKLAQQ RHLTERAVVT LHITITTAAI LYPVLVILGC DSAFLFGVIL
        p._frutescens_(q9fv16)     SFLVEKLVKL NYIPEWVAVF LHVTITTVEI LFPVVVILRC DSAVLSGVTL

                                   251                                                 300
           o._sativa_(d43212)      ~~~~~~~~~~ ~~~~~~~~~~ ~~~~~~~~~~ ~~~~~~~~~~ ~~~~~~~~~~
ryegrass_exon10-15_frame1_1        ~~~~~~~~~~ ~~~~~~~~~~ ~~~~~~~~~~ ~~~~~~~~~~ ~~~~~~~~~~
           o._sativa_(deduced)     MFLASIIWLK LVSFAHTNYD IRMLSKSIEK ........DP ENIKWPTFKR
        a._thaliana_(cab45373)     MLLTCIVWLK LVSYAHTSYD IRSLANAADK .......ANP EVSYYVSLKS
            b._napus_(q9m4v2)      MLLTCIVWLK LVSYAHTNYD IRTLANSSDK .......ANP EVSYYVSLKS
     m._truncatula_(al381190)      ~~~~~~~~~~ ~~~~~~~~~~ ~~~~~~~~~~ ~~~~~~~~~~ ~~~~~~~~~~
            g._max_(aw349274)      ~~~~~~~~~~ ~~~~~~~~~~ ~~~~~~~~~~ ~~~~~~~~~~ ~~~~~~~~~~
             n._tabaccum-dgat      MLVACIVWMK LVSYAHTNHD MRQLAKSTDK DETSDG.... DFSYDVSFKS
        p._frutescens_(q9fv16)     MLFACTVWLK LVSYAHTNYD LRVLAKSLDK WEAMSRYWNL DYAYDVSFKS
```

FIGURE 7

```
                               301                                                  350
           o._sativa_(d43212)  ~~~~~~~~~~ ~~~~~~~~~~ ~~~~~~~~~~ ~~~~~~~~~~ ~~~~~~~~~~
ryegrass_exon10-15_frame1_1    ~~~~~~~~~~ ~~~~~~~~~~ ~~~~~~~~~~ ~~~~~~~~~~ ~~~~~~~~~~
           o._sativa_(deduced) LSYFMLAPTL CYQGASLHDF SWYFIYIAVC ILNM...... ..SFIFQYIN
      a._thaliana_(cab45373)   LAYFMVAPTL CYQPSYPRSA CIRKGWVARQ FAKLVIFTGF MGFIIEQYIN
           b._napus_(q9m4v2)   LAYFMLAPTL CYQPSYPRSP CIRKGWVARQ FAKLIIFTGF MGFIIEQYIN
    m._truncatula_(al381190)   ~~~~~~~~~~ ~~~~~~~~~~ ~~~~~~~~~~ ~~~~~~~~~~ ~~~~~~~~~~
            g._max_(aw349274)  ~~~~~~~~~~ ~~~~~~~~~~ ~~~~~~~~~~ ~~~~~~~~~~ ~~~~~~~~~~
             n._tabaccum-dgat  LAYFMVAPTL CYQLSYPHTP CIRKGWVARQ FIKLVIFTGL MGFIIEQYIN
      p._frutescens_(q9fvl6)   LAYFMVAPTL CYQPSYPRTA CIRKGWVVRQ LIKLVIFTGL MGFIIEQYIN

                               351                                                  400
           o._sativa_(d43212)  ~~~~~~~~~~ ~~~~~~~~~~ ~~~~~~~~~~ ~~~~~~~~~~ ~~~~~~~~~~
ryegrass_exon10-15_frame1_1    ~~~~~~~~~~ ~~~~~~~~~~ ~~~~~~~~~~ ~~~~~~~~~~ ~~~~~~~~~~
           o._sativa_(deduced) PIVKNSKHPL KGNFLNAIER VLKLSVPTLY VWLCMFYCFF HLWLNILAEL
      a._thaliana_(cab45373)   PIVRNSKHPL KGDLLYAIER VLKLSVPNLY VWLCMFYCFF HLWLNILAEL
           b._napus_(q9m4v2)   PIVRNSKHPL KGDLLYGVER VLKLSVPNLY VWLCMFYCFF HLWLNILAEL
    m._truncatula_(al381190)   ~~~~~~~~~~ ~~~~~~~~~~ ~~~~~~~~~~ ~~~~~~~~~~ ~~~~~~~~~~
            g._max_(aw349274)  ~~~~~~~~~~ ~~~~~~~~~~ ~~~~~~~~~~ ~~~~~~~~~~ ~~~~NILAEL
             n._tabaccum-dgat  PIVQNSQHPL KGNLLYAIER VLKLSVPNLY VWLCMFYCFF HLWLNILAEL
      p._frutescens_(q9fvl6)   PIVQNSQHPL KGNLLYAIER VLKLSVPNLY VWLCMFYCFF HLWLNILAEL

                               401                                                  450
           o._sativa_(d43212)  ~~~~~~~~~~ ~~~~~~~~~~ ~~~~~~~~~~ ~~~VRHIYFP CMRNGISKEV
ryegrass_exon10-15_frame1_1    ~~~~~~~~~~ ~~~~~~~~~~ YWRMWNMPVH KWVVRHIYFP PRRSGISKEV
           o._sativa_(deduced) LCFGDREFYK DWWNAKTVEE YWRMWNMPVH KWVIRHIYFP CIRNGFSKGV
      a._thaliana_(cab45373)   LCFGDREFYK DWWNAKSVGD YWRMWNMPVH KWMVRHIYFP CLRSKIPKTL
           b._napus_(q9m4v2)   LCFGDREFYK DWWNAKSVGD YWRMWNMAVH KWMVRHVYFP CLRRNIPKVP
    m._truncatula_(al381190)   ~~~~~~~~~~ ~~~~~~~~~~ ~~~~~~~~~~ ~~~~~~~~~~ ~~~~~~PKGA
            g._max_(aw349274)  LRFGDREFYK DWWNAKTVED YWRMWNMPVH KWMIRHLYFP CLRHGLPKAA
             n._tabaccum-dgat  LCFGDREFYK DWWNAKTIDE YWRMWNMPVH KWMVRHLYFP CLRNGIPKGV
      p._frutescens_(q9fvl6)   LCFGDREFYK DWWNARTVEE YWRMWNMPVH KWMVRHIYCP CLQNGIPKIV

                               451                                                  500
           o._sativa_(d43212)  ALLISFLVSA VLHEICVAVP CRILKFWAFL GIMLQIPLIV LTA~~~~~~~
ryegrass_exon10-15_frame1_1    AVFVSFFVSA VLHELCVAVP CRIVKFWAFL GIMLQIPLII LTSYLKSKFR
           o._sativa_(deduced) AILISFLVSA AFHELCVAVP CHIFKFWAFI GIMFQIPLVF LTKYLQDKFN
      a._thaliana_(cab45373)   AIIIAFLVSA VFHELCIAVP CRLFKLWAFL GIMFQVPLVF ITNYLQERF.
           b._napus_(q9m4v2)   AIILAFLVSA VFHELCIAVP CRLFKLWAFL GIMFQVPLVF ITNYLQERF.
    m._truncatula_(al381190)   AVLIAFMVSA LFHELCIAVP CHIFKLWAFS GIMFQVPLVL ITNYLQNKFS
            g._max_(aw349274)  ALLIXXLVSA LFHELCIAVP CHIFKLWAFG GIMFQVPLVL ITNYLQNKFR
             n._tabaccum-dgat  AILIAFLVSA VFHELCIAVP CRLFKWWAFM GIMFQVPLVI LTNFLQNKFQ
      p._frutescens_(q9fvl6)   AVLIAFLVSA IFHELCVAVP CQIFKFWAFS GIMLQVPLVI VTNYLQEKFK

                               501                                  539
           o._sativa_(d43212)  ~~~~~~~~~~ ~~~~~~~~~~ ~~~~~~~~~~ ~~~~~~~~~~
ryegrass_exon10-15_frame1_1    DTMAGNMIFW FFFCIYGQPM CVLLYYHDVM NRIGKTG~~
           o._sativa_(deduced) NTMVGNMIFW FFFSILGQPM CVLLYYHDVM NRQQAQTNR
      a._thaliana_(cab45373)   GSTVGNMIFW FIFCIFGQPM CVLLYYHDLM NRKGSMS~~
           b._napus_(q9m4v2)   GSMVGNMIFW FTFCIFGQPM CVLLYYHDLM NRKGKMS~~
    m._truncatula_(al381190)   NSMVGNMFFW FTFCILGQPM CVLLYYHDLM NRNSKLD~~
            g._max_(aw349274)  NSMVGNMIFW FIFSILGQPM CVLLYYHDLM NRKGKLD~~
             n._tabaccum-dgat  SSMVGNMMFW CFFCILGQPM CVLLYYHDVM NRKSSAR~~
      p._frutescens_(q9fvl6)   NSMVGNMMFW CFFCIFGQPM CVLLYYHDIM NRKASAR~~
```

FIGURE 7 (cont.)

MODIFICATION OF FATTY ACID BIOSYNTHESIS USING RECOMBINANT DIACYLGLYCEROL ACYLTRANSFERASE SEQUENCES FROM RYEGRASS (*LOLIUM*) AND FESCUE (*FESTUCA*)

The present invention relates to nucleic acid fragments encoding amino acid sequences for fatty acid biosynthesis enzymes in plants, and the use thereof for the modification of fatty acid biosynthesis in plants.

In most plants (including *Lolium perenne*) the majority of leaf lipids are attached to a glycerol backbone and exist as diacylglycerols. These are incorporated into lipid bi-layers where they function as membranes of multiple sub-cellular organelles or the as the membrane of the cell itself. The majority of lipid bilayer in the leaf is the chloroplast thylakoid membrane. A smaller amount of leaf lipid exists as epicuticular waxes and an even smaller percentage is present in the form of triacylglycerol (TAG).

Most plants (including *Lolium perenne*) synthesise and store TAG in developing embryos and pollen cells where it is subsequently utilised to provide catabolizable energy during germination and pollen tube growth. Dicotyledonous plants can accumulate up to approximately 60% of their seed weight as TAG. Ordinarily, this level is considerably lower in the monocotyledonous seeds where the main form of energy storage is carbohydrates (e.g., starch).

The only committed step in TAG biosynthesis is the last one, i.e., the addition of a third fatty acid to an existing diacylglycerol, thus generating TAG. In plants this step is performed by one of three enzymes including: acyl CoA: diacylglycerol acyltransferase (DGAT1); an unrelated acyl CoA:diacylglycerol acyl transferase (DGAT2); and phospholipid:diacylglycerol acyltransferase (PDAT) (Zou et al., 1999; Bouvier-Navé et al., 2000; Dahlqvist et al., 2000; Lardizabal et al., 2001). The feeding value of grazed pastures is defined as an animal production response and is quantified by weight gain or milk yield. Nutritive value is a response per unit of feed intake and therefore feeding value is a function of both intake and the efficiency with which the animal utilises the products of digestion (Ulyatt 1973). The plant factors that influence feeding value include species, cultivar, plus responses to environment and grazing management. Examples of differences in feeding value among species include the lower performance of animals grazing subtropical grasses such as kikuyu in comparison to temperate grasses such as perennial ryegrass and timothy (Buxton and Mertens 1995). Differences also occur among temperate grass species. The high feeding value of timothy relative to perennial ryegrass is associated with its later flowering, endophyte-free status and slower decline in digestibility as tillers become reproductive (Chariton and Stewart 2000). The higher feeding value of legumes such as white clover is a major reason for their inclusion in temperate pastures. White clover improves feeding value for young sheep by 50-100% over grasses and by 15-35% over other forage legume species (Ulyatt 1981). This results from greater intake, higher N content, more rapid particle breakdown, and more efficient use of digested nutrients by the animals fed white clover. Herbs such as chicory have also been introduced over the past decade to improve feeding value.

The impact of plant improvement within species to improve nutritive value is probably more contentious. Traditionally pasture plant improvement has focussed on the development of high yielding, pest and disease resistant, and persistent cultivars. While these traits continue to be important for the commercial success of released cultivars, breeding objectives have diversified to include improved protein/energy balance, increased by-pass protein levels, leaf properties affecting intake, and manipulation of compounds that affect animal health, animal welfare, reproductive fertility, animal product flavour and texture (Caradus et al. 2000). Typically pasture plants are relatively rich in protein in comparison to their energy content, as a result, much of the ingested protein is degraded by rumen micro-organisms and lost from the animal in the form of urea (Ulyatt et al., 1988). Nitrogen losses can be reduced by improving the energy content of the forage (Ulyatt 1981; Ulyatt et al., 1988).

Primary and secondary fermentation within the rumen leads to the production of hydrogen, acetate, propionate, butyrate and carbon dioxide. Methanogens are able to use the hydrogen and acetate (as well as formate, methanol and mono-, di- and tri-methylamine) but not propionate or butyrate, as substrates for producing methane (McAllister et al., 1996). The production of methane is believed to act as an electron sink for unwanted hydrogen, thus allowing all ruminal fermentation microorganisms to achieve higher yields of ATP. The interspecies hydrogen transfer between the rumen methanogens and other rumen microorganisms enables a more complete digestion of poor quality feeds that have relatively high fibre levels. However, methane production also represents a 2-15% loss of gross energy intake to the ruminant (Sauer et al., 1998), and methane has been identified as a major contributor to green house gases. The combination of these two negative factors has lead industry to identify the mitigation of methanogenesis as a major target. The challenge is to mitigate methanogenesis in ruminants without causing a negative impact on ruminant production.

Typically, artificial ruminant diets containing high concentrations of fatty acids leads to both reduced methane production and reduced fibre degradation. The reduced methane production is partly due to a) the direct toxic effect of long chain fatty acids on methanogens; and b) the reduction of one of the substrates (hydrogen and acetate) used in the synthesis of methane. The latter is caused by the relative toxic effects of fatty acids to both protozoa and gram-positive cellulolytic acetate producing bacteria but not to the propionate-producing gram-negative bacteria; thus resulting in a reduction of hydrogen, total volatile fatty acid concentration and acetate: proprionate ratio in the rumen (Wettstein et al., 2000). The concomitant reduction in fibre degradation is caused by the physical coating of fibres by lipids and by the toxic effects of fatty acids on the protozoa and gram-positive cellulolytic bacteria (Jalč and Čerešňáková, 2001). However, when lipids are supplied in a partially rumen-protected form (e.g., whole crushed oilseeds) the negative influence on fibre digestion appears to be greatly negated (Machmüller et al., 2000; Wettstein et al., 2000). The degree of unsaturation of dietary lipid was also found to influence methanogenesis (Fievez et al., 2003).

It has been demonstrated that the lipid profile of ruminant animal feed in turn influences the lipid profile of meat and dairy products. Different plants have different lipid profiles; by selectively feeding animals only plants with the desired lipid profile it is possible to positively influence the lipid profile of downstream meat and dairy products. Given the relatively low level of lipid accumulation in the bulk of plant tissue the efficacy of this change is less than desirable. However, by supplemental feeding with TAG (made up of the preferred lipids) it is possible to make dramatic changes in the lipid profile of the final products.

The majority of the supplemented high ω-3 foods are using either ω-3-eicosapentanoic acid (EPA, C20:5n-3) or dosohexanoic acid (DHA, C22:6n-3) or a mixture of both; these are usually sourced from fish oil which is both expensive and potentially in limiting supply. A cheap and sustainable alternative would be to modify the feed intake of the animal to effect the same positive downstream changes in the lipid profiles of meat and dairy products. In unprotected supplementation feeding trials it is apparent that selection of the fatty acid composition to feed is important in determining the fatty acid composition of the resulting milk and meat fat. While the results were variable, supplementation (with no additional protection) with ω-3 rich oils including linseed oil (approximately 50% linolenic, C18:3n-3) and fish oils lead to 2 fold increases in their corresponding lipid in the meat while also lowering ω-6 fats (for reviews see: Chilliard et al., 2001; Demeyer and Doreau 1999; Ponnampalam et al., 2001; McNamee et al., 2002). In general, elevated levels of C18:2 only result in increased levels of Conjugated Linoleic Acid (CLA) whereas elevated levels of the ω3 fatty acid C18:3n-3 results in increased levels of CLA and C18:3n-3; fish oil supplements resulted in increased levels of longer chain ω-3 polyunsaturated fatty acids (PUFAs).

CLA is formed as an intermediate during the biohydrogenation of linoleic acid by the rumen bacterium *Butyrivibrio fibrisolvens* (Dhinman et al., 2000); hence complete protection of fatty acids would prohibit the production of CLA. A large portion of human dietary CLA comes from dairy and beef products that are relatively rich in CLA with the highest levels of CLA being found in pasture fed animals (Dewhurst and Scollan 1998; Demeyer and Doreau 1999; Kay et al., 2002). Numerous feeding trials have evaluated supplemental feeding with a variety of TAG sources and the effect on the formation of CLA in the milk and muscle (for reviews see: Scollan et al., 2001a; Kelly et al., 1998; Demeyer and Doreau 1999; Wood et al., 1999; Bauman et al., 2000; Chilliard et al., 2001; Kay et al., 2002). The efficacy of these trials ranged from 28% increase to over 500% increase in the CLA level. The higher levels were achieved under continuous infusion rather than single or double administrations during the day. Supplemental oils varied from linoleic, linolenic and fish oils which are rich in long chain polyunsaturates in particular C20:5n-3 and C22-6n-3. The most efficient supplement appeared to be linoleic, although all other supplements were frequently reported to result in 2-3 fold increases (Scollan et al., 2001a&b).

Accordingly there is a need for a system to mitigate methane production to reduce nitrogen losses and increase healthy lipids in the meat and milk of ruminants.

It is an object of the present invention to overcome, or at least alleviate, one or more of these needs in light of the prior art.

In one aspect, the present invention provides substantially purified or isolated nucleic acids encoding amino acid sequences of diacylglycerol acyltransferase (DGAT1) enzymes, and functionally active fragments and variants thereof.

The present invention also provides substantially purified or isolated nucleic acid fragments encoding amino acid sequences for a class of polypeptides which are related to DGAT1. Such polypeptides are referred to herein as DGAT1-like. The genes which encode these polypeptides are expressed in a similar manner to DGAT1. The invention also encompasses functionally active fragments and variants of nucleic acids encoding such polypeptides.

As used herein the term DGAT1-like relates to polypeptides that are produced in the plant in substantially the same organs and at substantially the same developmental stages as DGAt1.

The nucleic acid fragments may be obtained from ryegrass (*Lolium*) or fescue (*Festuca*) species. These species may be of any suitable type, including Italian or annual ryegrass, perennial ryegrass, tall fescue, meadow fescue and red fescue. Preferably the species is a ryegrass, more preferably perennial ryegrass (*L. perenne*).

Nucleic acids according to the invention may be full-length genes or part thereof, and are also referred to as "nucleic acid fragments" and "nucleotide sequences" in this specification.

The nucleic acid fragment may be of any suitable type and includes DNA (such as cDNA or genomic DNA) and RNA (such as mRNA) that is single- or double-stranded, optionally containing synthetic, non-natural or altered nucleotide bases, and combinations thereof.

The term "isolated" means that the material is removed from its original environment (eg. the natural environment if it is naturally occurring). For example, a naturally occurring nucleic acid fragment or polypeptide present in a living plant is not isolated, but the same nucleic acid fragment or polypeptide separated from some or all of the coexisting materials in the natural system, is isolated. Such an isolated nucleic acid fragment could be part of a vector and/or such nucleic acid fragments could be part of a composition, and still be isolated in that such a vector or composition is not part of its natural environment.

By "functionally active" in respect of a nucleotide sequence is meant that the fragment or variant (such as an analogue, derivative or mutant) is capable of modifying fatty acid biosynthesis in a plant. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence, more preferably at least approximately 90% identity, most preferably at least approximately 95% identity. Such functionally active variants and fragments include, for example, those having nucleic acid changes which result in conservative amino acid substitutions of one or more residues in the corresponding amino acid sequence. Preferably the fragment has a size of at least 30 nucleotides, more preferably at least 45 nucleotides, most preferably at least 60 nucleotides.

By "functionally active" in the context of a polypeptide is meant that the fragment or variant has one or more of the biological properties of the enzyme DGAT1. Additions, deletions, substitutions and derivatizations of one or more of the amino acids are contemplated so long as the modifications do not result in loss of functional activity of the fragment or variant. Preferably the functionally active fragment or variant has at least approximately 60% identity to the relevant part of the above mentioned sequence, more preferably at least approximately 80% identity, most preferably at least approximately 90% identity. Such functionally active variants and fragments include, for example, those having conservative amino acid substitutions of one or more residues in the corresponding amino acid sequence. Preferably the fragment has a size of at least 10 amino acids, more preferably at least 15 amino acids, most preferably at least 20 amino acids.

By "operatively linked" is meant that said regulatory element is capable of causing expression of said nucleic acid in a plant cell and said terminator is capable of terminating expression of said nucleic acid in a plant cell. Preferably, said regulatory element is upstream of said nucleic acid and said terminator is downstream of said nucleic acid.

By "an effective amount" is meant an amount sufficient to result in an identifiable phenotypic trait in said plant, or a plant, plant seed or other plant part derived therefrom. Such amounts can be readily determined by an appropriately skilled person, taking into account the type of plant, the route of administration and other relevant factors. Such a person will readily be able to determine a suitable amount and method of administration. See, for example, Maniatis et al, Molecular Cloning: A Laboratory Manual, Cold Spring Harbor Laboratory, Cold Spring Harbor, the entire disclosure of which is incorporated herein by reference.

It will also be understood that the term "comprises" (or its grammatical variants) as used in this specification is equivalent to the term "includes" and should not be taken as excluding the presence of other elements or features.

Reference to any prior art in the specification is not, and should not be taken as, an acknowledgment or any form of suggestion that this prior art forms part of the common general knowledge in Australia or any other jurisdiction.

In a preferred embodiment of this aspect of the invention, the substantially purified or isolated nucleic acid fragment encoding a DGAT1 protein includes a nucleotide sequence selected from the group consisting of (a) the sequence shown in FIG. 5 hereto; (b) complements of the sequence recited in (a); (c) sequences antisense to the sequence recited in (a) and (b); (d) functionally active fragments and variants of the sequences recited in (a), (b) and (c); and (e) RNA sequences corresponding to the sequences recited in (a), (b), (c) and (d).

The nucleic acid fragments of the present invention may be used to isolate cDNAs and genes encoding homologous proteins from the same or other plant species.

Additionally, genes encoding other DGAT1 enzymes, either as cDNAs or genomic DNAs, may be isolated directly by using all or a portion of the nucleic acid fragments of the present invention as hybridisation probes to screen libraries from the desired plant employing the methodology known to those skilled in the art. Specific oligonucleotide probes based upon the nucleic acid sequences of the present invention can be designed and synthesized by methods known in the art. Moreover, the entire sequences can be used directly to synthesize DNA probes by methods known to the skilled artisan such as random primer DNA labelling, nick translation, or end-labelling techniques, or RNA probes using available in vitro transcription systems. In addition, specific primers can be designed and used to amplify a part or all of the sequences of the present invention. The resulting amplification products can be labelled directly during amplification reactions or labelled after amplification reactions, and used as probes to isolate full length cDNA or genomic fragments under conditions of appropriate stringency.

In addition, two short segments of the nucleic acid fragments of the present invention may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the nucleic acid fragments of the present invention, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, those skilled in the art can follow the RACE protocol (Frohman et al. (1988) *Proc. Natl. Acad Sci. USA* 85:8998, the entire disclosure of which is incorporated herein by reference) to generate cDNAs by using PCR to amplify copies of the region between a single point in the transcript and the 3' or 5' end. Using commercially available 3' RACE and 5' RACE systems (BRL), specific 3' or 5' cDNA fragments can be isolated (Ohara et al. (1989) *Proc. Natl. Acad Sci USA* 86:5673; Loh et al. (1989) *Science* 243:217). Products generated by the 3' and 5' RACE procedures can be combined to generate full-length cDNAs.

In a second aspect of the present invention there is provided a substantially purified or isolated polypeptide from a ryegrass (*Lolium*) or fescue (*Festuca*) species, selected from the group consisting DGAT1 enzymes, DGAT1-like polypeptides and functionally active fragments and variants thereof.

The ryegrass (*Lolium*) or fescue (*Festuca*) species may be of any suitable type, including Italian or annual ryegrass, perennial ryegrass, tall fescue, meadow fescue and red fescue. Preferably the species is a ryegrass, more preferably perennial ryegrass (*L. perenne*).

In a preferred embodiment of this aspect of the invention, there is provided a substantially purified or isolated DGAT1 polypeptide including an amino acid sequence selected from the group of sequences translated from nucleotide sequence shown in FIG. 5 hereto; and functionally active fragments and variants thereof.

In a further embodiment of this aspect of the invention, there is provided a polypeptide recombinantly produced from a nucleic acid according to the present invention. Techniques for recombinantly producing polypeptides are known to those skilled in the art.

Availability of the nucleotide sequences of the present invention and deduced amino acid sequences facilitates immunological screening of cDNA expression libraries. Synthetic peptides representing portions of the instant amino acid sequences may be synthesized. These peptides can be used to immunise animals to produce polyclonal or monoclonal antibodies with specificity for peptides and/or proteins comprising the amino acid sequences. These antibodies can be then used to screen cDNA expression libraries to isolate full-length cDNA clones of interest.

A genotype is the genetic constitution of an individual or group. Variations in genotype are essential in commercial breeding programs, in determining parentage, in diagnostics and fingerprinting, and the like. Genotypes can be readily described in terms of genetic markers. A genetic marker identifies a specific region or locus in the genome. The more genetic markers, the finer defined is the genotype. A genetic marker becomes particularly useful when it is allelic between organisms because it then may serve to unambiguously identify an individual. Furthermore, a genetic marker becomes particularly useful when it is based on nucleic acid sequence information that can unambiguously establish a genotype of an individual and when the function encoded by such nucleic acid is known and is associated with a specific trait. Such nucleic acids and/or nucleotide sequence information including single nucleotide polymorphisms (SNPs), variations in single nucleotides between allelic forms of such nucleotide sequence, can be used as perfect markers or candidate genes for the given trait. In a further aspect of the present invention, there is provided use of nucleic acids of the present invention including SNP's, and/or nucleotide sequence information thereof, as molecular genetic markers.

In a further aspect of the present invention there is provided a method of isolating a nucleic acid of the present invention including a single nucleotide polymorphism (SNP). Nucleic acids and fragments thereof from a nucleic acid library may desirably be sequenced.

The nucleic acid library may be of any suitable type and is preferably a cDNA library. The nucleic acid fragments may be isolated from recombinant plasmids or may be amplified, for example using polymerase chain reaction. The sequencing may be performed by techniques known to those skilled in the art.

In a further aspect of the present invention there is provided use of a nucleic acid according to the present invention, and/or nucleotide sequence information thereof, as a molecular genetic marker. More particularly, nucleic acids according to the present invention and/or nucleotide sequence information thereof may be used as a molecular genetic marker for quantitative trait loci (QTL) tagging, QTL mapping, DNA fingerprinting and in marker assisted selection, particularly in ryegrasses and fescues. Even more particularly, nucleic acids according to the present invention and/or nucleotide sequence information thereof may be used as molecular genetic markers in forage and turf grass improvement, e.g. tagging QTLs for herbage quality traits, dry matter digestibility, mechanical stress tolerance, disease resistance, insect pest resistance, plant stature, leaf and stem colour. Even more particularly, sequence information revealing SNPs in allelic variants of the nucleic acids of the present invention and/or nucleotide sequence information thereof may be used as molecular genetic markers for QTL tagging and mapping and in marker assisted selection, particularly in ryegrasses and fescues.

In a still further aspect of the present invention there is provided a construct including a nucleic acid according to the present invention. The construct may be a vector. In a preferred embodiment of this aspect of the invention, the vector may include at least one regulatory element, such as a promoter, a nucleic acid according to the present invention and a terminator; said regulatory element, nucleic acid and terminator being operatively linked.

The vector may be of any suitable type and may be viral or non-viral. The vector may be an expression vector. Such vectors include chromosomal, non-chromosomal and synthetic nucleic acid sequences, eg. derivatives of plant viruses; bacterial plasmids; derivatives of the Ti plasmid from *Agrobacterium tumefaciens*, derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable, or integrative or viable in the plant cell.

The regulatory element and terminator may be of any suitable type and may be endogenous to the target plant cell or may be exogenous, provided that they are functional in the target plant cell.

In another embodiment, the construct or vector may include more than one nucleic acid. The nucleic acids within the same construct or vector may have identical or differing sequences. In one preferred embodiment, the construct or vector has at least two nucleic acids encoding functionally similar enzymes.

Preferably one of the regulatory elements is a promoter. A variety of promoters which may be employed in the vectors of the present invention are well known to those skilled in the art. Factors influencing the choice of promoter include the desired tissue specificity of the vector, and whether constitutive or inducible expression is desired and the nature of the plant cell to be transformed (eg. monocotyledon or dicotyledon). Particularly suitable constitutive promoters include the Cauliflower Mosaic Virus 35S (CaMV 35S) promoter, the maize Ubiquitin promoter, and the rice Actin promoter.

A variety of terminators which may be employed in the vectors of the present invention are also well known to those skilled in the art. It may be from the same gene as the promoter sequence or a different gene. Particularly suitable terminators are polyadenylation signals, such as the CaMV 35S polyA and other terminators from the nopaline synthase (nos) and the octopine synthase (ocs) genes.

The vector, in addition to the regulatory element, the nucleic acid of the present invention and the terminator, may include further elements necessary for expression of the nucleic acid, in different combinations, for example vector backbone, origin of replication (ori), multiple cloning sites, spacer sequences, enhancers, introns (such as the maize Ubiquitin Ubi intron), antibiotic resistance genes and other selectable marker genes (such as the neomycin phosphotransferase (npt2) gene, the hygromycin phosphotransferase (hph) gene, the phosphinothricin acetyltransferase (bar or pat) gene), and reporter genes (such as green fluorescence protein (GFP), beta-glucuronidase (GUS) gene (gusA)). The vector may also contain a ribosome binding site for translation initiation. The vector may also include appropriate sequences for amplifying expression.

As an alternative to use of a selectable marker gene to provide a phenotypic trait for selection of transformed host cells, the presence of the construct vector in transformed cells may be determined by other techniques well known in the art, such as PCR (polymerase chain reaction), Southern blot hybridisation analysis, histochemical GUS assays, northern and Western blot hybridisation analyses.

Those skilled in the art will appreciate that the various components of the construct or vector are operatively linked, so as to result in expression of said nucleic acid. Techniques for operatively linking the components of the construct or vector of the present invention are well known to those skilled in the art. Such techniques include the use of linkers, such as synthetic linkers, for example including one or more restriction enzyme sites.

The constructs and vectors of the present invention may be incorporated into a variety of plants, including monocotyledons (such as grasses from the genera *Lolium, Festuca, Paspalum, Pennisetum, Panicum* and other forage and turfgrasses, corn, rice, sugarcane, oat, wheat and barley) dicotyledons (such as *arabidopsis*, tobacco, soybean, canola, cotton, potato, chickpea, medics, white clover, red clover, subterranean clover, alfalfa, eucalyptus, poplar, hybrid aspen, and gymnosperms (pine tree)). In a preferred embodiment, the constructs and vectors are used to transform monocotyledons, preferably grass species such as ryegrasses (*Lolium* species) and fescues (*Festuca* species), even more preferably a ryegrass, most preferably perennial ryegrass, including forage- and turf-type cultivars.

Techniques for incorporating the constructs and vectors of the present invention into plant cells (for example by transduction, transfection or transformation) are well known to those skilled in the art. Such techniques include *Agrobacterium* mediated introduction, electroporation to tissues, cells and protoplasts, protoplast fusion, injection into reproductive organs, injection into immature embryos and high velocity projectile introduction to cells, tissues, calli, immature and mature embryos. The choice of technique will depend largely on the type of plant to be transformed.

Cells incorporating the constructs and vectors of the present invention may be selected, as described above, and then cultured in an appropriate medium to regenerate transformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

In a further aspect of the present invention there is provided a plant cell, plant, plant seed or other plant part, including, e.g. transformed with, a construct or vector of the present invention.

The plant cell, plant, plant seed or other plant part may be from any suitable species, including monocotyledons, dicotyledons and gymnosperms. In a preferred embodiment the plant cell, plant, plant seed or other plant part is from a monocotyledon, preferably a grass species, more preferably a ryegrass (*Lolium* species) or fescue (*Festuca* species), even more preferably a ryegrass, most preferably perennial ryegrass, including both forage- and turf-type cultivars.

The present invention also provides a plant, plant seed or other plant part derived from a plant cell of the present invention. The present invention also provides a plant, plant seed or other plant part derived from a plant of the present invention.

In a further aspect of the present invention there is provided a method of modifying fatty acid biosynthesis in a plant, said method including introducing into said plant an effective amount of a nucleic acid, construct and/or vector according to the present invention.

Using the methods and materials of the present invention the lipid content of *L. perenne* leaves may be increased by over expressing the transcribed region of the *L. perenne* DGAT1 gene in the leaf. While applicants do not wish to be restricted by theory, it is predicted that this leads to the production of TAG (containing mainly long chain unsaturated fatty acids) within the cytoplasm of these cells.

In a further aspect of the present invention there is provided a method of reducing ruminant waste urea production by feeding a ruminant a plant according to the present invention. The method according to this aspect of the present invention has the potential to reduce nitrogen losses through a non supplemental, pasture only, feed system. It is predicted that by over expressing the transcribed region of the *L. perenne* DGAT1 gene in *L. perenne* leaves leads to an increase in the C18:3 n-3 lipid content of TAG within the cytoplasm of leaf cells. It is predicted that the ingestion of these leaves reduces the microbial production of urea by one or more of the methods described above.

In a further aspect of the present invention there is provided a method of reducing ruminant methane production by feeding a ruminant a plant according to the present invention. The method according to this aspect of the present invention has the potential to reduce ruminant methane production through a non supplemental, pasture only, feed system. It is predicted that over expressing the transcribed region of the *L. perenne* DGAT1 gene in *L. perenne* leaves leads to an increase in the long chain unsaturated lipid content of TAG within the cytoplasm of leaf cells. It is predicted that the ingestion of these leaves reduces the production of methane by one or more of the methods described above.

In a further aspect of the present invention there is provided a method of increasing ω3 and CLA lipid content in ruminant meat and dairy products by feeding a ruminant a plant according to the present invention. The method according to this aspect of the present invention has the potential to increase the level of ω3 and CLA lipid content in ruminant meat and dairy products through a non supplemental, pasture only, feed system. It is predicted that by over expressing the transcribed region of the *L. perenne* DGAT1 gene in *L. perenne* leaves leads to an increase in the C18:3 n-3 lipid content of TAG within the cytoplasm of leaf cells. It is predicted that the ingestion of these leaves increases the ω3 and CLA fatty acid content of meat and dairy products by one or more of the methods described above.

In a still further aspect of the present invention there is provided a fatty acid modified fatty acid substantially or partially purified or isolated from a plant, plant seed or other plant part of the present invention.

In a further aspect of the present invention there is provided a preparation for transforming a plant comprising at least one nucleic acid according to the present invention. The preparation may contain vectors or other constructs to facilitate administration to and/or transformation of the plant with the nucleic acid.

The present invention will now be more fully described with reference to the accompanying Examples and drawings. It should be understood, however, that the description following is illustrative only and should not be taken in any way as a restriction on the generality of the invention described above.

In the Figures:

FIG. 1 shows the alignment of a translated 267 base pair *Lolium perenne* DGAT1 DNA fragment from genomic DNA (Seq. ID No: 26) (containing a partial sequence from exon 12 and a partial sequence from exon 13; SEQ ID No. 2) with other plant DGAT peptide sequences (SEQ ID Nos. 1 and 3-9). Accession numbers are shown in parenthesis. Grey boxes indicate conserved identical residues. *Lolium perenne* DGAT1 sequence is underlined and in bold.

FIG. 2 shows the phylogenetic relationship of the translated 267 base pair *Lolium perenne* DGAT1 sequence (containing a partial sequence from exon 12 and a partial sequence from exon 13) to other translated plant DGAT1 sequences. Accession numbers are shown in parenthesis.

FIG. 3 shows an ethidium bromide stained agarose gel containing PCR products using isolated BACs (reputedly containing *Lolium perenne* DGAT genomic DNA) as template. The primers were the same primers used to amplify the original *Lolium perenne* DGAT1 267 base pair genomic fragment (Seq. ID No: 26); the positive control was a clone of the 267 bp genomic fragment. Arrows indicate products of the predicted size found in the lane containing product from the positive control and from the lane containing product from the BAC clone 72-12C.

FIG. 4 shows a schematic comparison of the transcribed regions from the *Oryza sativa* (rice) putative DGAT1 gene and the *Arabidopsis thaliana* DGAT1 genes. Exon and intron lengths are drawn to scale.

FIG. 5 shows the *Lolium perenne* DGAT1 genomic sequence from exons 10 through to exon 15 (SEQ ID Nos. 10-13). Predicted exon sequences and corresponding translated sequences are boxed in grey; the 3' UTR is underlined; and the poly-A signal sequence is shown in bold.

FIG. 6 shows a schematic comparison of the transcribed regions from the *Lolium perenne* (ryegrass) putative DGAT1 gene (containing complete sequence from exon 10 through to exon 15) the *Oryza sativa* (rice) putative DGAT1 gene and the *Arabidopsis thaliana* DGAT1 gene. Exon and intron lengths are drawn to scale.

FIG. 7 shows the alignment of the translated *Lolium perenne* DGAT1 genomic fragment (containing complete sequence from exon 10 through to exon 15) with other plant DGAT1 peptide sequences (SEQ ID Nos. 14-22). Accession numbers are shown in parenthesis. Grey boxes indicate conserved identical residues. *Lolium perenne* DGAT1 sequence is underlined and in bold.

EXAMPLES

1. Cloning *L. perenne* (Impact) DGAT

Prediction of Intron/Exon Boundaries for PCR Primer Design

The full length sequence of the DGAT1 transcribed and coding regions are published for *Arabidopsis thaliana*. Assuming conserved intron/exon splice sites between all plant DGAT genes we designed degenerate primers to rice and oat incomplete cDNA sequences (accession numbers D43212 and AL505251 respectively) that showed homology to *Arabidopsis* DGAT1 (DGAT-1-NR:22-23). PCR primers were as follows.

```
Top primer I
                                   (SEQ ID No. 23)
5' AGG AAG TTG CTG TYT TKR TAT CAT T 3'

Top primer II
                                   (SEQ ID No. 24)
5' TGT WTC TGC YGT RCT CCA TGA G 3'

Bottom primer I
                                   (SEQ ID No. 25)
5' CTA AGA ATG CCC AGA ACT TGA G 3'.
```

PCR Amplification and Sequencing of *L. perenne* DGAT Genomic Fragment

Optimisation of magnesium concentration, annealing temperature, template concentration and primer concentration was performed on *L. perenne* (Impact) genomic DNA (DGAT-1-NR:25-41). PCR products were gel purified and sequenced directly from both ends using the relevant PCR primers (DGAT-1-NR:45-53). The 267 bp sequence between top primer I and bottom primer I (not including primer sequence) was as follows:

```
5'TGTATCTGCCGTGCTCCATGAGGTAAAACATGCCCCTTTCTTTGCGCAGGCACTTCAT
ATATCCACACCAGTTATTTAGCTCTCTTTTCCGCTCTTTTGATCCAAGTTGGTTCTGAGC
TTATAATAATAAAATGTTGCAGTTGTGTGGTTACGTCATTTTTTAATGTTGTTAAATAAA
AAGTTGCTAGTTGGCCTGTTTTGATTAACTCATGATGCCTTATCTTAATTAATGTACACC
AGTTATGTGTTGCTGTCCCCTGCCGAATT 3'  (SEQ ID No. 26)
```

Based on the splice sites predicted for *Arabidopsis thaliana* we predicted the following: 5' underlined sequence indicates likely exon 12 sequence, grey block indicates likely intron 12, 3' double underlined sequence indicates likely exon 13 sequence.

Spliced the mRNA fragment would have the following nucleotide sequence:

```
                                              (SEQ ID No. 27)
5' TGTATCTGCCGTGCTCCATGAGTTATGTGTTGCTGTCCCCTGCCGAA
TT 3'
```

5' underlined sequence indicates likely exon 13 sequence, 3' double underlined sequence indicates likely exon 14 sequence.

Translated in the forward direction using frame two this sequence would encode for the peptide fragment which is shown in grey below the predicted codons:

```
T GTA TCT GCC GTG CTC CAT GAG TTA TGT GTT GCT GTC
  Val Ser Ala Val Leu His Glu Leu Sys Val Ala Val

  CCC TGC CGA ATT (SEQ ID No. 27)
  Pro Cys Arg Ile (SEQ ID No. 2)
```

Figure 2:
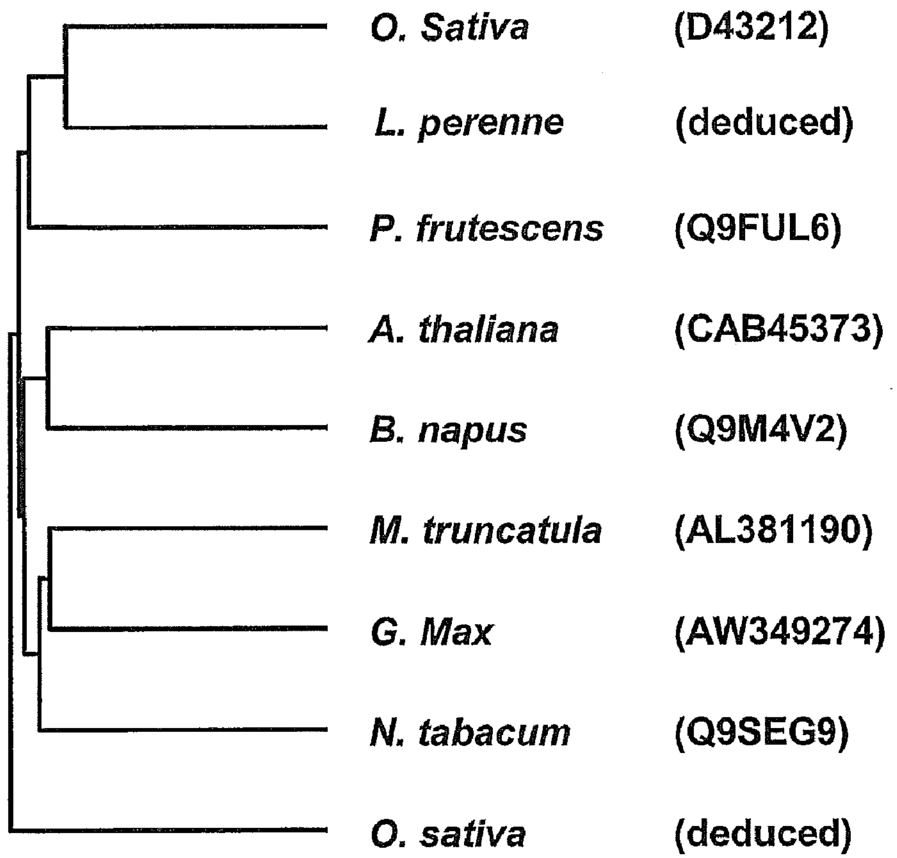

The homology of translated *L. perenne* DGAT1 fragment was compared to other DGAT1 sequences, as shown in FIGS. 1 and 2 (SEQ ID Nos. 1-9).

Identification of *L. perenne* DGAT BAC

The *Lolium perenne* DGAT1 267 base pair genomic fragment described above was PCR amplified from *L. perenne* (Impact) genomic DNA and was T/A TOPO cloned into pCR2.1 (Invitrogen) using the manufacturers protocols. PCR amplification was performed using the following primers:

```
Top primer
                                   (SEQ ID No. 28)
5' TGT ATC TGC CGT GCT CCA 3'

Bottom primer
                                   (SEQ ID No. 29)
5' AAT TCG GCA GGG GAC AGC 3'
```

This fragment was radiolabelled with $^{32}$P-dCTP using random primers as per Amersham Biosciences Rediprime™ II Random Prime Labelling System.

The probe was tested against *Lolium perenne* genomic DNA cut with Hind III, all lanes showed the presence of a single hybridizing band indicating the presence of a single copy of the 267 by DGAT1 genomic fragment.

The same fragment was then used to probe a nylon membrane ryegrass pBeloBAC11 library using standard methods detailed in Ausubel et al., (2001).

Three clones hybridised to the probe. Clones were recovered from 384 well plates.

Identified BACs were isolated from *E. coli* using alkaline lysis/PEG precipitation plasmid miniprep after overnight growth of cultures containing the selected BACs.

Figure 3:
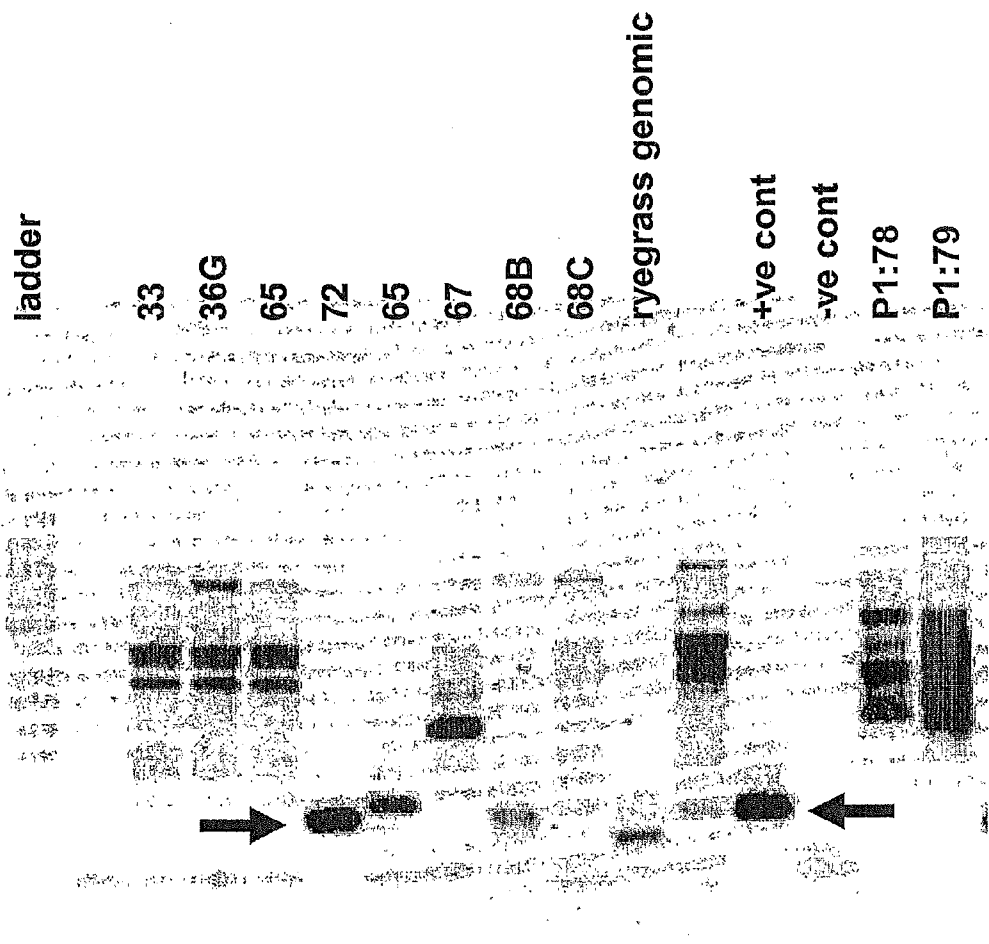

Isolated BACs were confirmed by both PCR (FIG. 3) and by Southern blot. One BAC, labelled 72-12C, produced a PCR product of the correct size and hybridised to the probe.

Shotgun Cloning, TempliPhi™ Amplification, Sequencing and Assembly of *L. perenne* BAC Clone 72-12C.

High quality *Lolium perenne* BAC clone 72-12C DNA was obtained using a Qiagen Large Construct Kit according to the manufacturers protocols. The DNA was sheared from approximately 140 kg into 1-2 kb fragments using an Invitrogen nebuliser according to the manufacturers protocols. Klenow (Invitrogen) was used to blunt end the fragments and cloned into pCR4Blunt-TOPO® Shotgun Subcloning Kit (Invitrogen) according to the manufacturers protocols. These were then transformed into *E. coli* grown on plates then individually picked and transferred to individual wells in 384 well plates.

A Beckman Coulter Biomek 2000 was used to transfer a sub sample of each colony to 384 well plates. The Biomek 2000 was also used to subsequently dilute the samples and directly amplify using Amersham TempliPhi™ (Amersham Biosciences). Each amplification product was sequenced directly using both the T7 and T3 primers. Sequencing was performed using the ABI 3100 Genetic Analyser fitted with a 50 cm array. Sequences were assembled into contigs using PHRED.

Figure 4:
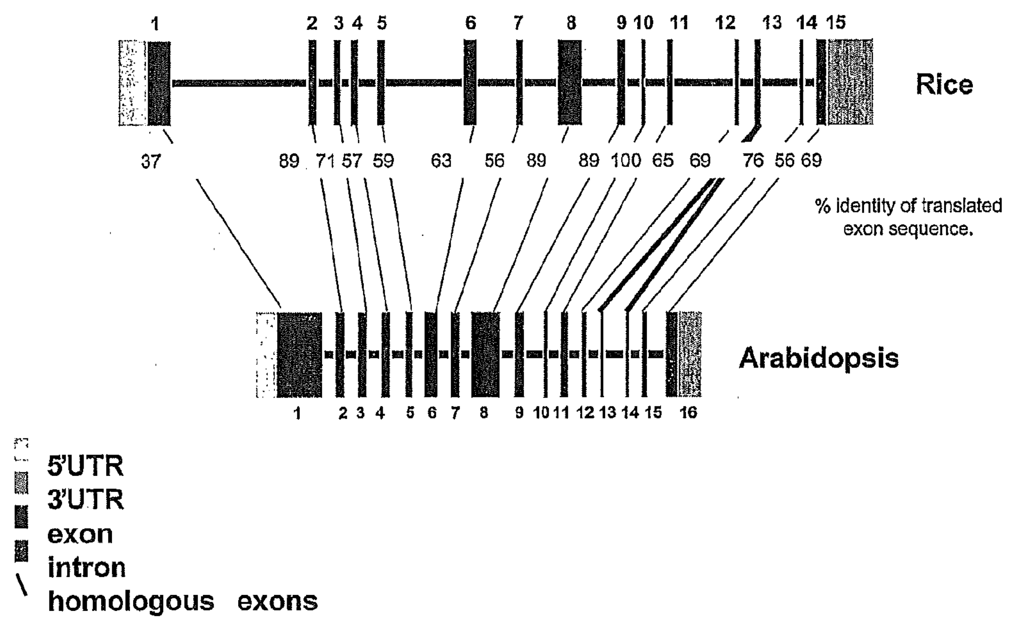

We predicted the structure and sequence of the *Oryza sativa* DGAT1 gene using the *Arabidopsis thaliana* DGAT1 gene structure as a model. A combination of NetGene2 (http://www.cbs.dtu.dk/services/NetGen2/), the *Arabidopsis thaliana* DGAT1 cDNA and the translated cDNA were used to predict intron/exon boundaries for genomic *Arabidopsis thaliana* DNA. Translated *Arabidopsis thaliana* exon sequences were used to run BLAST searches (protein-nucleic acid) against *Oryza sativa* genomic DNA. The region containing the *Oryza sativa* DGAT1 gene sequence was identified. SplicePredictor (http://bioinformatics.iastate.edu/cgi-bin/sp.cgi) and translated sequences from all three reading frames was used to predict intron/exon boundaries for the *Oryza sativa* genomic DGAT1 sequence of the relevant *Oryza sativa* genomic DNA sequence. A schematic comparison of the putative *Oryza sativa* DGAT1 gene structure was made with the DGAT1 gene structure from *Arabidopsis thaliana* (FIG. 4).

We used individual translated exons from the predicted rice DGAT1 gene to BLAST search the ryegrass BAC contig sequences. We identified one contig containing a significant portion of the corresponding putative ryegrass gene. This contig contains a fragment of intron 10 through to exon 15 and the 3' untranslated region.

Amplification and Cloning of *L. perenne* DGAT1 Exon10 and Intron 10 from *L. perenne* BAC Clone 72-12C.

The *Arabidopsis thaliana* DGAT1 gene sequence and our predicted *Oryza sativa* DGAT1 gene sequence were used to design a degenerate forward primer to exon 10 of both genes (DGAT-2-NR:32). The degenerate exon 10 PCR primer was as follows.

```
Exon 10 degenerate top primer.
                                    (SEQ ID No. 30)
5' TAY TGG AGA ATG TGG AAT ATG 3'
```

The BAC plasmid clone 72-12C was used as a PCR template with the Exon 11 top primer and a reverse primer designed to the ryegrass DGAT1 predicted Exon 11 sequence. The sequence of this primer was as follows:

```
Ryegrass DGAT1 Exon 11 reverse primer
                                    (SEQ ID No. 31)
5' CGA ACA ACC CAT TTA TGC ACA 3'
```

This produced a 378 bp product which was TA-TOPO cloned into pCR2.1 (Invitrogen) according to the manufacturers protocols. The clone was sequenced and found to contain the following sequence.

```
5'TACTGGAGAATGTGGAATATCGTATGCTTCTCTTTTCTCTACCATGTTACTTTCTTGC
AACCTTCTGGCAATTAGAGACCATATTTCTCCATAAGCTTGCTTGCATTTTTTTCCAAGG
AGTTACAATGTTAGAATGTTTATCTTATTCAAAGAAACAGCATGAGAATATGACAAACTC
AAATGAAACTGTTTGACAAGAACAGCACATTTTCTATGATTAAACTTTACCAAATTTCAG
TAGGTGAAGGAGTGGCAAATACCTCGAATTTTATTGATTTATGTTATATTGCTTGCTGTT
TCTCCACTAATTTGTTTATTTGTTTTTAACTATTTTTTATTTATGCTGCATTCACAGCCT
GTGCATAAATGGGTTGTTCG 3'   (SEQ ID No. 32)
```

The predicted intron boundaries are underlined, the primer sequences are shown in grey boxes; the 5' sequence of putative exon 11 (not included in the reverse primer sequence) is double underlined.

Comparison of *L. perenne, O. sativa* and *A. thaliana* DGAT Genes

Figure 8:
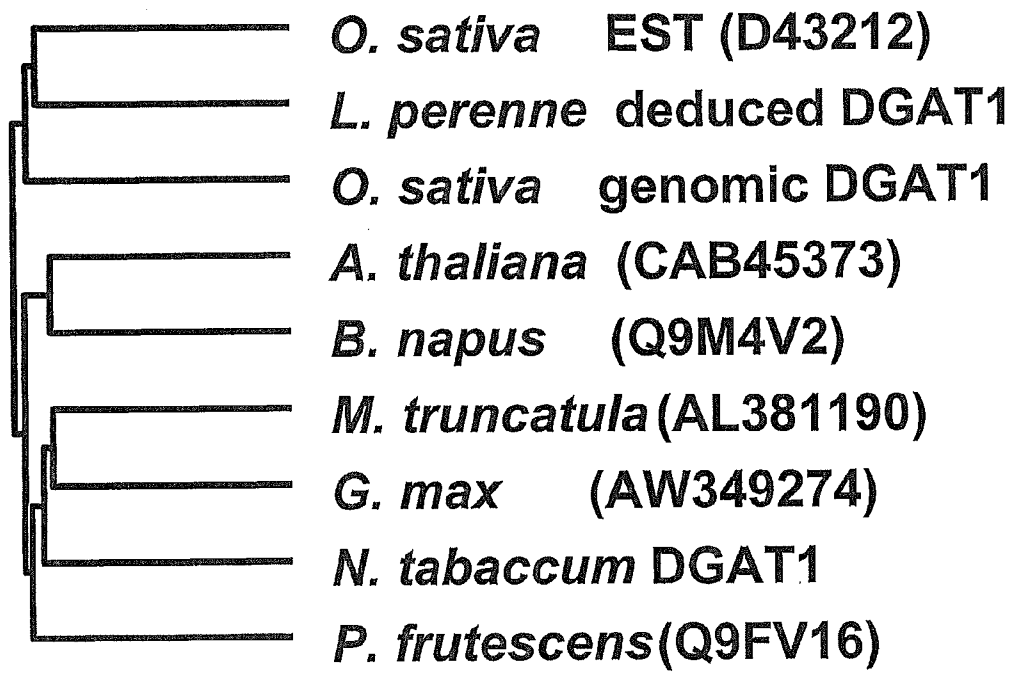
FIG. 8 shows the phylogenetic relationship of the translated *Lolium perenne* DGAT1 genomic sequence (containing complete sequence from exon 10 through to exon 15) to other translated plant DGAT1 sequences. Accession numbers are shown in parenthesis.
Figure 9:
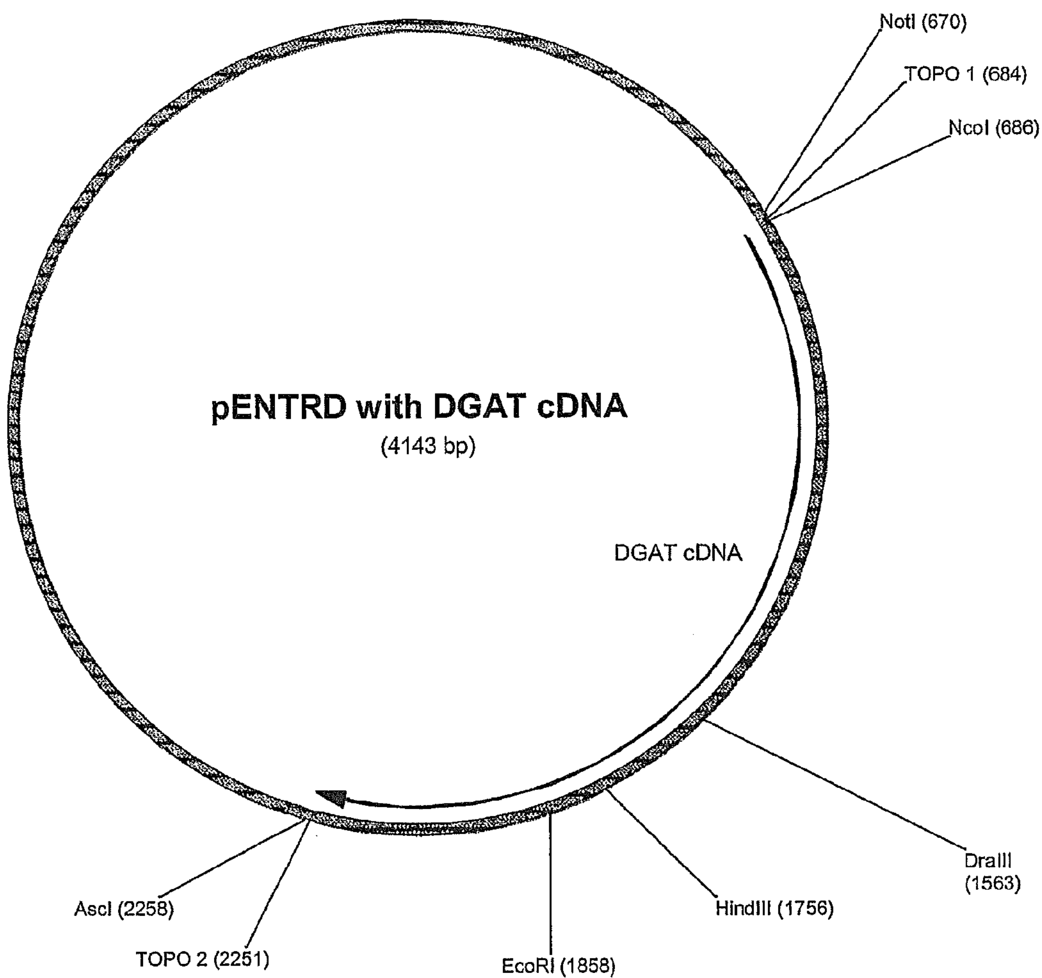
FIG. 9 shows a schematic representation of the of *Arabidopsis thaliana* DGAT1 cDNA open reading frame (black curved arrow) cloned into pENTR-D.
Figure 10:
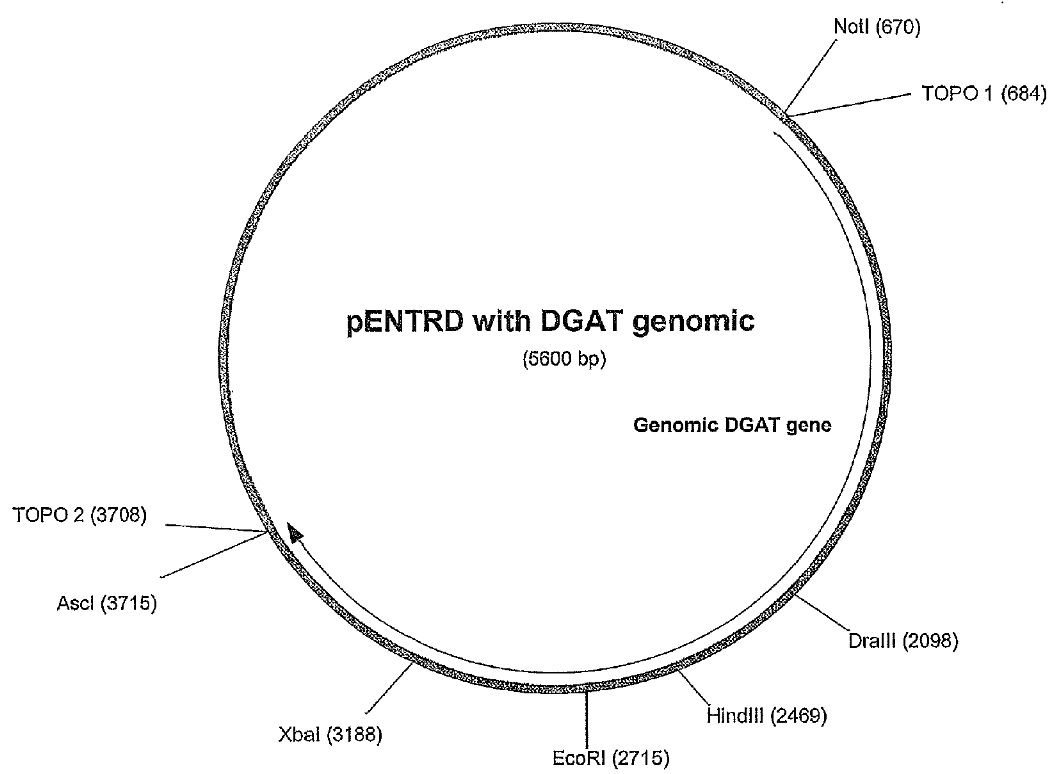
FIG. 10 shows a schematic representation of the of *Arabidopsis thaliana* DGAT1 transcribed genomic region (black curved arrow) cloned into pENTR-D.
Figure 11:
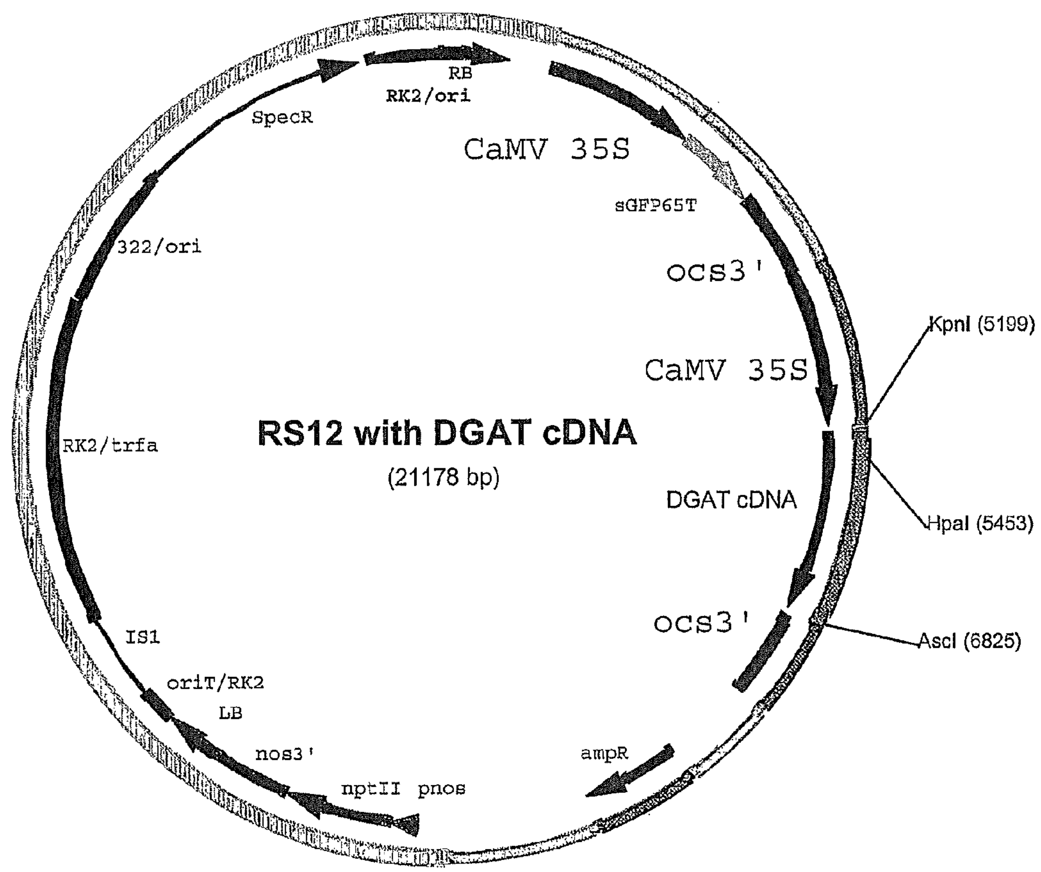
FIG. 11 shows a schematic representation of the of *Arabidopsis thaliana* DGAT1 cDNA open reading frame cloned into pRS12.
Figure 12:
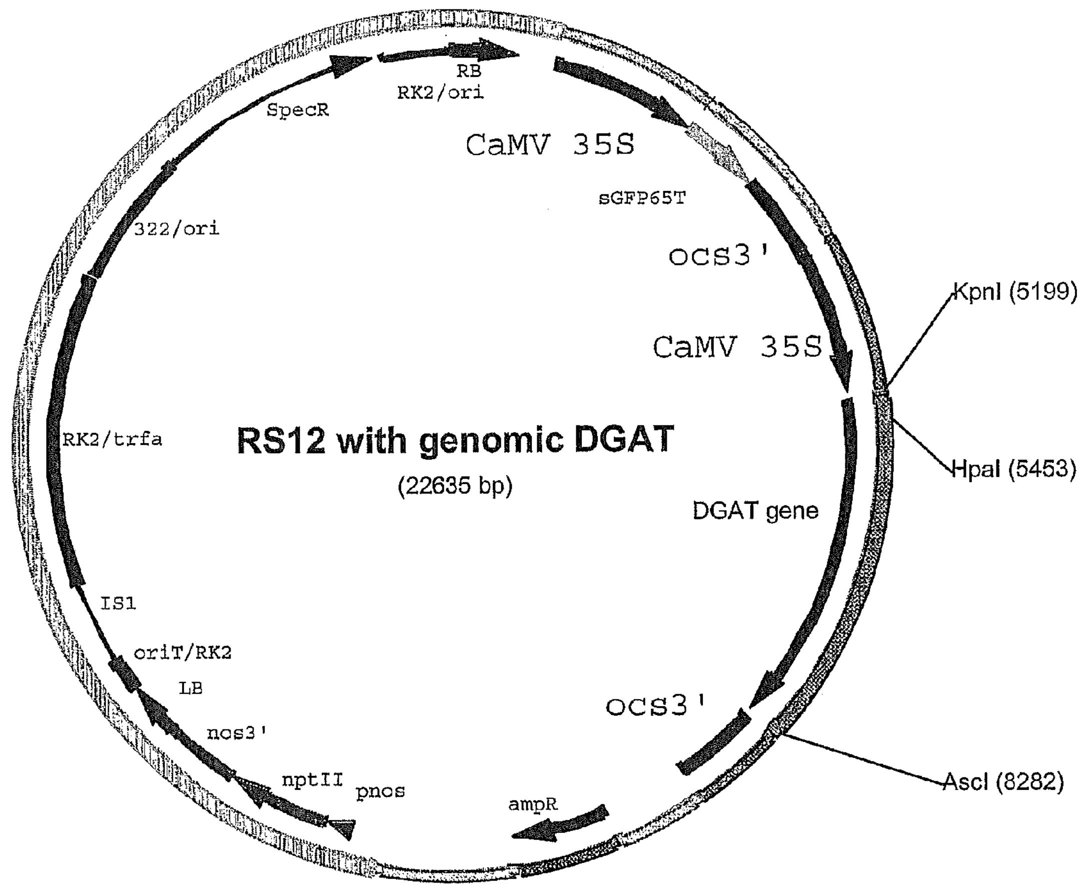
FIG. 12 shows a schematic representation of the of *Arabidopsis thaliana* DGAT1 transcribed genomic region cloned into pRS12.

The *Lolium perenne* DGAT1 contig (containing sequence from intron 10 through to exon 15) was combined with the sequence from the 378 bp PCR fragment obtained using degenerate exon 10 primer and the *Lolium perenne* DGAT1 exon 11 reverse primer. The predicted intron/exon boundaries and predicted translated sequence were determined by comparison of the *Lolium perenne* DGAT1 genomic sequence with the *Arabidopsis thaliana* DGAT1 genomic sequence and our predicted *Oryza sativa* DGAT1 genomic sequence. The *Lolium perenne* DGAT1 genomic sequence and its predicted intron/exon boundaries as well as theoretical translated sequence are shown in FIG. 8 FIG. 5 (SEQ ID Nos. 10-13).

Figure 6:
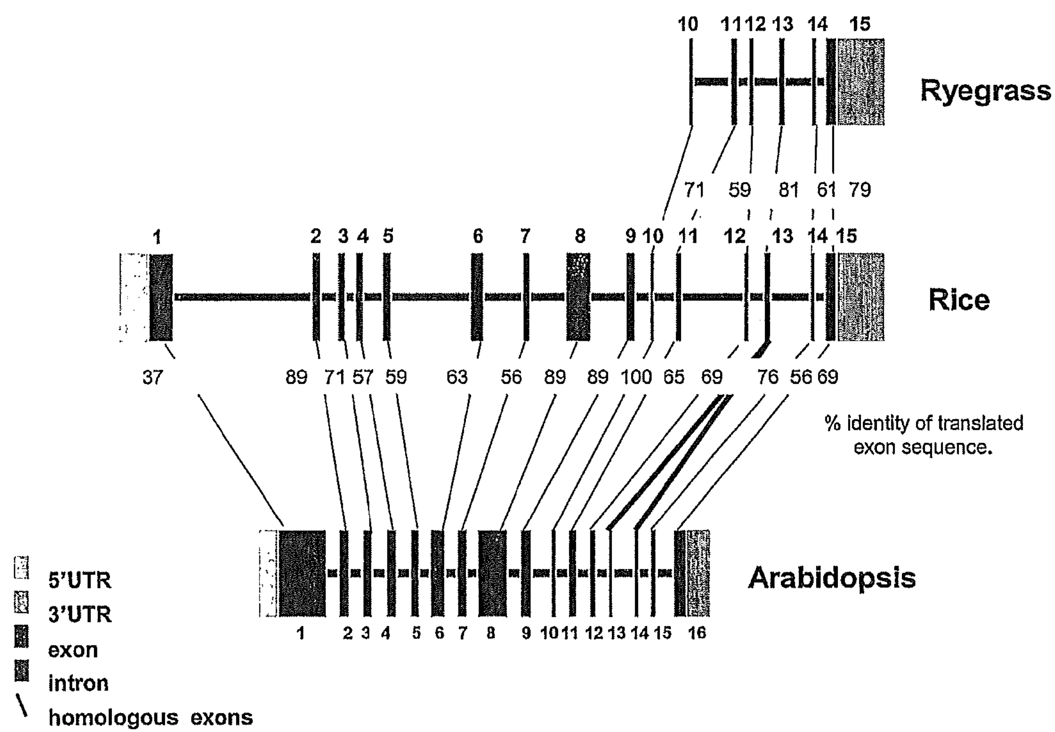

A schematic comparison of the predicted *Lolium perenne*, putative *Oryza sativa* and *Arabidopsis thaliana* DGAT1 gene structures is shown in FIG. 6. The predicted splice sites correspond with those of the *Oryza sativa* gene. This includes the predicted fused exons resulting in one less exon and intron than the *Arabidopsis thaliana* DGAT1 gene.

The predicted cDNA sequence and translated sequence of the *Lolium perenne* DGAT1 gene (exon 10 through to exon 15) is as follows:

TACTGGAGAATGTGGAATATGCCTGTGCATAAATGGGTTGTTCGCCATATATATTTTCCC
Y--W--R--M--W--N--M--P--V-I-H--R--W--V--V--R--H--I--Y--F--P--

CCCAGGCGCAGTGGTATATCAAAGGAAGTTGCTGTCTTTGTATCATTTTTTGTATCTGCC
P--R--R--S--G--I--S--K--E--V--A--V--F--V--S--F--F--V--S--A--

GTGCTCCATGAGTTATGTGTTGCTGTCCCCTGCCGAATTGTCAAGTTCTGGGCATTCTTA
V--L--H--E--L--C--V--A--V--P--C--R--I--V--K--F--W--A--F--L--

GGGATCATGCTGCAGATCCCTCTTATCATATTGACATCATACCTGAAGAGCAAATTCAGA
G--I--M--L--Q--I--P--L--I--I--L--T--S--Y--L--K--S--K--F--R--

GATACAATGGCCGGCAACATGATATTCTGGTTCTTTTTCTGCATCTACGGACAGCCTATG
D--T--M--A--G--N--M--I--F--W--F--F--F--C--I--Y--G--Q--P--M--

TGCGTTCTCCTGTACTACCATGATGTGATGAATACCATTGGGAAGACGGGATAGAAGAAC
C--V--I--L--Y--Y--H--D--V--M--N--R--I--C--K--T--G--*
(SEQ ID No. 15)

ACATATCGCTCTTCCTGTTTATGGCAAAAGGATGTTACGACATGGAGCTGCATAATTTCC
AACACTGGCATACATCCTTCCAGTCTTTCTTGGAAAATACAGTGCATAATTTTACCATGT
TTTGTGGCGGGTGGTTGCAGGCTTGTGACTGTACATAAGCTTCAGTCTATGATATAGAAT
CCTGCCTAATTGCTGGCGTGGCGGTGATAATTTTTTGTAGAGATGGAAGCTTTATTATCC
CTGGCCTGTGCGTTACATATGCATACGGCCTTAATTATTTTACCGTGTATCACAAATTGT
TAGGAAGCGTCCCCGTGCCCTTAGGGTAATTTGTTAATAAAAAATAATTACATTTGTTTC
TCTTTGAATAGAA (SEQ ID No. 33)

The predicted coding sequence and underlying translated peptide sequences are shaded grey. The predicted 3'UTR is underlined and the predicted polyadenylation signal sequence is shown in bold.

The putative *Lolium perenne* DGAT1 translated peptide sequence, encoded by exon 10 through to exon 15 from is:

(SEQ ID No. 15)

```
YWRMWNMPVHKWVVRHIYFPPRRSGISKEVAVFVSFFVSAVLHELCVAVP

CRIVKFWAFLGIMLQIPLIILTSYLKSKFRDTMAGNMIFWFFFCIYGQPM

CVLLYYHDVMNRIGKTG*
```

The predicted *Lolium perenne* DGAT1 translated sequence was compared to DGAT peptide sequences from other plants (FIG. 7; SEQ ID Nos. 14-22). The phylogenetic analysis identified a clade containing only monocotyledon sequences, including *Oryza sativa* (FIG. 8).

cDNA Cloning

Total RNA from *Lolium perenne* 4 day old seedlings was extracted using a Qiagen RNeasy kit as per the manufacturers protocols. This was primed with random primers and reverse transcribed using a Thermoscript Reverse Transcription kit (Invitrogen) as per the manufacturers protocols. An aliquot of the cDNA was used as a PCR template in combination with the following primers: predicted Exon 11 top primer and the predicted Exon 15 reverse primer. The sequence of these primers was as follows:

```
Ryegrass DGAT1 Exon 11 forward primer
                                  (SEQ ID No. 34)
5' CAG GCG CAG TGG TAT ATC A 3'

Ryegrass DGAT1 Exon 15 reverse primer
                                  (SEQ ID No. 35)
5' TGG TAG TAC AGG AGA ACG C 3'
```

This produced a 258 bp product which was TA-TOPO cloned into pCR2.1 (Invitrogen) according to the manufacturers protocols. The clone was sequenced and found to contain the following sequence (translated peptide sequence is shown in grey):

CAGGCGCAGTGGTATATCAAAGGAAAGTTGCTGTCTTTGTATCATTTTTTGTATCTGCCGT
R--R--S--G--I--S--K--E--V--A--V--F--V--S--F--F--V--S--A--V-

GCTCCATGAGTTATGTGTTGCTGTCCCCTGCCGAATTGTCAAGTTCTGGGCATTCTTAGG
-L--R--E--L--C--V--A--V--P--C--R--I--V--K--F--W--A--F--L--G-

GATCATGCTGCAGATCCCTCTTATCATATTGACATCATACCTGAAGAGCAAATTCAGAGA
-I--M--L--Q--I--P--L--I--I--L--T--S--Y--L--K--S--K--F--R--D-

-continued

```
TACAATGGCCGGCAACATGATATTCTGGTTCTTTTTCTGCATCTACGGACAGCCTATGTG
-T--M--A--G--N--M--I--F--W--F--F--F--C--I--Y--G--Q--P--M--C-

CGTTCTCCTGTACTACCA (SEQ ID No. 36)
-V--L--L--Y--Y- (SEQ ID No. 37)
```

The predicted *Lolium perenne* DGAT1 cDNA sequence (top sequence) derived from the genomic sequence aligns exactly (vertical bars) with the cloned cDNA *Lolium perenne* DGAT1 fragment (bottom sequence) as follows:

```
TACTGGAGAATGTGGAATATGCCTGTGCATAAATGGGTTGTTCGCCATAT

..................................................

ATATTTTCCCCCCAGGCGCAGTGGTATATCAAAGGAAGTTGCTGTCTTTG
             |||||||||||||||||||||||||||||||||||||
............CAGGCGCAGTGGTATATCAAAGGAAGTTGCTGTCTTTG

TATCATTTTTTGTATCTGCCGTGCTCCATGAGTTATGTGTTGCTGTCCCC
||||||||||||||||||||||||||||||||||||||||||||||||||
TATCATTTTTTGTATCTGCCGTGCTCCATGAGTTATGTGTTGCTGTCCCC

TGCCGAATTGTCAAGTTCTGGGCATTCTTAGGGATCATGCTGCAGATCCC
||||||||||||||||||||||||||||||||||||||||||||||||||
TGCCGAATTGTCAAGTTCTGGGCATTCTTAGGGATCATGCTGCAGATCCC

TCTTATCATATTGACATCATACCTGAAGAGCAAATTCAGAGATACAATGG
||||||||||||||||||||||||||||||||||||||||||||||||||
TCTTATCATATTGACATCATACCTGAAGAGCAAATTCAGAGATACAATGG

CCGGCAACATGATATTCTGGTTCTTTTTCTGCATCTACGGACAGCCTATG
||||||||||||||||||||||||||||||||||||||||||||||||||
CCGGCAACATGATATTCTGGTTCTTTTTCTGCATCTACGGACAGCCTATG

TGCGTTCTCCTGTACTACCATGATGTGATGAATAGGATTGGGAAGACGGG (SEQ ID No. 38)
||||||||||||||||||||
TGCGTTCTCCTGTACTACCA.............................. (SEQ ID No. 36)
```

The predicted *Lolium perenne* DGAT1 peptide sequence translated from the genomic sequence (top sequence) aligns exactly (vertical bars) with the predicted peptide sequence transcribed from the cloned cDNA *Lolium perenne* DGAT1 fragment (bottom sequence) as follows:

```
YWRMWNMPVHKWVVRHIYFPPRRSGISKEVAVFVSFFVSAVLHELCVAVP
                      ||||||||||||||||||||||||||||
......................RRSGISKEVAVFVSFFVSAVLHELCVAVP

CRIVKFWAFLGIMLQIPLIILTSYLKSKFRDTMAGNMIFWFFFCIYGQPM
||||||||||||||||||||||||||||||||||||||||||||||||||
CRIVKFWAFLGIMLQIPLIILTSYLKSKFRDTMAGNMIFWFFFCIYGQPM

CVLLYYHDVMNRIGKTG* (SEQ ID No. 15)
||||||
CVLLYY............ (SEQ ID No. 37)
```

2. Over Expressing *Arabidopsis Thaliana* DGAT1 in *Lotus japonicus* Roots

Sub-cloning *Arabidopsis thaliana* DGAT1 cDNA and Cloning *Arabidopsis thaliana* DGAT1 Genomic Transcribed Region.

GATEWAY™ (Invitrogen) compatible primers were designed to generate GATEWAY™ compatible clones containing either the open reading frame of the *Arabidopsis thaliana* DGAT1 cDNA or the full length transcribed region of the *A. thaliana* DGAT1 gene.

*Arabidopsis thaliana* DGAT1 top primer Theoretical Tm = 60° C.
5' CAC CAT GGC GAT TTT GGA TTC TGC 3' (SEQ ID No. 39)

Gateway compatible additional bases are boxed in grey. Nucleotides encoding for a methionine residue (corresponding to the translational start site) is underlined and bold faced.

*Arabidopsis thaliana* bottom primer Theoretical Tm = 60° C.
(SEQ ID No. 40)
5' TCA TGA CAT CGA TCC TTT TCG 3'

Nucleotides encoding a termination codon (corresponding to the end of the coding sequence) are underlined and bold faced.

These primers were used to engineer the transcripts to be GATEWAY™ (Invitrogen) compatible using standard PCR and cloning techniques. Briefly, the *Arabidopsis thaliana* DGAT1 cDNA was amplified from an existing cDNA clone (AtFLAGDGAT-pYeDP60) in the plasmid pYeDP60 (Pieret et al., 2001). The full length transcribed region of the *Arabidopsis thaliana* DGAT1 gene was amplified from an existing genomic *Arabidopsis thaliana* (ecotype Columbia) DGAT1 complete gene (Lipids-3-AT:50) in the plasmid pCR2.1 (Invitrogen).

The cDNA and genomic clones were amplified with the proof reading enzyme TripleMaster (Eppendorf) as per the manufacturers protocols. This enzyme produces a mixture of PCR products; some blunt ended fragments and some with Adenosine overhangs. Since pENTR-D (Invitrogen) cloning requires blunt ended inserts, 1 μl of T4 DNA polymerase was added to 10 μl of PCR product and left at 25° C. for 20 minutes then at 72° C. for 10 minutes to heat inactivate the protein.

The PCR amplification products were cloned into pENTR-D (Invitrogen) using the reactions outlined in Table 1.

TABLE 1

| Component | Cloning rxn 1 | Cloning rxn 2 | Control rxn |
|---|---|---|---|
| PCR product | 0.5 μl of Genomic DGAT DNA | 0.5 μl of DGAT cDNA | — |
| Salt | 0.5 μl | 0.5 μl | 0.5 μl |
| pENTR-D vector | 0.5 μl | 0.5 μl | 0.5 μl |
| Sterile water | 0.5 μl | 0.5 | 2.0 μl |

These reactions were left at room temp for 5 mins then transferred to ice.

Transformation of dH5α TOPO TOP 10 (Invitrogen) Cells by Heat Shock

Thawed 2 vials of cells on ice for ≈20 minutes

Added 2 μl of each cloning reaction to tubes of cell suspension

Mixed by gentle tapping and incubated on ice for 30 minutes.

Heat shocked cells for 30 seconds at 42° C. without shaking

Immediately transferred the cells to ice

Added 250 μl of room temperature SOC medium

Incubated cultures horizontally, shaking (220 rpm) at 37° C. for 1 hour

Plate cells onto LB-kanomycin plates (25 μl, 200 μl, & the rest)

Grew plates overnight in a 37° C. incubator

The next day colonies from the transformant plates were picked with toothpicks into 10 ml LB-kanomycin broths.

The plasmid DNA was extracted using the alkaline lysis method and sequenced (Sequences of the complete clones are shown in Appendicies I and II) (SEQ ID Nos. 41 and 42).

GATEWAY™ (Invitrogen) LR Reactions to Clone *Arabidopsis thaliana* DGAT1 from pENTR-D into pRS12 Plant Binary Vector LR reactions were set up as outlined in Table 2:

TABLE 2

| Component | LR rxn 1 | LR rxn 2 |
|---|---|---|
| Entry clone (400 ng) | 0.2 μl of Genomic DGAT DNA in pENTR-D (400 ng) | 0.5 μl of DGAT cDNA in pENTR-D |
| pRS12 binary vector | 0.2 μl (300 ng) | 0.2 μl (300 ng) |
| LR rxn mix | 1 μl | 1 μl |
| LR rxn buffer | 1 μl | 1 μl |
| Topo isomerase | 0.25 μl | 0.25 μl |
| Sterile water | 2.35 μl | 2.05 μl |

These reactions were incubated at 25° C. overnight.

The next day the whole 5 μl LR reactions were used to transform dH5α TOPO TOP 10 cells (Invitrogen) by heat shock as above. Cultures were plated on LB-spectomycin plates, transformants were picked and plasmid DNA was extracted using the alkaline lysis method.

The plasmid DNA was extracted using the alkaline lysis method and sequenced (sequences of the complete clones are shown in Appendices III and IV) (SEQ ID Nos. 43 and 44).

This plasmid DNA was then used to transform *Agrobacterium Rhizogenes.*

Transformation of *Agrobacterium rhizogenes* (A4T)

1. Streak a TY agar plate with *Agrobacterium rhizogenes* (A4T) glycerol stock and grow 28° C. overnight.

2. Innoculate 50 ml of YEB broth with a colony from *Agrobacterium* plate and grow at 28° C., shaking (220 rpm) until $OD_{600}$ is approx 0.5 (16 hrs)

3. Centrifuge cells for 15 mins @ 4000 rpm, discard supernatant and resuspend in 10 ml of 0.15 M NaCl 4. Centrifuge cells for 10 mins @ 400 rpm, discard supernatant, and resuspend in 1 mL of ice-cold 20 mM $CaCl_2$ 5. Aliquot 200 μL of cells into an eppendorf tube, add 5 μg of DNA and incubate on ice for 30 mins.

6. With what is left of the 1 ml aliquot 186 μL of cells and 14 μL of DMSO into eppendorf tubes and freeze in liquid $N_2$ then store at −70° C.

7. After incubation on ice for 30 mins freeze the DNA/cells in liquid $N_2$ for 1 min.

8. Thaw in a 37° C. waterbath

9. Repeat steps 7 & 8

10. Add 1 ml of YEB broth and incubate cells for 4 hours @ 28° C. with gentle shaking 11. Plate cells on TY agar containing spectomycin and grow for 2 days @ 28° C.

Pick colonies from the *Agrobacterium* plates into 10 ml TY broths containing spectomycin and grow for 2 days @ 28° C., shaking at 220 rpm.

0.15 M NaCl 0.375 μL 4M NaCl 9.625 mL $H_20$ 20 mM $CaCl_2$ 0.029 g $CaCl_2.2H_20$ in 10 ml $H_20$

Transformation of *Lotus japonicus* with *Agrobacterium rhizogenes* (A4T)

Day 1.

1. Scarify *Lotus japonicus* seeds using p220 wet/dry sand paper

2. Sterilise seeds by rotating for 20 mins in 10 ml sterilisation soln:

7 ml 100% ethanol 1 ml 30% $H_20$ 2 ml $H_20$

3. Wash 3 times in sterile $H_20$

4. Place seeds on 1% water agar plates

5. Wrap plates in tinfoil (dark) and germinate at 25° C. for 2 days

6. Streak TY agar plate with *Agrobacterium rhizogenes* (A4T) glycerol stock and grow overnight @ 28° C.

Day 2.

1. Inoculate 50 ml YEB culture broth with colony from A4T plate and grow overnight @ 28° C. shaking (220 rpm)

Day 3.

1. Make *Agrobacterium* competent cells and transform with binary plasmid containing gene of interest, plate on TY agar plates and grow for 2 days at 28° C. (refer: Transformation of *Agrobacerium*)

2. Transfer germinated seeds to ½ B5 media, approx 10 across each plate, roots pointing down. Tape plates together, grow vertically on lab bench.

| ½ B5 media (No sucrose) | |
|---|---|
| $NaH_2PO_4 \cdot 2H_20$ | 0.0425 g |
| $KN0_3$ | 0.625 g |
| $NH_{42}S0_4$ | 0.0335 g |
| $MgS0_4 \cdot 2H_20$ | 0.0625 g |
| Ferric EDTA | 0.01 g |
| Myo-Inositol | 0.025 g |
| Stock A | 0.25 mL |
| Stock B | 0.25 mL |
| Stock C | 0.25 mL |
| Stock D | 0.25 mL |
| Adjust pH to 5.5 with 0.2M KOH or 0.2M HCl | |
| Agar | 6 g |

Make up to 500 mL with sterile $H_20$

Day 5

Pick colonies from *Agrobacterium* plates into 10 ml TY-spectomycin broths and grow at 28° C. shaking (220 rpm) for 2 days.

Day 6.

Perform PCR on *Agrobacterium* broths to check for desired gene.

Day 7.

Inoculate *Lotus japonicus* plants by dipping a sterile scalpel into the *Agrobacterium* broth and cutting off the root. After inoculation tape plates together, wrap in tinfoil and leave overnight on lab bench Day 8.

Unwrap plates and grow for 2 days vertically on lab bench

Day 9.

Transfer plants to MS (CRO) media containing the antibiotic cephotaximine, 10 across a plate. Grow vertically on lab bench.

Roots can be viewed (for GFP) under a Microscope 10-20 days later.

MS/CRO Media

| | |
|---|---|
| MS Macro Stock | 50 ml/L |
| MS Fe (EDTA) Stock | 5 ml/L |
| B5B Vitamins stock | 1 ml/L |
| Sucrose | 30 g/L |
| Myo-Inositol | 100 mg/L |
| Phytagel agar | 8 g/L |

pH to 5.7 with NaOH

MS Macro Stock

| | |
|---|---|
| $NH_4NO_3$ | 33 g/900 ml |
| $KNO_3$ | 38 g/900 ml |
| $CaCl_2 \cdot 2H_2O$ | 8.8 g/900 ml |
| $KH_2PO_4$ | 3.4 g/900 ml |
| $MgSO_4 \cdot 7H_2O$ | 7.4 g/900 ml |
| MS Micro stock | 100 ml |
| 1000 ml | |

MS Fe (EDTA) Stock

Ferric EDTA (Ethylene diaminetetra acetic acidFe Na EDTA) 4 g/500 ml

MS Micro Stock

| | |
|---|---|
| H3BO3 | 1.24 g/L |
| MnSO4•4H20 | 4.46 g/L |
| ZnSO4•7H20 | 1.72 g/L |
| KI | 0.166 g/L |
| Na2MoO4•2H20 | 0.05 g/L |
| CuSO4•5H20 | 0.005 g/L |
| CoCl2•6H20 | 0.005 g/L |
| 1000 ml | |

B5B Vitamin Stock

| | |
|---|---|
| Nicotinic Acid | 0.1 g/100 ml |
| Thiamine HCl | 1.0 g/100 ml |
| Pyridoxine HCl | 0.1 g/100 ml |

1 ml aliquots into eppendorfs (Store in freezer)

Analysis of *Lotus japonicus* Roots Over Expressing *Arabidopsis thaliana* DGAT1 by Fatty Acid Methyl Ester Gas Chromatography-Mass Spectrometry (FAMEs GC-MS)

FAMEs Extraction Procedure:

Place frozen plant material (~50 mg fresh weight) in a 13×100 mm screw-capped tube and add the first internal standard (10 μL of 4 mg/mL 15:0 dissolved in heptane).

Add methanolic HCl reagent (1 mL of 3 M solution diluted to 1 M with dry methanol that has 2,2-dimethoxypropane (5%) as a water scavenger).

Purge the tube with nitrogen, seal with a Teflon-lined cap and heat at 80° C. for 1 hour.

Cool the tube; and add the premethylated standard (10 μL of 4 mg/mL 17:0 dissolved in heptane).

Add heptane (0.6 mL) and NaCl (1 mL, 0.9%) and shake vigorously to extract the FAMEs into the heptane.

Centrifuge (1000 g×30 sec) to break any emulsion and completely separate the phases.

Remove heptane layer and store in GC vials in a −4° C. freezer.

Using a syringe, inject the heptane layer (100 μL) into a separate vial containing a 250 μL glass insert (allows the GC/MS to analyse small volumes of samples).

Inject the phenol standard (3 μL of 2 mg/mL) into the vial before GC/MS analysis.

GC-MS Analysis.

Shimadzu GC/MS QP-2010 El with AOC-20i Autoinjector

Column (0.25 μm 50 m×0.22 mm I.D. BPX70).

Auto injector:

Rinse with solvent×6

Rinse with sample×2

Plunger speed (suction) high

Viscosity Comp. time 0.2 sec

Plunger speed (injection) high

Syringe insertion speed high

Inject 1 uL

Injection mode Split (20:1)

Carrier Gas He2 (pressure 150 kPa, flow rate 40 ml/min)

Column oven temp 80° C. (2 min)−[15° C./min]−150° C. (0 min)−[8° C./min]−250° C. (10 min)

MS ion source 200° C.

Interface temp 260° C.

Start time 6 min

End time 29 min

Acquisition mode scan

Interval 0.5 sec

Scan speed 625

Start m/z 50.00

End m/z 350.00

Lipid Results from Transformed *Lotus japonicus* Hairy Roots.

The *Arabidopsis thaliana* DGAT1 cDNA (under the control of the CaMV35s promoter in pRS12) was transformed into *Lotus japonicus* roots as described. Similarly, the *Arabidopsis thaliana* DGAT1 complete transcribed region of the genomic sequence (under the control of the CaMV35s promoter in pRS12) was transformed into *Lotus japonicus* roots as described. Approximately 15 independent hairy root phenotypes were generated for each construct; these were analysed for GFP expression and the highest GFP expressers were subcultured and grown in liquid media. After approximately 12 weeks growth samples of roots were ground in liquid nitrogen. From this, duplicate samples of each transformant were analysed by GC-MS. The results are presented in Table 3. Within each transformant type the clones are arranged in ascending order of total lipid content.

TABLE 3

| Transformant type and number | Total lipid content of root (mg/g DM) | % C16:0 of total lipids | % C18:0 of total lipds | % C18:1 of total lipds | % C18:2 of total lipds | % C18:3 of total lipds |
|---|---|---|---|---|---|---|
| A4T control Transgenic 1 | 4.03 | 30.30 | 1.88 | 0.74 | 57.53 | 9.55 |
| A4T control Transgenic 3 | 4.58 | 29.84 | 1.55 | 0.87 | 54.66 | 13.08 |
| A4T control Transgenic 2 | 5.24 | 27.98 | 1.46 | 0.81 | 56.73 | 13.02 |
| A4T control Transgenic 4 | 5.33 | 27.83 | 1.79 | 0.90 | 57.34 | 12.15 |
| DGAT1 cDNA Transgenic 4 | 7.89 | 22.59 | 0.39 | 0.80 | 55.64 | 20.59 |
| DGAT1 cDNA Transgenic 3 | 8.27 | 23.14 | 1.93 | 0.94 | 57.07 | 16.93 |
| DGAT1 cDNA Transgenic 7 | 8.75 | 22.67 | 1.56 | 1.25 | 58.17 | 16.36 |
| DGAT1 cDNA Transgenic 6 | 9.21 | 21.12 | 1.15 | 1.99 | 59.52 | 16.23 |
| DGAT1 cDNA Transgenic 10 | 10.04 | 26.53 | 1.10 | 0.66 | 54.01 | 17.70 |
| DGAT1 cDNA Transgenic 1 | 12.30 | 21.78 | 1.47 | 2.99 | 56.27 | 17.50 |
| DGAT1 cDNA Transgenic 8 | 12.37 | 23.26 | 2.13 | 1.77 | 49.29 | 23.56 |
| DGAT1 cDNA Transgenic 2 | 12.44 | 20.50 | 1.23 | 1.18 | 60.61 | 16.48 |
| DGAT1 cDNA Transgenic 5 | 12.87 | 22.22 | 1.40 | 1.65 | 59.16 | 15.56 |
| DGAT1 cDNA Transgenic 9 | 13.02 | 19.71 | 2.05 | 2.55 | 47.20 | 28.50 |
| DGAT1 genomic DNA Transgenic 1 | 7.78 | 25.75 | 2.11 | 1.06 | 54.30 | 16.78 |
| DGAT1 genomic DNA Transgenic 5 | 7.94 | 23.38 | 0.34 | 0.00 | 57.81 | 18.47 |
| DGAT1 genomic DNA Transgenic 6 | 8.49 | 25.70 | 0.65 | 0.00 | 50.26 | 23.39 |
| DGAT1 genomic DNA Transgenic 3 | 9.75 | 24.29 | 1.30 | 0.13 | 54.82 | 19.46 |
| DGAT1 genomic DNA Transgenic 2 | 10.88 | 22.14 | 1.77 | 4.08 | 43.13 | 28.89 |
| DGAT1 genomic DNA Transgenic 7 | 11.40 | 23.37 | 1.46 | 1.10 | 48.18 | 25.89 |
| DGAT1 genomic DNA Transgenic 4 | 11.79 | 19.64 | 1.19 | 1.66 | 44.88 | 32.63 |

3. Transformation of *Lolium perenne* by Microprojectile Bombardment of Embryogenic Callus Protocol adapted from Altpeter et al 2000, Molecular Breeding 6.

Materials

TABLE 4

| florally induced tillers of *Lolium perenne* |
|---|
| Na-hypochlorite (5% available chlorine) |
| sterile $ddH_2O$ |
| 100 mm Petri plates containing LP5 medium* |
| 100 mm Petri plates containing LP3-OS medium |
| 100 mm Petri plates containing LP3 medium |
| 100 mm Petri plates containing LP3 medium + 200 mg/L Hygromycin (Hm) |
| 100 mm Petri plates containing MSK medium + 200 mg/L Hm |
| 250 ml culture vessels containing MSO medium + 200 mg/L |
| Hygromycin stock solution (50 mg/ml in PDS, sterile) |

Procedure

Harvest and surface sterilise floral tillers of *Lolium perenne* in 5% available chlorine Na-hypochlorite for 15 minutes using a Mason jar (or equivalent) under constant agitation.

Rinse tillers with autoclaved $ddH_2O$.

Aseptically dissect floral meristems.

Culture meristems on callus induction medium LP5 (16-20 explants per plate) and incubate in the dark for four to six weeks.

On the day of transformation transfer embryogenic callus material to high osmotic medium LP3-OS. Arrange approximately 4 $cm^2$ of calli in the centre of the Petri dish.

Incubate calli for 4-6 hours at room temperature.

Prepare particles and perform biolistic transformation following the protocol: "Biolistic Transformation of *Lolium perenne* with the Bio-Rad Particle Delivery System (PDS)". Plasmids are co-transformed. One plasmid (pAcH1) contains the hygromycin phosphotransferase gene conferring resistance to the antibiotic hygromycin expressed from the rice actin promoter and the second plasmid contains the genetic construct of interest for transformation. Plasmids are mixed in a one to one ratio at 1 μg/μL and simultaneously coated onto the microcarriers.

Incubate bombarded calli on high osmotic medium LP3-OS for an additional 12-16 hours (overnight) at 25° C. in the dark.

Transfer bombarded calli to LP3 medium and incubate for 48 hours at 25° C. in the dark Plate calli on selection medium (LP3+200 mg/l Hygromycin (Hm)). Incubate at 25° C. in the dark on selection medium for two weeks.

Transfer all Hm-resistant callus material to regeneration medium MSK+200 mg/l Hm and incubate for four weeks at 25° C. under a 16 hour photoperiod.

Transfer developed shoots to MS0+200 mg/l Hm and incubate for another two to four weeks at 25° C. under 16 hour photoperiod.

Screen by PCR Hm-resistant plants growing on MSO+200 mg/L Hm.

Microprojectile Bombardment of *Lolium perenne* with the Bio-Rad Particle Delivery System (PDS-1000/He)

Taken from the PDS-100/He manual. These procedures were developed by Sanford et al. (1992).

Materials and Solutions

TABLE 5

| Bio-Rad Biolistic ® PDS-1000/He Particle Delivery System |
|---|
| Rupture disks (900 PSI) |
| Macrocarriers |
| Macrocarrier holders |
| Microcarriers (1.0 μm) |
| Stopping screens |
| Autoclaved 1.5 ml eppendorf tubes |
| Micropipette tips |
| Vortex and microfuge |
| Torque wrench tool |
| Pen vac |
| 70% Ethanol |
| Absolute Ethanol |
| 2.5M $CaCl_2$ |
| 100 mM Spermidine |

(A) Microcarrier Preparation

For 120 bombardments using 500 μg per bombardment.

1. In a 1.5 ml microfuge tube, weigh out 60 mg of microparticles.
2. Add 1 ml of 70% ethanol, freshly prepared.
3. Vortex on a platform vortexer for 3-5 minutes.
4. Incubate for 15 minutes.
5. Pellet the microparticles by spinning for 5 seconds in a microfuge.
6. Remove the liquid and discard.
7. Repeat the following steps three times:
   a. Add 1 ml of sterile water
   b. Vortex for 1 minute
   c. Allow the particles to settle for 1 minute
   d. Pellet the microparticles by spinning for 2 seconds in a microfuge.
   e. Remove the liquid and discard.
8. Add sterile 50% glycerol to bring the microparticle concentration to 60 mg/ml (assume no loss during preparation).
9. Store the microparticles at room temperature for up to 2 weeks.

(B) Coating DNA onto Microcarriers

The following procedure is sufficient for six bombardments; if fewer bombardments are needed, prepare enough microcarriers for three bombardments by reducing all volumes by one half. When removing aliquots of microcarriers, it is important to vortex the tube containing the microcarriers continuously in order to maximise uniform sampling.

1. Vortex the microcarriers prepared in 50% glycerol (60 mg/ml) for 5 minutes on a platform vortexer to resuspend and disrupt agglomerated particles.
2. Remove 50 μl (3 mg) of microcarriers to a 1.5 ml microfuge tube.
3. While vortexing vigorously, add in order:
   5 μl DNA (1 μg/μl)
   50 μl $CaCl_2$ (2.5 M)
   20 μl spermidine (0.1 M)
4. Continue vortexing for 2-3 minutes
5. Allow the microcarriers to settle for 1 minute
6. Pellet the microcarriers by spinning for 2 seconds in a microfuge
7. Remove the liquid and discard
8. Add 140 μl of 70% ethanol without disturbing the pellet
9. Remove the liquid and discard
10. Add 140 μl of 100% ethanol without disturbing the pellet
11. Remove the liquid and discard
12. Add 48 μl of 100% ethanol
13. Gently resuspend the pellet by tapping the side of the tube several times, and then by vortexing at low speed for 2-3 seconds
14. Remove six 6 μl aliquots of microcarriers and transfer them to the centre of a macrocarrier. An effort is made to remove equal amounts (500 μg) of microcarriers each time and to spread them evenly over the central 1 cm of the macrocarrier using the pipette tip. Desiccate immediately.

C) Bombardment Procedure

Open valve of helium cylinder

Adjust helium regulator by turning the helium pressure regulator to 200 PSI above chosen rupture disk (e.g. if a 900 PSI rupture disk will be used, the working pressure has to be adjusted to 1100 PSI)

Turn on vacuum pump

Place 900 psi rupture disk in the rupture disk-retaining cap. Screw on and tighten retaining cap.

Place macrocarriers in sterile macrocarrier holder

Place stop screen and macrocarrier holder in the launch assembly, tighten screw lid and place below rupture disk-retaining cap. Launch assembly should be set to a Gap distance of ¼ inch and macrocarrier travel distance of 11 mm.

Place tissue sample at a target distance of 90 mm.

Turn on main switch of PDS

Apply vacuum to 27 inches of Hg

Hold vacuum and press "fire" button until shot is performed (automatic)

Release "fire" button and vent chamber

After shooting close valve of helium cylinder and loosen pressure valve

TABLE 6

Compositions of the media used

| | Media component | | | | |
|---|---|---|---|---|---|
| | LP3 | LP5 | LP3-OS | MSK | MS0 |
| Macro elements (mg/l final concentration) | | | | | |
| $KNO_3$ | 1900 | 1900 | 1900 | 1900 | 1900 |
| $NH_4NO_3$ | 1650 | 1650 | 1650 | 1650 | 1650 |

TABLE 6-continued

Compositions of the media used

| | Media component | | | | |
|---|---|---|---|---|---|
| | LP3 | LP5 | LP3-OS | MSK | MS0 |
| $CaCl_2x2H_2O$ | 440 | 440 | 440 | 440 | 440 |
| $MgSO_4x2H_2OKH_2PO_4$ | 370 | 370 | 370 | 370 | 370 |
| KCl | 170 | 170 | 170 | 170 | 170 |
| Micro elements (mg/l final concentration) | | | | | |
| $Na_2EDTA$ | 37.3 | 37.3 | 37.3 | 37.3 | 37.3 |
| $FeSO_4x7H_2O$ | 27.8 | 27.8 | 27.8 | 27.8 | 27.8 |
| $H_3BO_3$ | 6.2 | 6.2 | 6.2 | 6.2 | 6.2 |
| KI | 0.83 | 0.83 | 0.83 | 0.83 | 0.83 |
| $MnSO_4xH_2O$ | 16.9 | 16.9 | 16.9 | 16.9 | 16.9 |
| $ZnSO_4x7H_2O$ | 8.6 | 8.6 | 8.6 | 8.6 | 8.6 |
| $CuSO_4x5H_2O$ | 0.025 | 0.025 | 0.025 | 0.025 | 0.025 |
| $Na_2MoO_4x2H_2O$ | 0.25 | 0.25 | 0.25 | 0.25 | 0.25 |
| $CoCl_2x6H_2O$ | 0.025 | 0.025 | 0.025 | 0.025 | 0.025 |
| Carbohydrates (g/l final concentration) | | | | | |
| Maltose | 30 | 30 | 30 | 30 | 30 |
| D-Mannitol | | | 64 | | |
| Hormones (mg/l final concentration) | | | | | |
| 2,4-D | 3.0 | 5.0 | 3.0 | | |
| Kinetin | | | | 0.2 | |
| Vitamins (mg/l final concentration) | | | | | |
| Pyridoxine HCl | 0.5 | 0.5 | 0.5 | 0.5 | |
| Thiamine HCl | 0.1 | 0.1 | 0.1 | 0.1 | |
| Nicotinic acid | 0.5 | 0.5 | 0.5 | 0.5 | |
| Myo-Inositol | 100 | 100 | 100 | 100 | |
| Other organics (mg/l final concentration) | | | | | |
| Glycine | 2 | 2 | 2 | 2 | 2 |

Culture Media

Weights and volumes required of each individual ingredient are specified in Table 6. Adjust media pH to 5.8 with KOH. The addition of a solidifying agent is required. Use agarose (for LP3, LP5 and LP3-OS) and 0.8% (w/v) Agar for MS0 and MSK prior to sterilising. Media LP3, LP5 and MSK are modified from Murashige and Skoog (1962).

Those skilled in the art will appreciate that the invention described above is susceptible to variations and modifications other than those specifically described. It is to be understood that the invention includes all such variations and modifications. The invention also includes all of the steps, features, compositions and products referred to or indicated in this specification, individually or collectively, and any and all combinations of two or more of said steps or features.

4. Reducing Ruminant Methane Production by Feeding a Ruminant Plants Over Expressing DGAT1 in the Leaf.

Elevated levels of dietary lipids was correlated with reduced methane output in ruminants (Holter and Young, 1992; Johnson et al., 2002; Dohme et al., 2001; Fievez et al., 2003; Machmuller et al., 2003; Jalc et al., 2002; Jalc and Ceresnakova, 2001; Sauer et al., 1998). The single committed step in the formation of triacylglycerides is catalysed by acyl CoA:diacylglycerol acyltransferase (DGAT1) which was recently cloned from *Arabidopsis thaliana* (Zou et al., 1999). When the *A. thaliana* DGAT1 cDNA was placed under the control of a constitutive promoter in tobacco, triacylglycerol accumulated as oil drops in the cytoplasm of leaf cells; plants were otherwise phenotypically unchanged (Bouvier-Navé et al., 2000). We propose that modifying the expression pattern of ryegrass DGAT1 to be expressed at high levels in the leaf would result in the generation and accumulation of TAG in the leaves of these plants. In turn this will influence the efficiency of pasture conversion by the ruminant into useful products (e.g., meat or dairy) or waste products (e.g., methane, hydrogen, urea).

Ruminants can tolerate up to 10% lipid content (on a dry matter basis) in their diet (Garnsworthy, 1997). From this maximal value we can determine how much triacylglyceride can be accumulated in ryegrass (by over expressing DGAT1 in the leaves) to reach this value. Subsequently, when animals are fed ryegrass over expressing DGAT1 in the leaves the effect on methane production can be calculated.

The maximum allowable lipid content of the DMI for ruminants is 10% (Gamsworthy 1997). The average total lipid content of forage grasses is 5% (varying from 2-6% w/w) on a dry matter basis (Weenink, 1959; Shorland, 1961; Weenink, 1961; Dewhurs and King, 1998; Elgersma et al., 2003). Hence, the 5 maximum allowable accumulation of triacylglycerol by over expression of DGAT1 in the leaf is 5% of the dry matter.

Bouvier-Nave et al., (2000) reported in their first round of trangenics there was up to a 7 fold increase in the triacylglycerol content of transgenic tobacco by overexpressing a full length open reading frame of DGAT1. We have found that over expressing DGAT1 in the roots of *Lotus japonicus* led to up to a doubling of the total lipid content when compared with roots transformed with the *Agrobacterium rhizogenes* Ri gene alone. Combined, these results show that it should be possible to increase the lipid content of ryegrass leaves from 5% to 10% DM by over expressing DGAT1 which would lead to the accumulation of triacylglyceride.

Supplementation of ruminant feeds with plant based oils (consisting of predominantly C16:0, C18:0, C18:1, C18:2 and C18:3 in similar ratios to those we report in ryegrass) to give a total of 8-10% lipid (DM) have been reported to reduce ruminant methane production by 20 to 56% and are summarised in the Table 7.

TABLE 7

| Supplemental oil type | Reduction in CH4 production compared to control feed | Reference |
|---|---|---|
| Palmitic | 38% | Czerkaski et al., (1966) |
| Oleic | 27% | Czerkaski et al., (1966) |
| Linoleic | 26% | Czerkaski et al., (1966) |
| Linolenic | 33.3% | Czerkaski et al., (1966) |
| Soybean Oil | 47% | Fievez et al., (2003) |
| Canola Oil | 21% | Dong et al., (1997) |
| Linoleic | 19.5% | Dome et al., (2001) |

The mechanism for methane reduction appears to be a combination of providing a competing sink for hydrogen (a substrate required by methanogens) as well altering the rumen methanogenic population. Combined, the results indicate that feeding ruminants ryegrass in which the expression of DGAT1 in the leaves has been upregulated (leading to the accumulation of triacylglycerol in the leaf and a total lipid content of approximately 8% DM) would lead to a 20-50% reduction in methane production.

5. Increasing Meat and Milk Production and Altering Their Lipid Profile by Feeding a Ruminant Plants Over Expressing DGAT1 in the Leaf.

Casler and Vogel (1999) report an average increase of 3.2% in liveweight gain for each 1% increase in digestibility without negatively affecting forage yield and/or agronomic fitness. If we increased the lipid level by 5% we can predict the increase in energy content of the forage. Purified lipids provide 37.7 J/g, carbohydrate and protein both provide 16.7 J/g. Currently, the carbohydrate and protein constitute approximately 70 and 18% of ryegrass dry matter while lipids make up approximately 5%. An increase in lipid content to 10% would reduce the DM contribution from carbohydrate and protein combined by 5%. Hence, the total energy content would rise to would rise from approximately 16.6 J/g to 17.6 J/g DM or a 6% rise over the existing level Lean beef and lamb are wholesome foods which provide a variety of caloric and essential fatty acids. Among the beneficial, health promoting fatty acids (FA) are conjugated linoleic acid (CLA), especially the cis-9, trans-11 isomer, trans-vaccenic acid (TVA; trans-11 C18:1), and the long chain omega-3 polyunsaturated FA (LC n-3 PUFA). CLA reduces the severity of cancer in a number of animal models exposed to a range of acute carcinogenic stimulants (Belury 1995; Kritchevsky 2000). TVA, the major precursor of CLA, is found mainly in meat and milk of ruminants (Corl et al. 2001) and dietary TVA is known to be converted to CLA in situ in mice (Santora et al. 2000) and humans (Salminen et al. 1998). The LC n-3 PUFA include eicosapentaenoic (EPA; C20:5), docosapentaenoic (DPA; C22:5), and docosahexaenoic (DHA; C22:6) acids, which can reduce the potential for coronary heart disease, cancer, and arthritis (Simopoulos 1996). Less beneficial FA include the saturated FA, especially the intermediate chain length lauric (C12:0), myristic (C14:0), and palmitic (C16:0) acids that can promote the development of atherosclerosis (Ulbricht & Southgate 1991).

Two studies were conducted to test the affects on sheep of proposed modifications to the lipid profile in ryegrass. The materials and methods, results and conclusions from these trials are reported as follows:

Trial 1

An indoor study was conducted in autumn using rumen-fistulated sheep in metabolism crates, to determine the effect of increasing lipid concentration on energy balance. Sheep were fed ad-libitum on ryegrass that had been harvested daily, and stored in a chiller at 4 deg C. A fresh allocation of feed was provided twice daily at 9:00 am and 5:00 pm. For periods of 2 hours, commencing when the morning and afternoon feed was allocated, oil was infused directly into the rumen to simulate the ingestion of ryegrass with 6 different levels of total lipid; 4% (the basal concentration of total lipid in the diet) 5.25%, 6.50%, 7.75%, 9.0% and 10.25%. The amount of oil infused to simulate the 5 nominal dietary levels was calculated based on the amount of dry matter intake sheep consumed in each preceding 24-hour period.

The fourteen sheep were allocated in pairs to 6 levels (3 sheep were used for the two highest levels) and received this level for 17 days. This was comprised of an adjustment period of 8 days followed by 10 days to determine energy balance. During this first period, sheep receiving the highest dose (10.25%) reacted adversely (stopped eating) and this treatment was discontinued. Sheep were then allowed 8 days without infusion as a treatment 'washout period' and reassigned to another treatment level for a further 17 days. During the second period with 5 treatment levels, 3 sheep were used for 5.25, 6.50% and 7.75%, 2 for 9.00% and 2 for the control.

Figure 13:
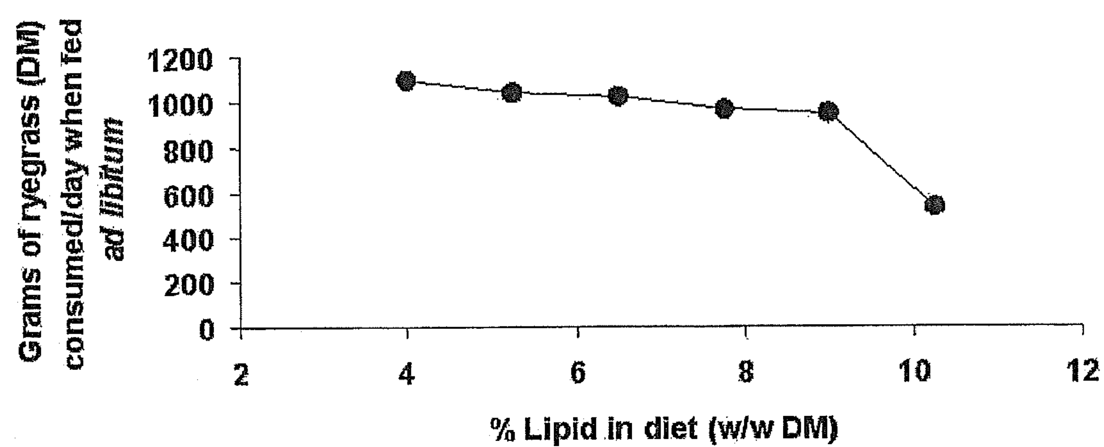
FIG. 13 shows the average *Lolium perenne* dry matter intake for lambs infused with supplementary lipid in feeding Trial 1. (Effect of dietary lipid on *Lolium perenne* DM intake/day in sheep).

The results of this study indicated that sheep tolerated up to approximately 8% total lipid in the diet without reduction in daily dry matter intake (FIG. 13). This study confirmed that a target for plant modification of 8% total lipid in the diet was feasible (from an animal health and nutrition view point).

Trial 2

The purpose of the second study was a) to confirm that the target of 8%, established with sheep indoors, would also apply for sheep at pasture and b) to determine effects of elevated lipid concentration on liveweight gain, feed intake and the fatty acid profiles of carcass meat. For this grazing study 90 weaned lambs (approximately 14 weeks of age) were randomly allocated to 3 treatments (n=30);

control—nominal 4% total lipid in diet (i.e. the concentration in ryegrass)

medium—nominal 6% total lipid in diet high—nominal 8% total lipid in diet.

The medium and high levels of total dietary lipid were simulated by giving the lambs an oral dose of a blend of sunflower and linseed oil twice daily for 6 weeks. The volume of oil dosed each day was calculated to raise the total concentration of dietary lipid from 4% present in ryegrass to the nominal targets of 6% and 8%, and was 28 ml/day and 56 ml/day, respectively. The control lambs were also yarded twice daily and given a dose of water (28 ml/day). The lipid profile of each diet is shown in Table 8.

TABLE 8

| | mg lipid/g DM intake | | | | | | |
|---|---|---|---|---|---|---|---|
| DIET | 14:0 | 16:0 | 16:1 | 18:0 | 18:1 | 18:2 | 18:3 |
| Control | 0.01 | 5.38 | 0.99 | 0.42 | 0.43 | 4.33 | 32.90 |
| Medium | 0.01 | 6.74 | 0.94 | 1.23 | 6.59 | 11.29 | 41.05 |
| High | 0.01 | 7.92 | 0.84 | 2.08 | 13.18 | 18.51 | 48.08 |

The study was conducted over 6 weeks during November and December. All lambs grazed together as a single group on hybrid (*perenne*×*multiflorum*) ryegrass pasture. They were offered an ad-libitum allowance and were shifted to a fresh allocation every 2 days.

Measurements were made to determine liveweight gain, and daily dry matter intake. Lambs were slaughtered at the end of the trial and carcass weight recorded and samples of meat collected for analysis of total fatty acid composition Trial 2 Materials and Methods Extraction, Saponification, and Methylation of Fatty Acid Extraction of FA from the muscle was by the method described by Knight et al. (2003a) for beef. Part of the extract was used to gravimetrically determine the lipid content of the dried tissue, and the rest was used for gas-liquid chromatography (GLC) analysis. In brief the muscle samples were cut into 1 cm cubes, weighed, freeze dried, weighed again to determine the dry matter content of the meat (DM), and then finely ground. Lipids were extracted from the freeze-dried samples by a modified of the method used by Folch et al. (1957). The saponification, methylation, and analyses of FA in the extracts were based on the methods of Slover and Lanza (1979) and the American Oil Chemists Society (2001). An internal standard of 2 mg tridecanoic acid (C13:0) in 2 ml isooctane was added to 10-25 ml of the extracted lipids. Lipids were saponified using methanolic NaOH and methylated using a freshly prepared methanolic $BF_3$ solution. The dry isooctane solution of fatty acid methyl esters was stored in a refrigerator until analysed. The extract was blanketed with nitrogen at all steps in the procedure.

Plasma samples were extracted by the method of Caruso et al. (1991). 0.8 ml of plasma was mixed with an internal standard of 1.0 ml of a solution of 1 mg n-heneicosanoic acid (C21:0)/ml isooctane and extracted with 8 ml of methanol: chloroform. (1:1). After centrifuging at 2000 g for 5 min. the supernatant was transferred to a clean tube and washed with 4 ml chloroform and 2.4 ml water. The mixture was again centrifuged for 5 min. and, after discarding the upper aqueous layer, the lower chloroform layer was evaporated to dryness under a stream of nitrogen gas while heating to 40° C. using a dry block. Saponification, methylation, and analyses of FA in the plasma extracts were the same as for the extracts of muscle.

GLC Analysis

GLC was performed with a Hewlett Packard model 6890 equipped with a flame ionization detector and a SGE BPX70 column 120 m length, 0.25 mm ID, and 0.25 μm film thickness. 1 μl of the sample or standards was injected into the GLC with a split ratio of 50:1. Helium was used as the carrier gas at a linear velocity of 19 cm/sec or 1.2 ml/min in a constant flow mode; the starting column pressure was 45 psi. The injector temperature was 250° C. and the initial temperature on the column was 130° C. increasing at 1° C./min. to 190° C. and then 2° C./min. to 245° C. and this temperature was held for 5 min. The total run time was 95 min. Fatty acids were identified by comparing their retention time with known standards and using effective chain length calculations from data contained in technical publications for the SGE BPX 70 phase columns. The GLC analyses of the plasma extracts used a column of 30 m length, 3.2 mm internal diameter, and 0.25 μm thick with an injection volume of 1 μl.

The FA peaks identified were the same as those reported in Knight et al. (2003a) but only those FA that were present at more than 0.2 g/100 g total fatty acid (TFA) are presented in this paper. Although the FA with less than 0.2 g/100 g TFA were not presented they were included in the groups of saturated (SATFA), monounsaturated (MUFA) and polyunsaturated FA (PUFA) where appropriate. The C18:1 c/t included a mixture of cis and trans isomers of C18:1 other than cis-9 C18:1 or TVA which cannot be separated, cis C18:1 includes cis isomers of other than cis-9 C18:1 and trans C18:1 includes trans isomers of C18:1 other than TVA. The FA compositions for the muscle and plasma extracts are given as g per 100 g TFA.

Statistical Analysis

Data for the proportions of FA in the TFA extracted from the muscle and plasma were analysed using Analysis of Variance (GenStat 2000). Means are presented with standard errors of difference (s.e.d) for the comparison between treatments with the minimum and maximum number of lambs in the group.

Trial 2 Results

Fatty Acids in Muscle

There were no effects of the twice day drenching with oil on the proportion of lipid in the raw lean meat but it did have an effect on the composition of the FA in the meat (Table 1). Compared with the control lambs the lambs drenched with the high dose of oil had significantly lower proportions of C16:0, C16:1; C17:0, C17:1, and cis-9 C18:1. Conversely, the lambs drenched with the high dose of oil had significantly higher proportions than the control lambs of TVA and the other trans isomers of C18:1, of the mixed cis-trans isomers of C18:1, of C18:2 and the mixture of cis-trans isomers of C18:2, and of C18:3. Despite the drenching with oil increasing the proportions of TVA in the meat the increases in the proportions of cis-9, trans-11 CLA were not significant ($P=0.082$). In all these comparisons for individual FA the lambs receiving the medium dose of oil were intermediate between the controls and the lambs receiving the high dose of oil.

Over all, the high dose of oil increased the proportions of PUFA and reduced the proportions of SATFA compared with the control lambs and the lambs drenched with the medium dose of oil whereas both doses of oil lowered the proportions of MUFA in the meat compared with the control lambs. The ratio of PUFA:SATFA was higher ($P<0.001$) for the lambs drenched with the high dosed of oil than for the control lambs and lambs drenched with the medium dose of oil. There were no effects of the drenching with oil on the ratio of omega-6: omega-3 PUFA but the lambs drenched with the medium dose of oil had a lower ratio of linoleic:linolenic acid than the control lambs with the lambs drenched with the high dose of oil being intermediate.

Fatty Acids in Plasma

Drenching with the medium dose of oil increased the total lipid content of the plasma by 23% and the high dose increased it by 34% compared to the control lambs ($P<0.01$; Table 2). The differences among treatments in the FA composition of the plasma largely mirror the differences found in the meat. All the C14:0 to C17:0 saturated FA and their mono-unsaturated FA were higher ($P<0.05$) for the control lambs than the lambs drenched with the high dose of oil. There were no effects of drenching the lambs with oil on C18:0 but cis-9 C18:1 was lower ($P<0.001$) in the lambs drenched with the high dose of oil than the control lambs.

Conversely, the other C18:1 isomers, including TVA, were higher in the lambs drenched with the high dose than the control lambs. Surprisingly given the lower TVA in the control lambs, the cis-9 trans-11 CLA and trans trans CLA were higher ($P<0.05$) in the plasma of the control lambs than in the lambs drenched with the high dose of oil. Drenching lambs with the high dose of oil increased the proportion of C18:2 and cis trans C18:2 compared with the control lambs. In all the above mentioned FA the proportions of the FA in the lambs drenched with the medium dose of oil were intermediate between the control lambs and the lambs drenched with the high dose of oil. This changed for C18:3 and the longer chained poly-unsaturated FA where the lambs drenched with the medium dose of oil had the higher proportion of these FA compared with the control lambs and/or lambs drenched with the high dose of oil.

Trial 2 Discussion and Conclusion

Fatty Acids in Muscle and Plasma

Drenching the lambs with oil did not increase the TFA content of the meat despite increasing in the lipid content in the plasma. However, there was a change in the composition of the FA in the meat from drenching the lambs with oil containing C18:2 and C18:3 with proportions of these FA being increased in the meat. This was offset by a large reduction in the proportion of cis-9 C18:1 and to a lesser extent the proportions of the saturated and mono-unsaturated C16 and C17 FA. The increase in the proportions of the other isomers of C18:1 including TVA with drenching with the oil suggest there was some disruption of the rumen micro flora involved in the biohydrogenation of C18:2 and C18:3 from the diet. Despite the increase in the proportion of TVA in the meat and plasma from drenching with oil the proportion of cis-9 trans-11 CLA was lower in the plasma from the drenched lambs and only marginally higher in the meat from the drenched lambs. Increasing the dietary intake of C18:2 and C18:3 in the lambs did not increase the proportions of the longer chain omega-6 or omega-3 PUFA in the meat despite C18:2 and C18:3 being the precursors in tissues for these groups of longer chain FA.

TABLE 9

The content of TFA and the proportions of individual and groups of FA in the meat from the Control group of lambs and the lambs drenched daily with Medium or High doses of oil.

| | Control | Medium | High | s.e.d. | Sign. diff. |
|---|---|---|---|---|---|
| Number | 13 | 10 | 15 | | |
| TFA (mg/g DM) | 79.2 | 93.2 | 87.7 | 9.70 | NS |
| (g/100 g TFA) | | | | | |
| C14:0 | 2.30 | 2.44 | 2.35 | 0.196 | NS |
| C15:0 | 0.33 | 0.37 | 0.34 | 0.018 | NS |
| C16:0 | 20.69$^{a}$ | 20.32$^{ab}$ | 18.73$^{b}$ | 0.648 | ** |
| C17:0 | 0.94$^{a}$ | 0.92$^{ab}$ | 0.85$^{b}$ | 0.033 | * |
| C18:0 | 19.96 | 21.17 | 20.42 | 0.832 | NS |
| SATFA | 44.21$^{ab}$ | 45.20$^{a}$ | 42.68$^{b}$ | 0.858 | * |
| C17:1 | 0.44$^{a}$ | 0.34$^{b}$ | 0.26$^{c}$ | 0.021 | *** |
| C16:1 | 0.97$^{a}$ | 0.81$^{b}$ | 0.72$^{b}$ | 0.068 | *** |
| Cis-9 C18:1 | 33.04$^{a}$ | 29.45$^{b}$ | 27.95$^{b}$ | 1.006 | *** |
| Cis C18:1 | 1.74 | 1.60 | 1.78 | 0.138 | NS |
| C18:1 c/t | 0.34$^{c}$ | 0.46$^{b}$ | 0.57$^{a}$ | 0.026 | *** |
| Trans C18:1 | 0.48$^{c}$ | 0.60$^{b}$ | 0.67$^{a}$ | 0.026 | *** |
| TVA | 3.36$^{c}$ | 4.33$^{b}$ | 5.49$^{a}$ | 0.329 | *** |
| MUFA | 40.60$^{a}$ | 37.82$^{b}$ | 37.66$^{b}$ | 0.862 | *** |
| Cis-9, trans-11 CLA | 0.84 | 0.92 | 1.02 | 0.084 | NS |
| C18:2 | 2.37$^{c}$ | 3.26$^{b}$ | 4.36$^{a}$ | 0.387 | *** |
| Cis, trans C18:2 | 0.21$^{b}$ | 0.34$^{ab}$ | 0.43$^{a}$ | 0.066 | ** |
| Trans, trans C18:2 | 0.26 | 0.36 | 0.36 | 0.071 | NS |
| C18:3 | 1.59$^{c}$ | 2.54$^{b}$ | 3.27$^{a}$ | 0.212 | *** |
| C20:4 n-6 | 0.99 | 0.77 | 0.81 | 0.147 | NS |
| C20:5 | 0.94 | 0.77 | 0.86 | 0.131 | NS |

TABLE 9-continued

The content of TFA and the proportions of individual and groups of FA in the meat from the Control group of lambs and the lambs drenched daily with Medium or High doses of oil.

| | Control | Medium | High | s.e.d. | Sign. diff. |
|---|---|---|---|---|---|
| C22:5 | 0.86 | 0.63 | 0.70 | 0.110 | NS |
| C22:6 | 0.22 | 0.18 | 0.19 | 0.032 | NS |
| PUFA | 8.49$^{b}$ | 10.01$^{b}$ | 12.17$^{a}$ | 0.900 | *** |
| Unknowns | 6.22 | 6.47 | 6.95 | 0.35 | NS |
| PUFA:SATFA | 0.195$^{b}$ | 0.224$^{b}$ | 0.287$^{a}$ | 0.0242 | *** |
| Omega-6:omega-3 | 1.14 | 1.20 | 1.23 | 0.051 | NS |
| Linoleic:linolenic | 1.46$^{a}$ | 1.27$^{b}$ | 1.34$^{ab}$ | 0.078 | P = 0.063 |

TABLE 10

The content of TFA and the proportions of individual and groups of FA in the plasma from the Control group of lambs and the lambs drenched daily with Medium or High doses of oil

| | Control | Medium | High | s.e.d. | Sign diff. |
|---|---|---|---|---|---|
| μg lipid/ml plasma | 1135$^{b}$ | 1400$^{a}$ | 1524$^{a}$ | 114.6 | ** |
| FA (g/100 g TFA) | | | | | |
| C14:0 | 1.29$^{a}$ | 1.29$^{a}$ | 0.86$^{b}$ | 0.174 | * |
| C15:0 | 1.14$^{a}$ | 0.86$^{b}$ | 0.69$^{c}$ | 0.047 | *** |
| C16:0 | 13.89$^{a}$ | 12.09$^{b}$ | 10.57$^{c}$ | 0.487 | *** |
| C16:1 | 0.98$^{a}$ | 0.51$^{b}$ | 0.28$^{c}$ | 0.071 | *** |
| C17:0 | 1.14$^{a}$ | 0.80$^{b}$ | 0.70$^{c}$ | 0.032 | *** |
| C17:1 | 0.64$^{a}$ | 0.37$^{b}$ | 0.16$^{c}$ | 0.099 | *** |
| C18:0 | 22.09 | 21.11 | 21.52 | 1.055 | NS |
| cis C18:1 | 1.58$^{b}$ | 1.73$^{b}$ | 2.24$^{a}$ | 0.0.121 | *** |
| cis-9 C18:1 | 21.14$^{a}$ | 13.96$^{b}$ | 11.44$^{c}$ | 0.686 | *** |
| C18:1 c/t | 1.04$^{c}$ | 2.27$^{b}$ | 2.58$^{a}$ | 0.136 | *** |
| trans C18:1 | 0.58$^{b}$ | 0.76$^{a}$ | 0.86$^{a}$ | 0.052 | *** |
| TVA | 3.05$^{b}$ | 3.04$^{b}$ | 4.83$^{a}$ | 0.331 | *** |
| cis 9, trans-11 CLA | 0.96$^{a}$ | 0.76$^{b}$ | 0.73$^{b}$ | 0.098 | * |
| All trans CLA | 0.39$^{a}$ | 0.38$^{a}$ | 0.26$^{b}$ | 0.036 | *** |
| C18:2 | 6.70$^{c}$ | 12.73$^{b}$ | 14.21$^{a}$ | 0.714 | *** |
| cis trans C18:2 | 0.21$^{c}$ | 0.48$^{b}$ | 1.20$^{a}$ | 0.086 | *** |
| trans trans C18:2 | 0.40 | 0.43 | 0.33 | 0.057 | NS |
| C18:3 | 5.08$^{b}$ | 9.44$^{a}$ | 9.33$^{a}$ | 0.783 | *** |
| C20:4 n-6 | 0.76$^{b}$ | 0.90$^{a}$ | 0.65$^{b}$ | 0.061 | *** |
| C20:5 | 1.71$^{b}$ | 2.18$^{a}$ | 1.61$^{b}$ | 0.191 | ** |
| C22:5 | 1.53$^{ab}$ | 1.75$^{a}$ | 1.28$^{b}$ | 0.156 | * |
| C22:6 | 1.01$^{a}$ | 1.19$^{a}$ | 0.76$^{b}$ | 0.123 | ** |
| Miscellaneous | 1.38 | 1.10 | 1.31 | 0.133 | NS |
| Unknowns | 11.45$^{a}$ | 9.96$^{b}$ | 11.63$^{a}$ | 0.705 | * |

Miscellaneous includes all the FA that were identified but the proportions were less than 0.2 g/100 g TFA.

REFERENCES

Ausubel et al., (2001) Current Protocols in Molecular Biology, Current Protocols, John Wiley and Sons Inc. (2001) and Sambrook and Russel (eds) Molecular Cloning, A Laboratory Manual, Cold Spring Harbour Laboratory Press, Cold Spring Harbour, N.Y.

Bauman D E, Barbano D M, Dwyer D A, Griinari J M. (2000) Technical note: production of butter with enhanced conjugated linoleic acid for use in biomedical studies with animal models. *J. Dairy Sci.,* 83, 2422-5.

Belury, M. A. 1995: Conjugated dienoic linoleate: A polyunsaturated fatty acid with unique chemoprotective properties. *Nutrition Reviews* 53: 83-89.

Bouvier-Nave P, Benveniste P, Oelkers P, Sturley S L, Schaller H. (2000) Expression in yeast and tobacco of plant cDNAs encoding acyl CoA:diacylglycerol acyltransferase. *Eur. J. Biochem.* 267, 85-96.

Buxton, D. R.; Mertens, D. R. (1995) Quality-related characteristics of forages. Pp 83-96. In: Forages, Volume II. (eds) Barnes, R. F.; Miller, D. A.; Nelson, J. C. Iowa State University Press, Ames.

Caradus, J. R.; Woodfield, D. R.; Easton, H. S. 2000. Improved grazing value of pasture cultivars for temperate environments. In: Stone, G. M. (ed) Animal Production for a Consuming World Vol. B: 5-8

Caruso, U.; Fowler, B.; Erceg, M.; Romano, C. 1991: Determination of very long chain fatty acids in plasma by a simplified gas chromatographic-mass spectrometric procedure. *Journal of Chromatography* 526: 147-152.

Corl, B. A.; Baumgard, L. H.; Dwyer, D. A.; Griinari, J. M.; Phillips, B. S.; Bauman, D. E. 2001: The role of delta 9-desaturase in the production of cis-9, trans-11 CLA. *Journal of Nutritional Biochemistry* 12: 622-630.

Chilliard Y, Ferlay A, Doreau M. (2000) Effect of different types of forages, animal fat or marine oils in cow's diet on milk fat secretion and composition, especially conjugated linoleic acid (CLA) and polyunsaturated fatty acids. *Livest. Prod. Sci.,* 70, 31-48.

Czerkawski J W, Blaxter K L, Wainman F W. (1966) The metabolism of oleic, linoleic and linolenic acids by sheep with reference to their effects on methane production. Br. J. Nutr., 20, 349-362.

Dahlqvist A, Stahl U, Lenman M, Banas A, Lee M, Sandager L, Ronne H, Stymne S. (2000) Phospholipid:diacylglycerol acyltransferase: an enzyme that catalyzes the acyl-CoA-independent formation of triacylglycerol in yeast and plants. Proc Natl Acad Sci USA. 97, 6487-6492.

Demeyer D, Doreau M. (1999) Targets and procedures for altering ruminant meat and milk lipids. *Proc Nutr Soc.,* 58, 593-607.

Dhiman T R, Satter L D, Pariza M W, Galli M P, Albright K, Tolosa M X. (2000) Conjugated linoleic acid (CLA) content of milk from cows offered diets rich in linoleic and linolenic acid. *J. Dairy Sci.,* 83, 1016-27.

Dewhurst R., Scollan N. (1998) Forages, Fat Fitness and Flavour. IGER Innovations 1998, 36-39.

Dohme F, Machmuller A, Wasserfallen A, Kreuzer M. (2001) Ruminal methanogenesis as influenced by individual fatty acids supplemented to complete ruminant diets. Letters in Applied Micro. 32, 47-51.

Dong Y, Bae H D, McAllister T A, Mathison G W, Cheng K-J. (1997) Lipid-induced depression of methane production and digestibility in the artificial rumen system (RUSTITEC). Can. J. Anim. Sci., 77, 269-278.

Fievez V., Dohme F., Danneels M., Raes K., Demeyer D. (2003) Fish oils as potent rumen methane inhibitors and associated effects on rumen fermentation in vitro and in vivo. *Animal Feed Science and Technology* 104, 41-58

Folch, J.; Lee, M.; Sloane-Stanley, G. A. 1957: A simple method for the isolation and purification of total lipid from animal tissue. *Journal of Biological Chemistry* 226: 497-509.

GenStat 2000: GenStat for Windows. Release 4.2. 5th ed. Oxford, VSN International Ltd.

Holter J B, Young A J. (1992) Nutrition, Feeding and Calves: Methane prediction in dry and lactating Holstein cows. J. Dairy Sci., 75, 2165-2175.

Jalč D, Čerešňáková Z. (2001) Effect of plant oils and aspartate on rumen fermentation in vitro. J Anim Physiol Anim Nutr (Berl). 85, 378-84.

Jalć D, Kisidayova S, Nerud F. (2002) Effect of plant oils and organic acids on rumen fermentation in vitro. Folia Microbiol. (Praha). 47, 171-177.

Johnson K A, Kincaid R L, Westberg H H, Gaskins C T, Lamb B K, Conrath J K. (2002) The effect of oilseeds in diets of lactating cows on milk production and methane emmissions. J. Dairy Sci., 85, 1509-1515.

Kay J K, Mackle T R, Auldist M J, Thomson N A, Bauman D E. (2002). Endogenous synthesis and enhancement of conjugated linoleic acid in pasture-fed dairy cows. *Proc. NZ Soc. Anim. Prod.* 62, 12-15.

Kelly M L, Berry J R, Dwyer D A, Griinari J M, Chouinard P Y, Van Amburgh M E, Bauman D E. (1998). Dietary fatty acid sources affect conjugated linoleic acid concentrations in milk from lactating dairy cows. *J Nutr.,* 128, 881-885.

Knight, T. W.; Knowles, S.; Death, A. F.; West, J.; Agnew, M.; Morris, C. A.; Purchas, R. W. 2003a: Factors affecting the variation in fatty acid concentrations in lean beef from grass-fed cattle in New Zealand and the implications for human health. *New Zealand Journal of Agricultural Research* 46: 83-95.

Kritchevsky, D. 2000: Antimutagenic and some other effects of conjugated linoleic acid. *British Journal of Nutrition* 83:459-465.

Lardizabal K D, Mai J T, Wagner N W, Wyrick A, Voelker T, Hawkins D J. (2001) DGAT2 Is a new diacylglycerol acyltransferase gene family. J.B.C. 276, 38862-38869.

Machmuller A, Soliva C R, Kreuzer M. (2003) Effect of coconut oil and defaunation treatment on methanogenesis in sheep. Reprod. Nutr. Dev., 43, 41-55.

McAllister T A, Okine E K, Mathison G W, Cheng K-J. (1996) Dietary, environmental and microbiological aspects of methane production in ruminants. Can. J. Anim. Sci. 76, 231-243.

McNamee B F, Fearon A M, Pearce J. (2002) Effect of feeding oilseed supplements to dairy cows on ruminal and milk fatty acid composition. *J. Sci. Food Agric.* 82, 677-684.

Machmüller A, Ossowski D A, Kreuzer M. (2000) Comparative evaluation of the effects of coconut oil, oilseeds and crystalline fat on methane release, digestion and energy balance in lambs. Anim. Feed Sci. Technol. 85, 41-60.

Ponnampalam E N, Sinclair A J, Egan A R, Blakeley S J, Leury B J. (2001) Effect of diets containing n-3 fatty acids on muscle long-chain n-3 fatty acid content in lambs fed low- and medium-quality roughage diets. *J Anim Sci.,* 79, 698-706.

Salminen, I.; Mutanen, M.; Jauhiainen, M.; Aro, A. 1998: Dietary trans fatty acids increase conjugated linoleic acid levels in human serum. *Journal of Nutritional Biochemistry* 9: 93-98.

Santora, J. E.; Palmquist, D. L.; Roehrig, K. 2000: Trans-vaccenic acid is desaturated to conjugated linoleic acid in mice. *Journal of Nutrition* 130: 208-215.

Sauer F D, Fellner V, Kinsman R, Kramer J K, Jackson H A, Lee A J, Chen S. (1998) Methane output and lactation response in Holstein cattle with monensin or unsaturated fat added to the diet. J Anim Sci. 76, 906-914.

Scollan N D, Choi N J, Kurt E, Fisher A V, Enser M, Wood J D. (2001a) Manipulating the fatty acid composition of muscle and adipose tissue in beef cattle. *Br J Nutr.,* 85, 115-124.

Scollan N D, Dhanoa M S, Choi N J, Maeng W J, Enser M, Wood J D (2001b) Biohydrogenation and digestion of long chain fatty acids in steers fed on different sources of lipid. *J. Agric. Sci. Camb.* 136, 345-355.

Simopoulos, A. P. 1996: Omega-3 fatty acids Part 1: Metabolic effects of omega-3 fatty acids and essentiality. Pp. 51-73 in: Handbook of Lipids in Human Nutrition. Spiller, G. A. ed. NY, CRC Press.

Slover, H. T.; Lanza, E. 1979: Quantitative analysis of food fatty acids by capillary gas chromatography. *Journal of the American Oil Chemistry Society* 56: 933-943.

Ulbricht, T. L.; Southgate, D. A. T. 1991: Coronary heart disease: seven dietary factors. *The Lancet* 338: 985-992.

Ulyatt, M. J. (1973) The feeding value of herbage. pp 131-178 In: Chemistry and Biochemistry of Herbage. Butler, G. W.; Bailey, R. W. (eds) Volume 3. Academic Press, London Ulyatt, M. J. (1981) The feeding value of herbage: can it be improved? *New Zealand Journal of Agricultural Science,* 15. 200-205.

Ulyatt, M. J.; Thomson, D. J.; Beever, D. E.; Evans, R. T.; Haines, M. J. (1988) The digestion of perennial ryegrass and white clover by grazing cattle. *British journal of nutrition* 60: 137-149.

Wettstein H, Machmuller A, Kreuzer M. (2000) Effects of raw and modified canola lecithins compared to canola oil, canola seed and soy lecithin on ruminal fermentation measured with rumen simulation technique. Anim. Feed Sci. Technol. 85, 153-169.

Wood J D, Enser M, Fisher A V, Nute G R, Richardson R I, Sheard P R. (1999) Manipulating meat quality and composition. *Proc Nutr Soc.,* 58, 363-70.

Zou J, Wei Y, Jako C, Kumar A, Selvaraj G, Taylor D C. (1999) The *Arabidopsis thaliana* TAG1 mutant has a mutation in a diacylglycerol acyltransferase gene. *Plant J.* 19, 645-653.

APPENDICIES

Appendix I

Sequence of *Arabidopsis thaliana* DGAT1 cDNA open Reading Frame (Grey Box) Cloned into pENTR-D

```
5'CTTTCCTGCGTTATCCCCTGATTCTGTGGATAACCGTATTACCGCCTTTGAGTGAGCT
GATACCGCTCGCCGCAGCCGAACGACCGAGCGCAGCGAGTCAGTGAGCGAGGAAGCGGAA
GAGCGCCCAATACGCAAACCGCCTCTCCCCGCGCGTTGGCCGATTCATTAATGCAGCTGG
CACGACAGGTTTCCCGACTGGAAAGCGGGCAGTGAGCGCAACGCAATTAATACGCGTACC
GCTAGCCAGGAAGAGTTTGTAGAAACGCAAAAAGGCCATCCGTCAGGATGGCCTTCTGCT
TAGTTTGATGCCTGGCAGTTTATGGCGGGCGTCCTGCCCGCCACCCTCCGGGCCGTTGCT
TCACAACGTTCAAATCCGCTCCCGGCGGATTTGTCCTACTCAGGAGAGCGTTCACCGACA
AACAACAGATAAAACGAAAGGCCCAGTCTTCCGACTGAGCCTTTCGTTTTATTTGATGCC
TGGCAGTTCCCTACTCTCGCGTTAACGCTAGCATGGATGTTTTCCCAGTCACGACGTTGT
AAAACGACGGCCAGTCTTAAGCTCGGGCCCCAAATAATGATTTTATTTTGACTGATAGTG
ACCTGTTCGTTGCAACAAATTGATGAGCAATGCTTTTTTATAATGCCAACTTTGTACAAA
AAAGCAGGCTCCGCGGCCGCCCCCTTCACCATGGCGATTTTGGATTCTGCTGGCGTTACT

ACGGTGACGGAGAACGGTGGCGGAGAGTTCGTCGATCTTGATAGGCTTCGTCGACGGAAA
TCGAGATCGGATTCTTCTAACGGACTTCTTCTCTCTGGTTCCGATAATAATTCTCCTTCG
GATGATGTTGGAGCTCCCGCCGACGTTAGGGATCGGATTGATTCCGTTGTTAACGATGAC
GCTCAGGGAACAGCCAATTTGGCCGGAGATAATAACGGTGGTGGCGATAATAACGGTGGT
GGAAGAGGCGGCGGAGAAGGAAGAGGAAACGCCGATGCTACGTTTACGTATCGACCGTCG
GTTCCAGCTCATCGGAGGGCGAGAGAGAGTCCACTTAGCTCCGACGCAATCTTCAAACAG
AGCCATGCCGGATTATTCAACCTCTGTGTAGTAGTTCTTATTGCTGTAAACAGTAGACTC
ATCATCGAAAATCTTATGAAGTATGGTTGGTTGATCAGAACGGATTTCTGGTTTAGTTCA
AGATCGCTGCGAGATTGGCCGCTTTTCATGTGTTGTATATCCCTTTCGATCTTTCCTTTG
GCTGCCTTTACGGTTGAGAAATTGGTACTTCAGAAATACATATCAGAACCTGTTGTCATC
TTTCTTCATATTATTATCACCATGACAGAGGTTTTGTATCCAGTTTACGTCACCCTAAGG
TGTGATTCTGCTTTTTTATCAGGTGTCACTTTGATGCTCCTCACTTGCATTGTGTGGCTA
AAGTTGGTTTCTTATGCTCATACTAGCTATGGACATAAGATCCCTAGCCAATGCAGTGAT
AAGGCCAATCCTGAAGTCTCCTACTACGTTAGCTTGAAGAGCTTGGCATATTTCATGGTC
GCTCCCACATTGTGTTATCAGCCAAGTTATCCACGTTCTGCATGTATACGGAAGGGTTGG

GTGGCTCGTCAATTTGCAAAACTGGTCATATTCACCGGATTCATGGGATTTATAATAGAA
CAATATATAAATCCTATTGTCAGGAACTCAAAGCATCCTTTGAAAGGCGATCTTCTATAT
GCTATTGAAAGAGTGTTGAAGCTTTCAGTTCCAAATTTATATGTGTGGCTCTGCATGTTC
TACTGCTTGTTCCACCTTTGGTTAAACATATTGGCAGAGCTTCTCTGCTTCGGGGATCGT
GAATTCTACAAAGATTGGTGGAATGCAAAAAGTGTGGGAGATTACTGGAGAATGTGGAAT
ATGCCTGTTCATAAATGGATGGTTCGACATATATACTTCCCGTGCTTGCGCAGCAAGATA
CCAAAGACACTCGCCATTATCATTGCTTTCCTAGTCTCTGCAGTCTTTCATGAGCTATGC
ATCGCAGTTCCTTGTCGTCTCTTCAAGCTATGGGCTTTTCTTGGGATTATGTTTCAGGTG
CCTTTGGTCTTCATCACAAACTATCTACAGGAAAGGTTTGGCTCAACGGTGGGGAACATG
ATCTTCTGGTTCATCTTCTGCATTTTCGGACAACCGATGTGTGTGCTTCTTTATTACCAC
GACCTGATGAACCGAAAAGGATCGATGTCATGAAAGGGTGGGCGCGCCGACCCAGCTTTC
TTGTACAAAGTTGGCATTATTAGAAAGCATTGCTTATGAATTTGTTGCAACGAACAGGTC

TTGTACAAAGTTGGCATTATAAGAAAGCATTGCTTATCAATTTGTTGCAACGAACAGGTC
TATTACATGGTCATAGCTGTTTCCTGGCAGCTCTGGCCCGTGTCTCAAAATCTCTGATGT
TACATTGCACAAGATAAAAATATATCATCATGAACAATAAAACTGTCTGCTTACATAAAC
AGTAATACAAGGGGTGTTATGAGCCATATTCAACGGGAAACGTCGAGGCCGCGATTAAAT
TCCAACATGGATGCTGATTTATATGGGTATAAATGGGCTCGCGATAATGTCGGGCAATCA
GGTGCGACAATCTATCGCTTGTATGGGAAGCCCGATGCGCCAGAGTTGTTTCTGAAACAT
GGCAAAGGTAGCGTTGCCAATGATGTTACAGATGAGATGGTCAGACTAAACTGGCTGACG
GAATTTATGCCTCTTCCGACCATCAAGCATTTTATCCGTACTCCTGATGATGCATGGTTA
CTCACCACTGCGATCCCCGGAAAAACAGCATTCCAGGTATTAGAAGAATATCCTGATTCA
GGTGAAAATATTGTTGATGCGCTGGCAGTGTTCCTGCGCCGGTTGCATTCGATTCCTGTT

TGTAATTGTCCTTTTAACAGCGATCGCGTATTTCGTCTCGCTCAGGCGCAATCACGAATG
AATAACGGTTTGGTTCATGCGAGTGATTTTGATGACGAGCGTAATGGCTGGCCTGTTGAA
CAAGTCTGGAAAGAAATGCATAAACTTTTGCCATTCTCACCGGATTCAGTCGTCACTCAT
GGTGATTTCTCACTTGATAACCTTATTTTTGACGAGGGGAAATTAATAGGTTGTATTGAT
GTTGGACGAGTCGGAATCGCAGACCGATACCAGGATCTTGCCATCCTATGGAACTGCCTC
GGTGAGTTTTCTCCTTCATTACAGAAACGGCTTTTTCAAAAATATGGTATTGATAATCCT
GATATGAATAAATTGCAGTTTCATTTGATGCTCGATGAGTTTTTCTAATCAGAATTGGTT
AATTGGTTGTAACACTGGCAGAGCATTACGCTGACTTGACGGGACGGCGCAAGCTCATGA
CCAAAATCCCTTAACGTGAGTTACGCGTCGTTCCACTGAGCGTCAGACCCCGTAGAAAAG
ATCAAAGGATCTTCTTGAGATCCTTTTTTTCTGCGCGTAATCTGCTGCTTGCAAACAAAA
AAACAACCGCTACCAGCGGTGGTTTGTTTGCCGGATCAAGAGCTACCAACTCTTTTTCCG
AAGGTAACTGGCTTCAGCAGAGCGCAGATACCAAATACTGTCCTTCTAGTGTAGCCGTAG
```

-continued

```
TTAGGCCACCACTTCAAGAACTCTGTAGCACCGCCTACATACCTCGCTCTGCTAATCCTG
TTACCAGTGGCTGCTGCCAGTGGCGATAAGTCGTGTCTTACCGGGTTGGACTCAAGACGA
TAGTTACCGGATAAGGCGCAGCGGTCGGGCTGAACGGGGGGTTCGTGCACACAGCCCAGC
TTGGAGCGAACGACCTACACCGAACTGAGATACCTACAGCGTGAGCATTGAGAAAGCGCC
ACGCTTCCCGAAGGGAGAAAGGCGGACAGGTATCCGGTAAGCGGCAGGGTCGGAACAGGA
GAGCGCACGAGGGAGCTTCCAGGGGGAAACGCCTGGTATCTTTATAGTCCTGTCGGGTTT
CGCCACCTCTGACTTGAGCGTCGATTTTTGTGATGCTCGTCAGGGGGGCGGAGCCTATGG
AAAAACGCCAGCAACGCGGCCTTTTTACGGTTCCTGGCCTTTTGCTGGCCTTTTGCTCAC
ATGTT 3'
```

Appendix II

Sequence of *Arabidopsis thaliana* DGAT1 Transcribed Genomic Region (Grey Box) Cloned into pENTR-D

```
5'CTTTCCTGCGTTATCCCCTGATTCTGTGGATAACCGTATTACCGCCTTTGAGTGAGCT
GATACCGCTCGCCGCAGCCGAACGACCGAGCCGAGCGAGTCAGTGAGCGAGGAAGCGGAA
GAGCGCCCAATACGCAAACCGCCTCTCCCCGCGCGTTGGCCGATTCATTAATGCAGCTGG
CACGACAGGTTTCCCGACTGGAAAGCGGGCAGTGAGCGCAACGCAATTAATACGCGTACC
GCTAGCCAGGAAGAGTTTGTAGAAACGCAAAAAGGCCATCCGTCAGGATGGCCTTCTGCT
TAGTTTGATGCCTGGCAGTTTATGGCGGGCGTCCTGCCCGCCACCCTCCGGGCCGTTGCT
TCACAACGTTCAAATCCGCTCCCGGCGGATTTGTCCTACTCAGGAGAGCGTTCACCGACA
AACAACAGATAAAACGAAAGGCCCAGTCTTCCGACTGAGCCTTTCGTTTTATTTGATGCC
TGGCAGTTCCCTACTCTCGCGTTAACGCTAGCATGGATGTTTTCCCAGTCACGACGTTGT
AAAACGACGGCCAGTCTTAAGCTCGGGCCCCAAATAATGATTTTATTTTGACTGATAGTG
ACCTGTTCGTTGCAACAAATTGATGAGCAATGCTTTTTTATAATGCCAACTTTGTACAAA
AAAGCAGGCTCCGCGGCCGCCCCCTTCACCATGGCCATTTTGGATTCTGCTGGCGTTACT
ACGGTGACGGAGAACGGTGGCGGAGAGTTCGTCGATCTTGATAGGCTTCGTCGACGGAAA

TCGAGATCGGATTCTTCTAACGGACTTCTTCTCTCTGGTTCCGATAATAATTCTCCTTCC
GATGATGTTGGAGCTCCCGCCGACGTTAGGGATCGGATTGATTCCGTTGTTAACGATGAC
GCTCAGGGAACAGCCAATTTGGCCGGACATAATAACGGTGGTGGCGATAATAACGGTGGT
GGAAGAGGCGGCGGAGAAGGAAGAGGAAACGCCGATGCTACGTTTACGTATCGACCGTCG
GTTCCAGCTCATCGGAGGGCGAGAGAGAGTCCACTTAGCTCCGACGCAATCTTCAAACAC
GTTTAAAATCTCAGAAATCTTCGAATTTGGTGTTTGCTTGTTCTTTTATATGGAATTGAG
TTTGGTGATTGTTTTGCATTGCAGAGCCATGCCGGATTATTCAACCTCTGTGTAGTAGTT
CTTATTGCTGTAAACAGTACACTCATCATCGAAAATCTTATGAAGGTTTGCTGTTACTTG
TTTCTCCTTTTAGGAATTGAATTGCTTGAAAATTTATCAGAGACGAATAACTTTGTTGTT
GCTATCATTCATGTAGTATGGTTGGTTGATCAGAACGGATTTCTGGTTTAGTTCAAGATC
GCTGCGAGATTGGCCGCTTTTCATGTGTTGGTAAAAGAAGATGTTTTTTATTTCCAGCAA
TGTTACATTGTTATACGTATAATGATGAGTTTAGTGATCAAGTTCCTCTTTGATTCTTCT
TTCTTGTTGCAGTATATCCCTTTCGATCTTTCCTTTGGCTGCCTTTACGGTTGAGAAATT
GGTACTTCAGAAATACATATCAGAACCTGTGAGTAATTACTATTCTCCAGCCATTACTGT
AATTTTTATTGAAGACAAGTTTGTATCATGAAGAACTTACAAGTTCTGTTTTGAAAATGC
TCAAGGTTGTCATCTTTCTTCATATTATTATCACCATGACAGAGGTTTTGTATCCAGTTT

ACGTCACCCTAAGGTGATACTGTTTTTCTGGTCTCAGTTTGTGATACTGTTTTTAAGTTT
AGTTGTCTGACCCGGTGATCTTGAAAATGGACAGGTGTGATTCTGCTTTTTTATCAGGTG
TCACTTTGATGCTCCTCACTTGCATTGTGTGGCTAAAGTTGGTTTCTTATGCTCATACTA
GCTATGACATAAGATCCCTAGCCAATGCAGCTGATAAGGTAAAATACGAAAAAGAAGCGT
ATGTATTAGTCACTTGCACTGTGTTACTGTTTTAACCAAACACTGTTATGAACTTTAGGC
CAATCCTGAAGTCTCCTACTACGTTAGCTTGAAGAGCTTGGCATATTTCATGGTCGCTCC
CACATTGTGTTATCAGGTAACTGCAAAGTGCATCAACCATTCTTATACTTGCAAGAGTTT
CTTGTCTAAACCTCGGATCTTTGCTTTTCCCCAGCCAAGTTATCCACGTTCTGCATGTAT
ACGGAAGGGTTGGGTGGCTCGTCAATTTGCAAAACTGGTCATATTCACCGGATTCATGGG
ATTTATAATAGAACAAGTACGTTTTCACATCTTGCTTTATTAGTTTTCCTTGGTGAAAAT
CATCATCCCTGCGTTGTCACCACTTGACTTCATGTTCTTTTGTTACATTTTGGCAGTATA
TAAATCCTATTGTCAGGAACTCAAAGCATCCTTTGAAAGGCGATCTTCTATATGCTATTG
AAAGAGTGTTGAAGCTTTCAGTTCCAAATTTATATGTGTGGCTCTGCATGTTCTACTGCT
TCTTCCACCTTTGGTATGCTGTGATGCCATCTCTTTCAAAATAATTTGCAAATTCGAAAA

ACCGAAAAAGGCTAAATCTCATACCAATTTGATATTTTTAGTTTCTTAGAGTCGGTGATG
ATTTTTCAGTTACTGAACGCAAATCTCTTGTCCAAAGGTTAAACATATTGGCAGAGCTTC
TCTGCTTCGGGGATCGTGAATTCTGCAAAGATTGGTGGAATGCAAAAAGTGTGGGAGATG
TGAGGTATTTTACTCAAAAGAAAACTTATGATTTTTAATGTTGTGGTTGTTTTTGGGTGA
TCTAACTAACCAAATTCATGTATTCACTGTCTTCCTTTATCAGTACTGGAGAATGTGGAA
TATGGTATGGTTCTCTTCCTAAACATCACCTTCTTTTGTACACAGGGTAGAAGAAGAGAG
CTAATTAAGATCTTGTTTTCCTTGACACCCTGTTCATAAATGGATGGTTCGACATATATA
CTTCCCGTGCTTGCGCAGCAAGATACCAAAGGTGAGTGAGATATATACCGATATGCAATT
GTCGAGATTTGTTTCTGTGATATAAATTTAACCCTCCACACACTTGTTTTTCAGACACTC
GCCATTATCATTGCTTTCCTAGTCTCTGCAGTCTTTCATGAGGTATACATACTTTCTGCA
TTGCCCTGTCTCTAGACGCATGAACACACGCTAGTGAAAGAAATGCTAATATTCAAAGCA
TTGTTTTTACTTAACGATCTTGTGTTACAAATTTCCTTTTGACAGCTATGCATCGCAGTT
CCTTGTCGTCTCTTCAAGCTATGGGCTTTTCTTGGGATTATCTTTCAGGTTAAAAAATTA
CTAAACTGCTGCAGTCGATTTTTACTAAACTCTAATCTCATATTCTGACCAACCAATTTG
```

-continued

```
TTTGAGTAGGTGCCTTTGGTCTTCATCACAAACTATCTACAGGAAAGGTTTGGCTCAACG
GTATGCTCTCAAAACCCGAGAAAATAGAACGAATAACTCTTTCTTTCATAGCCTAGCCAT
TTAAATCGCAATGCTGAAACTTAATAATAAAGGTGATCTGTTTTGGAATGGGATCATATT
ATTAGGTGGGGAACATGATCTTCTGGTTCATCTTCTGCATTTTCGGACAACCGATGTGTG
TGCTTCTTTATTACCACGACCTGATGAACCGAAAAGGATCGATGTCATGAAAGGGTGGGC
GCGCCGACCCAGCTTTCTTGTACAAAGTTGGCATTATAAGAAAGCATTGCTTATCAATTT

GTTGCAACGAACAGGTCACTATCAGTCAAAATAAAATCATTATTTGCCATCCAGCTGATA
TCCCCTATAGTGAGTCGTATTACATGGTCATAGCTGTTTCCTGGCAGCTCTGGCCCGTGT
CTCAAAATCTCTGATGTTACATTGCACAAGATAAAAATATATCATCATGAACAATAAAAC
TGTCTGCTTACATAAACAGTAATACAAGGGGTGTTATGAGCCATATTCAACGGGAAACGT
CGAGGCCGCGATTAAATTCCAACATGGATGCTGATTTATATGGGTATAAATGGGCTCGCG
ATAATGTCGGGCAATCAGGTGCGACAATCTATCGCTTGTATGGGAAGCCCGATGCGCCAG
AGTTGTTTCTGAAACATGGCAAAGGTAGCGTTGCCAATGATGTTACAGATGAGATGGTCA
GACTAAACTGGCTGACGGAATTTATGCCTCTTCCGACCATCAAGCATTTTATCCGTACTC
CTGATGATGCATGGTTACTCACCACTGCGATCCCCGGAAAAACAGCATTCCAGGTATTAG
AAGAATATCCTGATTCAGGTGAAAATATTGTTGATGCGCTGGCAGTGTTCCTGCGCCGGT
TGCATTCGATTCCTGTTTGTAATTGTCCTTTTAACAGCGATCGCGTATTTCGTCTCGCTC
AGGCGCAATCACGAATGAATAACGGTTTGGTTGATGCGAGTGATTTTGATGACGAGCGTA

ATGGCTGGCCTGTTGAACAAGTCTGGAAAGAAATGCATAAACTTTTGCCATTCTCACCGG
ATTCAGTCGTCACTCATGGTGATTTCTCACTTGATAACCTTATTTTTGACGAGGGGAAAT
TAATAGGTTGTATTGATGTTGGACGAGTCGGAATCGCAGACCGATACCAGGATCTTGCCA
TCCTATGGAACTGCCTCGGTGAGTTTTCTCCTTCATTACAGAAACGGCTTTTTCAAAAAT
ATGGTATTGATAATCCTGATATGAATAAATTGCAGTTTCATTTGATGCTCGATGAGTTTT
TCTAATCAGAATTGGTTAATTGGTTGTAACACTGGCAGAGCATTACGCTGACTTGACGGG
ACGGCGCAAGCTCATGACCAAAATCCCTTAACGTGAGTTACGCGTCGTTCCACTGAGAGT
CAGACCCCGTAGAAAAGATCAAAGGATCTTCTTGAGATCCTTTTTTTCTGCGCGTAATCT
GCTGCTTGCAAACAAAAAAACCACCGCTACCAGCGGTGGTTTGTTTGCCGGATCAAGAGC
TACCAACTCTTTTTCCGAAGGTAACTGGCTTCAGCAGAGCGCAGATACCAAATACTGTCC

TTCTAGTGTAGCCGTAGTTAGGCCACCACTTCAAGAACTCTGTAGCACCGCCTACATACC
TCGCTCTGCTAATCCTGTTACCAGTGGCTGCTGCCAGTGGCGATAAGTCGTGTCTTACCG
GGTTGGACTCAAGACGATAGTTACCGGATAAGGCGCAGCGGTCGGGCTGAACGGGGGGTT
CGTGCACACAGCCCAGCTTGGAGCGAACGACCTACACCGAACTGAGATACCTACAGCGTG
AGCATTGAGAAAGCGCCACGCTTCCCGAAGGGAGAAAGGCGGACAGGTATCCGGTAAGCG
GCAGGGTCGGAACAGGAGAGCGCACGAGGGAGCTTCCAGGGGGAAACGCCTGGTATCTTT
ATAGTCCTGTCGGGTTTCGCCACCTCTGACTTGAGCGTCGATTTTTGTGATGCTCGTCAG
GGGGGCGGAGCCTATGGAAAAACGCCAGCAACGCGGCCTTTTTACGGTTCCTGGCCTTTT
GCTGGCCTTTTGCTCACATGTT 3'
```

Appendix III

Sequence of *Arabidopsis thaliana* DGAT1 cDNA Open Reading Frame (Grey Box) Cloned into pRS12

```
5'TCGACATCTTGCTGCGTTCGGATATTTTCGTGGAGTTCCCGCCACAGACCCGGATTGA
AGGCGAGATCCAGCAACTCGCGCCAGATCATCCTGTGACGGAACTTTGGCGCGTGATGAC
TGGGCCAGGACGTCGGCCGAAAGAGCGACAAGCAGATCACATTTTCGACAGCGTCGGATT
TGCGATCGAGGATTTTTCGGCGCTGCGCTACGTCCGCGACCGCGTTGAGGGATCAAGCCA
CAGCAGCCCACTCGACCTTCTAGCCGACCCAGACGAGCCAAGGGATCTTTTTGGAATGCT
GCTCCGTCGTCAGGCTTTCCGACGTTTGGGTGGTTGAACAGAAGTCATTATCGTACGGAA
TGCCAGCACTCCCGAGGGGAACCCTGTGGTTGGCATGCACATACAAATGGACGAACGGAT
AAACCTTTTCACGCCCTTTTAAATATCCGTTATTCTAATAAACGCTCTTTTCTCTTAGGT
TTACCCGCCAATATATCCTGTCAAACACTGATAGTTTAAACTGAAGGCGGGAAACGACAA
TCTGATCATGAGCGGAGAATTAAGGGAGTCACGTTATGACCCCCGCCGATGACGCGGGAC

AAGCCGTTTTACGTTTGGAACTGACAGAACCGCAACGATTGAAGGAGCCACTCAGCCCCA
ATACGCAAACCGCCTCTCCCCGCGCGTTGGCCGATTCATTAATGCAGCTGGCACGACAGG
TTTCCCGACTGGAAAGCGGGCAGTGAGCGCAACGCAATTAATGTGAGTTAGCTCACTCAT
TAGGCACCCCAGGCTTTACACTTTATGCTTCCGGCTCGTATGTTGTGTGGAATTGTGAGC
GGATAACAATTTCACACAGGAAACAGCTATGACCATGATTACGCCAAGCTATTTAGGTGA
CACTATAGAATACTCAAGCTATGCATCCAACGCGTTGGGAGCTCTCCCATATCGACCTGC
AGGCGGCCGCTCGACGAATTAATTCCAATCCCACAAAAATCTGAGCTTAACAGCACAGTT
GCTCCTCTCAGAGCAGAATCGGGTATTCAACACCCTCATATCAACTACTACGTTGTGTAT
AACGGTCCACATGCCGGTATATACGATGACTGGGGTTGTACAAAGGCGGCAACAAACGGC
GTTCCCGGAGTTGCACACAAGAAATTTGCCACTATTACAGAGGCAAGAGCAGCAGCTGAC

GCGTACACAAGAAGTCAGCAAACAGACAGGTTGAACTTCATCCCCAAAGGAGAAGCTCAA
CTCAAGCCCAAGAGCTTTGCTAAGGCCCTAACAAGCCCACCAAAGCAAAAAGCCCACTGG
CTCACGCTAGGAACCAAAAGGCCCAGCAGTGATCCAGCCCCAAAAGAGATCTCCTTTGCC
CCGGAGATTACAATGGACGATTTCCTCTATCTTTACGATCTAGGAAGGAAGTTCGAAGGT
GAAGGTGACGACACTATGTTCACCACTGATAATGAGAAGGTTAGCCTCCTCAATTTCAGA
AAGAATGCTGACCCACAGATGGTTAGAGAGGCCTACGCAGCAGGTCTCATCAAGACGATC
TACCCGAGTAACAATCTCCAGGAGATCAAATACCTTCCCAAGAAGGTTAAAGATGCAGTC
AAAAGATTCAGGACTAATTGCATCAAGAACACAGAGAAAGACATATTTCTCAAGATCAGA
AGTACTATTCCAGTATGGACGATTCAAGGCTTGCTTCATAAACCAAGGCAAGTAATAGAG
```

-continued

```
ATTGGAGTCTCTAAAAAGGTAGTTCCTACTGAATCTAAGGCCATGCATGGAGTCTAAGAT
TCAAATCGAGGATCTAACAGAACTCGCCGTGAAGACTGGCGAACAGTTCATACAGAGTCT
TTTACGACTCAATGACAAGAAGAAAATCTTCGTCAACATGGTGGAGCACGACACTCTGGT
CTACTCCAAAAATGTCAAAGATACAGTCTCAGAAGACCAAAGGGCTATTGAGACTTTTCA
ACAAAGGATAATTTCGGGAAACCTCCTCGGATTCCATTGCCCAGCTATCTGTCACTTCAT
CGAAAGGACAGTAGAAAAGGAAGGTGGCTCCTACAAATGCCATCATTGCGATAAAGGAAA
GGCTATCATTCAAGATCTCTCTGCCGACAGTGGTCCCAAAGATGGACCCCCACCCACGAG
GAGCATCGTGGAAAAAGAAGACGTTCCAACCACGTCTTCAAAGCAAGTGGATTGATGTGA
CATCTCCACTGACGTAAGGGATGACGCACAATCCCACTATCCTTCGCAAGACCCTTCCTC
TATATAAGGAAGTTCATTTCATTTGGAGAGGACACGCTCGAGGAATTCCATGGTGAGCAA

GGGCCACGAGCTGTTCACCGGGGTGGTGCCCATCCTGGTCGAGCTGGACGGCGACGTAAA
CGGCCACAAGTTCAGCGTGTCCGGCGAGGGCGAGGGCGATGCCACCTACGGCCATCTGAC
CCTGAAGTTCATCTGCACCACCGGCAAGCTGCCCGTGCCCTGGCCCACCCTCGTGACCAC
CTTCACCTACGGCGTGCAGTGCTTCAGCCGCTACCCCGACCACATGAAGCAGCACGACTT
CTGCAAGTCCGCCATGCCCGAAGGCTACGTCCAGGAGCGCACCATCTTCTTCAAGGACGA
CGGCAACTACCAGACCCGCGCCGAGGTGAAGTTCGAGGGCGACACCCTGGTGAACCGCAT
CGAGCTGAAGGGCATCGACTTCAAGGAGGACGGCAACATCCTGGGGCACAAGCTGGAGTA
CAACTACAACAGCCACAACGTCTATATCATGGCCGACAAGCAGAAGAACGGCATCAAGGT
GAACTTCAAGATCCGCCACAACATCGAGGACGGCAGCGTGCAGCTCGCCGACCACTACCA
GCAGAACACGGGGGATCGGCGACGGCCCCGTGCTGCTGCCCGACAACCACTACCTGAGCAC

CCAGTCCGCCCTGAGCAAAGACCCCAACGAGAAGCGCGATCACATGGTCCTGCTGGAGTT
CGTGACCGCCGCCGGGATCACTCACGGCATGGACGAGCTGTACAAGTAAGATCGATCCTC
TAGAGTCCTGCTTTAATGAGATATGCGAGACGCCTATGATCGCATGATATTTGCTTTCAA
TTCTGTTGTGCACGTTGTAAAAAACCTGAGCATGTGTAGCTCAGATCCTTACCGCCGGTT
TCGGTTCATTCTAATGAATATATCACCCGTTACTATCGTATTTTTATGAATAATATTCTC
CGTTCAATTTACTGATTGTACCCTACTACTTATATGTACAATATTAAAATGAAAACAATA
TATTGTGCTGAATAGGTTTATAGCGACATCTATGATAGAGCGCCACAATAACAAACAATT
GCGTTTTATTATTACAAATCCAATTTTAAAAAAAGCGGCAGAACCGGTCAAACCTAAAAG
ACTGATTACATAAATCTTATTCAAATTTCAAAAGGCCCCAGGGGCTAGTATCTACGACAC
ACCGAGCGGCGAACTAATAACGTTCACTGAAGGGAACTCCGGTTCCCCGCGGGCGCGCAT
GGGTGAGATTCCTTGAAGTTGAGTATTGGCCGTCCGCTCTACCGAAAGTTACGGGCACCA
TTCAACCCGGTCCAGCACGGCGGCCGGGTAACCGACTTGCTGCCCCGAGAATTATGCAGC
ATTTTTTTGGTGTATGTGGGCCCCAAATGAAGTGCAGGTCAAACCTTGACAGTGACGACA
AATCGTTGGGCGGGTCCAGGGCGAATTTTGCGACGGCATGTCGAGGCTCAGCAGGACCTG

CAGGCATGCAAGCTAGCTTACTAGTGATGCATATTCTATAGTGTCACCTAAATCTGCGGC
CGCTCGACGAATTAATTCCAATCCCACAAAAATCTGAGCTTAACAGCACAGTTGCTCCTC
TCAGAGCAGAATCGGGTATTCAACACCCTCATATCAACTACTACGTTGTGTATAACGGTC
CACATGCCGGTATATACGATGACTGGGGTTGTACAAAGGCGGCAACAAACGGCGTTCCCG
GAGTTGCACACAAGAAATTTGCCACTATTACAGAGGCAAGAGCAGCAGCTGACGCGTACA
CAACAAGTCAGCAAACAGACAGGTTGAACTTCATCCCCAAAGGACAAGCTCAACTCAAGC
CCAAGAGCTTTGCTAAGGCCCTAACAAGCCCACCAAAGCAAAAAGCCCACTGGCTCACGC
TAGGAACCAAAAGGCCCAGCAGTGATCCAGCCCCAAAAGAGATCTCCTTTGCCCCGGAGA
TTACAATGGACGATTTCCTCTATCTTTACGATCTAGGAAGGAAGTTCGAAGGTGAAGGTG
ACGACACTATGTTCACCACTGATAATGAGAAGGTTAGCCTCTTCAATTTCAGAAAGAATG
CTGACCCACAGATGGTTAGAGAGGCCTACGCAGCAGGTCTCATCAAGACGATCTACCCGA

GTAACAATCTCCAGGAGATCAAATACCTTCCCAAGAAGGTTAAAGATGCAGTCAAAAGAT
TCAGGACTAATTGCATCAAGAACACAGAGAAAGACATATTTCTCAAGATCAGAAGTACTA
TTCCAGTATGGACGATTCAAGGCTTGCTTCATAAACCAAGGCAAGTAATAGAGATTGGAG
TCTCTAAAAAGGTAGTTCCTACTGAATCTAAGGCCATGCATGGAGTCTAAGATTCAAATC
GAGGATCTAACAGAACTCGCCGTGAAGACTGGCGAACAGTTCATACAGAGTCTTTTACGA
CTCAATGACAAGAAGAAAATCTTCGTCAACATGGTGGAGCACGACACTCTGGTCTACTCC
AAAAATGTCAAAGATACAGTCTCAGAAGACCAAAGGGCTATTGAGACTTTTCAACAAAGG
ATAATTTCGGGAAACCTCCTCGGATTCCATTGCCCAGCTATCTGTCACTTCATCGAAAGG
ACAGTAGAAAAGGAAGGTGGCTCCTACAAATGCCATCATTGCGATAAAGGAAAGGCTATC
ATTCAAGATCTCTCTGCCGACAGTCCTCCCAAAGATGGACCCCCACCCACGAGGAGCATC
GTGGAAAAAGAAGACGTTCCAACCACGTCTTCAAAGCAAGTGGATTGATGTGACATCTCC
ACTGACGTAAGGATGACGCACAATCCCACTATCCTTCGCAAGACCCTTCCTCTATATAA
GGAAGTTCATTTCATTTGGAGAGGACACGCTCGAGGAATTCGGTACCCCATCACAAGTTT

GTACAAAAAAGCAGGCTCCGCGGCCGCCCCCTTCACCATGGCGATTTTGGATTCTGCTGG
CGTTACTACGGTGACGGAGAACGGTGGCGGAGAGTTCGTCGATCTTGATAGGCTTCGTCG
ACGGAAATCGAGATCGGATTCTTCTAACGGACTTCTTCTCTCTGGTTCCCATAATAATTC
TCCTTCGGATGATGTTGGAGCTCCCGCCGACGTTAGGGATCGGATTGATTCCGTTGTTAA
CGATGACGCTCAGGGAACAGCCAATTTGGCCGGAGATAATAACGGTGGTGGCGATAATAA
CGGTGGTGGAAGAGGCGGCGGAGAAGGAAGAGGAAACGCCGATGCTACGTTTACGTATCG
ACCGTCGGTTCCAGCTCATCGGAGGGCGAGAGAGAGTCCACTTAGCTCCGACGCAATCTT
CAAACAGAGCCATGCCGGATTATTCAACCTCTGTGTAGTAGTTCTTATTGCTGTAAACAG
TAGACTCATCATCGAAAATCTTATGAAGTATCCTTCCTTGATCAGAACGGATTTCTGGTT
TAGTTCAAGATCGCTGCGAGATTGGCCGCTTTTCATGTGTTGTATATCCCTTTCGATCTT

TCCTTTGGCTGCCTTTACGGTTGAGAAATTGGTACTTCAGAAATACATATCAGAACCTGT
TGTCATCTTTCTTCATATTATTATCACCATGACAGAGGTTTTGTATCCAGTTTACGTCAC
CCTAAGGTGTGATTCTGCTTTTTTATCAGGTGTGACTTTGATGCTCCTCACTTGCATTGT
GTGGCTAAAGTTGGTTTCTTATGCTCATACTAGCTATGACATAAGATCCCTAGCCAATGC
AGCTGATAAGGCCAATCCTGAAGTCTCCTACTACGTTAGCTTGAAGAGCTTGGCATATTT
CATGGTCGCTCCCACATTGTGTTATCAGCCAAGTTATCCACGTTCTGCATGTATACGGAA
GGGTTGGGTGGCTCGTCAATTTGCAAAACTGGTCATATTCACCGGATTCATGGGATTTAT
AATAGAACAATATATAAATCCTATTGTCAGGAACTCAAAGCATCCTTTGAAAGGCGATCT
CTCATATGCTATTGAAAGAGTGTTGAAGCTTTCAGTTCCAAATTTATATGTGTGGCTCTG
CATGTTCTGCTGCTTCTTCCACCTTTGGTTAAACATATTGGCAGAGCTTCTCTGCTTCGG
```

-continued

```
GGATCGTGAATTCTACAAAGATTGGTGGAATGCAAAAAGTGTGGGAGATTACTGGAGAAT
GTGGAATATGCCTGTTCATAAATGGATGGTTCGACATATATACTTCCCGTGCTTGCGCAG
CAACATACCAAAGACACTCGCCATTATGATTGCTTTCCTAGTCTCTGCAGTCTTTCATGA
GCTATGCATCGGAGTTCCTTGTGGTCTCTTCAAGCTATGGGCTTTTCTTGGGATTATGTT
TCAGGTGCCTTTGGTCTTCATCACAAACTATCTACAGGAAAGGTTTGGCTCAACGGTGGG
GAACATGATCTTCTGGTTCATCTTCTGCATTTTCGGACAACCGATGTGTGTGCTTCTTTA
TTACCACGACCTGATGAACCCAAAAGGATCGATGTCATGAAAGGGTGGGCGCGCCGACCC
AGCTTTCTTGTACAAAGTGGTGATGGGTTCGAAATCGATAAGCTTGGATCCTCTAGAGTC
CTGCTTTAATGAGATATGCGAGACGCCTATGATCGCATGATATTTGCTTTCAATTCTGTT
GTGCACGTTGTAAAAACCTGAGCATGTGTAGCTCCAGATCCTTACCGCCGGTTTCGGTTC

ATTCTAATGAATATATCACCCGTTACTATCGTATTTTTATGAATAATATTCTCCGTTCAA
TTTACTGATTGTACCCTACTACTTATATGTACAATATTAAAATGAAAACAATATATTGTG
CTGAATAGGTTTATAGCGACATCTATGATAGAGCGCCACAATAACAAACAATTGCGTTTT
ATAATTACAAATCCAATTTTAAAAAAAGCGGCAGAACCGGTCAAACCTAAAAGACTGATT
ACATAAATCTTATTCAAATTTCAAAAGGCCCCAGGGGCTAGTATCTACGACACACCGAGC
GGCGAACTAATAACGTTCACTGAAGGGAACTCCGGTTCCCCGCCGGCGCGCATGGGTGAG
ATTCCTTGAAGTTGAGTATTGGCCGTCCGCTCTACCGAAAGTTACGGGCACCATTCAACC
CGGTCCAGCACGGCGGCCGGGTAACCGACTTGCTGCCCCGAGAATTATGCAGCATTTTTT
TCCTCTGTGTGGGCCCCAAATGAAGTGCAGGTCAAACCTTGACAGTGACGACAAATCGTT
GGGCGGGTCCAGGGCGAATTTTGCGACAACATGTCGAGGCTCAGCAGGACCTGCAGGCAT
GCAAGCTAGCTTACTAGTGATGCATATTCTATAGTGTCACCTAAATCTGCGGCCGCTGAC
CAAGTCAGCTTGGCACTGGCCGTCGTTTTACAACGTCGTGACTGGGAAAACCCTGGCGTT
ACCCAACTTAATCGCCTTGCAGCACATCCCCCTTTCGCCAGCTGGCGTAATAGCGAAGAG
GCCCGCACCGATCGCCCTTCCCAACAGTTTGCGAGCCTGAATGGCGAATGGGAAATTGTA

AACGTTAATATTTTGTTAATATTTTGTTAAAATTCGCGTTAAATTTTTGTTAAATCAGCT
CATTTTTTAACCAATAGGCCGAAATCGGCAAAATCCCTTATAAATCAAAAGAATAGACCG
AGATAGGGTTGAGTGTTGTTCCAGTTTGGAACAAGAGTCCACTATTAAAGAACGTGGACT
CCAACGTCAAAGGGCGAAAAACCGTCTATCAGGGCGATGGCCCACTACGTGAACCATCAC
CCTAATCAAGTTTTTTGGGGTCGAGGTGCCGTAAAGCACTAAATCGGAACCCTAAAGGGA
TGCCCCGATTTAGAGCTTGACGGGGAAAGCCGGCGAACGTGGCGAGAAAGGAAGGGAAGA
AAGCGAAAGGAGCGGGCGCTAGGGCGCTGGCAAGTGTAGCGGTCACGCTGCGCGTAACCA
CCACACCCGCCGCGCTTAATGCGCCGCTACAGGGCGCGTCAGGTGGCACTTTTCGGGGAA
ATGTGCGCGGAACCCCTATTTGTTTATTTTTCTAAATACATTCAAATATGTATCCGCTCA
TGAGACAATAACCCTGATAAATGCTTCAATAATATTGAAAAAGGAAGAGTATGAGTATTC
AACATTTCCGTGTCGCCCTTATTCCCTTTTTTGCGGCATTTTGCCTTCCTGTTTTTGCTC

ACCCAGAAACGCTGGTGAAAGTAAAAGATGCTGAAGATCAGTTGGGTGCACGAGTGGGTT
ACATCGAACTGGATCTCAACAGCGGTAAGATCCTTGAGAGTTTTCGCCCCGAAGAACGTT
TTCCAATGATGAGCACTTTTAAAGTTCTGCTATGTGGCGCGGTATTATCCCGTATTGACG
CCGGGCAAGAGCAACTCGGTCGCCGCATACACTATTCTCAGAATGACTTGGTTGAGTACT
CACCAGTCACAGAAAAGCATCTTACGGATGGCATGACAGTAAGAGAATTATGCAGTGCTG
CCATAACCATGAGTGATAACACTGCGGCCAACTTACTTCTGACAACGACTGGAGGACCGA
AGGAGCTAACCGCTTTTTTGCACAACATGGGGGATCATGTAACTCGCCTTGATCGTTGGG
AACCGGAGCTGAATGAAGCCATACCAAACGACGAGCGTGACACCACGATGCCTGTAGCAA
TGGCAACAACGTTGCGCAAACTATTAACTGGCGAACTACTTACTCTAGCTTCCCGGCAAC
AATTAATAGACTGGATGGAGGCGGATAAAGTTGCAGGACCACTTCTGCGCTCGGCCCTTC

CGGCTGGCTGGTTTATTGCTGATAAATCTGGAGCCGGTGAGCGTGGGTCTCGCGGTATCA
TTGCAGCACTGGGGCCAGATGGTAAGCCCTCCCGTATCGTAGTTATCTACACGACGGGGA
GTCAGGCAACTATGGATGAACGAAATAGACAGATCGCTGAGATAGGTGCCTCACTGATTA
AGCATTGGTAACTGTCAGACCAAGTTTACTCATATATACTTTAGATTGATTTAAAACTTC
ATTTTTAATTTAAAAGGATCTAGGTGAAGATCCTTTTTGATAATCTCATGACCAAAATCC
CTTAACGTGAGTTTTCGTTCCACTGAGCGTCAGACCCCGTCGAAAAGATCAAAGGATCTT
CTTGAGATCCTTTTTTTCTGCGCGTAATCTGCTGCTTGCAAACAAAAAAACCACCGCTAC
CAGCGGTGGTTTGTTTGCCGGATCAAGAGCTACCAACTCTTTTTCCGAAGGTAACTGGCT
TCAGCAGAGCGCAGATACCAAATACTGTCCTTCTAGTGTAGCCGTAGTTAGGCCACCACT
TCAAGAACTCTGTAGCACCGCCTACATACCTCGCTCTGCTAATCCTGTTACCAGTGGCTG
CTGCCAGTGGCGATAAGTCGTGTCTTACCGGGTTGGACTCAAGACGATAGTTACCGGATA
AGGCGCAGCGGTCGGGCTGAACGGGGGGTTCGTGCACACAGCCCAGCTTGGAGCGAACGA
CCTACACCGAACTGAGATACCTACAGCGTGAGCTATGAGAAAGCGCCACGCTTCCCGAAG

GGAGAAAGGCGGACAGGTATCCGGTAAGCGGCAGGGTCGGAACAGGAGAGCGCACGAGGG
AGCTTCCAGGGGGAAACGCCTGGTATCTTTATAGTCCTGTCGGGTTTCGCCACCTCTGAC
TTGAGCGTCGATTTTTGTGATGCTCGTCAGGGGGGCGGAGCCTATGGAAAAACGCCAGCA
ACGCGGCCTTTTTACGGTTCCTGGCCTTTTGCTGGCCTTTTGCTCACATGTTCTTTCCTG
CGTTATCCCCTGATTCTGTGGATAACCGTATTACCGCCTTTGAGTGAGCTGATACCGCTC
GCCGCAGCCGAACGACCGAGCGCAGCGAGTCAGTGAGCGAGGAAGCGGAAGAGCGCCCAA
TACGCAAACCGCCTCTCCCCGCGCGTTGGCCGATTCATTAATGCAGCTGGCACGACAGGT
TTCCCGACTGGAAAGCGGGCAGTGAGCGCAACGCAATTAATGTGAGTTAGCTCACTCATT
AGGCACCCCAGGCTTTACACTTTATGCTTCCGGCTCGTATGTTGTGTGGAATTGTGAGCG
GATAACAATTTCACACAGGAAACAGCTATGACCATGATTACGAATTTGGCCAAGTCGGCC

TCTAATACGACTCACTATAGGAGCTCGTCGAGCGGCCGCACTAGTGATATCCCGCGGGCC
ATGGCGGCCGGGAGCATGCGACGTCGGGCCCAATTCGCCCTATAGTGAGTCGTATTACAA
TTCACTGGCCGTCGTTTTACAACGTCGTGACTGGGAAAACCCTGGCGTTACCCAACTTAA
TCGCCTTGCAGCACATCCCCCTTTCGCCAGCTGGCGTAATAGCGAAGAGGCCCGCACCGA
TCGCCCTTCCCAACAGTTGCGCAGCCTGAATGGCGAATGGAAATTGTAAACGTTAATGGG
TTTCTGGAGTTTAATGAGCTAAGCACATACGTCAGAAACCATTATTGCGCGTTCAAAAGT
CGCCTAAGGTCACTATCAGCTAGCAAATATTTCTTGTCAAAAATGCTCCACTGACGTTCC
ATAAATTCCCCTCGGTATCCAATTAGAGTCTCATATTCACTCTCAATCCAAATAATCTGC
AATGGCAATTACCTTATCCGCAACTTCTTTACCTATTTCCGCCCGGATCCGGGCAGGTTC
TCCGGCCGCTTGGGTGGAGAGGCTATTCGGCTATGACTGGGCACAACAGACAATCGGCTG
CTCTGATGCCGCCGTGTTCCGGCTGTCAGCGCAGGGGCGCCCGGTTCTTTTTGTCAAGAC
```

-continued

CGACCTGTCCGGTGCCCTGAATGAACTGCAGGACGAGGCAGCGCGGCTATCGTGGCTGGC
CACGACGGGCGTTCCTTGCGCAGCTGTGCTCGACGTTGTCACTGAAGCGGGAAGGGACTG
GCTGCTATTGGGCGAAGTGCCGGGGCAGGATCTCCTGTCATCTCACCTTGCTCCTGCCGA
GAAAGTATCCATCATGGCTGATGCAATGCGGCGGCTGCATACGCTTGATCCGGCTACCTG
CCCATTCGACCACCAAGCGAAACATCGCATCGAGCGAGCACGTACTCGGATGGAAGCCGG
TCTTGTCGATCAGGATGATCTGGACGAAGAGCATCAGGGGCTCGCGCCAGCCGAACTGTT
CGCCAGGCTCAAGGCGCGCATGCCCGACGGCGAGGATCTCGTCGTGACCCATGGCGATGC
CTGCTTGCCGAATATCATGGTGGAAAATGGCCGCTTTTCTGGATTCATCGACTGTGGCCG
GCTGGGTGTGGCGGACCGCTATCAGGACATAGCGTTGGCTACCCGTGATATTGCTGAAGA
GCTTGGCGGCGAATGGGCTGACCGCTTCCTCGTGCTTTACGGTATCGCCGCTCCCGATTC
GCAGCGCATCGCCTTCTATCGCCTTCTTGACGAGTTCTTCTGAGCGGGACTCTGGGGTTC
GAAATGACCGACCAAGCGACGCCCAACCTGCCATCACGAGATTTCGATTCCACCGCCGCC
TTCTATGAAAGGTTGGGCTTCGGAATCGTTTTCCGGGACGCCGGCTGGATGATCCTCCAG

CGCGGGGATCTCATGCTGGAGTTCTTCGCCCACCCCGATCCAACACTTACGTTTGCAACG
TCCAAGAGCAAATAGACCACGAACGCCGGAAGGTTGCCGCAGCGTGTGGATTGCGTCTCA
ATTCTCTCTTGCAGGAATGCAATGATGAATATGATACTGACTATGAAACTTTGAGGGAAT
ACTGCCTAGCACCGTCACCTCATAACGTGCATCATGCATGCCCTGACAACATGGAACATC
GCTATTTTTCTGAAGAATTATGCTCGTTGGAGGATGTCGCGGCAATTGCAGCTATTGCCA
ACATCGAACTACCCCTCACGCATGCATTCATCAATATTATTCATGCGGGGAAAGGCAAGA
TTAATCCAACTGGCAAATCATCCAGCGTGATTGGTAACTTCAGTTCCAGCGACTTGATTC
GTTTTGGTGCTACCCACGTTTTCAATAAGGACGAGATGGTGGAGTAAAGAAGGAGTGCGT
CGAAGCAGATCGTTCAAACATTTGGCAATAAAGTTTCTTAAGATTGAATCCTGTTGCCGG
TCTTGCGATGATTATCATATAATTTCTGTTGAATTACGTTAAGCATGTAATAATTAACAT
GTAATGCATGACGTTATTTATGAGATGGGTTTTTATGATTAGAGTCCCGCAATTATACAT

TTAATACGCGATAGAAAACAAAATATAGCGCGCAAACTGGGATAAATTATCGCGCGCGGT
GTCATCTATGTTACTAGATCGAATTAATTCAGTACATTAAAAACGTCCGCAATGTGTTAT
TAAGTTGTCTAAGCGTCAATTTGTTTACACCACAATATATCCTGCCACCAGCCAGCCAAC
AGCTCCCCGACCGGCAGCTCGGCACAAAATCACCACTCGATACAGGCAGCCCATCAGTCC
GGGACGGCGTCAGCGGGAGAGCCGTTGTAAGGCGGCAGACTTTGCTCATGTTACCGATGC
TATTCGGAAGAACGGCAACTAAGCTGCCGGGTTTGAAACACGGATGATCTCGCGGAGGGT
AGCATGTTGATTGTAACGATGACAGAGCGTTGCTGCCTGTGATCAAATATCATCTCCCTC
GCAGAGATCCGAATTATCAGCCTTCTTATTCATTTCTCGCTTAACCGTGACAGGCTGTCG
ATCTTGAGAACTATGCCGACATAATAGGAAATCGCTGGATAAAGCCGCTGAGGAAGCTGA
GTGGCGCTATTTCTTTAGAAGTGAACGTTGACGATGTCGACGGATCTTTTCCGCTGCATA
ACCCTGCTTCGGGGTCATTATAGCGATTTTTTCGGTATATCCATCCTTTTTCGCACGATA

TACAGGATTTTGCCAAAGGGTTCGTGTAGACTTTCCTTGGTGTATCCAACGGCGTCAGCC
GGGCAGGATAGGTGAAGTAGGCCCACCCGCGAGCGGGTGTTCCTTCTTCACTGTCCCTTA
TTCGCACCTGGCGGTGCTCAACGGGAATCCTGCTCTGCGAGGCTGGCCGGCTACCGCCGG
CGTAACAGATGAGGGCAAGCGGATGGCTGATGAAACCAAGCCAACCAGGGGTGATGCTGC
CAACTTACTGATTTAGTGTATGATGGTGTTTTTGAGGTGCTCCAGTGGCTTCTGTTTCTA
TCAGCTGTCCCTCCTGTTCAGCTACTGACGGGGTGGTGCGTAACGGCAAAAGCACCGCCG
GACATCAGCGCTATCTCTGCTCTCACTGCCGTAAAACATGGCAACTGCAGTTCACTTACA
CCGCTTCTCAACCCGGTACGCACCAGAAAATCATTGATATGGCCATGAATGGCGTTGGAT
GCCGGGCAACAGCCCGCATTATGGGCGTTGGCCTCAACACGATTTTACGTCACTTAAAAA
ACTCAGGCCGCAGTCGGTAACCTCGCGCATACAGCCGGGCAGTGACGTCATCGTCTGCGC
GGAAATGGACGAACAGTGGGGCTATGTCGGGGCTAAATCGCGCCAGCGCTGGCTGTTTTA
CGCGTATGACAGTCTCCGGAAGACGGTTGTTGCGCACGTATTCGGTGAACGCACTATGGC

GACGCTGGGGCGTCTTATGAGCCTGCTGTCACCCTTTGACGTGGTGATATGGATGACGGA
TGGCTGGCCGCTGTATGAATCCCGCCTGAAGGGAAAGCTGCACGTAATCAGCAAGCGATA
TACGCAGCGAATTGAGCGGCATAACCTGAATCTGAGGCAGCAGGTGGCACGGCTGGGACG
GAAGTCGCTGTCGTTCTCAAAATCGGTGGAGCTGCATGACAAAGTCATCGGGCATTATCT
GAACATAAAACACTATCAATAAGTTGGAGTCATTACCCAACCAGGAAGGGCAGCCCACCT
ATCAAGGTGTACTGCCTTCCAGACGAACGAAGAGCGATTGAGGAAAAGGCGGCGGCGGCC
GGCATGAGCCTGTCGGCCTACCTGCTGGCCGTCGGCCAGGGCTACAAAATCACGGGCGTC
GTGGACTATGAGCACGTCCGCGAGCTGGCCCGCATCAATGGCGACCTGGGCCGCCTGGGC
GGCCTGCTGAAACTCTGGCTCACCGACGACCCGCGCACGGCGCGGTTCGGTGATGCCACG
ATCCTCGCCCTGCTGGCGAAGATCGAAGAGAAGCAGGACGAGCTTGGCAAGGTCATGATG
GGCGTGGTCCGCCCGAGGGCAGAGCCATGACTTTTTTAGCCGCTAAAACGGCCGGGGGGT

GCGCGTGATTGCCAAGCACGTCCCCATGCGCTCCATCAAGAAGAGCGACTTCGCGGAGCT
GGTATTCGTGCAGGGCAAGATTCGGAATACCAAGTACGAGAAGGACGGCCAGACGGTCTA
CGGGACCGACTTCATTGCCGATAAGGTGGATTATCTGGACACCAAGGCACCAGGCGGGTC
AAATCAGGAATAAGGGCACATTGCCCCGGCGTGAGTCGGGGCAATCCCGCAAGGAGGGTG
AATGAATCGGACGTTTGACCGGAAGGCATACAGGCAAGAACTGATCGACGCGGGGTTTTC
CGCCGAGGATGCCGAAACCATCGCAAGCCGCACCGTCATGCGTGCGCCCCGCGAAACCTT
CCAGTCCGTCGGCTCGATGGTCCAGCAAGCTACGGCCAAGATCGAGCGCGACAGCGTGCA
ACTGGCTCCCCCTGCCCTGCCCGCGCCATCGGCCGCCGTGGAGCGTTCGCGTCGTCTCGA
ACAGGAGGCGGCAGGTTTGGCGAAGTCGATGACCATCGACACGCGAGGAACTATGACGAC
CAAGAAGCGAAAAACCGCCGGCGAGGACCTGGCAAAACAGGTCAGCGAGGCCAAGCAGGC
CGCGTTGCTGAAACACACGAAGCAGCAGATCAAGGAAATGCAGCTTTCCTTGTTCGATAT

TGCGCCGTGGCCGGACACGATGCGAGCGATGCCAAACGACACGGCCCGCTCTGCCCTGTT
CACCACGCGCAACAAGAAAATCCCGCGCGAGGCGCTGCAAAACAAGGTCATTTTCCACGT
CAACAAGGACGTCAAGATCACCTACACCGGCGTCGAGCTGCGGGCCGACGATGACGAACT
GGTGTGGCAGCAGGTGTTGGAGTACGCGAAGCGCACCCCTATCGGCGAGCCGATCACCTT
CACGTTCTACGAGCTTTGCCAGGACCTGGGCTGGTCGATCAATGGCCGGTATTACACGAA
GGCCGAGGAATGCCTGTCGCGCCTACAGGCGACGGCGATGGGCTTCACGTCCGACCGCGT
TGGGCACCTGGAATCGGTGTCGCTGCTGCACCGCTTCCGCGTCCTGGACCGTGGCAAGAA
AACGTCCCGTTGCCAGGTCCTGATCGACGAGGAAATCGTCGTGCTGTTTGCTGGCGACCA
CTACACGAAATTCATATGGGAGAAGTACCGCAAGCTGTCGCCGACGGCCCGACGGATGTT
CGACTATTTCAGCTCGCACCGGGAGCCGTACCCGCTCAAGCTGGAAACCTTCCGCCTCAT
GTGCGGATCGGATTCCACCCGCGTGAAGAAGTGGCGCGAGCAGGTCGGCGAAGCCTGCGA
AGAGTTGCGAGGCAGCGGCCTGGTGGAACACGCCTGGGTCAATGATGACCTGGTGCATTG

-continued

```
CAAACGCTAGGGCCTTGTGGGGTCAGTTCCGGCTGGGGGTTCAGCAGCCAGCGCTTTACT
GGCATTTCAGGAACAAGCGGGCACTGCTCGACGCACTTGCTTCGCTCAGTATCGCTCGGG
ACGCACGGCGCGCTCTACGAACTGCCGATAAACAGAGGATTAAAATTGACAATTGTGATT
AAGGCTCAGATTCGACGGCTTGGAGCGGCCGACGTGCAGGATTTCCGCGAGATCCGATTG
TCGGCCCTGAAGAAAGCTCCAGAGATGTTCGGGTCCGTTTACGAGCACGAGGAGAAAAAG
CCCATGGAGGCGTTCGCTGAACGGTTGCGAGATGCCGTGGCATTCGGCGCCTACATCGAC
GGCGAGATCATTGGGCTGTCGGTCTTCAAACAGGAGGACGGCCCCAAGGACGCTCACAAG
GCGCATCTGTCCGGCGTTTTCGTGGAGCCCGAACAGCGAGGCCGAGGGGTCGCCGGTATG
CTGCTGCGGGCGTTGCCGGCGGGTTTATTGCTCGTGATGATCGTCCGACAGATTCCAACG
GGAATCTGGTGGATGCGCATCTTCATCCTCGGCGCACTTAATATTTCGCTATTCTGGAGC
TTGTTGTTTATTTCGGTCTACCGCCTGCCGGGCGGGGTCGCGGCGACGGTAGGCGCTGTG

CAGCCGCTGATGGTCGTGTTCATCTCTGCCGCTCTGCTAGGTAGCCCGATACGATTGATG
GCGGTCCTGGGGGCTATTTGCGGAACTGCGGGCGTGGCGCTGTTGGTGTTGACACCAAAC
GCAGCGCTAGATCCTGTCGGCGTCGCAGCGGGCCTGGCGGGGGCGGTTTCCATGGCGTTC
GGAACCGTGCTGACCCGCAAGTGGCAACCTCCCGTGCCTCTGCTCACCTTTACCGCCTGG
CAACTGGCGGCCGGAGGACTTCTGCTCGTTCCAGTAGCTTTAGTGTTTGATCCGCCAATC
CCGATGCCTACAGGAACCAATGTTCTCGGCCTGGCGTGGCTCGGCCTGATCGGAGCGGGT
TTAACCTACTTCCTTTGGTTCCGGGGGATCTCGCGACTCGAACCTACAGTTGTTTCCTTA
CTGGGCTTTCTCAGCCGGGATGGCGCTAAGAAGCTATTGCCGCCGATCTTCATATGCGGT
GTGAAATACCGCACAGATGCGTAAGGAGAAAATACCGCATCAGGCGCTCTTCCGCTTCCT
CGCTCACTGACTCGCTGCGCTCGGTCGTTCGGCTGCGGCGAGCGGTATCAGCTCACTCAA

AGGCGGTAATACGGTTATCCACAGAATCAGGGGATAACGCAGGAAAGAACATGTGAGCAA
AAGGCCAGCAAAAGGCCAGGAACCGTAAAAAGGCCGCGTTGCTGGCGTTTTTCCATAGGC
TCCGCCCCCCTGACGAGCATCACAAAAATCGACGCTCAAGTCAGAGGTGGCGAAACCCGA
CAGGACTATAAAGATACCAGGCGTTTCCCCCTGGAAGCTCCCTCGTGCGCTCTCCTGTTC
CGACCCTGCCGCTTACCGGATACCTGTCCGCCTTTCTCCCTTCGGGAAGCGTGGCGCTTT
CTCAATGCTCACGCTGTAGGTATCTCAGTTCGGTGTAGGTCGTTCGCTCCAAGCTGGGCT
GTGTGCACGAACCCCCCGTTCAGCCCGACCGCTGCGCCTTATCCGGTAACTATCGTCTTG
AGTCCAACCCGGTAAGACACGACTTATCGCCACTGGCAGCAGCCACTGGTAACAGGATTA
GCAGAGCGAGGTATGTAGGCGGTGCTACAGAGTTCTTGAAGTGGTGGCCTAACTACGGCT
ACACTAGAAGGACAGTATTTGGTATCTGCGCTCTGCTGAAGCCAGTTACCTTCGGAAAAA
GAGTTGGTAGCTCTTGATCCGGCAAACAAACCACCGCTGGTAGCGGTGGTTTTTTTGTTT
GCAAGCAGCAGATTACGCGCAGAAAAAAAGGATATCAAGAAGATCCTTTGATCTTTTCTA
CGGGGTCTGACGCTCAGTGGAACGAAAACTCACGTTAGGGATTTTGGTCATGAGATTAT

CAAAAAGGATCTTCACCTAGATCCTTTTAAATTAAAAATGAAGTTTTAAATCAATCTAAA
GTATATATGAGTAAACTTGGTCTGACAGTTACCAATGCTTAATCAGTGAGGCACCTATCT
CAGCGATCTGTCTATTTCGTTCATCCATAGTTGCCTGACTCCCCGTCGTGTAGATAACTA
CGATACGGGAGGGCTTACCATCTGGCCCCAGTGCTGCAATGATACCGCGAGACCCACGCT
CACCGGCTCCAGATTTATCAGCAATAAACCAGCCAGCCGGAAGGGCCGAGCGCAGAAGTG
GTCCTGCAACTTTATCCGCCTCCATCCAGTCTATTAAACAAGTGGCAGCAACGGATTCGC
AAACCTGTCACGCCTTTTGTGCCAAAAGCCGCGCCAGGTTTGCGATCCGCTGTGCCAGGC
GTTAGGCGTCATATGAAGATTTCGGTGATCCCTGAGCAGGTGGCGGAAACATTGGATGCT
GAGAACCATTTCATTGTTCGTGAAGTGTTCGATGTGCAGGTATCCGACCAAGGCTTTGAA
CTATCTGCCAGAAGTGTGAGCCCCTACCGGAAGGATTACATCTCGGATGATGACTCTGAT
GAAGACTCTGCTTGCTATGGCGCATTCATCGACCAAGAGCTTGTCGGGAAGATTGAACTC

AACTCAACATGGAACGATCTAGCCTCTATCGAACACATTGTTGTGTCGCACACGCACCGA
GGCAAAGGAGTCGCGCACAGTCTCATCGAATTTGCGAAAAAGTGGGCACTAAGCAGACAG
CTCCTTGGCATACGATTAGAGACACAAACGAACAATGTACCTGCCTGCAATTTGTACGCA
AAATGTGGCTTTACTCTCGGCGGCATTGACCTGTTCACGTATAAAACTAGACCTCAAGTC
TCGAACGAAACAGCGATGTACTGGTACTGGTTCTCGGGAGCACAGGATGACGCCTAACAA
TTCATTCAAGCCGACACCGCTTCGCGGCGCGGCTTAATTCAGGAGTTAAACATCATGAGG
GAAGCGGTGATCGCCGAAGTATCGACTCAACTATCAGAGGTAGTTGGCGTCATCGAGCGC
CATCTCGAACCGACGTTGCTGGCCGTACATTTGTACGGCTCCGCAGTGGATGGCGGCCTG
AAGCCAGAGAGTGATATTGATTTGCTGGTTACGGTGACCGTAAGGCTTGATGAAACAACG
CGGCGAGCTTTGATCAACGACCTTTTGGAAACTTCGGCTTCCCCTGGAGAGAGCGAGATT
CTCCGCGCTGTAGAAGTCACCATTGTTCTGCACGACGACATCATTCCGTGGCGTTATCCA

GCTAAGCGCGAACTGCAATTTGGAGAATGGCAGCGCAATGACATTCTTGCAGGTATCTTC
GAGCCAGCCACGATCGACATTGATCTGGCTATCTTGCTGACAAAAGCAAGAGAACATAGC
GTTGCCTTGGTAGGTCCAGCGGCGGAGGAACTCTTTGATCCGGTTCCTGAACAGGATCTA
TTTGAGGCGCTAAATGAAACCTTAACGCTATGGAACTCGCCGCCCGACTGGGCTGGCGAT
GAGCGAAATGTAGTGCTTACGTTGTCCCGCATTTGGTACAGCGCAGTAACCGGCAAAATC
GCGCCGAAGGATGTCGCTGCCGACTGGGCAATGGAGCGCCTGCCGGCCCAGTATCAGCCC
GTCATACTTGAAGCTAGGCAGGCTTATCTTGGACAAGAAGATCGCTTGGCCTCGCGCGCA
GATCAGTTGGAAGAATTTGTTCACTACGTGAAAGGCGAGATCACCAAGGTAGTCGGCAAA
TAATGTCTAACAATTCGTTCAAGCCGACGCCGCTTCGCGGCGCGGCTTAACTCAAGCGTT
AGAGAGCTGGGGAAGACTATGCGCGATCTGTTGAAGGTGGTTCTAAGCCTCGTACTTGCG
ATGGCATCGGGGCAGGCACTTGCTGACCTGCCAATTGTTTTAGTGGATGAAGCTCGTCTT
CCCTATGACTACTCCCCATCCAACTACGACATTTCTCCAAGCAACTACGACAACTCCATA

AGCAATTACGACAATAGTCCATCAAATTACGACAACTCTGAGAGCAACTACGATAATAGT
TCATCCAATTACGACAATAGTCGCAACGGAAATCGTAGGCTTATATATAGCGCAAATGGG
TCTCGCACTTTCGCCGGCTACTACGTCATTGCCAACAATGGGACAACGAACTTCTTTTCC
ACATCTGGCAAAAGGATGTTCTACACCCCAAAAGGGGGGCGCGGCGTCTATGGCGGCAAA
GATGGGAGCTTCTGCGGGGCATTGGTCGTCATAAATGGCCAATTTTCGCTTGCCCTGACA
GATAACGGCCTGAAGATCATGTATCTAAGCAACTAGCCTGCTCTCTAATAAAATGTTAGG
AGCTTGGCTGCCATTTTTGGGGTGAGGCCGTTCGCGGCCGAGGGGCGCAGCCCCTGGGGG
GATGGGAGGCCCGCGTTAGCGGGCCGGGAGGGTTCGAGAAGGGGGGGCAGGGGGGTTCGG
CGTGCGCGGTCACGCGCCAGGGCGCAGCCCTGGTTAAAAACAAGGTTTATAAATATTGGT
TTAAAAGCAGGTTAAAAGACAGGTTAGCGGTGGCCGAAAAACGGGCGGAAACCCTTGCAA

ATGCTGGATTTTCTGCCTGTGGACAGCCCCTCAAATGTCAATAGGTGCGCCCCTCATCTG
TCAGCACTCTGCCCCTCAAGTGTCAAGGATCGCGCCCCTCATCTGTCAGTAGTCGCGCCC
CTCAAGTGTCAATACCGCAGGGCACTTATCCCCAGGCTTGTCCACATCATCTGTGGGAAA
CTCGCGTAAAATCAGGCGTTTTCGCCGATTTGCGAGGCTGGCCAGCTCCACGTCGCCGGC
CGAAATCGAGCCTGCCCCTCATCTGTCAACGCCGCGCCGGGTCAGTCGGCCCCTCAAGTG
TCAACGTCCGCCCCTCATCTGTCAGTGAGGGCCAAGTTTTCCGCGAGGTATCCACAACGC
CGGCGGCCGGCCGCGGTGTCTCGCACACGGCTTCGACGGCGTTTCTGGCGCGTTTGCAGG
GCCATAGACGGCCGCCAGCCCAGCGGCGAGGGCAACCAGCCCGGTGAGCGTCGGAAAGGG
3'
```

Appendix IV

Sequence of *Arabidopsis thaliana* DGAT1 Transcribed Genomic Region (Grey Box) Cloned into pRS12

```
5'TCGACATCTTGCTGCGTTCGGATATTTTCGTGGAGTTCCCGCCACAGACCCGGATTGA
AGGCGAGATCCAGCAACTCGCGCCAGATCATCCTGTGACGGAACTTTGGCGCGTGATGAC
TGGCCAGGACGTCGGCCGAAAGAGCGACAAGCAGATCACGATTTTCGACAGCGTCGGATT
TGCGATCGAGGATTTTTCGGCGCTGCGCTACGTCCGCGACCGCGTTGAGGGATCAAGCCA
CAGCAGCCCACTCGACCTTCTAGCCGACCCAGACGAGCCAAGGGATCTTTTTGGAATGCT
GCTCCGTCGTCAGGCTTTCCGACGTTTGGGTGGTTGAACAGAAGTCATTATCGTACGGAA
TGCCAGCACTCCCGAGGGGAACCCTGTGGTTGGCATGCACATACAAATGGACGAACGGAT
AAACCTTTTCACGCCCTTTTAAATATCCGTTATTCTAATAAACGCTCTTTTCTCTTAGGT
TTACCCGCCAATATATCCTGTCAAACACTGATAGTTTAAACTGAAGGCGGGAAACGACAA
TCTGATCATGAGCGGAGAATTAAGGGAGTCACGTTATGACCCCCGCCGATGACGCGGGAC
AAGCCGTTTTACGTTTGGAACTGACAGAACCGCAACGATTGAAGGAGCCACTCAGCCCCA

ATACGCAAACCGCCTCTCCCCGCGCGTTGGCCGATTCATTAATGCAGCTGGCACGACAGG
TTTCCCGACTGGAAAGCGGGCAGTGAGCGCAACGCAATTAATGTGAGTTAGCTCACTCAT
TAGGCACCCCAGGCTTTACACTTTATGCTTCCGGCTCGTATGTTGTGTGGAATTGTGAGC
GGATAACAATTTCACACAGGAAACAGCTATGACCATGATTACGCCAAGCTATTTAGGTGA
CACTATAGAATACTCAAGCTATGCATCCAACGCGTTGGGAGCTCTCCCATATCGACCTGC
AGGCGGCCGCTCGACGAATTAATTCCAATCCCACAAAAATCTGAGCTTAACAGCACAGTT
GCTCCTCTCAGAGCAGAATCGGGTATTCAACAGGGTCATATCAACTACTACGTTGTGTAT
AACGGTCCACATGCCGGTATATACGATGACTGGGGTTGTACAAAGGCGGCAACAAACGGC
GTTCCCGGAGTTGCACACAAGAAATTTGCCACTATTACAGAGGCAAGAGCAGCAGCTGAC
GCGTACACAACAAGTCAGCAAACAGACAGGTTGAACTTCATCCCCAAAGGAGAAGCTCAA

CTCAAGCCCAAGAGCTTTGCTAAGGCCCTAACAAGCCCACCAAAGCAAAAAGCCCACTGG
CTCACGCTAGGAACCAAAAGGCCCAGCAGTGATCCAGCCCCAAAAGAGATCTCCTTTGCC
CCGGAGATTACAATGGACGATTTCCTCTATCTTTACGATCTAGGAAGGAAGTTCGAAGGT
GAAGGTGACGACACTATGTTCACCACTGATAATGAGAAGGTTAGCCTCTTCAATTTCAGA
AAGAATGCTGACCCACAGATGGTTAGAGAGGCCTACGCAGCAGGTCTCATCAAGACGATC
TACCCGAGTAACAATCTCCAGGAGATCAAATACCTTCCCAAGAAGGTTAAAGATGCAGTC
AAAAGATTCAGGACTAATTGCATCAAGAACACAGAGAAAGACATATTTCTCAAGATCAGA
AGTACTATTCCAGTATGGACGATTCAAGGCTTGCTTCATAAACCAAGGCAAGTAATAGAG

ATTGGAGTCTCTAAAAAGGTAGTTCCTACTGAATCTAAGGCCATGCATGGAGTCTAAGAT
TCAAATCGAGGATCTAACAGAACTCGCCGTGAAGACTGGCGAACAGTTCATACAGAGTCT
TTTACGACTCAATGACAAGAAGAAAATCTTCGTCAACATGGTGGAGCACGACACTCTGGT
CTACTCCAAAAATGTCAAAGATACAGTCTCAGAAGACCAAAGGGCTATTGAGACTTTTCA
ACAAAGGATAATTTCGGGAAACCTCCTCGGATTCCATTGCCCAGCTATCTGTCACTTCAT
CGAAAGGACAGTAGAAAAGGAAGGTGGCTCCTACAAATGCCATCATTGCGATAAAGGAAA
GGCTATCATTCAAGATCTCTCTGCCGACAGTGGTCCCAAAGATGGACCCCCACCCACGAG
GAGCATCGTGGAAAAAGAAGACGTTCCAACCACGTCTTCAAAGCAAGTGGATTGATGTGA
CATCTCCACTGACGTAAGGGATGACGCACAATCCCACTATCCTTCGCAAGACCCTTCCTC
TATATAAGGAAGTTCATTTCATTTGGAGAGGACACGCTCGAGGAATTCCATGGTGAGCAA
GGGCCACGAGCTGTTCACCGGGGTGGTGCCCATCCTGGTCGAGCTGGACGGCGACGTAAA

CGGCCACAAGTTCAGCGTGTCCGGCGAGGGCGAGGGCGATGCCACCTACGGCCATCTGAC
CCTGAAGTTCATCTGCACCACCGGCAAGCTGCCCGTGCCCTGGCCCACCCTCGTGACCAC
CTTCACCTACGGCGTGCAGTGCTTCAGCCGCTACCCCGACCACATGAAGCAGCACGACTT
CTGCAAGTCCGCCATGCCCGAAGGCTACGTCCAGGAGCGCACCATCTTCTTCAAGGACGA
CGGCAACTACAAGACCCGCGCCGAGGTGAAGTTCGAGGGCGACACCCTGGTGAACCGCAT
CGAGCTGAAGGGCATCGACTTCAAGGAGGACGGCAACATCCTGGGGCACAAGCTGGAGTA
CAACTACAACAGCCACAACGTCTATATCATGGCCGACAAGCAGAAGAACGGCATCAAGGT
GAACTTCAAGATCCGCCACAACATCGAGGACGGCAGCGTGCAGCTCGCCGACCACTACCA
GCAGAACACCCCCATCGGCGACGGCCCCGTGCTGCTGCCCGACAACCACTACCTGAGCAC
CCAGTCCGCCCTGAGCAAAGACCCCAACGAGAAGCGCGATCACATGGTCCTGCTGGAGTT
CGTGACCGCCGCCGGGATCACTCACGGCATGGACGAGCTGTACAAGTAAGATCGATCCTC
TAGAGTCCTGCTTTAATGAGATATGCGAGACGCCTATGATCGCATGATATTTGCTTTCAA
TTCTGTTGTGCACGTTGTAAAAAACCTGAGCATGTGTAGCTCAGATCCTTACCGCCGGTT

TCGGTTCATTCTAATGAATATATCACCCGTTACTATCGTATTTTTATGAATAATATTCTC
CGTTCAATTTACTGATTGTACCCTACTACTTATATGTACAATATTAAAATGAAAACAATA
TATTGTGCTGAATAGGTTTATAGCGACATCTATGATAGAGCGCCACAATAACAAACAATT
GCGTTTTATTATTACAAATCCAATTTTAAAAAAAGCGGCAGAACCGGTCAAACCTAAAAG
ACTGATTACATAAATCTTATTCAAATTTCAAAAGGCCCCAGGGGCTAGTATCTACGACAC
ACCGAGCGGCGAACTAATAACGTTCACTGAAGGGAACTCCGGTTCCCCGCCGGCGCGCAT
GGGTGAGATTCCTTGAAGTTGAGTATTGGCCGTCCGCTCTACCGAAAGTTACGGGCACCA
TTCAACCCGGTCCAGCACGGCGGCCGGGTAACCGACTTGCTGCCCCGAGAATTATGCAGC
ATTTTTTTGGTGTATGTGGGCCCCAAATGAAGTGCAGGTCAAACCTTGACAGTGACGACA
AATCGTTGGGCGGGTCCAGGGCGAATTTTGCGACAACATGTCGAGGCTCAGCAGGACCTG

CAGGCATGCAAGCTAGCTTACTAGTGATGCATATTCTATAGTGTCACCTAAATGTGCGGC
CGCTCGACGAATTAATTCCAATCCCACAAAAATCTGAGCTTAACAGCACAGTTGCTCCTC
TCAGAGCAGAATCGGGTATTCAACACCCTCATATCAACTACTACGTTGTGTATAACGGTC
CACATGCCGGTATATACGATGACTGGGGTTGTACAAAGGCGGCAACAAACGGCGTTCCCG
GAGTTGCACACAAGAAATTTGCCACTATTACAGAGGCAAGAGCAGCAGCTGACGCGTACA
CAACAAGTCAGCAAACAGACAGGTTGAACTTCATCCCCAAAGGAGAAGCTCAACTCAAGC
CCAAGAGCTTTGCTAAGGCCCTAACAAGCCCACCAAAGCAAAAAGCCCACTGGCTCACGC
TAGGAACCAAAAGGCCCAGCAGTGATCCAGCCCCAAAAGAGATCTCCTTTGCCCCGGAGA
TTACAATGGACGATTTCCTCTATCTTTACGATCTAGGAAGGAAGTTCGAAGGTGAAGGTG
ACGACACTATGTTCACCACTGATAATGAGAAGGTTAGCCTCTTCAATTTCAGAAAGAATG
CTGACCCACAGATGGTTAGAGAGGCCTACGCAGCAGGTCTCATCAAGACGATCTACCCGA
```

-continued

```
GTAACAATCTCCAGGAGATCAAATACCTTCCCAAGAAGGTTAAAGATGCAGTCAAAAGAT
TCAGGACTAATTGCATCAAGAACACAGAGAAAGACATATTTCTCAAGATCAGAAGTACTA
TTCCAGTATGGACGATTCAAGGCTTGCTTCATAAACCAAGGCAAGTAATAGAGATTGGAG
TCTCTAAAAAGGTAGTTCCTACTGAATCTAAGGCCATGCATGGAGTCTAAGATTCAAATC
GAGGATCTAACAGAACTCGCCGTGAAGACTGGCGAACAGTTCATACAGAGTCTTTTACGA
CTCAATGACAAGAAGAAAATCTTCGTCAACATGGTGGAGCACGACACTCTGGTCTACTCC
AAAAATGTCAAAGATACAGTCTCAGAAGACCAAAGGGCTATTGAGACTTTTCAACAAAGG
ATAATTTCGGGAAACCTCCTCGGATTCCATTGCCCAGCTATCTGTCACTTCATCGAAAGG
ACAGTAGAAAAGGAAGGTGGCTCCTACAAATGCCATCATTGCGATAAAGGAAAGGCTATC
ATTCAAGATCTCTCTGCCGACAGTGGTCCCAAAGATGGACCCCCACCCACGAGGAGCATC

GTGGAAAAAGAAGACGTTCCAACCACGTCTTCAAAGCAAGTGGATTGATGTGACATCTCC
ACTGACGTAAGGGATGACGCACAATCCCACTATCCTTCGCAAGACCCTTCCTCTATATAA
GGAAGTTCATTTCATTTGGAGAGGACACGCTCGAGGAATTCGGTACCCCATCACAAGTTT
GTACAAAAAAGCAGGCTCCGCGGCCGCCCCCTTCACCATGGCGATTTTGGATTCTGCTGG
CGTTACTACGGTGACGGAGAACGGTGGCGGAGAGTTCGTCGATCTTGATAGGCTTCGTCG
ACGGAAATCGAGATCGGATTCTTCTAACGGACTTCTTCTCTCTGGTTCCGATAATAATTC
TCCTTCGGATGATGTTGGAGCTCCCGCCGACGTTAGGGATCGGATTGATTCCGTTGTTAA
CGATGACGCTCAGGGAACAGCCAATTTGGCCGGAGATAATAACGGTGGTGGCGATAATAA
CGGTGGTGGAAGAGGCGGCGGAGAAGGAAGAGGAAACGCCGATGCTACGTTTACGTATCG
ACCGTCGGTTCCAGCTCATCGGAGGGCGAGAGAGAGTCCACTTAGCTCCGACGCAATCTT
CAAACAGGTTTAAAATCTCAGAAATCTTCGAATTTGGTGTTTGCTTGTTGTTTTATATGG
AATTGAGTTTGGTGATTGTTTTGCATTGCAGAGCCATGCCGGATTATTCAACCTCTGTGT
AGTAGTTCTTATTGCTGTAAACAGTAGACTCATCATCGAAAATCTTATGAAGGTTTGCTG

TTACTTGTTTCTCCTTTTAGGAATTGAATTGCTTGAAAATTTATCAGAGACGAATAACTT
TGTTGTTGCTATCATTCATGTAGTATGGTTGGTTGATCAGAACGGATTTCTGGTTTAGTT
CAAGATCGCTGCGAGATTGGCCGCTTTTCATGTGTTGGTAAAAGAAGATGTTTTTTATTT
CCAGCAATGTTACATTGTTATACGTATAATGATGAGTTTAGTGATGAAGTTCCTCTTTGA
TTCTTCTTTCTTGTTGCAGTATATCCCTTTCGATCTTTCCTTTGGCTGCCTTTACGGTTG
AGAAATTGGTACTTCAGAAATACATATCAGAACCTGTGAGTAATTACTATTCTCCAGCCA
TTACTGTAATTTTTATTGAAGACAAGTTTGTATCATGAAGAACTTACAAGTTCTGTTTTG
AAAATGCTCAAGGTTGTCATCTTTCTTCATATTATTATCACCATGACAGAGGTTTTGTAT
CCAGTTTACGTCACCCTAAGGTGATACTGTTTTTCTGGTCTCAGTTTGTGATACTGTTTT
TAAGTTTAGTTGTCTGACCCGGTGATCTTGAAAATGGACAGGTGTGATTCTGCTTTTTTA
TCAGGTGTCACTTTGATGCTCCTCACTTGCATTGTGTGGCTAAAGTTGGTTTCTTATGCT
CATACTAGCTATGACATAAGATCCCTAGCCAATGCAGCTGATAAGGTAAAATACGAAAAA

GAAGCGTATGTATTAGTCACTTGCACTGTGTTACTGTTTTAACCAAACACTGTTATGAAC
TTTAGGCCAATCCTGAAGTCTCCTACTACGTTAGCTTGAAGAGCTTGGCATATTTCATGG
TCGCTCCCACATTGTGTTATCAGGTAACTGCAAAGTGCATCAACCATTCTTATACTTGCA
AGAGTTTCTTGTCTAAACCTCGGATCTTTGCTTTTCCCCAGCCAAGTTATCCACGTTCTG
CATGTATACGGAAGGGTTGGGTGGCTCGTCAATTTGCAAAACTGGTCATATTCACCGGAT
TCATGGGATTTATAATAGAACAAGTACGTTTTCACATCTTGCTTTATTAGTTTTCCTTGG
TGAAAATCATCATCCCTGCGTTGTCACCACTTGACTTCATGTTCTTTTGTTACATTTTGG
CAGTATATAAATCCTATTGTCAGGAACTCAAAGCATCCTTTGAAAGGCGATCTTCTATAT
GCTATTGAAAGAGTGTTGAAGCTTTCAGTTCCAAATTTATATGTGTGGCTCTGCATGTTC
TACTGCTTCTTCCACCTTTGGTATGCTGTGATCCCATGTCTTTCAAAATAATTTGCAAAT
TCGAAAAACCGAAAAAGGCTAAATCTCATACGAATTTGATATTTTTAGTTTCTTAGAGTC
GGTGATGTAATTTCAGTTACTGAACGCAAATCTCTTGTCCAAAGGTTAAACATATTGGCA

GAGCTTCTCTGCTTCGGGGATCGTGAATTCTACAAAGATTGGTGGAATGCAAAAAGTGTG
GGAGATGTGAGCTATTTTACTCAAAAGAAAACTTATGATTTTTAATGTTGTCGTTGTTTT
TGGGTCATCTAACTAACCAAATTCATGTATTCACTGTCTTCCTTTATCAGTACTGGAGAA
TGTGGAATATGGTATGGTTCTCTTCCTAAACATCACCTTCTTTTGTACACAAAATAGAAG
AAGAGAGCTAATTAAGATCTTGTTTTCCTTGACAGCCTGTTCATAAATGGATGGTTCGAC
ATATATACTTCCCGTGCTTGCGCAGCAAGATACCAAAGGTGAGTGAGATATATACCGATA
TGCAATTGTCGAGATTTGTTTCTGTGATATAAATTTAACCCTCCACACACTTGTTTTTCA
GACACTCGCCATTATCATTGCTTTCCTAGTCTCTGCAGTCTTTCATGAGGTATACATACT
TTCTACATTGCCCTGTCTCTAGACGCATGAACACACGCTAGTGAAAGAAATGCTAATATT
CAAAGCATTGTTTTTACTTAACGATCTTGTGTTACAAATTTCCTTTTGACAGCTATGCAT

CGCAGTTCCTTGTCGTCTCTTCAAGCTATGGGCTTTTCTTGGGATTATGTTTCAGGTTAA
AAAATTACTAAACTGCTGCAGTCGATTTTTACTAAACTCTAATCTCATATTCTGACCAAC
CAATTTGTTTGAGTAGGTGCCTTTGGTCTTCATCACAAACTATGTACAGGAAAGGTTTGG
CTCAACGGTATGCTCTCAAAACCCGAGAAAATAGAACGAATAACTCTTTCTTTCATAGCC
TAGCCATTTAAATCGCAATGCTGAAACTTAATAATAAAGGTGATCTGTTTTGGAATGGGA
TCATATTATTAGGTGGGGAACATGATCTTCTGGTTCATCTTCTGCATTTTCGGACAACCG
ATGTGTGTGCTTCTTTATTACCACGACCTGATGAACCGAAAAGGATCGATGTCATGAAAG
GGTGGGCGCGCCGACCCAGCTTTCTTGTACAAAGTGGTGATGGGTTCGAAATCGATAAGC
TTGGATCCTCTAGAGTCCTGCTTTAATGAGATATGCGAGACGCCTATGATCGCATGATAT
TTGCTTTCAATTCTGTTGTGCACGTTGTAAAAAACCTGAGCATGTGTAGCTCAGATCCTT
ACCGCCGGTTTCGGTTCATTCTAATGAATATATCACCCGTTACTATCGTATTTTTATGAA

TAATATTCTCCGTTCAATTTACTGATTGTACCCTACTACTTATATGTACAATATTAAAAT
GAAAACAATATATTGTGCTGAATAGGTTTATAGCGACATCTATGATAGAGCGCCACAATA
ACAAACAATTGCGTTTTATTATTACAAATCCAATTTTAAAAAAAGCGGCAGAACCGGTCA
AACCTAAAAGACTGATTACATAAATCTTATTCAAATTTCAAAAGGCCCCAGGGGCTAGTA
TCTACGACACACCGAGCGGCGAACTAATAACGTTCACTGAAGGGAACTCCGGTTCCCCGC
CGGCGCGCATGGGTGAGATTCCTTGAAGTTGAGTATTGGCCGTCCGCTCTACCGAAAGTT
ACGGGCACCATTCAACCCGGTCCAGCACGGCGGCCGGGTAACCGACTTGCTGCCCCGAGA
ATTATGCAGCATTTTTTTGGTGTATGTGGGCCCCAAATGAAGTGCAGGTCAAACCTTGAC
AGTGACGACAAATCGTTGGGCGGGTCCAGGGCGAATTTTGCGACAACATGTCGAGGCTCA
GCAGGACCTGCAGGCATGCAAGCTAGCTTACTAGTGATGCATATTCTATAGTGTCACCTA
AATCTGCGGCCGCTGACCAAGTCAGCTTGGCACTGGCCGTCGTTTTACAACGTCGTGACT
```

-continued

```
GGGAAAACCCTGGCGTTACCCAACTTAATCGCCTTGCAGCACATCCCCCTTTCGCCAGCT
GGCGTAATAGCGAAGAGGCCCGCACCGATCGCCCTTCCCAACAGTTGCGCAGCCTGAATG
GCGAATGGGAAATTGTAAACGTTAATATTTTGTTAATATTTTGTTAAAATTCGCGTTAAA
TTTTTGTTAAATCAGCTCATTTTTTAACCAATAGGCCGAAATCGGCAAAATCCCTTATAA
ATCAAAAGAATAGACCGAGATAGGGTTGAGTGTTGTTCCAGTTTGGAACAAGAGTCCACT
ATTAAAGAACGTGGACTCCAACGTCAAAGGGCGAAAAACCGTCTATCAGGGCGATGGCCC
ACTACGTGAACCATCACCCTAATCAAGTTTTTTGGGGTCGAGGTGCCGTAAAGCACTAAA
TCGGAACCCTAAAGGGATGCCCCGATTTAGAGCTTGACGGGGAAAGCCGGCGAACGTGGC
GAGAAAGGAAGGGAAGAAAGCGAAAGGAGCGGGCGCTAGGGCGCTGGCAAGTGTAGCGGT
CACGCTGCGCGTAACCACCACAGGGGCCGCGCTTAATGCGCCGCTACAGGGCGCGTCAGG
TGGCACTTTTCGGGGAAATGTGCGCGGAACCCCTATTTCTTTATTTTTCTAAATACATTC
AAATATGTATCCGCTCATGAGACAATAACCCTGATAAATGCTTCAATAATATTGAAAAAG

GAAGAGTATGAGTATTCAACATTTCCGTGTCGCCCTTATTCCCTTTTTTGCGGCATTTTG
CCTTCCTGTTTTTGCTCACCCAGAAACGCTGGTGAAAGTAAAAGATGCTGAAGATCAGTT
GGGTGCACGAGTGGGTTACATCGAACTGGATCTCAACAGCGGTAAGATCCTTGAGAGTTT
TCGCCCCGAAGAACGTTTTCCAATGATGATGCATTTTAAAGTTCTGCTATGTGGCGCGGT
ATTATCCCGTATTGACGCCGGGCAAGAGCAACTCGGTCGCCGCATACACTATTCTCAGAA
TGACTTGGTTGAGTACTCACCAGTCACAGAAAAGCATCTTACGGATGGCATGACAGTAAG
AGAATTATGCAGTGCTGCCATAACCATGAGTGATAACACTGCGGCCAACTTACTTCTGAC
AACGATCGGAGGACCGAAGGAGCTAACCGCTTTTTTGCACAACATGGGGGATCATGTAAC
TCGCCTTGATCGTTGGGAACCGGAGCTGAATGAAGCCATACCAAAGCACGAGCGTGACAC
CACGATGCCTGTAGCAATGGCAACAACGTTGCGCAAACTATTAACTGGCGAACTACTTAC
TCTAGCTTCCCGGCAACAATTAATAGACTGGATGGAGGCGGATAAAGTTGCAGGACCACT

TCTGCGCTCGGCCCTTCCGGCTGGCTGGTTTATTGCTGATAAATCTGGAGCCGGTGAGCG
TGGGTCTCGCGGTATCATTGCAGCACTGGGGCCAGATGGTAAGCCCTCCCGTATCGTAGT
TATCTACACGACGGGGAGTCAGGCAACTATGGATGAACGAAATAGACAGATCGCTGAGAT
AGGTGCCTCACTGATTAAGCATTGGTAACTGTCAGACCAAGTTTACTCATATATACTTTA
GATTGATTTAAAACTTCATTTTTAATTTAAAAGGATCTAGGTGAAGATCCTTTTTGATAA
TCTCATGACCAAAATCCCTTAACGTGAGTTTTCGTTCCACTGAGCGTCAGACCCCGTAGA
AAAGATCAAAGGATCTTCTTGAGATCCTTTTTTTCTGCGCGTAATCTGCTGCTTGCAAAC
AAAAAAACCACCGCTACCAGCGGTGGTTTGTTTGCCGGATCAAGAGCTACCAACTCTTTT
TCCGAAGGTAACTGGCTTCAGCAGAGCGCAGATACCAAATACTGTCCTTCTAGTGTAGCC
GTAGTTAGGCCACCACTTCAAGAACTCTGTAGCACCGCCTACATACCTCGCTCTGCTAAT
CCTGTTACCAGTGGCTGCTGCCAGTGGCGATAAGTCGTGTCTTACCGGGTTGGACTCAAG

ACGATAGTTACCGGATAAGGCGCAGCGGTCGGGCTGAACGGGGGGTTCGTGCACACAGCC
CAGCTTGGAGCGAACGACCTACAGGCAACTGAGATACCTACAGCGTGAGCTATGAGAAAG
CGCCACGCTTCCCGAAGGGAGAAAGGCGGACAGGTATCCGGTAAGCGGCAGGGTCGGAAC
AGGAGAGCGCACGAGGGAGCTTCCAGGGGGAAACGCCTGGTATCTTTATAGTCCTGTCGG
GTTTCGCCACCTCTGACTTGAGCGTCGATTTTTGTGATGCTCGTCAGGGGGGCGGAGCCT
ATGGAAAAACGCCAGCAACGCGGCCTTTTTACGGTTCCTGGCCTTTTGCTGGCCTTTTGC
TCACATGTTCTTTCCTGCGTTATCCCCTGATTCTGTGGATAACCGTATTACCGCCTTTGA
GTGAGCTGATACCGCTCGCCGCAGCCGAACGACCGAGCGCAGCGAGTCAGTGAGCGAGGA
AGCGGAAGAGCGCCCAATACGCAAACCGCCTCTCCCCGCGCGTTGGCCGATTCATTAATG
CAGCTGGCACGACAGGTTTCCCGACTGGAAAGCGGGCAGTGAGCGCAACGCAATTAATGT
GAGTTAGCTCACTCATTAGGCACCCCAGGCTTTACACTTTATGCTTCCGGCTCGTATGTT
GTGTGGAATTGTGAGCGGATAACAATTTCACACAGGAAACAGCTATGACCATGATTACGA

ATTTGGCCAAGTCGGCCTCTAATACGACTCACTATAGGGAGCTCGTCGAGCGGCCGCACT
AGTGATATCCCGCGGCCATGGCGGCCGGGAGCATGCGACGTCGGGCCCAATTCGCCCTAT
AGTGAGTCGTATTACAATTCACTGGCCGTCGTTTTACAACGTCGTGACTGGGAAAACCCT
GGCGTTACCCAACTTAATCGCCTTGCAGCACATCCCCCTTTCGCCAGCTGGCGTAATAGC
GAAGAGGCCCGCACCGATCGCCCTTCCCAACAGTTGCGCAGCCTGAATGGCGAATGGAAA
TTGTAAACGTTATTGGGTTTCTGGAGTTTAATGAGCTAAGCACATACGTCAGAAACCATT
ATTGCGCGTTCAAAAGTCGCCTAAGGTCACTATCAGCTAGCAAATATTTCTTGTCAAAAA
TGCTCCACTGACGTTCCATAAATTCCCCTCGGTATCCAATTAGAGTCTCATATTCACTCT
CAATCCAAATAATCTGCAATGGCAATTACCTTATCCGCAACTTCTTTACCTATTTCCGCC
CGGATCCGGGCAGGTTCTCCGGCCGCTTGGGTGGAGAGGCTATTCGGCTATGACTGGGCA
CAACAGACAATCGGCTGCTCTGATGCCGCCGTGTTCCGGCTGTCAGCGCAGGGGCGCCCG

GTTCTTTTTCTGAAGACCGACCTGTCCGGTGCCCTGAATGAACTGCAGGACGAGGCAGCG
CGGCTATCGTGGCTGGCCACGACGGGCGTTCCTTGCGCAGCTGTGCTCGACGTTGTCACT
GAAGCGGGAAGGGACTGGCTGCTATTGGGCGAAGTGCCGGGGCAGGATCTCCTGTCATCT
CACCTTGCTCCTGCCGAGAAAGTATCCATCATGGCTGATGCAATGCGGCGGCTGCATACG
CTTGATCCGGCTACCTGCCCATTCGACCACCAAGCGAAACATCGCATCGAGCGAGCACGT
ACTCGGATGGAAGCCGGTCTTGTCGATCAGGATGATCTGGACGAAGAGCATCAGGGGCTC
GCGCCAGCCGAACTGTTCGCCAGGCTCAAGGCGCGCATGCCCGACGGCGAGGATCTCGTC
GTGACCCATGGCGATGCCTGCTTGCCGAATATCATGGTGGAAAATGGCCGCTTTTCTGGA
TTCATCGACTGTGGCCGGCTGGGTGTGGCGGACCGCTATCAGGACATAGCGTTGGCTACC
CGTGATATTGCTGAAGAGCTTGGCGGCGAATGGGCTGACCGCTTCCTCGTGCTTTACGGT
ATCGCCGCTCCCGATTCGCAGCGCATCGCCTTCTATCGCCTTCTTGACGAGTTCTTCTGA

GCGGGACTCTGGGGTTCGAAATGACCGACCAAGCGACGCCCAACCTGCCATCACGAGATT
TCGATTCCACCGCCGCCTTCTATGAAAGGTTGGGCTTCGGAATCGTTTTCCGGGACGCCG
GCTGGATGATCCTCCAGCGCGGGGATCGCATGCTGGAGTTCTTCGCCCACCCCGATCCAA
CACTTACGTTTGCAACGTCCAAGAGCAAATAGACCACGAACGCCGGAAGGTTGCCGCAGC
GTGTGGATTGCGTCTCAATTCTCTCTTGCAGGAATGCAATGATGAATATGATACTGACTA
TGAAACTTTGAGGGAATACTGCCTAGCACCGTCACCTCATAACGTGCATCATGCATGCCC
TGACAACATGGAACATCGCTATTTTTCTGAAGAATTATGCTCGTTGGAGGATGTCGCGGC
AATTGCAGCTATTGCCAACATCGAACTACCCCTCACGCATGCATTCATCAATATTATTCA
TGCGGGGAAAGGCAAGATTAATCCAACTGGCAAATCATCCAGCGTGATTGGTAACTTCAG
TTCCAGCGACTTGATTCGTTTTCCTGCTACCCACGTTTTCAATAAGGACGAGATGGTGGA
GTAAAGAAGGAGTGCGTCGAAGCAGATCGTTCAAACATTTGGCAATAAAGTTTCTTAAGA
TTGAATCCTGTTGCCGGTCTTGCGATGATTATCATATAATTTCTGTTGAATTACGTTAAG
```

-continued

```
CATGTAATAATTAACATGTAATGCATGACGTTATTTATGAGATGGGTTTTTATGATTAGA
GTCCCGCAATTATACATTTAATACGCGATAGAAAACAAAATATAGCGCGCAAACTAGGAT
AAATTATCGCGCGCGGTGTCATCTATGTTACTAGATCGAATTAATTCAGTACATTAAAAA
CGTCCGCAATGTGTTATTAAGTTGTCTAAGCGTCAATTTGTTTACACCACAATATATCCT
GCCACCAGCCAGCCAACAGCTCCCCGACCGGCAGCTCGGCACAAAATCACCACTCGATAC
AGGCAGCCCATCAGTCCGGGACGGCGTCAGCGGGAGAGCCGTTGTAAGGCGGCAGACTTT
GCTCATGTTACCGATGCTATTCGGAAGAACGGCAACTAAGCTGCCGGGTTTGAAACACGG
ATGATCTCGCGGAGGGTAGCATGTTGATTGTAACGATGACAGAGCGTTGCTGCCTGTGAT
CAAATATCATCTCCCTCGCAGAGATCCGAATTATCAGCCTTCTTATTCATTTCTCGCTTA
ACCGTGACAGGCTGTCGATCTTGAGAACTATGCCGACATAATAGGAAATCGCTGGATAAA
GCCGCTGAGGAAGCTGAGTGGCGCTATTTCTTTAGAAGTGAACGTTGACGATGTCGACGG

ATCTTTTCCGCTGCATAACCCTGCTTCGGGGTCATTATAGCGATTTTTTCGGTATATCCA
TCCTTTTTCGCACGATATACAGGATTTTGCCAAAGGGTTCGTGTAGACTTTCCTTGGTGT
ATCCAACGGCGTCAGCCGGGCAGGATAGGTGAAGTAGGCCCACCCGCGAGCGGGTGTTCC
TTGTTCACTGTCCCTTATTCGCACCTGGCGGTGCTCAACGGGAATCCTGCTCTGCGAGGC
TGGCCGGCTACCGCCGGCGTAACAGATGAGGGCAAGCGGATGGCTGATGAAACCAAGCCA
ACCAGGGGTGATGCTGCCAACTTACTGATTTAGTGTATGATGGTGTTTTTGAGGTGCTCC
AGTGGCTTCTGTTTCTATCAGCTGTCCCTCCTGTTCAGCTACTGACGGGGTGGTGCGTAA
CGGCAAAAGCACCGCCGGACATCAGCGCTATCTCTGCTCTCACTGCCGTAAAACATGGCA
ACTGCAGTTCACTTACACCGCTTCTCAACCCGGTACGCACCAGAAAATCATTGATATGGC
CATGAATGGCGTTGGATGCCGGGCAACAGCCCGCATTATGGGCGTTGGCCTCAACACGAT
TTTACGTCACTTAAAAAACTCAGGCCGCAGTCGGTAACCTCGCGCATACAGCCGGGCAGT

GACGTCATCGTCTGCGCGGAAATGGACGAACAGTGGGGCTATGTCGGGGCTAAATCGCGC
CAGCGCTGGCTGTTTTACGCGTATGACAGTCTCCGGAAGACGGTTGTTGCGCACGTATTC
GGTGAACGCACTATGGCGACGCTGGGGCGTCTTATGAGCCTGCTGTCACCCTTTGACGTG
GTGATATGGATGACGGATGGCTGGCCGCTGTATGAATCCCGCCTGAAGGGAAAGCTGCAC
GTAATCAGCAAGCGATATACGCAGCGAATTGAGCGGCATAACCTGAATCTGAGGCAGCAC
CTGGCACGGCTGGGACGGAAGTCGCTGTCGTTCTCAAAATCGGTGGAGCTGCATGACAAA
GTCATCGGGCATTATCTGAACATAAAACACTATCAATAAGTTGGAGTCATTACCCAACCA
GGAAGGGCAGCCCACCTATCAAGGTGTACTGCCTTCCAGACGAACGAAGAGCGATTGAGG
AAAAGGCGGCGGCGGCCGGCATGAGCCTGTCGGCCTACCTGCTGGCCGTCGGCCAGGGCT
ACAAAATCACGGGCGTCGTGGACTATGAGCACGTCCGCGAGCTGGCCCGCATCAATGGCG
ACCTGGGCCGCCTGGGCGGCCTGCTGAAACTCTGGCTCACCGACGACCCGCGCACGGCGC
GGTTCGGTGATGCCACGATGGTCGCCCTGCTGGCGAAGATCGAAGAGAAGCAGGACGAGC

TTGGCAAGGTCATGATGGGCGTGGTCCGCCCGAGGGCAGAGCCATGACTTTTTTAGCCGC
TAAAACGGCCGGGGGGTGCGCGTGATTGCCAAGCACGTCCCCATGCGCTCCATCAAGAAG
AGCGACTTCGCGGAGCTGGTATTCGTGCAGGGCAAGATTCGGAATACCAAGTACGAGAAG
GACGGCCAGACGGTCTACGGGACCGACTTCATTGCCGATAAGGTGGATTATCTGGACACC
AAGGCACCAGGCGGGTCAAATCAGGAATAAGGGCACATTGCCCCGGCGTGAGTCGGGGCA
ATCCCGCAAGGAGGGTGAATGAATCGGACGTTTGACCGGAAGGCATACAGGCAAGAACTG
ATCGACGCGGGGTTTTCCGCCGAGGATGCCGAAACCATCGCAAGCCGCACCGTCATGCGT
GCGCCCCGCGAAACCTTCCAGTCCGTCGGCTCGATGGTCCAGCAAGCTACGGCCAAGATC
GAGCGCGACAGCGTGCAACTGGCTCCCCCTGCCCTGCCCGCGCCATCGGCCGCCGTGGAG
CGTTCGCGTCGTCTCGAACAGGAGGCGGCAGGTTTGGCGAAGTCGATGACCATCGACACG
CGAGGAACTATGACGACCAAGAAGCGAAAAACCGCCGGCGAGGACCTGGCAAAACAGGTC

AGCGAGGCCAAGCAGGCCGCGTTGCTGAAACACACGAAGCAGCAGATCAAGGAAATGCAG
CTTTCCTTGTTCGATATTGCGCCGTGGCCGGACACGATGCGAGCGATGCCAAACGACACG
GCCCGCTCTGCCCTGTTCACCACGCGCAACAAGAAAATCCCGCGCGAGGCGCTGCAAAAC
AAGGTCATTTTCCACGTCAACAAGGACGTGAAGATCACCTACACCGGCGTCGAGCTGCGG
GCCGACGATGACGAACTGGTGTGGCAGCAGGTGTTGGAGTACGCGAAGCGCACCCCTATC
GGCGAGCCGATCACCTTCACGTTCTACGAGCTTTGCCAGGACCTGGGCTGGTCGATCAAT
GGCCGGTATTACACGAAGGCCGAGGAATGCCTGTCGCGCCTACAGGCGACGGCGATGGGC
TTCACGTCCGACCGCGTTGGGCACCTGGAATCGGTGTCGCTGCTGCACCGCTTCCGCGTC
CTGGACCGTGGCAAGAAAACGTCCCGTTGCCAGGTCCTGATCGACGAGGAAATCGTCGTG
CTGTTTGCTGGCGACCACTACACGAAATTCATATGGGAGAAGTACCGCAAGCTGTCGCCG
ACGGCCCGACGGATGTTCGACTATTTCAGCTCGCACCGGGAGCCGTACCCGCTCAAGCTG

GAAACCTTCCGCCTCATGTGCGGATCGGATTCCACCCGCGTGAAGAAGTGGCGCGAGCAG
GTCGGCGAAGCCTGCGAAGAGTTGCGAGGCAGCGGCCTGGTGGAACACGCCTGGGTCAAT
GATGACCTGGTGCATTGCAAACGCTAGGGCCTTGTGGGGTCAGTTCCGGCTGGGGGTTCA
GCAGCCAGCGCTTTACTGGCATTTCAGGAACAAGCGGGCACTGCTCGACGCACTTGCTTC
GCTCAGTATCGCTCGGGACGCACGGCGCGCTCTACGAACTGCCGATAAACAGAGGATTAA
AATTGACAATTGTGATTAAGGCTCAGATTCGACGGCTTGGAGCGGCCGACGTGCAGGATT
TCCGCGAGATCCGATTGTCGGCCCTGAAGAAAGCTCCAGAGATGTTCGGGTCCGTTTACG
AGCACGAGGAGAAAAAGCCCATGGAGGCGTTCGCTGAACGGTTGCGAGATGCCGTGGCAT
TCGGCGCCTACATCGACGGCGAGATCATTGGGCTGTCGGTCTTCAAACAGGAGGACGGCC
CCAAGGACGCTCACAAGGCGCATCTGTCCGGCGTTTTCGTGGAGCCCGAACAGCGAGGCC
GAGGGGTCGCCGGTATGCTGCTGCGGGCGTTGCCGGCGGGTTTATTGCTCGTGATGATCG
TCCGACAGATTCCAACGGGAATCTGGTGGATGCGCATCTTCATCCTCGGCGCACTTAATA

TTTCGCTATTCTGGAGCTTGTTGTTTATTTCGGTCTACCGCCTGCCGGGCGGGGTCGCGG
CGACGGTAGGCGCTGTGCAGCCGCTGATGGTCGTGTTCATCTCTGCCGCTCTGCTAGGTA
GCCCGATACGATTGATGGCGGTCCTGGGGGCTATTTGCGGAACTGCGGGCGTGGCGCTGT
TGGTGTTGACACCAAACGCAGCGCTAGATCCTGTCGGCGTCGCAGCGGGCCTGGCGGGGG
CGGTTTCCATGGCGTTCGGAACCGTGCTGACCCGCAAGTGGCAACCTCCCGTGCCTCTGC
TCACCTTTACCGCCTGGCAACTGGCGGCCGGAGGACTTCTGCTCGTTCCAGTAGCTTTAG
TGTTTGATCCGCCAATCCCGATGCCTACAGGAACCAATGTTCTCGGCCTGGCGTGGCTCG
GCCTGATCGGAGCGGGTTTAACCTACTTCCTTTGGTTCCGGGGGATCTCGCGACTCGAAC
CTACAGTTGTTTCCTTACTGGGCTTTCTCAGCCGGGATGGCGCTAAGAAGCTATTGCCGC
CGATCTTCATATGCGGTGTGAAATACCGCACAGATGCGTAAGGAGAAAATACCGCATCAG
GCGCTCTTCCGCTTCCTCGCTCACTGACTCGCTGCGCTCGGTCGTTCGGCTGCGGCGAGC
```

-continued

```
GGTATCAGCTCACTCAAAGGCGGTAATACGGTTATCCACAGAATCAGGGGATAACGCAGG
AAAGAACATGTGAGCAAAAGGCCAGCAAAAGGCCAGGAACCGTAAAAAGGCCGCGTTGCT
GGCGTTTTTCCATAGGCTCCGCCCCCCTGACGAGCATCACAAAAATCGACGCTCAAGTCA
GAGGTGGCGAAACCCGACAGGACTATAAAGATACCAGGCGTTTCCCCCTGGAAGCTCCCT
CGTGCGTTCTCCTGTTCCGACCCTGCCGCTTACCGGATACCTGTCCGCCTTTCTCCCTTC
GGGAAGCGTGGCGCTTTCTCAATGCTCACGCTGTAGGTATCTCAGTTCGGTGTAGGTCGT
TCGCTCCAAGCTGGGCTGTGTGCACGAACCCCCCGTTCAGCCCGACCGCTGCGCCTTATC
CGGTAACTATCGTCTTGAGTCCAACCCGGTAAGACACGACTTATCGCCACTGGCAGCAGC
CACTGGTAACAGGATTAGCAGAGCGAGGTATGTAGGCGGTGCTACAGAGTTCTTGAAGTG
GTGGCCTAACTACGGCTACACTAGAAGGACAGTATTTGGTATCTGCGCTCTGCTGAAGCC
AGTTACCTTCGGAAAAAGAGTTGGTAGCTCTTGATCCGGCAAACAAACCACCGCTGGTAG

CGGTGGTTTTTTTGTTTGCAAGCAGCAGATTACGCGCAGAAAAAAAGGATATCAAGAAGA
TCCTTTGATCTTTTCTACGGGGTCTGACGCTCAGTGGAACGAAAACTCACGTTAAGGGAT
TTTGGTCATGAGATTATCAAAAAGGATCTTCACCTAGATCCTTTTAAATTAAAAATGAAG
TTTTAAATCAATCTAAAGTATATATGAGTAAACTTGGTCTGACAGTTACCAATGCTTAAT
CAGTGAGGCACCTATCTCAGCGATCTGTCTATTTCGTTCATCCATAGTTGCCTGACTCCC
CGTCGTGTAGATAACTACGATACGGGAGGGCTTACCATCTGGCCCCAGTGCTGCAATGAT
ACCGCGAGACCCACGCTCACCGGCTCCAGATTTATCAGCAATAAACCAGCCAGCCGGAAG
GGCCGAGCGCAGAAGTGGTCCTGCAACTTTATCCGCCTCCATCCAGTCTATTAAACAAGT
GGCAGCAACGGATTCGCAAACCTGTCACGCCTTTTGTGCCAAAAGCCGCGCCAGGTTTGC
GATCCGCTGTGCCAGGCGTTAGGCGTCATATGAAGATTTCGGTGATCCCTGAGCAGGTGG
CGGAAACATTGGATGCTGAGAACCATTTCATTGTTCGTGAAGTGTTCGATGTGCACCTAT
CCGACCAAGGCTTTGAACTATCTACCAGAAGTGTGAGCCCCTACCGGAAGGATTACATCT

CGGATGATGACTCTGATGAAGACTCTGCTTGCTATGGCGCATTCATCGACCAAGAGCTTG
TCGGGAAGATTGAACTCAACTCAACATGGAACGATCTAGCCTCTATCGAACACATTGTTG
TGTCGCACACGCACCGAGGCAAAGGAGTCGCGCACAGTCTCATCGAATTTGCGAAAAAGT
GGGCACTAAGCAGACAGCTCCTTGGCATACGATTAGAGACACAAACGAACAATGTACCTG
CCTGCAATTTGTACGCAAAATGTGGCTTTACTCTCGGCGGCATTGACCTGTTCACGTATA
AAACTAGACCTCAAGTCTCGAACGAAACAGCGATGTACTGGTACTGGTTCTCGGGAGCAC
AGGATGACGCCTAACAATTCATTCAAGCCGACACCGCTTCGCGGCGCGGCTTAATTCAGG
AGTTAAACATCATGAGGGAAGCGGTGATCGCCGAAGTATCGACTCAACTATCAGAGGTAG
TTGGCGTCATCGAGCGCCATCTCGAACCGACGTTGCTGGCCGTACATTTGTACGGCTCCG
CAGTGGATGGCGGCCTGAAGCCACACAGTGATATTGATTTGCTGGTTACGGTGACCGTAA
GGCTTGATGAAACAACGCGGCGAGCTTTGATCAACGACCTTTTGGAAACTTCGGCTTCCC
CTGGAGAGAGCGAGATTCTCCGCGCTGTAGAAGTCACCATTGTTGTGCACGACGACATCA

TTCCGTGGCGTTATCCAGCTAAGCGCGAACTGCAATTTGGAGAATGGCAGCGCAATGACA
TTCTTGCAGGTATCTTCGAGCCAGCCACGATCGACATTGATCTGGCTATCTTGCTGACAA
AAGCAAGAGAACATAGCGTTGCCTTGGTAGGTCCAGCGGCGGAGGAACTCTTTGATCCGG
TTCCTGAACAGGATCTATTTGAGGCGCTAAATGAAACCTTAACGCTATGGAACTCGCCGC
CCGACTGGGCTGGCGATGAGCGAAATGTAGTGCTTACGTTGTCCCGCATTTGGTACAGCG
CAGTAACCGGCAAAATCGCGCCGAAGGATGTCGCTGCCGACTGGGCAATGGAGCGCCTGC
CGGCCCAGTATCAGCCCGTCATACTTGAAGCTAGGCAGGCTTATCTTGGACAAGAAGATC
GCTTGGCCTCGCGCGCAGATCAGTTGGAAGAATTTGTTCACTACGTGAAAGGCGAGATCA
CCAAGGTAGTCGGCAAATAATGTCTAACAATTCGTTCAAGCCGACGCCGCTTCGCGGCGC
GGCTTAACTCAAGCGTTAGAGAGCTGGGGAAGACTATGCGCGATCTGTTGAAGGTGGTTC

TAAGCCTCGTACTTGCGATGGCATCGGGGCAGGCACTTGCTGACCTGCCAATTGTTTTAG
TGGATGAAGCTCGTCTTCCCTATGACTACTCCCCATCCAACTACGACATTTCTCCAAGCA
ACTACGACAACTCCATAAGCAATTACGACAATAGTCCATCAAATTACGACAACTCTGAGA
GCAACTACGATAATAGTTCATCCAATTACGACAATAGTCGCAACGGAAATCGTAGGCTTA
TATATAGCGCAAATGGGTCTCGCACTTTCGCCGGCTACTACGTCATTGCCAACAATGGGA
CAACGAACTTCTTTTCCACATCTGGCAAAAGGATGTTCTACACCCCAAAAGGGGGCGCG
GCGTCTATGGCGGCAAAGATGGGAGCTTCTGCGGGGCATTGGTCGTCATAAATGGCCAAT
TTTCGCTTGCCCTGACAGATAACGGCCTGAAGATCATGTATCTAAGCAACTAGCCTGCTC
TCTAATAAAATGTTAGGAGCTTGGCTGCCATTTTTGGGGTGAGGCCGTTCGCGGCCGAGG
GGCGCAGCCCCTGGGGGGATGGGAGGCCCGCGTTAGCGGGCCGGGAGGGTTCGAGAAGGG
GGGGCACCCCCCTTCGGCGTGCGCGGTCACGCGCCAGGGCGCAGCCCTGGTTAAAAACAA
GGTTTATAAATATTGGTTTAAAAGCAGGTTAAAAGACAGGTTAGCGGTGGCCGAAAAACG

GGCGGAAACCCTTGCAAATGCTGGATTTTCTGCCTGTGGACAGCCCCTCAAATGTCAATA
GGTGCGCCCCTCATCTGTCAGCACTGTGCCCCTCAAGTGTCAAGGATCGCGCCCCTCATC
TGTCAGTAGTCGCGCCCCTCAAGTGTCAATACCGCAGGGCACTTATCCCCAGGCTTGTCC
ACATCATCTGTGGGAAACTCGCGTAAAATCAGGCGTTTTCGCCGATTTGCGAGGCTGGCC
AGCTCCACGTCGCCGGCCGAAATCGAGCCTGCCCCTCATCTGTCAACGCCGCGCCGGGTG
AGTCGGCCCCTCAAGTGTCAACGTCCGCCCCTCATCTGTCAGTGAGGGCCAAGTTTTCCG
CGAGGTATCCACAACGCCGGCGGCCGGCCGCGGTGTCTCGCACACGGCTTCGACGGCGTT
TCTGGCGCGTTTGCAGGGCCATAGACGGCCGCCAGCCCAGCGGCGAGGGCAACCAGCCCG
GTGAGCGTCGGAAAGGG 3'
```

The invention claimed is:

1. A substantially purified or isolated nucleic acid, said nucleic acid consisting of a nucleotide sequence selected from the group consisting of:

(a) SEQ ID No: 10;

(b) SEQ ID No: 38;

(c) a variant of SEQ ID No: 38, wherein the variant is different from SEQ ID NO.: 38 as a consequence of one or more nucleotide changes and wherein all of the changes result in conservative amino acid substitutions, with the proviso that the variant of SEQ ID No 38 has at least 95% sequence identity with SEQ ID No: 38;

(d) the complement of SEQ ID No: 10;

(e) the complement of SEQ ID No: 38;

(f) the complement of the variant as defined in (c); and (g) a nucleic acid fragment that has a length of at least 60 nucleotides wherein the entire sequence of the nucleic acid fragment is the same as or the complement of a sequence of the same length within SEQ ID No: 10.

2. The nucleic acid of claim 1, said nucleic acid consisting of a nucleotide sequence selected from the group consisting of:

(a) SEQ ID No: 10;

(b) SEQ ID No: 38;

(c) the complement of SEQ ID No: 10;

(d) the complement of SEQ ID No: 38; and (e) a nucleic acid fragment that has a length of at least 60 nucleotides wherein the entire sequence of the nucleic acid fragment is the same as or the complement of a sequence of the same length within SEQ ID No: 10.

3. The nucleic acid of claim 1, said nucleic acid consisting of a nucleotide sequence selected from the group consisting of:

(a) SEQ ID No: 10;

(b) SEQ ID No: 38;

(c) the complement of SEQ ID No: 10;

(d) the complement of SEQ ID No: 38; and (e) a variant of SEQ ID No: 38, wherein the variant is different from SEQ ID NO.: 38 as a consequence of one or more nucleotide changes and wherein all of the changes result in conservative amino acid substitutions, with the proviso that the variant of SEQ ID No 38 has at least 95% sequence identity with SEQ ID No: 38.

4. A construct including one or more nucleic acids according to claim 1.

5. A preparation for transforming a plant comprising a nucleic acid according to claim 1, or a construct according to claim 4.

6. A substantially purified or isolated nucleic acid, said nucleic acid consisting of a nucleotide sequence selected from the group consisting of:

(a) SEQ ID No: 26;

(b) SEQ ID No: 27;

(c) the complement of SEQ ID No: 26;

(d) the complement of SEQ ID No: 27; and (e) a nucleic acid fragment that has a length of at least 60 nucleotides wherein the sequence is the same as or the complement of a sequence of the same length within SEQ ID No: 26.

7. A construct including one or more nucleic acids according to claim 6.

8. A construct according to claim 7 wherein the one or more nucleic acids are operably linked to one or more regulatory elements, such that the one or more nucleic acids are each expressed.

9. A construct according to claim 8, wherein the one or more regulatory elements include a promoter and a terminator, said promoter, nucleic acid or nucleic acid fragment and terminator being operably linked.

10. A preparation for transforming a plant comprising a nucleic acid according to claim 6, or a construct according to claim 7.

11. A substantially purified or isolated nucleic acid, said nucleic acid comprising a nucleotide sequence selected from the group consisting of:

(a) SEQ ID No: 26;

(b) SEQ ID No: 27;

(c) the complement of SEQ ID No: 26; and (d) the complement of SEQ ID No: 27.

12. A substantially purified or isolated nucleic acid, said nucleic acid comprising a nucleotide sequence selected from the group consisting of:

(a) SEQ ID No: 10;

(b) SEQ ID No: 38;

(c) the complement of SEQ ID No: 10; and (d) the complement of SEQ ID No: 38.

* * * * *

SEQUENCE LISTING

```
<160> NUMBER OF SEQ ID NOS: 44

<210> SEQ ID NO 1
<211> LENGTH: 59
<212> TYPE: PRT
<213> ORGANISM: Oryza sativa

<400> SEQUENCE: 1

Val Arg His Ile Tyr Phe Pro Cys Met Arg Asn Gly Ile Ser Lys Glu
1               5                   10                  15
```

```
Val Ala Leu Ile Ser Phe Leu Val Ser Ala Val Leu His Glu Ile Cys
            20                  25                  30

Val Ala Val Pro Cys Arg Ile Leu Lys Phe Trp Ala Phe Leu Gly Ile
        35                  40                  45

Met Leu Gln Ile Pro Leu Ile Val Leu Thr Ala
    50                  55


<210> SEQ ID NO 2
<211> LENGTH: 16
<212> TYPE: PRT
<213> ORGANISM: Lolium perenne

<400> SEQUENCE: 2

Val Ser Ala Val Leu His Glu Leu Cys Val Ala Val Pro Cys Arg Ile
1               5                   10                  15


<210> SEQ ID NO 3
<211> LENGTH: 534
<212> TYPE: PRT
<213> ORGANISM: Perilla frutescens

<400> SEQUENCE: 3

Met Ala Ile Leu Asp Ser Pro Glu Ile Leu Asp Thr Thr Ser Ser Ser
1               5                   10                  15

Ala Asp Asn Gly Ala Ala His His Thr Thr Leu Arg Arg Arg Gln Ser
            20                  25                  30

Ala Arg Ser Val Pro Pro Leu Leu Asp Ser Asp Ser Asn Ser Leu Glu
        35                  40                  45

Ala Glu Ser Ala Ile Asn Asp Ser Glu Asn Val Arg Asn Asp Ala Asn
    50                  55                  60

Leu Ile Glu Asn Leu Arg Gly Gly Ala Val Glu Ser Glu Asn Glu Lys
65                  70                  75                  80

Gln Glu Ser Tyr Gly Lys Glu Glu Gly Ala Lys Val Lys Glu Asn Gly
                85                  90                  95

Glu Thr Ser Asn Gly Asn Gly Thr Asp Val Met Ala Val Lys Phe Thr
            100                 105                 110

Phe Arg Pro Ala Ala Pro Ala His Arg Lys Asn Lys Glu Ser Pro Leu
        115                 120                 125

Ser Ser Asp Ala Ile Phe Lys Gln Ser His Ala Gly Leu Phe Asn Leu
    130                 135                 140

Cys Ile Val Val Leu Val Ala Val Asn Ser Arg Leu Ile Ile Glu Asn
145                 150                 155                 160

Leu Met Lys Tyr Gly Trp Leu Ile Lys Ser Gly Phe Trp Phe Ser Ser
                165                 170                 175

Thr Ser Leu Arg Asp Trp Pro Leu Leu Met Cys Cys Leu Ser Leu Pro
            180                 185                 190

Val Phe Ala Leu Ala Ser Phe Leu Val Glu Lys Leu Val Lys Leu Asn
        195                 200                 205

Tyr Ile Pro Glu Trp Val Ala Val Phe Leu His Val Thr Ile Thr Thr
    210                 215                 220

Val Glu Ile Leu Phe Pro Val Val Val Ile Leu Arg Cys Asp Ser Ala
225                 230                 235                 240

Val Leu Ser Gly Val Thr Leu Met Leu Phe Ala Cys Thr Val Trp Leu
                245                 250                 255

Lys Leu Val Ser Tyr Ala His Thr Asn Tyr Asp Leu Arg Val Leu Ala
            260                 265                 270
```

```
Lys Ser Leu Asp Lys Trp Glu Ala Met Ser Arg Tyr Trp Asn Leu Asp
        275                 280                 285

Tyr Ala Tyr Asp Val Ser Phe Lys Ser Leu Ala Tyr Phe Met Val Ala
    290                 295                 300

Pro Thr Leu Cys Tyr Gln Pro Ser Tyr Pro Arg Thr Ala Cys Ile Arg
305                 310                 315                 320

Lys Gly Trp Val Val Arg Gln Leu Ile Lys Leu Val Ile Phe Thr Gly
                325                 330                 335

Leu Met Gly Phe Ile Ile Glu Gln Tyr Ile Asn Pro Ile Val Gln Asn
            340                 345                 350

Ser Gln His Pro Leu Lys Gly Asn Leu Leu Tyr Ala Ile Glu Arg Val
        355                 360                 365

Leu Lys Leu Ser Val Pro Asn Leu Tyr Val Trp Leu Cys Met Phe Tyr
    370                 375                 380

Cys Phe Phe His Leu Trp Leu Asn Ile Leu Ala Glu Leu Leu Cys Phe
385                 390                 395                 400

Gly Asp Arg Glu Phe Tyr Lys Asp Trp Trp Asn Ala Arg Thr Val Glu
                405                 410                 415

Glu Tyr Trp Arg Met Trp Asn Met Pro Val His Lys Trp Met Val Arg
            420                 425                 430

His Ile Tyr Cys Pro Cys Leu Gln Asn Gly Ile Pro Lys Ile Val Ala
        435                 440                 445

Val Leu Ile Ala Phe Leu Val Ser Ala Ile Phe His Glu Leu Cys Val
    450                 455                 460

Ala Val Pro Cys Gln Ile Phe Lys Phe Trp Ala Phe Ser Gly Ile Met
465                 470                 475                 480

Leu Gln Val Pro Leu Val Ile Val Thr Asn Tyr Leu Gln Glu Lys Phe
                485                 490                 495

Lys Asn Ser Met Val Gly Asn Met Met Phe Trp Cys Phe Phe Cys Ile
            500                 505                 510

Phe Gly Gln Pro Met Cys Val Leu Leu Tyr Tyr His Asp Leu Met Asn
        515                 520                 525

Arg Lys Ala Ser Ala Arg
    530


<210> SEQ ID NO 4
<211> LENGTH: 520
<212> TYPE: PRT
<213> ORGANISM: Arabidopsis thaliana

<400> SEQUENCE: 4

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Gly Arg Gly Gly Gly Glu
                85                  90                  95

Gly Arg Gly Asn Ala Asp Ala Thr Phe Thr Tyr Arg Pro Ser Val Pro
            100                 105                 110
```

```
Ala His Arg Arg Ala Arg Glu Ser Pro Leu Ser Ser Asp Ala Ile Phe
        115                 120                 125

Lys Gln Ser His Ala Gly Leu Phe Asn Leu Cys Val Val Val Leu Ile
    130                 135                 140

Ala Val Asn Ser Arg Leu Ile Ile Glu Asn Leu Met Lys Tyr Gly Trp
145                 150                 155                 160

Leu Ile Arg Thr Asp Phe Trp Phe Ser Ser Arg Ser Leu Arg Asp Trp
                165                 170                 175

Pro Leu Phe Met Cys Cys Ile Ser Leu Ser Ile Phe Pro Leu Ala Ala
            180                 185                 190

Phe Thr Val Glu Lys Leu Val Leu Gln Lys Tyr Ile Ser Glu Pro Val
        195                 200                 205

Val Ile Phe Leu His Ile Ile Ile Thr Met Thr Glu Val Leu Tyr Pro
    210                 215                 220

Val Tyr Val Thr Leu Arg Cys Asp Ser Ala Phe Leu Ser Gly Val Thr
225                 230                 235                 240

Leu Met Leu Leu Thr Cys Ile Val Trp Leu Lys Leu Val Ser Tyr Ala
                245                 250                 255

His Thr Ser Tyr Asp Ile Arg Ser Leu Ala Asn Ala Ala Asp Lys Ala
            260                 265                 270

Asn Pro Glu Val Ser Tyr Tyr Val Ser Leu Lys Ser Leu Ala Tyr Phe
        275                 280                 285

Met Val Ala Pro Thr Leu Cys Tyr Gln Pro Ser Tyr Pro Arg Ser Ala
    290                 295                 300

Cys Ile Arg Lys Gly Trp Val Ala Arg Gln Phe Ala Lys Leu Val Ile
305                 310                 315                 320

Phe Thr Gly Phe Met Gly Phe Ile Ile Glu Gln Tyr Ile Asn Pro Ile
                325                 330                 335

Val Arg Asn Ser Lys His Pro Leu Lys Gly Asp Leu Leu Tyr Ala Ile
            340                 345                 350

Glu Arg Val Leu Lys Leu Ser Val Pro Asn Leu Tyr Val Trp Leu Cys
        355                 360                 365

Met Phe Tyr Cys Phe Phe His Leu Trp Leu Asn Ile Leu Ala Glu Leu
    370                 375                 380

Leu Cys Phe Gly Asp Arg Glu Phe Tyr Lys Asp Trp Trp Asn Ala Lys
385                 390                 395                 400

Ser Val Gly Asp Tyr Trp Arg Met Trp Asn Met Pro Val His Lys Trp
                405                 410                 415

Met Val Arg His Ile Tyr Phe Pro Cys Leu Arg Ser Lys Ile Pro Lys
            420                 425                 430

Thr Leu Ala Ile Ile Ile Ala Phe Leu Val Ser Ala Val Phe His Glu
        435                 440                 445

Leu Cys Ile Ala Val Pro Cys Arg Leu Phe Lys Leu Trp Ala Phe Leu
    450                 455                 460

Gly Ile Met Phe Gln Val Pro Leu Val Phe Ile Thr Asn Tyr Leu Gln
465                 470                 475                 480

Glu Arg Phe Gly Ser Thr Val Gly Asn Met Ile Phe Trp Phe Ile Phe
                485                 490                 495

Cys Ile Phe Gly Gln Pro Met Cys Val Leu Leu Tyr Tyr His Asp Leu
            500                 505                 510

Met Asn Arg Lys Gly Ser Met Ser
        515                 520
```

<210> SEQ ID NO 5

<211> LENGTH: 501
<212> TYPE: PRT
<213> ORGANISM: Brassica napus

<400> SEQUENCE: 5

```
Met Glu Ile Leu Asp Ser Gly Gly Val Thr Met Pro Thr Glu Asn Gly
1               5                   10                  15

Gly Ala Asp Leu Asp Thr Leu Arg His Arg Lys Pro Arg Ser Asp Ser
            20                  25                  30

Ser Asn Gly Leu Leu Pro Asp Ser Val Thr Val Ser Asp Ala Asp Val
        35                  40                  45

Arg Asp Arg Val Asp Ser Ala Val Glu Asp Thr Gln Gly Lys Ala Asn
    50                  55                  60

Leu Ala Gly Glu Asn Glu Ile Arg Glu Ser Gly Gly Glu Ala Gly Gly
65                  70                  75                  80

Asn Val Asp Val Arg Tyr Thr Tyr Arg Pro Ser Val Pro Ala His Arg
                85                  90                  95

Arg Val Arg Glu Ser Pro Leu Ser Ser Asp Ala Ile Phe Lys Gln Ser
            100                 105                 110

His Ala Gly Leu Phe Asn Leu Cys Val Val Val Leu Val Ala Val Asn
        115                 120                 125

Ser Arg Leu Ile Ile Glu Asn Leu Met Lys Tyr Gly Trp Leu Ile Arg
    130                 135                 140

Thr Asp Phe Trp Phe Ser Ser Thr Ser Leu Arg Asp Trp Pro Leu Phe
145                 150                 155                 160

Met Cys Cys Leu Ser Leu Ser Ile Phe Pro Leu Ala Ala Phe Thr Val
                165                 170                 175

Glu Lys Leu Val Leu Gln Lys Cys Ile Ser Glu Pro Val Val Ile Ile
            180                 185                 190

Leu His Ile Ile Ile Thr Met Thr Glu Val Leu Tyr Pro Val Tyr Val
        195                 200                 205

Thr Leu Arg Cys Asp Ser Ala Phe Leu Ser Gly Val Thr Leu Met Leu
    210                 215                 220

Leu Thr Cys Ile Val Trp Leu Lys Leu Val Ser Tyr Ala His Thr Asn
225                 230                 235                 240

Tyr Asp Ile Arg Thr Leu Ala Asn Ser Ser Asp Lys Ala Asn Pro Glu
                245                 250                 255

Val Ser Tyr Tyr Val Ser Leu Lys Ser Leu Ala Tyr Phe Met Leu Ala
            260                 265                 270

Pro Thr Leu Cys Tyr Gln Pro Ser Tyr Pro Arg Ser Pro Cys Ile Arg
        275                 280                 285

Lys Gly Trp Val Ala Arg Gln Phe Ala Lys Leu Ile Ile Phe Thr Gly
    290                 295                 300

Phe Met Gly Phe Ile Ile Glu Gln Tyr Ile Asn Pro Ile Val Arg Asn
305                 310                 315                 320

Ser Lys His Pro Leu Lys Gly Asp Leu Leu Tyr Gly Val Glu Arg Val
                325                 330                 335

Leu Lys Leu Ser Val Pro Asn Leu Tyr Val Trp Leu Cys Met Phe Tyr
            340                 345                 350

Cys Phe Phe His Leu Trp Leu Asn Ile Leu Ala Glu Leu Leu Cys Phe
        355                 360                 365

Gly Asp Arg Glu Phe Tyr Lys Asp Trp Trp Asn Ala Lys Ser Val Gly
    370                 375                 380

Asp Tyr Trp Arg Met Trp Asn Met Pro Val His Lys Trp Met Val Arg
385                 390                 395                 400
```

```
His Val Tyr Phe Pro Cys Leu Arg Arg Asn Ile Pro Lys Val Pro Ala
                405                 410                 415

Ile Ile Leu Ala Phe Leu Val Ser Ala Val Phe His Glu Leu Cys Ile
            420                 425                 430

Ala Val Pro Cys Arg Leu Phe Lys Leu Trp Ala Phe Leu Gly Ile Met
        435                 440                 445

Phe Gln Val Pro Leu Val Phe Ile Thr Asn Tyr Leu Gln Glu Arg Phe
    450                 455                 460

Gly Ser Met Val Gly Asn Met Ile Phe Trp Phe Thr Phe Cys Ile Phe
465                 470                 475                 480

Gly Gln Pro Met Cys Val Leu Leu Tyr Tyr His Asp Leu Met Asn Arg
                485                 490                 495

Lys Gly Lys Met Ser
            500


<210> SEQ ID NO 6
<211> LENGTH: 91
<212> TYPE: PRT
<213> ORGANISM: Medicago truncatula

<400> SEQUENCE: 6

Pro Lys Gly Ala Ala Val Leu Ile Ala Phe Met Val Ser Ala Leu Phe
1               5                   10                  15

His Glu Leu Cys Ile Ala Val Pro Cys His Ile Phe Lys Leu Trp Ala
            20                  25                  30

Phe Ser Gly Ile Met Phe Gln Val Pro Leu Val Leu Ile Thr Asn Tyr
        35                  40                  45

Leu Gln Asn Lys Phe Ser Asn Ser Met Val Gly Asn Met Phe Phe Trp
    50                  55                  60

Phe Thr Phe Cys Ile Leu Gly Gln Pro Met Cys Val Leu Leu Tyr Tyr
65                  70                  75                  80

His Asp Leu Met Asn Arg Asn Ser Lys Leu Asp
                85                  90


<210> SEQ ID NO 7
<211> LENGTH: 143
<212> TYPE: PRT
<213> ORGANISM: Glycine max
<220> FEATURE:
<221> NAME/KEY: misc_feature
<222> LOCATION: (61)..(62)
<223> OTHER INFORMATION: Xaa can be any naturally occurring amino acid

<400> SEQUENCE: 7

Asn Ile Leu Ala Glu Leu Leu Arg Phe Gly Asp Arg Glu Phe Tyr Lys
1               5                   10                  15

Asp Trp Trp Asn Ala Lys Thr Val Glu Asp Tyr Trp Arg Met Trp Asn
            20                  25                  30

Met Pro Val His Lys Trp Met Ile Arg His Leu Tyr Phe Pro Cys Leu
        35                  40                  45

Arg His Gly Leu Pro Lys Ala Ala Ala Leu Leu Ile Xaa Xaa Leu Val
    50                  55                  60

Ser Ala Leu Phe His Glu Leu Cys Ile Ala Val Pro Cys His Ile Phe
65                  70                  75                  80

Lys Leu Trp Ala Phe Gly Gly Ile Met Phe Gln Val Pro Leu Val Leu
                85                  90                  95

Ile Thr Asn Tyr Leu Gln Asn Lys Phe Arg Asn Ser Met Val Gly Asn
            100                 105                 110
```

```
Met Ile Phe Trp Phe Ile Phe Ser Ile Leu Gly Gln Pro Met Cys Val
        115                 120                 125

Leu Leu Tyr Tyr His Asp Leu Met Asn Arg Lys Gly Lys Leu Asp
    130                 135                 140


<210> SEQ ID NO 8
<211> LENGTH: 532
<212> TYPE: PRT
<213> ORGANISM: Nicotiana tabacum

<400> SEQUENCE: 8

Met Val Ile Met Glu Leu Pro Glu Ser Val Glu Met Thr Thr Thr Thr
1               5                   10                  15

Thr Thr Ser Gly Ile Glu Asn Leu Asn Ser Asp Leu Asn His Ser Val
            20                  25                  30

Arg Arg Arg Arg Gly Ser Asn Gly Phe Glu Ala Ala Ser Ala Ile Asn
        35                  40                  45

Ser Ser Asp Ala Asn Met Ser Glu Asp Arg Arg Asp Val Cys Gly Ser
    50                  55                  60

Gly Ala Gly Leu Glu Thr Val Asn Glu Arg Ser Lys Ser Val Gly Glu
65                  70                  75                  80

Ser Ser Asp Val Ile Arg Lys Glu Asp Asp Arg Asn Asp Asn Val Ala
                85                  90                  95

Asn Gly Glu Glu Ser Lys Ser Thr Glu Thr Thr Thr Thr Pro Phe Lys
            100                 105                 110

Phe Ala Tyr Arg Ala Ser Ala Pro Ala His Arg Arg Ile Lys Glu Ser
        115                 120                 125

Pro Leu Ser Ser Asp Ala Ile Phe Lys Gln Ser His Ala Gly Leu Phe
    130                 135                 140

Asn Leu Cys Val Val Val Leu Ile Ala Val Asn Ser Arg Leu Ile Ile
145                 150                 155                 160

Glu Asn Leu Met Lys Tyr Gly Leu Leu Ile Arg Ala Gly Phe Trp Phe
                165                 170                 175

Ser Ser Lys Ser Leu Arg Asp Trp Pro Leu Leu Met Cys Cys Leu Ser
            180                 185                 190

Leu Gln Ile Leu Pro Leu Ala Ala Phe Leu Val Glu Lys Leu Ala Gln
        195                 200                 205

Gln Arg His Leu Thr Glu Arg Ala Val Val Thr Leu His Ile Thr Ile
    210                 215                 220

Thr Thr Ala Ala Ile Leu Tyr Pro Val Leu Val Ile Leu Gly Cys Asp
225                 230                 235                 240

Ser Ala Phe Leu Phe Gly Val Ile Leu Met Leu Val Ala Cys Ile Val
                245                 250                 255

Trp Met Lys Leu Val Ser Tyr Ala His Thr Asn His Asp Met Arg Gln
            260                 265                 270

Leu Ala Lys Ser Thr Asp Lys Asp Glu Thr Ser Asp Gly Asp Phe Ser
        275                 280                 285

Tyr Asp Val Ser Phe Lys Ser Leu Ala Tyr Phe Met Val Ala Pro Thr
    290                 295                 300

Leu Cys Tyr Gln Leu Ser Tyr Pro His Thr Pro Cys Ile Arg Lys Gly
305                 310                 315                 320

Trp Val Ala Arg Gln Phe Ile Lys Leu Val Ile Phe Thr Gly Leu Met
                325                 330                 335

Gly Phe Ile Ile Glu Gln Tyr Ile Asn Pro Ile Val Gln Asn Ser Gln
            340                 345                 350
```

```
His Pro Leu Lys Gly Asn Leu Leu Tyr Ala Ile Glu Arg Val Leu Lys
        355                 360                 365

Leu Ser Val Pro Asn Leu Tyr Val Trp Leu Cys Met Phe Tyr Cys Phe
    370                 375                 380

Phe His Leu Trp Leu Asn Ile Leu Ala Glu Leu Leu Cys Phe Gly Asp
385                 390                 395                 400

Arg Glu Phe Tyr Lys Asp Trp Trp Asn Ala Lys Thr Ile Asp Glu Tyr
                405                 410                 415

Trp Arg Met Trp Asn Met Pro Val His Lys Trp Met Val Arg His Ile
            420                 425                 430

Tyr Phe Pro Cys Leu Arg Asn Gly Ile Pro Lys Gly Val Ala Ile Leu
        435                 440                 445

Ile Ala Phe Leu Val Ser Ala Val Phe His Glu Leu Cys Ile Ala Val
    450                 455                 460

Pro Cys Arg Leu Phe Lys Trp Trp Ala Phe Met Gly Ile Met Phe Gln
465                 470                 475                 480

Val Pro Leu Val Ile Leu Thr Asn Phe Leu Gln Asn Lys Phe Gln Ser
                485                 490                 495

Ser Met Val Gly Asn Met Met Phe Trp Cys Phe Phe Cys Ile Leu Gly
            500                 505                 510

Gln Pro Met Cys Val Leu Leu Tyr Tyr His Asp Val Met Asn Arg Lys
        515                 520                 525

Ser Ser Ala Arg
    530


<210> SEQ ID NO 9
<211> LENGTH: 458
<212> TYPE: PRT
<213> ORGANISM: Oryza sativa

<400> SEQUENCE: 9

Met Ala Pro Pro Pro Ser Leu Ala Pro Asp Arg Gly Gly Gly Glu Pro
1               5                   10                  15

Asp Asp Ala Leu Arg Leu Arg Ala Arg Ala Ala Ala Ala Ala Gly Asp
            20                  25                  30

Ala Pro Ala Pro Gln Gln Gln Gln Glu Gln Arg His Gln Glu Gln Gln
        35                  40                  45

Gln Gln Leu Leu Trp Tyr Arg Ala Ser Ala Pro Ala His Arg Arg Val
    50                  55                  60

Arg Glu Ser Pro Leu Ser Ser Asp Ala Ile Phe Arg Gln Ser His Ala
65                  70                  75                  80

Gly Leu Leu Asn Leu Cys Ile Val Val Leu Val Ala Val Asn Ser Arg
                85                  90                  95

Leu Ile Ile Glu Asn Leu Met Lys Tyr Gly Leu Leu Ile Arg Ala Gly
            100                 105                 110

Phe Trp Phe Ser Gly Thr Ser Leu Ala Asp Trp Pro Leu Leu Met Cys
        115                 120                 125

Cys Leu Thr Leu Pro Thr Phe Pro Leu Ala Ala Leu Met Val Glu Lys
    130                 135                 140

Leu Ala Gln Arg Lys Leu Ile Val Val Ile Leu Leu His Ile Val Ile
145                 150                 155                 160

Thr Thr Ser Val Leu Val Tyr Pro Val Val Val Ile Leu Lys Cys Asp
                165                 170                 175

Ser Ala Val Leu Ser Gly Phe Val Leu Met Phe Leu Ala Ser Ile Ile
            180                 185                 190
```

```
Trp Leu Lys Leu Val Ser Phe Ala His Thr Asn Tyr Asp Ile Arg Met
        195                 200                 205

Leu Ser Lys Ser Ile Glu Lys Asp Pro Glu Asn Ile Lys Trp Pro Thr
    210                 215                 220

Phe Lys Arg Leu Ser Tyr Phe Met Leu Ala Pro Thr Leu Cys Tyr Gln
225                 230                 235                 240

Gly Ala Ser Leu His Asp Phe Ser Trp Tyr Phe Ile Tyr Ile Ala Val
                245                 250                 255

Cys Ile Leu Asn Met Ser Phe Ile Phe Gln Tyr Ile Asn Pro Ile Val
            260                 265                 270

Lys Asn Ser Lys His Pro Leu Lys Gly Asn Phe Leu Asn Ala Ile Glu
        275                 280                 285

Arg Val Leu Lys Leu Ser Val Pro Thr Leu Tyr Val Trp Leu Cys Met
    290                 295                 300

Phe Tyr Cys Phe Phe His Leu Trp Leu Asn Ile Leu Ala Glu Leu Leu
305                 310                 315                 320

Cys Phe Gly Asp Arg Glu Phe Tyr Lys Asp Trp Trp Asn Ala Lys Thr
                325                 330                 335

Val Glu Glu Tyr Trp Arg Met Trp Asn Met Pro Val His Lys Trp Val
            340                 345                 350

Ile Arg His Ile Tyr Phe Pro Cys Ile Arg Asn Gly Phe Ser Lys Gly
        355                 360                 365

Val Ala Ile Leu Ile Ser Phe Leu Val Ser Ala Ala Phe His Glu Leu
    370                 375                 380

Cys Val Ala Val Pro Cys His Ile Phe Lys Phe Trp Ala Phe Ile Gly
385                 390                 395                 400

Ile Met Phe Gln Ile Pro Leu Val Phe Leu Thr Lys Tyr Leu Gln Asp
                405                 410                 415

Lys Phe Asn Asn Thr Met Val Gly Asn Met Ile Phe Trp Phe Phe Phe
            420                 425                 430

Ser Ile Leu Gly Gln Pro Met Cys Val Leu Leu Tyr Tyr His Asp Val
        435                 440                 445

Met Asn Arg Gln Gln Ala Gln Thr Asn Arg
    450                 455

<210> SEQ ID NO 10
<211> LENGTH: 1863
<212> TYPE: DNA
<213> ORGANISM: Lolium perenne

<400> SEQUENCE: 10

tactggagaa tgtggaatat ggtatgcttc tcttttctct accatgttac tttcttgcaa      60

ccttctggca attagagacc atatttctcc ataagcttgc ttgcattttt ttccaaggag     120

ttacaatgtt agaatgttta tcttattcaa agaaacagca tgagaatatg acaaactcaa     180

atgaaactgt ttgacaagaa cagcacattt tctatgatta aactttacca aatttcagta     240

ggtgaaggag tggcaaatac ctcgaatttt attgatttat gttatattgc ttgctgtttc     300

tccactaatt tgtttatttg tttttaacta ttttttattt atgtctgcat tcacagcctg     360

tgcataaatg ggttgttcgc catatatatt ttccccccag gcgcagtggt atatcaaagg     420

taaactgcta gctgttagac tactaagctc ttcatgcttt ggacatagtt taagctgggt     480

cctttgtgct gtttttcttg caggaagttg ctgtctttgt atcatttttt gtatctgccg     540

tgctccatga ggtaaaacat gccccttttct ttcgcaggca cttcatatat ccacaccagt    600
```

```
tatttagctc tcttttccgc tcttttgatc caagttggtt ctgagcttat aataataaaa    660

tgttgcagtt gtgtggttac gtcatttttt aatgttgtta aataaaaagt tgctagttgg    720

cctgttttga ttaactcatg atgccttatc ttaattaatg tacaccagtt atgtgttgct    780

gtcccctgcc gaattgtcaa gttctgggca ttcttaggga tcatgctgca ggtatgtcaa    840

aaattactgc tgaatggatg atgtgccatc tcattcactt cattgattag tatgttgcta    900

ctttctaagt aaaaatgtgt ctgcttttga ggatcatctt gcattttgta tatatgtgga    960

aatttatttg taagcaggat ggatgggccc atcctgttat accatctgag acaatgaact   1020

ttgcttattc catatccttt cctcccttgt taccagatcc ctcttatcat attgacatca   1080

tacctgaaga gcaaattcag agatacaatg gttagccatc tttaccatgt ttgtactaaa   1140

aggatatata ctttgatgtt agaccagttc taatttgtgc caccttcaac aggccggcaa   1200

catgatattc tggttctttt tctgcatcta cggacagcct atgtgcgttc tcctgtacta   1260

ccatgatgtg atgaatagga ttgggaagac gggatagaag aacacatatc gctcttcctg   1320

tttatggcaa aaggatgtta cgacatggag ctgcataatt tccaacactg gcatacatcc   1380

ttccagtctt tcttggaaaa tacagtgcat aattttacca tgttttgtgg cgggtggttg   1440

caggcttgtg actgtacata agcttcagtc tatgatatag aatcctgcct aattgctggc   1500

gtggcggtga taattttttg tagagatgga agctttatta tccctggcct gtgcgttaca   1560

tatgcatacg gccttaatta ttttaccgtg tatcacaaat tgttaggaag cgtccccgtg   1620

cccttagggt aatttgttaa taaaaaataa ttacatttgt ttctcttgaa tagaagaggc   1680

aactgatgat gtagtatttt ttgtttttgt tttgtacaga tgtatctaga cacaaataca   1740

tgtatctaga aaaagttcag actattaata ttgttgccgt aaggtgattg tggggcaatc   1800

taagataagg tactattcaa tctttttttct cgaaaagaga cgatgtacat ggagtattta   1860

ttt                                                                  1863
```

```
<210> SEQ ID NO 11
<211> LENGTH: 596
<212> TYPE: PRT
<213> ORGANISM: Lolium perenne

<400> SEQUENCE: 11

Tyr Trp Arg Met Trp Asn Met Val Cys Phe Ser Phe Leu Tyr His Val
1               5                   10                  15

Thr Phe Leu Gln Pro Ser Gly Asn Arg Pro Tyr Phe Ser Ile Ser Leu
            20                  25                  30

Leu Ala Phe Phe Ser Lys Glu Leu Gln Cys Asn Val Tyr Leu Ile Gln
        35                  40                  45

Arg Asn Ser Met Arg Ile Gln Thr Gln Met Lys Leu Phe Asp Lys Asn
    50                  55                  60

Ser Thr Phe Ser Met Ile Lys Leu Tyr Gln Ile Ser Val Gly Glu Gly
65                  70                  75                  80

Val Ala Asn Thr Ser Asn Phe Ile Asp Leu Cys Tyr Ile Ala Cys Cys
                85                  90                  95

Phe Ser Thr Asn Leu Phe Ile Cys Phe Leu Phe Phe Ile Tyr Val Cys
            100                 105                 110

Ile His Ser Leu Cys Ile Asn Gly Leu Phe Ala Ile Tyr Ile Phe Pro
        115                 120                 125

Pro Gly Ala Val Val Tyr Gln Arg Thr Ala Ser Cys Thr Thr Lys Leu
    130                 135                 140

Phe Met Leu Trp Thr Phe Lys Leu Gly Pro Leu Cys Cys Phe Ser Cys
```

```
145                 150                 155                 160

Arg Lys Leu Leu Ser Leu Tyr His Phe Leu Tyr Leu Pro Cys Ser Met
                165                 170                 175

Arg Asn Met Pro Leu Ser Phe Ala Gly Thr Ser Tyr Ile His Thr Ser
            180                 185                 190

Tyr Leu Ala Leu Phe Ser Ala Leu Leu Ile Gln Val Gly Ser Glu Leu
        195                 200                 205

Ile Ile Ile Lys Cys Cys Ser Cys Val Val Thr Ser Phe Phe Asn Val
    210                 215                 220

Val Lys Lys Val Ala Ser Trp Pro Val Leu Ile Asn Ser Cys Leu Ile
225                 230                 235                 240

Leu Ile Asn Val His Gln Leu Cys Val Ala Val Pro Cys Arg Ile Val
                245                 250                 255

Lys Phe Trp Ala Phe Leu Gly Ile Met Leu Gln Val Cys Gln Lys Leu
            260                 265                 270

Leu Leu Asn Gly Cys Ala Ile Ser Phe Thr Ser Leu Ile Ser Met Leu
        275                 280                 285

Leu Leu Ser Lys Lys Cys Val Cys Phe Gly Ser Ser Cys Ile Leu Tyr
    290                 295                 300

Ile Cys Gly Asn Leu Phe Val Ser Arg Met Asp Gly Pro Ile Leu Leu
305                 310                 315                 320

Tyr His Leu Arg Gln Thr Leu Leu Ile Pro Tyr Pro Phe Leu Pro Cys
                325                 330                 335

Tyr Gln Ile Pro Leu Ile Ile Leu Thr Ser Tyr Leu Lys Ser Lys Phe
            340                 345                 350

Arg Asp Thr Met Val Ser His Leu Tyr His Val Cys Thr Lys Arg Ile
        355                 360                 365

Tyr Thr Leu Met Leu Asp Gln Phe Phe Val Pro Pro Ser Thr Gly Arg
    370                 375                 380

Gln His Asp Ile Leu Val Leu Phe Leu His Leu Arg Thr Ala Tyr Val
385                 390                 395                 400

Arg Ser Pro Val Leu Pro Cys Asp Glu Asp Trp Glu Asp Gly Ile Glu
                405                 410                 415

Glu His Ile Ser Leu Phe Leu Phe Met Ala Lys Gly Cys Tyr Asp Met
            420                 425                 430

Glu Leu His Asn Phe Gln His Trp His Thr Ser Phe Gln Ser Phe Leu
        435                 440                 445

Glu Asn Thr Val His Asn Phe Thr Met Phe Cys Gly Gly Trp Leu Gln
    450                 455                 460

Ala Cys Asp Cys Thr Ala Ser Val Tyr Asp Ile Glu Ser Cys Leu Ile
465                 470                 475                 480

Ala Gly Val Ala Val Ile Ile Phe Cys Arg Asp Gly Ser Phe Ile Ile
                485                 490                 495

Pro Gly Leu Cys Val Thr Tyr Ala Tyr Gly Leu Asn Tyr Phe Thr Val
            500                 505                 510

Tyr His Lys Leu Leu Gly Ser Val Pro Val Pro Leu Gly Phe Val Asn
        515                 520                 525

Lys Lys Leu His Leu Phe Leu Leu Asn Arg Arg Gly Asn Cys Ser Ile
    530                 535                 540

Phe Cys Phe Cys Phe Val Gln Met Tyr Leu Asp Thr Asn Thr Cys Ile
545                 550                 555                 560

Lys Lys Phe Arg Leu Leu Ile Leu Leu Pro Gly Asp Cys Gly Ala Ile
                565                 570                 575
```

```
Asp Lys Val Leu Phe Asn Leu Phe Ser Arg Lys Glu Thr Met Tyr Met
            580                 585                 590

Glu Tyr Leu Phe
        595


<210> SEQ ID NO 12
<211> LENGTH: 588
<212> TYPE: PRT
<213> ORGANISM: Lolium perenne
<220> FEATURE:
<221> NAME/KEY: misc_feature
<222> LOCATION: (588)..(588)
<223> OTHER INFORMATION: Xaa can be any naturally occurring amino acid

<400> SEQUENCE: 12

Thr Gly Glu Cys Gly Ile Trp Tyr Ala Ser Leu Phe Ser Thr Met Leu
1               5                   10                  15

Leu Ser Cys Asn Leu Leu Ala Ile Arg Asp His Ile Ser Pro Ala Cys
            20                  25                  30

Leu His Phe Phe Pro Arg Ser Tyr Asn Val Arg Met Phe Ile Leu Phe
        35                  40                  45

Lys Glu Thr Ala Glu Tyr Asp Lys Leu Lys Asn Cys Leu Thr Arg Thr
    50                  55                  60

Ala His Phe Leu Leu Asn Phe Thr Lys Phe Gln Val Lys Glu Trp Gln
65                  70                  75                  80

Ile Pro Arg Ile Leu Leu Ile Tyr Val Ile Leu Leu Ala Val Ser Pro
                85                  90                  95

Leu Ile Cys Leu Phe Val Phe Asn Tyr Phe Leu Phe Met Ser Ala Phe
            100                 105                 110

Thr Ala Cys Ala Met Gly Cys Ser Pro Tyr Ile Phe Ser Pro Gln Ala
        115                 120                 125

Gln Trp Tyr Ile Lys Gly Lys Leu Leu Ala Val Arg Leu Leu Ser Ser
    130                 135                 140

Ser Cys Phe Gly His Ser Leu Ser Trp Val Leu Cys Ala Val Phe Leu
145                 150                 155                 160

Ala Gly Ser Cys Cys Leu Cys Ile Ile Phe Cys Ile Cys Arg Ala Pro
                165                 170                 175

Gly Lys Thr Cys Pro Phe Leu Ser Gln Ala Leu His Ile Ser Thr Pro
            180                 185                 190

Val Ile Leu Ser Phe Pro Leu Phe Ser Lys Leu Val Leu Ser Leu Asn
        195                 200                 205

Val Ala Val Val Trp Leu Arg His Phe Leu Met Leu Leu Asn Lys Lys
    210                 215                 220

Leu Leu Val Gly Leu Phe Leu Thr His Asp Ala Leu Ser Leu Met Tyr
225                 230                 235                 240

Thr Ser Tyr Val Leu Leu Ser Pro Ala Glu Leu Ser Ser Ser Gly His
                245                 250                 255

Ser Gly Ser Cys Cys Arg Tyr Val Lys Asn Tyr Cys Met Asp Asp Val
            260                 265                 270

Pro Ser His Ser Leu His Leu Val Cys Cys Tyr Phe Leu Ser Lys Asn
        275                 280                 285

Val Ser Ala Phe Glu Asp His Leu Ala Phe Cys Ile Tyr Val Glu Ile
    290                 295                 300

Tyr Leu Ala Gly Trp Met Gly Pro Ser Cys Tyr Thr Ile Asp Asn Glu
305                 310                 315                 320

Leu Cys Leu Phe His Ile Leu Ser Ser Leu Val Thr Arg Ser Leu Leu
                325                 330                 335
```

```
Ser Tyr His His Thr Arg Ala Asn Ser Glu Ile Gln Trp Leu Ala Ile
            340                 345                 350

Phe Thr Met Phe Val Leu Lys Gly Tyr Ile Leu Cys Thr Ser Ser Asn
        355                 360                 365

Leu Cys His Leu Gln Gln Ala Gly Asn Met Ile Phe Trp Phe Phe Phe
    370                 375                 380

Cys Ile Tyr Gly Gln Pro Met Cys Val Leu Leu Tyr Tyr His Asp Val
385                 390                 395                 400

Met Asn Arg Ile Gly Lys Thr Gly Lys Asn Thr Tyr Arg Ser Ser Cys
                405                 410                 415

Leu Trp Gln Lys Asp Val Thr Thr Trp Ser Cys Ile Ile Ser Asn Thr
            420                 425                 430

Gly Ile His Pro Ser Ser Leu Ser Trp Lys Ile Gln Cys Ile Ile Leu
        435                 440                 445

Pro Cys Phe Val Ala Gly Gly Cys Arg Leu Val Thr Val His Lys Leu
    450                 455                 460

Gln Ser Met Ile Asn Pro Ala Leu Leu Ala Trp Arg Phe Phe Val Glu
465                 470                 475                 480

Met Glu Ala Leu Leu Ser Leu Ala Cys Ala Leu His Met His Thr Ala
                485                 490                 495

Leu Ile Ile Leu Pro Cys Ile Thr Asn Cys Glu Ala Ser Pro Cys Pro
            500                 505                 510

Gly Asn Leu Leu Ile Lys Asn Asn Tyr Ile Cys Phe Ser Ile Glu Glu
        515                 520                 525

Ala Thr Asp Asp Val Val Phe Phe Val Phe Val Leu Tyr Arg Cys Ile
    530                 535                 540

Thr Gln Ile His Val Ser Arg Lys Ser Ser Asp Tyr Tyr Cys Cys Arg
545                 550                 555                 560

Lys Val Ile Val Gly Gln Ser Lys Ile Arg Tyr Tyr Ser Ile Phe Phe
                565                 570                 575

Leu Glu Lys Arg Arg Cys Thr Trp Ser Ile Tyr Xaa
            580                 585


<210> SEQ ID NO 13
<211> LENGTH: 588
<212> TYPE: PRT
<213> ORGANISM: Lolium perenne
<220> FEATURE:
<221> NAME/KEY: misc_feature
<222> LOCATION: (588)..(588)
<223> OTHER INFORMATION: Xaa can be any naturally occurring amino acid

<400> SEQUENCE: 13

Leu Glu Asn Val Glu Tyr Gly Met Leu Leu Phe Ser Leu Pro Cys Tyr
1               5                   10                  15

Phe Leu Ala Thr Phe Trp Gln Leu Glu Thr Ile Phe Leu His Lys Leu
            20                  25                  30

Ala Cys Ile Phe Phe Gln Gly Val Thr Met Leu Glu Cys Leu Ser Tyr
        35                  40                  45

Ser Lys Lys Gln His Glu Asn Met Thr Asn Ser Asn Glu Thr Val Gln
    50                  55                  60

Glu Gln His Ile Phe Tyr Asp Thr Leu Pro Asn Phe Ser Arg Arg Ser
65                  70                  75                  80

Gly Lys Tyr Leu Glu Phe Tyr Phe Met Leu Tyr Cys Leu Leu Phe Leu
                85                  90                  95

His Phe Val Tyr Leu Phe Leu Thr Ile Phe Tyr Leu Cys Leu His Ser
```

```
            100                 105                 110

Gln Pro Val His Lys Trp Val Val Arg His Ile Tyr Phe Pro Pro Arg
        115                 120                 125

Arg Ser Gly Ile Ser Lys Val Asn Cys Leu Leu Asp Tyr Ala Leu His
    130                 135                 140

Ala Leu Asp Ile Val Ala Gly Ser Phe Val Leu Phe Phe Leu Gln Glu
145                 150                 155                 160

Val Ala Val Phe Val Ser Phe Phe Val Ser Ala Val Leu His Glu Val
                165                 170                 175

Lys His Ala Pro Phe Phe Arg Arg His Phe Ile Tyr Pro His Gln Leu
            180                 185                 190

Phe Ser Ser Leu Phe Arg Ser Phe Asp Pro Ser Trp Phe Ala Tyr Asn
        195                 200                 205

Asn Lys Met Leu Gln Leu Cys Gly Tyr Val Ile Phe Cys Cys Ile Lys
    210                 215                 220

Ser Cys Leu Ala Cys Phe Asp Leu Met Met Pro Tyr Leu Asn Cys Thr
225                 230                 235                 240

Pro Val Met Cys Cys Cys Pro Leu Pro Asn Cys Gln Val Leu Gly Ile
                245                 250                 255

Leu Arg Asp His Ala Ala Gly Met Ser Lys Ile Thr Ala Glu Trp Met
            260                 265                 270

Met Cys His Leu Ile His Phe Ile Asp Tyr Val Ala Thr Phe Val Lys
        275                 280                 285

Met Cys Leu Leu Leu Arg Ile Ile Leu His Phe Val Tyr Met Trp Lys
    290                 295                 300

Phe Ile Cys Lys Gln Asp Gly Trp Ala His Pro Val Ile Pro Ser Glu
305                 310                 315                 320

Thr Met Asn Phe Ala Tyr Ser Ile Ser Phe Pro Pro Leu Leu Pro Asp
                325                 330                 335

Pro Ser Tyr His Ile Asp Ile Ile Pro Glu Glu Gln Ile Gln Arg Tyr
            340                 345                 350

Asn Gly Pro Ser Leu Pro Cys Leu Tyr Lys Asp Ile Tyr Phe Asp Val
        355                 360                 365

Arg Pro Val Leu Ile Cys Ala Thr Phe Asn Arg Pro Ala Thr Tyr Ser
    370                 375                 380

Gly Ser Phe Ser Ala Ser Thr Asp Ser Leu Cys Ala Phe Ser Cys Thr
385                 390                 395                 400

Thr Met Met Ile Gly Leu Gly Arg Arg Asp Arg Arg Thr His Ile Ala
                405                 410                 415

Leu Pro Val Tyr Gly Lys Arg Met Leu Arg His Gly Ala Ala Phe Pro
            420                 425                 430

Thr Leu Ala Tyr Ile Leu Pro Val Phe Leu Gly Lys Tyr Ser Ala Phe
        435                 440                 445

Tyr His Val Leu Trp Arg Val Val Ala Gly Leu Leu Tyr Ile Ser Phe
    450                 455                 460

Ser Leu Tyr Arg Ile Leu Pro Asn Cys Trp Arg Gly Gly Asp Asn Phe
465                 470                 475                 480

Leu Arg Trp Lys Leu Tyr Tyr Pro Trp Pro Val Arg Tyr Ile Cys Ile
                485                 490                 495

Arg Pro Leu Phe Tyr Arg Val Ser Gln Ile Val Arg Lys Arg Pro Arg
            500                 505                 510

Ala Leu Arg Val Ile Cys Lys Ile Ile Thr Phe Val Ser Leu Glu Lys
        515                 520                 525
```

```
Arg Gln Leu Met Met Tyr Phe Leu Phe Leu Phe Cys Thr Asp Val Ser
    530                 535                 540

Arg His Lys Tyr Met Tyr Leu Glu Lys Val Gln Thr Ile Asn Ile Val
545                 550                 555                 560

Ala Val Arg Leu Trp Gly Asn Leu Arg Gly Thr Ile Gln Ser Phe Phe
                565                 570                 575

Ser Lys Arg Asp Asp Val His Gly Val Phe Ile Xaa
            580                 585


<210> SEQ ID NO 14
<211> LENGTH: 59
<212> TYPE: PRT
<213> ORGANISM: Oryza sativa

<400> SEQUENCE: 14

Val Arg His Ile Tyr Phe Pro Cys Met Arg Asn Gly Ile Ser Lys Glu
1               5                   10                  15

Val Ala Leu Ile Ser Phe Leu Val Ser Ala Val Leu His Glu Ile Cys
            20                  25                  30

Val Ala Val Pro Cys Arg Ile Leu Lys Phe Trp Ala Phe Leu Gly Ile
        35                  40                  45

Met Leu Gln Ile Pro Leu Ile Val Leu Thr Ala
    50                  55


<210> SEQ ID NO 15
<211> LENGTH: 117
<212> TYPE: PRT
<213> ORGANISM: Lolium perenne

<400> SEQUENCE: 15

Tyr Trp Arg Met Trp Asn Met Pro Val His Lys Trp Val Val Arg His
1               5                   10                  15

Ile Tyr Phe Pro Pro Arg Arg Ser Gly Ile Ser Lys Glu Val Ala Val
            20                  25                  30

Phe Val Ser Phe Phe Val Ser Ala Val Leu His Glu Leu Cys Val Ala
        35                  40                  45

Val Pro Cys Arg Ile Val Lys Phe Trp Ala Phe Leu Gly Ile Met Leu
    50                  55                  60

Gln Ile Pro Leu Ile Ile Leu Thr Ser Tyr Leu Lys Ser Lys Phe Arg
65                  70                  75                  80

Asp Thr Met Ala Gly Asn Met Ile Phe Trp Phe Phe Phe Cys Ile Tyr
                85                  90                  95

Gly Gln Pro Met Cys Val Leu Leu Tyr Tyr His Asp Val Met Asn Arg
            100                 105                 110

Ile Gly Lys Thr Gly
        115


<210> SEQ ID NO 16
<211> LENGTH: 458
<212> TYPE: PRT
<213> ORGANISM: Oryza sativa

<400> SEQUENCE: 16

Met Ala Pro Pro Pro Ser Leu Ala Pro Asp Arg Gly Gly Gly Glu Pro
1               5                   10                  15

Asp Asp Ala Leu Arg Leu Arg Ala Arg Ala Ala Ala Ala Ala Gly Asp
            20                  25                  30

Ala Pro Ala Pro Gln Gln Gln Gln Glu Gln Arg His Gln Glu Gln Gln
        35                  40                  45
```

```
Gln Gln Leu Leu Trp Tyr Arg Ala Ser Ala Pro Ala His Arg Arg Val
    50                  55                  60

Arg Glu Ser Pro Leu Ser Ser Asp Ala Ile Phe Arg Gln Ser His Ala
65                  70                  75                  80

Gly Leu Leu Asn Leu Cys Ile Val Val Leu Val Ala Val Asn Ser Arg
                85                  90                  95

Leu Ile Ile Glu Asn Leu Met Lys Tyr Gly Leu Leu Ile Arg Ala Gly
            100                 105                 110

Phe Trp Phe Ser Gly Thr Ser Leu Ala Asp Trp Pro Leu Leu Met Cys
        115                 120                 125

Cys Leu Thr Leu Pro Thr Phe Pro Leu Ala Ala Leu Met Val Glu Lys
    130                 135                 140

Leu Ala Gln Arg Lys Leu Ile Val Val Ile Leu Leu His Ile Val Ile
145                 150                 155                 160

Thr Thr Ser Val Leu Val Tyr Pro Val Val Val Ile Leu Lys Cys Asp
                165                 170                 175

Ser Ala Val Leu Ser Gly Phe Val Leu Met Phe Leu Ala Ser Ile Ile
            180                 185                 190

Trp Leu Lys Leu Val Ser Phe Ala His Thr Asn Tyr Asp Ile Arg Met
        195                 200                 205

Leu Ser Lys Ser Ile Glu Lys Asp Pro Glu Asn Ile Lys Trp Pro Thr
    210                 215                 220

Phe Lys Arg Leu Ser Tyr Phe Met Leu Ala Pro Thr Leu Cys Tyr Gln
225                 230                 235                 240

Gly Ala Ser Leu His Asp Phe Ser Trp Tyr Phe Ile Tyr Ile Ala Val
                245                 250                 255

Cys Ile Leu Asn Met Ser Phe Ile Phe Gln Tyr Ile Asn Pro Ile Val
            260                 265                 270

Lys Asn Ser Lys His Pro Leu Lys Gly Asn Phe Leu Asn Ala Ile Glu
        275                 280                 285

Arg Val Leu Lys Leu Ser Val Pro Thr Leu Tyr Val Trp Leu Cys Met
    290                 295                 300

Phe Tyr Cys Phe Phe His Leu Trp Leu Asn Ile Leu Ala Glu Leu Leu
305                 310                 315                 320

Cys Phe Gly Asp Arg Glu Phe Tyr Lys Asp Trp Trp Asn Ala Lys Thr
                325                 330                 335

Val Glu Glu Tyr Trp Arg Met Trp Asn Met Pro Val His Lys Trp Val
            340                 345                 350

Ile Arg His Ile Tyr Phe Pro Cys Ile Arg Asn Gly Phe Ser Lys Gly
        355                 360                 365

Val Ala Ile Leu Ile Ser Phe Leu Val Ser Ala Ala Phe His Glu Leu
    370                 375                 380

Cys Val Ala Val Pro Cys His Ile Phe Lys Phe Trp Ala Phe Ile Gly
385                 390                 395                 400

Ile Met Phe Gln Ile Pro Leu Val Phe Leu Thr Lys Tyr Leu Gln Asp
                405                 410                 415

Lys Phe Asn Asn Thr Met Val Gly Asn Met Ile Phe Trp Phe Phe Phe
            420                 425                 430

Ser Ile Leu Gly Gln Pro Met Cys Val Leu Leu Tyr Tyr His Asp Val
        435                 440                 445

Met Asn Arg Gln Gln Ala Gln Thr Asn Arg
    450                 455
```

<210> SEQ ID NO 17
<211> LENGTH: 520
<212> TYPE: PRT
<213> ORGANISM: Arabidopsis thaliana

<400> SEQUENCE: 17

```
Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Lys Gln Ser His Ala Gly Leu Phe Asn Leu Cys Val Val Val Leu Ile
    130                 135                 140

Ala Val Asn Ser Arg Leu Ile Ile Glu Asn Leu Met Lys Tyr Gly Trp
145                 150                 155                 160

Leu Ile Arg Thr Asp Phe Trp Phe Ser Ser Arg Ser Leu Arg Asp Trp
                165                 170                 175

Pro Leu Phe Met Cys Cys Ile Ser Leu Ser Ile Phe Pro Leu Ala Ala
            180                 185                 190

Phe Thr Val Glu Lys Leu Val Leu Gln Lys Tyr Ile Ser Glu Pro Val
        195                 200                 205

Val Ile Phe Leu His Ile Ile Ile Thr Met Thr Glu Val Leu Tyr Pro
    210                 215                 220

Val Tyr Val Thr Leu Arg Cys Asp Ser Ala Phe Leu Ser Gly Val Thr
225                 230                 235                 240

Leu Met Leu Leu Thr Cys Ile Val Trp Leu Lys Leu Val Ser Tyr Ala
                245                 250                 255

His Thr Ser Tyr Asp Ile Arg Ser Leu Ala Asn Ala Ala Asp Lys Ala
            260                 265                 270

Asn Pro Glu Val Ser Tyr Tyr Val Ser Leu Lys Ser Leu Ala Tyr Phe
        275                 280                 285

Met Val Ala Pro Thr Leu Cys Tyr Gln Pro Ser Tyr Pro Arg Ser Ala
    290                 295                 300

Cys Ile Arg Lys Gly Trp Val Ala Arg Gln Phe Ala Lys Leu Val Ile
305                 310                 315                 320

Phe Thr Gly Phe Met Gly Phe Ile Ile Glu Gln Tyr Ile Asn Pro Ile
                325                 330                 335

Val Arg Asn Ser Lys His Pro Leu Lys Gly Asp Leu Leu Tyr Ala Ile
            340                 345                 350

Glu Arg Val Leu Lys Leu Ser Val Pro Asn Leu Tyr Val Trp Leu Cys
        355                 360                 365

Met Phe Tyr Cys Phe Phe His Leu Trp Leu Asn Ile Leu Ala Glu Leu
    370                 375                 380

Leu Cys Phe Gly Asp Arg Glu Phe Tyr Lys Asp Trp Trp Asn Ala Lys
```

```
385                 390                 395                 400

Ser Val Gly Asp Tyr Trp Arg Met Trp Asn Met Pro Val His Lys Trp
                405                 410                 415

Met Val Arg His Ile Tyr Phe Pro Cys Leu Arg Ser Lys Ile Pro Lys
            420                 425                 430

Thr Leu Ala Ile Ile Ile Ala Phe Leu Val Ser Ala Val Phe His Glu
        435                 440                 445

Leu Cys Ile Ala Val Pro Cys Arg Leu Phe Lys Leu Trp Ala Phe Leu
    450                 455                 460

Gly Ile Met Phe Gln Val Pro Leu Val Phe Ile Thr Asn Tyr Leu Gln
465                 470                 475                 480

Glu Arg Phe Gly Ser Thr Val Gly Asn Met Ile Phe Trp Phe Ile Phe
                485                 490                 495

Cys Ile Phe Gly Gln Pro Met Cys Val Leu Leu Tyr Tyr His Asp Leu
            500                 505                 510

Met Asn Arg Lys Gly Ser Met Ser
        515                 520


<210> SEQ ID NO 18
<211> LENGTH: 501
<212> TYPE: PRT
<213> ORGANISM: Brassica napus

<400> SEQUENCE: 18

Met Glu Ile Leu Asp Ser Gly Gly Val Thr Met Pro Thr Glu Asn Gly
1               5                   10                  15

Gly Ala Asp Leu Asp Thr Leu Arg His Arg Lys Pro Arg Ser Asp Ser
            20                  25                  30

Ser Asn Gly Leu Leu Pro Asp Ser Val Thr Val Ser Asp Ala Asp Val
        35                  40                  45

Arg Asp Arg Val Asp Ser Ala Val Glu Asp Thr Gln Gly Lys Ala Asn
    50                  55                  60

Leu Ala Gly Glu Asn Glu Ile Arg Glu Ser Gly Gly Glu Ala Gly Gly
65                  70                  75                  80

Asn Val Asp Val Arg Tyr Thr Tyr Arg Pro Ser Val Pro Ala His Arg
                85                  90                  95

Arg Val Arg Glu Ser Pro Leu Ser Ser Asp Ala Ile Phe Lys Gln Ser
            100                 105                 110

His Ala Gly Leu Phe Asn Leu Cys Val Val Val Leu Val Ala Val Asn
        115                 120                 125

Ser Arg Leu Ile Ile Glu Asn Leu Met Lys Tyr Gly Trp Leu Ile Arg
    130                 135                 140

Thr Asp Phe Trp Phe Ser Ser Thr Ser Leu Arg Asp Trp Pro Leu Phe
145                 150                 155                 160

Met Cys Cys Leu Ser Leu Ser Ile Phe Pro Leu Ala Ala Phe Thr Val
                165                 170                 175

Glu Lys Leu Val Leu Gln Lys Cys Ile Ser Glu Pro Val Val Ile Ile
            180                 185                 190

Leu His Ile Ile Ile Thr Met Thr Glu Val Leu Tyr Pro Val Tyr Val
        195                 200                 205

Thr Leu Arg Cys Asp Ser Ala Phe Leu Ser Gly Val Thr Leu Met Leu
    210                 215                 220

Leu Thr Cys Ile Val Trp Leu Lys Leu Val Ser Tyr Ala His Thr Asn
225                 230                 235                 240

Tyr Asp Ile Arg Thr Leu Ala Asn Ser Ser Asp Lys Ala Asn Pro Glu
```

```
                245                 250                 255

Val Ser Tyr Tyr Val Ser Leu Lys Ser Leu Ala Tyr Phe Met Leu Ala
            260                 265                 270

Pro Thr Leu Cys Tyr Gln Pro Ser Tyr Pro Arg Ser Pro Cys Ile Arg
        275                 280                 285

Lys Gly Trp Val Ala Arg Gln Phe Ala Lys Leu Ile Ile Phe Thr Gly
    290                 295                 300

Phe Met Gly Phe Ile Ile Glu Gln Tyr Ile Asn Pro Ile Val Arg Asn
305                 310                 315                 320

Ser Lys His Pro Leu Lys Gly Asp Leu Leu Tyr Gly Val Glu Arg Val
                325                 330                 335

Leu Lys Leu Ser Val Pro Asn Leu Tyr Val Trp Leu Cys Met Phe Tyr
            340                 345                 350

Cys Phe Phe His Leu Trp Leu Asn Ile Leu Ala Glu Leu Leu Cys Phe
        355                 360                 365

Gly Asp Arg Glu Phe Tyr Lys Asp Trp Trp Asn Ala Lys Ser Val Gly
    370                 375                 380

Asp Tyr Trp Arg Met Trp Asn Met Pro Val His Lys Trp Met Val Arg
385                 390                 395                 400

His Val Tyr Phe Pro Cys Leu Arg Arg Asn Ile Pro Lys Val Pro Ala
                405                 410                 415

Ile Ile Leu Ala Phe Leu Val Ser Ala Val Phe His Glu Leu Cys Ile
            420                 425                 430

Ala Val Pro Cys Arg Leu Phe Lys Leu Trp Ala Phe Leu Gly Ile Met
        435                 440                 445

Phe Gln Val Pro Leu Val Phe Ile Thr Asn Tyr Leu Gln Glu Arg Phe
    450                 455                 460

Gly Ser Met Val Gly Asn Met Ile Phe Trp Phe Thr Phe Cys Ile Phe
465                 470                 475                 480

Gly Gln Pro Met Cys Val Leu Leu Tyr Tyr His Asp Leu Met Asn Arg
                485                 490                 495

Lys Gly Lys Met Ser
            500


<210> SEQ ID NO 19
<211> LENGTH: 91
<212> TYPE: PRT
<213> ORGANISM: Medicago truncatula

<400> SEQUENCE: 19

Pro Lys Gly Ala Ala Val Leu Ile Ala Phe Met Val Ser Ala Leu Phe
1               5                   10                  15

His Glu Leu Cys Ile Ala Val Pro Cys His Ile Phe Lys Leu Trp Ala
            20                  25                  30

Phe Ser Gly Ile Met Phe Gln Val Pro Leu Val Leu Ile Thr Asn Tyr
        35                  40                  45

Leu Gln Asn Lys Phe Ser Asn Ser Met Val Gly Asn Met Phe Phe Trp
    50                  55                  60

Phe Thr Phe Cys Ile Leu Gly Gln Pro Met Cys Val Leu Leu Tyr Tyr
65                  70                  75                  80

His Asp Leu Met Asn Arg Asn Ser Lys Leu Asp
                85                  90


<210> SEQ ID NO 20
<211> LENGTH: 143
<212> TYPE: PRT
```

<213> ORGANISM: Glycine max
<220> FEATURE:
<221> NAME/KEY: misc_feature
<222> LOCATION: (61)..(62)
<223> OTHER INFORMATION: Xaa can be any naturally occurring amino acid

<400> SEQUENCE: 20

```
Asn Ile Leu Ala Glu Leu Leu Arg Phe Gly Asp Arg Glu Phe Tyr Lys
1               5                   10                  15

Asp Trp Trp Asn Ala Lys Thr Val Glu Asp Tyr Trp Arg Met Trp Asn
            20                  25                  30

Met Pro Val His Lys Trp Met Ile Arg His Leu Tyr Phe Pro Cys Leu
        35                  40                  45

Arg His Gly Leu Pro Lys Ala Ala Ala Leu Leu Ile Xaa Xaa Leu Val
    50                  55                  60

Ser Ala Leu Phe His Glu Leu Cys Ile Ala Val Pro Cys His Ile Phe
65                  70                  75                  80

Lys Leu Trp Ala Phe Gly Gly Ile Met Phe Gln Val Pro Leu Val Leu
                85                  90                  95

Ile Thr Asn Tyr Leu Gln Asn Lys Phe Arg Asn Ser Met Val Gly Asn
            100                 105                 110

Met Ile Phe Trp Phe Ile Phe Ser Ile Leu Gly Gln Pro Met Cys Val
        115                 120                 125

Leu Leu Tyr Tyr His Asp Leu Met Asn Arg Lys Gly Lys Leu Asp
    130                 135                 140
```

<210> SEQ ID NO 21
<211> LENGTH: 532
<212> TYPE: PRT
<213> ORGANISM: Nicotiana tabacum

<400> SEQUENCE: 21

```
Met Val Ile Met Glu Leu Pro Glu Ser Val Glu Met Thr Thr Thr Thr
1               5                   10                  15

Thr Thr Ser Gly Ile Glu Asn Leu Asn Ser Asp Leu Asn His Ser Val
            20                  25                  30

Arg Arg Arg Arg Gly Ser Asn Gly Phe Glu Ala Ala Ser Ala Ile Asn
        35                  40                  45

Ser Ser Asp Ala Asn Met Ser Glu Asp Arg Arg Asp Val Cys Gly Ser
    50                  55                  60

Gly Ala Gly Leu Glu Thr Val Asn Glu Arg Ser Lys Ser Val Gly Glu
65                  70                  75                  80

Ser Ser Asp Val Ile Arg Lys Glu Asp Asp Arg Asn Asp Asn Val Ala
                85                  90                  95

Asn Gly Glu Glu Ser Lys Ser Thr Glu Thr Thr Thr Thr Pro Phe Lys
            100                 105                 110

Phe Ala Tyr Arg Ala Ser Ala Pro Ala His Arg Arg Ile Lys Glu Ser
        115                 120                 125

Pro Leu Ser Ser Asp Ala Ile Phe Lys Gln Ser His Ala Gly Leu Phe
    130                 135                 140

Asn Leu Cys Val Val Val Leu Ile Ala Val Asn Ser Arg Leu Ile Ile
145                 150                 155                 160

Glu Asn Leu Met Lys Tyr Gly Leu Leu Ile Arg Ala Gly Phe Trp Phe
                165                 170                 175

Ser Ser Lys Ser Leu Arg Asp Trp Pro Leu Leu Met Cys Cys Leu Ser
            180                 185                 190

Leu Gln Ile Leu Pro Leu Ala Ala Phe Leu Val Glu Lys Leu Ala Gln
```

```
        195                 200                 205

Gln Arg His Leu Thr Glu Arg Ala Val Val Thr Leu His Ile Thr Ile
    210                 215                 220

Thr Thr Ala Ala Ile Leu Tyr Pro Val Leu Val Ile Leu Gly Cys Asp
225                 230                 235                 240

Ser Ala Phe Leu Phe Gly Val Ile Leu Met Leu Val Ala Cys Ile Val
                245                 250                 255

Trp Met Lys Leu Val Ser Tyr Ala His Thr Asn His Asp Met Arg Gln
            260                 265                 270

Leu Ala Lys Ser Thr Asp Lys Asp Glu Thr Ser Asp Gly Asp Phe Ser
        275                 280                 285

Tyr Asp Val Ser Phe Lys Ser Leu Ala Tyr Phe Met Val Ala Pro Thr
    290                 295                 300

Leu Cys Tyr Gln Leu Ser Tyr Pro His Thr Pro Cys Ile Arg Lys Gly
305                 310                 315                 320

Trp Val Ala Arg Gln Phe Ile Lys Leu Val Ile Phe Thr Gly Leu Met
                325                 330                 335

Gly Phe Ile Ile Glu Gln Tyr Ile Asn Pro Ile Val Gln Asn Ser Gln
            340                 345                 350

His Pro Leu Lys Gly Asn Leu Leu Tyr Ala Ile Glu Arg Val Leu Lys
        355                 360                 365

Leu Ser Val Pro Asn Leu Tyr Val Trp Leu Cys Met Phe Tyr Cys Phe
    370                 375                 380

Phe His Leu Trp Leu Asn Ile Leu Ala Glu Leu Leu Cys Phe Gly Asp
385                 390                 395                 400

Arg Glu Phe Tyr Lys Asp Trp Trp Asn Ala Lys Thr Ile Asp Glu Tyr
                405                 410                 415

Trp Arg Met Trp Asn Met Pro Val His Lys Trp Met Val Arg His Ile
            420                 425                 430

Tyr Phe Pro Cys Leu Arg Asn Gly Ile Pro Lys Gly Val Ala Ile Leu
        435                 440                 445

Ile Ala Phe Leu Val Ser Ala Val Phe His Glu Leu Cys Ile Ala Val
    450                 455                 460

Pro Cys Arg Leu Phe Lys Trp Trp Ala Phe Met Gly Ile Met Phe Gln
465                 470                 475                 480

Val Pro Leu Val Ile Leu Thr Asn Phe Leu Gln Asn Lys Phe Gln Ser
                485                 490                 495

Ser Met Val Gly Asn Met Met Phe Trp Cys Phe Phe Cys Ile Leu Gly
            500                 505                 510

Gln Pro Met Cys Val Leu Leu Tyr Tyr His Asp Val Met Asn Arg Lys
        515                 520                 525

Ser Ser Ala Arg
    530


<210> SEQ ID NO 22
<211> LENGTH: 534
<212> TYPE: PRT
<213> ORGANISM: Perilla frutescens

<400> SEQUENCE: 22

Met Ala Ile Leu Asp Ser Pro Glu Ile Leu Asp Thr Thr Ser Ser Ser
1               5                   10                  15

Ala Asp Asn Gly Ala Ala His His Thr Thr Leu Arg Arg Arg Gln Ser
            20                  25                  30

Ala Arg Ser Val Pro Pro Leu Leu Asp Ser Asp Ser Asn Ser Leu Glu
```

```
        35                  40                  45

Ala Glu Ser Ala Ile Asn Asp Ser Glu Asn Val Arg Asn Asp Ala Asn
    50                  55                  60

Leu Ile Glu Asn Leu Arg Gly Gly Ala Val Glu Ser Glu Asn Glu Lys
65                  70                  75                  80

Gln Glu Ser Tyr Gly Lys Glu Glu Gly Ala Lys Val Lys Glu Asn Gly
                85                  90                  95

Glu Thr Ser Asn Gly Asn Gly Thr Asp Val Met Ala Val Lys Phe Thr
            100                 105                 110

Phe Arg Pro Ala Ala Pro Ala His Arg Lys Asn Lys Glu Ser Pro Leu
        115                 120                 125

Ser Ser Asp Ala Ile Phe Lys Gln Ser His Ala Gly Leu Phe Asn Leu
    130                 135                 140

Cys Ile Val Val Leu Val Ala Val Asn Ser Arg Leu Ile Ile Glu Asn
145                 150                 155                 160

Leu Met Lys Tyr Gly Trp Leu Ile Lys Ser Gly Phe Trp Phe Ser Ser
                165                 170                 175

Thr Ser Leu Arg Asp Trp Pro Leu Leu Met Cys Cys Leu Ser Leu Pro
            180                 185                 190

Val Phe Ala Leu Ala Ser Phe Leu Val Glu Lys Leu Val Lys Leu Asn
        195                 200                 205

Tyr Ile Pro Glu Trp Val Ala Val Phe Leu His Val Thr Ile Thr Thr
    210                 215                 220

Val Glu Ile Leu Phe Pro Val Val Val Ile Leu Arg Cys Asp Ser Ala
225                 230                 235                 240

Val Leu Ser Gly Val Thr Leu Met Leu Phe Ala Cys Thr Val Trp Leu
                245                 250                 255

Lys Leu Val Ser Tyr Ala His Thr Asn Tyr Asp Leu Arg Val Leu Ala
            260                 265                 270

Lys Ser Leu Asp Lys Trp Glu Ala Met Ser Arg Tyr Trp Asn Leu Asp
        275                 280                 285

Tyr Ala Tyr Asp Val Ser Phe Lys Ser Leu Ala Tyr Phe Met Val Ala
    290                 295                 300

Pro Thr Leu Cys Tyr Gln Pro Ser Tyr Pro Arg Thr Ala Cys Ile Arg
305                 310                 315                 320

Lys Gly Trp Val Val Arg Gln Leu Ile Lys Leu Val Ile Phe Thr Gly
                325                 330                 335

Leu Met Gly Phe Ile Ile Glu Gln Tyr Ile Asn Pro Ile Val Gln Asn
            340                 345                 350

Ser Gln His Pro Leu Lys Gly Asn Leu Leu Tyr Ala Ile Glu Arg Val
        355                 360                 365

Leu Lys Leu Ser Val Pro Asn Leu Tyr Val Trp Leu Cys Met Phe Tyr
    370                 375                 380

Cys Phe Phe His Leu Trp Leu Asn Ile Leu Ala Glu Leu Leu Cys Phe
385                 390                 395                 400

Gly Asp Arg Glu Phe Tyr Lys Asp Trp Trp Asn Ala Arg Thr Val Glu
                405                 410                 415

Glu Tyr Trp Arg Met Trp Asn Met Pro Val His Lys Trp Met Val Arg
            420                 425                 430

His Ile Tyr Cys Pro Cys Leu Gln Asn Gly Ile Pro Lys Ile Val Ala
        435                 440                 445

Val Leu Ile Ala Phe Leu Val Ser Ala Ile Phe His Glu Leu Cys Val
    450                 455                 460
```

```
Ala Val Pro Cys Gln Ile Phe Lys Phe Trp Ala Phe Ser Gly Ile Met
465                 470                 475                 480

Leu Gln Val Pro Leu Val Ile Val Thr Asn Tyr Leu Gln Glu Lys Phe
                485                 490                 495

Lys Asn Ser Met Val Gly Asn Met Met Phe Trp Cys Phe Phe Cys Ile
            500                 505                 510

Phe Gly Gln Pro Met Cys Val Leu Leu Tyr Tyr His Asp Leu Met Asn
        515                 520                 525

Arg Lys Ala Ser Ala Arg
    530


<210> SEQ ID NO 23
<211> LENGTH: 25
<212> TYPE: DNA
<213> ORGANISM: Artificial
<220> FEATURE:
<223> OTHER INFORMATION: synthetic primer sequence

<400> SEQUENCE: 23

aggaagttgc tgtyttkrta tcatt                                            25


<210> SEQ ID NO 24
<211> LENGTH: 22
<212> TYPE: DNA
<213> ORGANISM: Artificial
<220> FEATURE:
<223> OTHER INFORMATION: synthetic primer sequence

<400> SEQUENCE: 24

tgtwtctgcy gtrctccatg ag                                               22


<210> SEQ ID NO 25
<211> LENGTH: 22
<212> TYPE: DNA
<213> ORGANISM: Artificial
<220> FEATURE:
<223> OTHER INFORMATION: synthetic primer sequence

<400> SEQUENCE: 25

ctaagaatgc ccagaacttg ag                                               22


<210> SEQ ID NO 26
<211> LENGTH: 267
<212> TYPE: DNA
<213> ORGANISM: Lolium perenne

<400> SEQUENCE: 26

tgtatctgcc gtgctccatg aggtaaaaca tgcccctttc tttgcgcagg cacttcatat     60

atccacacca gttatttagc tctcttttcc gctcttttga tccaagttgg ttctgagctt    120

ataataataa aatgttgcag ttgtgtggtt acgtcatttt ttaatgttgt taaataaaaa    180

gttgctagtt ggcctgtttt gattaactca tgatgcctta tcttaattaa tgtacaccag    240

ttatgtgttg ctgtcccctg ccgaatt                                        267


<210> SEQ ID NO 27
<211> LENGTH: 49
<212> TYPE: DNA
<213> ORGANISM: Lolium perenne

<400> SEQUENCE: 27

tgtatctgcc gtgctccatg agttatgtgt tgctgtcccc tgccgaatt                 49
```

<210> SEQ ID NO 28
<211> LENGTH: 18
<212> TYPE: DNA
<213> ORGANISM: Artificial
<220> FEATURE:
<223> OTHER INFORMATION: synthetic primer sequence

<400> SEQUENCE: 28
tgtatctgcc gtgctcca 18

<210> SEQ ID NO 29
<211> LENGTH: 18
<212> TYPE: DNA
<213> ORGANISM: Artificial
<220> FEATURE:
<223> OTHER INFORMATION: synthetic primer sequence

<400> SEQUENCE: 29
aattcggcag gggacagc 18

<210> SEQ ID NO 30
<211> LENGTH: 21
<212> TYPE: DNA
<213> ORGANISM: Artificial
<220> FEATURE:
<223> OTHER INFORMATION: synthetic primer sequence

<400> SEQUENCE: 30
taytggagaa tgtggaatat g 21

<210> SEQ ID NO 31
<211> LENGTH: 21
<212> TYPE: DNA
<213> ORGANISM: Artificial
<220> FEATURE:
<223> OTHER INFORMATION: synthetic primer sequence

<400> SEQUENCE: 31
cgaacaaccc atttatgcac a 21

<210> SEQ ID NO 32
<211> LENGTH: 378
<212> TYPE: DNA
<213> ORGANISM: Lolium perenne

<400> SEQUENCE: 32
tactggagaa tgtggaatat ggtatgcttc tcttttctct accatgttac tttcttgcaa 60
ccttctggca attagagacc atatttctcc ataagcttgc ttgcattttt ttccaaggag 120
ttacaatgtt agaatgttta tcttattcaa agaaacagca tgagaatatg acaaactcaa 180
atgaaactgt ttgacaagaa cagcacattt tctatgatta aactttacca aatttcagta 240
ggtgaaggag tggcaaatac ctcgaatttt attgatttat gttatattgc ttgctgtttc 300
tccactaatt tgtttatttg tttttaacta ttttttattt atgctgcatt cacagcctgt 360
gcataaatgg gttgttcg 378

<210> SEQ ID NO 33
<211> LENGTH: 732
<212> TYPE: DNA
<213> ORGANISM: Lolium perenne

<400> SEQUENCE: 33
tactggagaa tgtggaatat gcctgtgcat aaatgggttg ttcgccatat atattttccc 60
cccaggcgca gtggtatatc aaaggaagtt gctgtctttg tatcattttt tgtatctgcc 120

```
gtgctccatg agttatgtgt tgctgtcccc tgccgaattg tcaagttctg ggcattctta    180

gggatcatgc tgcagatccc tcttatcata ttgacatcat acctgaagag caaattcaga    240

gatacaatgg ccggcaacat gatattctgg ttctttttct gcatctacgg acagcctatg    300

tgcgttctcc tgtactacca tgatgtgatg aataggattg ggaagacggg atagaagaac    360

acatatcgct cttcctgttt atggcaaaag gatgttacga catggagctg cataatttcc    420

aacactggca tacatccttc cagtctttct tggaaaatac agtgcataat tttaccatgt    480

tttgtggcgg gtggttgcag gcttgtgact gtacataagc ttcagtctat gatatagaat    540

cctgcctaat tgctggcgtg gcggtgataa ttttttgtag agatggaagc tttattatcc    600

ctggcctgtg cgttacatat gcatacggcc ttaattattt taccgtgtat cacaaattgt    660

taggaagcgt ccccgtgccc ttagggtaat ttgttaataa aaaataatta catttgtttc    720

tcttgaatag aa                                                        732


<210> SEQ ID NO 34
<211> LENGTH: 19
<212> TYPE: DNA
<213> ORGANISM: Artificial
<220> FEATURE:
<223> OTHER INFORMATION: synthetic primer sequence

<400> SEQUENCE: 34

caggcgcagt ggtatatca                                                  19


<210> SEQ ID NO 35
<211> LENGTH: 19
<212> TYPE: DNA
<213> ORGANISM: Artificial
<220> FEATURE:
<223> OTHER INFORMATION: synthetic primer sequence

<400> SEQUENCE: 35

tggtagtaca ggagaacgc                                                  19


<210> SEQ ID NO 36
<211> LENGTH: 258
<212> TYPE: DNA
<213> ORGANISM: Lolium perenne

<400> SEQUENCE: 36

caggcgcagt ggtatatcaa aggaagttgc tgtctttgta tcattttttg tatctgccgt     60

gctccatgag ttatgtgttg ctgtcccctg ccgaattgtc aagttctggg cattcttagg    120

gatcatgctg cagatccctc ttatcatatt gacatcatac ctgaagagca aattcagaga    180

tacaatggcc ggcaacatga tattctggtt ctttttctgc atctacggac agcctatgtg    240

cgttctcctg tactacca                                                  258


<210> SEQ ID NO 37
<211> LENGTH: 85
<212> TYPE: PRT
<213> ORGANISM: Lolium perenne

<400> SEQUENCE: 37

Arg Arg Ser Gly Ile Ser Lys Glu Val Ala Val Phe Val Ser Phe Phe
1               5                   10                  15

Val Ser Ala Val Leu His Glu Leu Cys Val Ala Val Pro Cys Arg Ile
            20                  25                  30

Val Lys Phe Trp Ala Phe Leu Gly Ile Met Leu Gln Ile Pro Leu Ile
```

```
        35                  40                  45

Ile Leu Thr Ser Tyr Leu Lys Ser Lys Phe Arg Asp Thr Met Ala Gly
    50                  55                  60

Asn Met Ile Phe Trp Phe Phe Phe Cys Ile Tyr Gly Gln Pro Met Cys
65                  70                  75                  80

Val Leu Leu Tyr Tyr
                85


<210> SEQ ID NO 38
<211> LENGTH: 400
<212> TYPE: DNA
<213> ORGANISM: Lolium perenne

<400> SEQUENCE: 38

tactggagaa tgtggaatat gcctgtgcat aaatgggttg ttcgccatat atattttccc     60

cccaggcgca gtggtatatc aaaggaagtt gctgtctttg tatcattttt tgtatctgcc    120

gtgctccatg agttatgtgt tgctgtcccc tgccgaattg tcaagttctg ggcattctta    180

gggatcatgc tgcagatccc tcttatcata ttgacatcat acctgaagag caaattcaga    240

gatacaatgg ccggcaacat gatattctgg ttctttttct gcatctacgg acagcctatg    300

ccggcaacat gatattctgg ttctttttct gcatctacgg acagcctatg tgcgttctcc    360

tgtactacca tgatgtgatg aataggattg ggaagacggg                          400


<210> SEQ ID NO 39
<211> LENGTH: 25
<212> TYPE: DNA
<213> ORGANISM: Artificial
<220> FEATURE:
<223> OTHER INFORMATION: synthetic primer sequence

<400> SEQUENCE: 39

caccatggcg attttggatt ctgct                                           25


<210> SEQ ID NO 40
<211> LENGTH: 21
<212> TYPE: DNA
<213> ORGANISM: Artificial
<220> FEATURE:
<223> OTHER INFORMATION: synthetic primer sequence

<400> SEQUENCE: 40

tcatgacatc gatccttttc g                                               21


<210> SEQ ID NO 41
<211> LENGTH: 4143
<212> TYPE: DNA
<213> ORGANISM: Arabidopsis thaliana

<400> SEQUENCE: 41

ctttcctgcg ttatcccctg attctgtgga taaccgtatt accgcctttg agtgagctga     60

taccgctcgc cgcagccgaa cgaccgagcg cagcgagtca gtgagcgagg aagcggaaga    120

gcgcccaata cgcaaaccgc ctctccccgc gcgttggccg attcattaat gcagctggca    180

cgacaggttt cccgactgga aagcgggcag tgagcgcaac gcaattaata cgcgtaccgc    240

tagccaggaa gagtttgtag aaacgcaaaa aggccatccg tcaggatggc cttctgctta    300

gtttgatgcc tggcagttta tggcgggcgt cctgcccgcc accctccggg ccgttgcttc    360

acaacgttca aatccgctcc cggcggattt gtcctactca ggagagcgtt caccgacaaa    420

caacagataa aacgaaaggc ccagtcttcc gactgagcct ttcgttttat ttgatgcctg    480
```

```
gcagttccct actctcgcgt taacgctagc atggatgttt tcccagtcac gacgttgtaa    540
aacgacggcc agtcttaagc tcgggcccca aataatgatt ttattttgac tgatagtgac    600
ctgttcgttg caacaaattg atgagcaatg cttttttata atgccaactt tgtacaaaaa    660
agcaggctcc gcggccgccc ccttcaccat ggcgattttg gattctgctg gcgttactac    720
ggtgacggag aacggtggcg gagagttcgt cgatcttgat aggcttcgtc gacggaaatc    780
gagatcggat tcttctaacg gacttcttct ctctggttcc gataataatt ctccttcgga    840
tgatgttgga gctcccgccg acgttaggga tcggattgat tccgttgtta acgatgacgc    900
tcagggaaca gccaatttgg ccggagataa taacggtggt ggcgataata acggtggtgg    960
aagaggcggc ggagaaggaa gaggaaacgc cgatgctacg tttacgtatc gaccgtcggt   1020
tccagctcat cggagggcga gagagagtcc acttagctcc gacgcaatct tcaaacagag   1080
ccatgccgga ttattcaacc tctgtgtagt agttcttatt gctgtaaaca gtagactcat   1140
catcgaaaat cttatgaagt atggttggtt gatcagaacg gatttctggt ttagttcaag   1200
atcgctgcga gattggccgc ttttcatgtg ttgtatatcc ctttcgatct ttcctttggc   1260
tgcctttacg gttgagaaat tggtacttca gaaatacata tcagaacctg ttgtcatctt   1320
tcttcatatt attatcacca tgacagaggt tttgtatcca gtttacgtca ccctaaggtg   1380
tgattctgct tttttatcag gtgtcacttt gatgctcctc acttgcattg tgtggctaaa   1440
gttggtttct tatgctcata ctagctatga cataagatcc ctagccaatg cagctgataa   1500
ggccaatcct gaagtctcct actacgttag cttgaagagc ttggcatatt tcatggtcgc   1560
tcccacattg tgttatcagc caagttatcc acgttctgca tgtatacgga agggttgggt   1620
ggctcgtcaa tttgcaaaac tggtcatatt caccggattc atgggattta taatagaaca   1680
atatataaat cctattgtca ggaactcaaa gcatcctttg aaaggcgatc ttctatatgc   1740
tattgaaaga gtgttgaagc tttcagttcc aaatttatat gtgtggctct gcatgttcta   1800
ctgcttcttc cacctttggt taaacatatt ggcagagctt ctctgcttcg gggatcgtga   1860
attctacaaa gattggtgga atgcaaaaag tgtgggagat tactggagaa tgtggaatat   1920
gcctgttcat aaatggatgg ttcgacatat atacttcccg tgcttgcgca gcaagatacc   1980
aaagacactc gccattatca ttgctttcct agtctctgca gtctttcatg agctatgcat   2040
cgcagttcct tgtcgtctct tcaagctatg ggcttttctt gggattatgt ttcaggtgcc   2100
tttggtcttc atcacaaact atctacagga aaggtttggc tcaacggtgg ggaacatgat   2160
cttctggttc atcttctgca ttttcggaca accgatgtgt gtgcttcttt attaccacga   2220
cctgatgaac cgaaaaggat cgatgtcatg aaagggtggg cgcgccgacc cagctttctt   2280
gtacaaagtt ggcattataa gaaagcattg cttatcaatt tgttgcaacg aacaggtcac   2340
tatcagtcaa aataaaatca ttatttgcca tccagctgat atcccctata gtgagtcgta   2400
ttacatggtc atagctgttt cctggcagct ctggcccgtg tctcaaaatc tctgatgtta   2460
cattgcacaa gataaaaata tatcatcatg aacaataaaa ctgtctgctt acataaacag   2520
taatacaagg ggtgttatga gccatattca acgggaaacg tcgaggccgc gattaaattc   2580
caacatggat gctgatttat atgggtataa atgggctcgc gataatgtcg ggcaatcagg   2640
tgcgacaatc tatcgcttgt atgggaagcc cgatgcgcca gagttgtttc tgaaacatgg   2700
caaaggtagc gttgccaatg atgttacaga tgagatggtc agactaaact ggctgacgga   2760
atttatgcct cttccgacca tcaagcattt tatccgtact cctgatgatg catggttact   2820
caccactgcg atccccggaa aaacagcatt ccaggtatta gaagaatatc ctgattcagg   2880
```

tgaaaatatt gttgatgcgc tggcagtgtt cctgcgccgg ttgcattcga ttcctgtttg 2940
taattgtcct tttaacagcg atcgcgtatt tcgtctcgct caggcgcaat cacgaatgaa 3000
taacggtttg gttgatgcga gtgattttga tgacgagcgt aatggctggc ctgttgaaca 3060
agtctggaaa gaaatgcata aacttttgcc attctcaccg gattcagtcg tcactcatgg 3120
tgatttctca cttgataacc ttatttttga cgaggggaaa ttaataggtt gtattgatgt 3180
tggacgagtc ggaatcgcag accgatacca ggatcttgcc atcctatgga actgcctcgg 3240
tgagttttct ccttcattac agaaacggct ttttcaaaaa tatggtattg ataatcctga 3300
tatgaataaa ttgcagtttc atttgatgct cgatgagttt ttctaatcag aattggttaa 3360
ttggttgtaa cactggcaga gcattacgct gacttgacgg gacggcgcaa gctcatgacc 3420
aaaatccctt aacgtgagtt acgcgtcgtt ccactgagcg tcagaccccg tagaaaagat 3480
caaaggatct tcttgagatc cttttttct gcgcgtaatc tgctgcttgc aaacaaaaaa 3540
accaccgcta ccagcggtgg tttgtttgcc ggatcaagag ctaccaactc tttttccgaa 3600
ggtaactggc ttcagcagag cgcagatacc aaatactgtc cttctagtgt agccgtagtt 3660
aggccaccac ttcaagaact ctgtagcacc gcctacatac ctcgctctgc taatcctgtt 3720
accagtggct gctgccagtg gcgataagtc gtgtcttacc gggttggact caagacgata 3780
gttaccggat aaggcgcagc ggtcgggctg aacggggggt tcgtgcacac agcccagctt 3840
ggagcgaacg acctacaccg aactgagata cctacagcgt gagcattgag aaagcgccac 3900
gcttcccgaa gggagaaagg cggacaggta tccggtaagc ggcagggtcg gaacaggaga 3960
gcgcacgagg gagcttccag ggggaaacgc ctggtatctt tatagtcctg tcgggtttcg 4020
ccacctctga cttgagcgtc gatttttgtg atgctcgtca ggggggcgga gcctatggaa 4080
aaacgccagc aacgcggcct ttttacggtt cctggccttt tgctggcctt ttgctcacat 4140
gtt 4143

<210> SEQ ID NO 42
<211> LENGTH: 5600
<212> TYPE: DNA
<213> ORGANISM: Arabidopsis thaliana

<400> SEQUENCE: 42
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggcccca aataatgatt ttattttgac tgatagtgac 600
ctgttcgttg caacaaattg atgagcaatg cttttttata atgccaactt tgtacaaaaa 660
agcaggctcc gcggccgccc ccttcaccat ggcgattttg gattctgctg gcgttactac 720
ggtgacggag aacggtggcg gagagttcgt cgatcttgat aggcttcgtc gacggaaatc 780
gagatcggat tcttctaacg gacttcttct ctctggttcc gataataatt ctccttcgga 840

```
tgatgttgga gctcccgccg acgttaggga tcggattgat tccgttgtta acgatgacgc    900
tcagggaaca gccaatttgg ccggagataa taacggtggt ggcgataata acggtggtgg    960
aagaggcggc ggagaaggaa gaggaaacgc cgatgctacg tttacgtatc gaccgtcggt   1020
tccagctcat cggagggcga gagagagtcc acttagctcc gacgcaatct tcaaacaggt   1080
ttaaaatctc agaaatcttc gaatttggtg tttgcttgtt gttttatatg gaattgagtt   1140
tggtgattgt tttgcattgc agagccatgc cggattattc aacctctgtg tagtagttct   1200
tattgctgta aacagtagac tcatcatcga aaatcttatg aaggtttgct gttacttgtt   1260
tctcctttta ggaattgaat tgcttgaaaa tttatcagag acgaataact ttgttgttgc   1320
tatcattcat gtagtatggt tggttgatca gaacggattt ctggtttagt tcaagatcgc   1380
tgcgagattg gccgcttttc atgtgttggt aaaagaagat gtttttttatt tccagcaatg   1440
ttacattgtt atacgtataa tgatgagttt agtgatcaag ttcctctttg attcttcttt   1500
cttgttgcag tatatccctt tcgatctttc ctttggctgc ctttacggtt gagaaattgg   1560
tacttcagaa atacatatca gaacctgtga gtaattacta ttctccagcc attactgtaa   1620
tttttattga agacaagttt gtatcatgaa gaacttacaa gttctgtttt gaaaatgctc   1680
aaggttgtca tctttcttca tattattatc accatgacag aggttttgta tccagtttac   1740
gtcaccctaa ggtgatactg tttttctggt ctcagtttgt gatactgttt ttaagtttag   1800
ttgtctgacc cggtgatctt gaaaatggac aggtgtgatt ctgctttttt atcaggtgtc   1860
actttgatgc tcctcacttg cattgtgtgg ctaaagttgg tttcttatgc tcatactagc   1920
tatgacataa gatccctagc caatgcagct gataaggtaa aatacgaaaa agaagcgtat   1980
gtattagtca cttgcactgt gttactgttt taaccaaaca ctgttatgaa ctttaggcca   2040
atcctgaagt ctcctactac gttagcttga agagcttggc atatttcatg gtcgctccca   2100
cattgtgtta tcaggtaact gcaaagtgca tcaaccattc ttatacttgc aagagtttct   2160
tgtctaaacc tcggatcttt gcttttcccc agccaagtta tccacgttct gcatgtatac   2220
ggaagggttg ggtggctcgt caatttgcaa aactggtcat attcaccgga ttcatgggat   2280
ttataataga acaagtacgt tttcacatct tgctttatta gttttccttg gtgaaaatca   2340
tcatccctgc gttgtcacca cttgacttca tgttcttttg ttacattttg gcagtatata   2400
aatcctattg tcaggaactc aaagcatcct ttgaaaggcg atcttctata tgctattgaa   2460
agagtgttga agctttcagt tccaaattta tatgtgtggc tctgcatgtt ctactgcttc   2520
ttccaccttt ggtatgctgt gatcccatct ctttcaaaat aatttgcaaa ttcgaaaaac   2580
cgaaaaaggc taaatctcat acgaatttga tatttttagt ttcttagagt cggtgatgta   2640
atttcagtta ctgaacgcaa atctcttgtc caaaggttaa acatattggc agagcttctc   2700
tgcttcgggg atcgtgaatt ctacaaagat tggtggaatg caaaaagtgt gggagatgtg   2760
agctatttta ctcaaaagaa aacttatgat ttttaatgtt gtcgttgttt ttgggtcatc   2820
taactaacca aattcatgta ttcactgtct tcctttatca gtactggaga atgtggaata   2880
tggtatggtt ctcttcctaa acatcacctt cttttgtaca caaaatagaa gaagagagct   2940
aattaagatc ttgttttcct tgacagcctg ttcataaatg gatggttcga catatatact   3000
tcccgtgctt gcgcagcaag ataccaaagg tgagtgagat atataccgat atgcaattgt   3060
cgagatttgt ttctgtgata taaatttaac cctccacaca cttgtttttc agacactcgc   3120
cattatcatt gctttcctag tctctgcagt ctttcatgag gtatacatac tttctacatt   3180
gccctgtctc tagacgcatg aacacacgct agtgaaagaa atgctaatat tcaaagcatt   3240
```

```
gtttttactt aacgatcttg tgttacaaat ttccttttga cagctatgca tcgcagttcc   3300
ttgtcgtctc ttcaagctat gggcttttct tgggattatg tttcaggtta aaaaattact   3360
aaactgctgc agtcgatttt tactaaactc taatctcata ttctgaccaa ccaatttgtt   3420
tgagtaggtg cctttggtct tcatcacaaa ctatctacag gaaaggtttg gctcaacggt   3480
atgctctcaa aacccgagaa aatagaacga ataactcttt ctttcatagc ctagccattt   3540
aaatcgcaat gctgaaactt aataataaag gtgatctgtt ttggaatggg atcatattat   3600
taggtgggga acatgatctt ctggttcatc ttctgcattt tcggacaacc gatgtgtgtg   3660
cttctttatt accacgacct gatgaaccga aaaggatcga tgtcatgaaa gggtgggcgc   3720
gccgacccag ctttcttgta caaagttggc attataagaa agcattgctt atcaatttgt   3780
tgcaacgaac aggtcactat cagtcaaaat aaaatcatta tttgccatcc agctgatatc   3840
ccctatagtg agtcgtatta catggtcata gctgtttcct ggcagctctg gcccgtgtct   3900
caaaatctct gatgttacat tgcacaagat aaaaatatat catcatgaac aataaaactg   3960
tctgcttaca taaacagtaa tacaaggggt gttatgagcc atattcaacg ggaaacgtcg   4020
aggccgcgat taaattccaa catggatgct gatttatatg ggtataaatg ggctcgcgat   4080
aatgtcgggc aatcaggtgc gacaatctat cgcttgtatg ggaagcccga tgcgccagag   4140
ttgtttctga aacatggcaa aggtagcgtt gccaatgatg ttacagatga gatggtcaga   4200
ctaaactggc tgacggaatt tatgcctctt ccgaccatca agcattttat ccgtactcct   4260
gatgatgcat ggttactcac cactgcgatc cccggaaaaa cagcattcca ggtattagaa   4320
gaatatcctg attcaggtga aaatattgtt gatgcgctgg cagtgttcct gcgccggttg   4380
cattcgattc ctgtttgtaa ttgtcctttt aacagcgatc gcgtatttcg tctcgctcag   4440
gcgcaatcac gaatgaataa cggtttggtt gatgcgagtg attttgatga cgagcgtaat   4500
ggctggcctg ttgaacaagt ctggaaagaa atgcataaac ttttgccatt ctcaccggat   4560
tcagtcgtca ctcatggtga tttctcactt gataacctta tttttgacga ggggaaatta   4620
ataggttgta ttgatgttgg acgagtcgga atcgcagacc gataccagga tcttgccatc   4680
ctatggaact gcctcggtga gttttctcct tcattacaga aacggctttt tcaaaaatat   4740
ggtattgata atcctgatat gaataaattg cagtttcatt tgatgctcga tgagtttttc   4800
taatcagaat tggttaattg gttgtaacac tggcagagca ttacgctgac ttgacgggac   4860
ggcgcaagct catgaccaaa atcccttaac gtgagttacg cgtcgttcca ctgagcgtca   4920
gaccccgtag aaaagatcaa aggatcttct tgagatcctt tttttctgcg cgtaatctgc   4980
tgcttgcaaa caaaaaaacc accgctacca gcggtggttt gtttgccgga tcaagagcta   5040
ccaactcttt ttccgaaggt aactggcttc agcagagcgc agataccaaa tactgtcctt   5100
ctagtgtagc cgtagttagg ccaccacttc aagaactctg tagcaccgcc tacatacctc   5160
gctctgctaa tcctgttacc agtggctgct gccagtggcg ataagtcgtg tcttaccggg   5220
ttggactcaa gacgatagtt accggataag gcgcagcggt cgggctgaac ggggggttcg   5280
tgcacacagc ccagcttgga gcgaacgacc tacaccgaac tgagatacct acagcgtgag   5340
cattgagaaa gcgccacgct tcccgaaggg agaaaggcgg acaggtatcc ggtaagcggc   5400
agggtcggaa caggagagcg cacgagggag cttccagggg gaaacgcctg gtatctttat   5460
agtcctgtcg ggtttcgcca cctctgactt gagcgtcgat ttttgtgatg ctcgtcaggg   5520
gggcggagcc tatggaaaaa cgccagcaac gcggcctttt tacggttcct ggccttttgc   5580
tggccttttg ctcacatgtt                                               5600
```

<210> SEQ ID NO 43
<211> LENGTH: 21178
<212> TYPE: DNA
<213> ORGANISM: Arabidopsis thaliana

<400> SEQUENCE: 43

```
tcgacatctt gctgcgttcg gatattttcg tggagttccc gccacagacc cggattgaag     60
gcgagatcca gcaactcgcg ccagatcatc ctgtgacgga actttggcgc gtgatgactg    120
gccaggacgt cggccgaaag agcgacaagc agatcacgat tttcgacagc gtcggatttg    180
cgatcgagga tttttcggcg ctgcgctacg tccgcgaccg cgttgaggga tcaagccaca    240
gcagcccact cgaccttcta gccgacccag acgagccaag ggatcttttt ggaatgctgc    300
tccgtcgtca ggctttccga cgtttgggtg gttgaacaga agtcattatc gtacggaatg    360
ccagcactcc cgaggggaac cctgtggttg gcatgcacat acaaatggac gaacggataa    420
accttttcac gccctttaa atatccgtta ttctaataaa cgctcttttc tcttaggttt    480
acccgccaat atatcctgtc aaacactgat agtttaaact gaaggcggga aacgacaatc    540
tgatcatgag cggagaatta agggagtcac gttatgaccc ccgccgatga cgcgggacaa    600
gccgttttac gtttggaact gacagaaccg caacgattga aggagccact cagccccaat    660
acgcaaaccg cctctccccg cgcgttggcc gattcattaa tgcagctggc acgacaggtt    720
tcccgactgg aaagcgggca gtgagcgcaa cgcaattaat gtgagttagc tcactcatta    780
ggcaccccag gctttacact ttatgcttcc ggctcgtatg ttgtgtggaa ttgtgagcgg    840
ataacaattt cacacaggaa acagctatga ccatgattac gccaagctat ttaggtgaca    900
ctatagaata ctcaagctat gcatccaacg cgttgggagc tctcccatat cgacctgcag    960
gcggccgctc gacgaattaa ttccaatccc acaaaaatct gagcttaaca gcacagttgc   1020
tcctctcaga gcagaatcgg gtattcaaca ccctcatatc aactactacg ttgtgtataa   1080
cggtccacat gccggtatat acgatgactg gggttgtaca aaggcggcaa caaacggcgt   1140
tcccggagtt gcacacaaga aatttgccac tattacagag gcaagagcag cagctgacgc   1200
gtacacaaca agtcagcaaa cagacaggtt gaacttcatc cccaaaggag aagctcaact   1260
caagcccaag agctttgcta aggccctaac aagcccacca aagcaaaaag cccactggct   1320
cacgctagga accaaaaggc ccagcagtga tccagcccca aaagagatct cctttgcccc   1380
ggagattaca atggacgatt tcctctatct ttacgatcta ggaaggaagt tcgaaggtga   1440
aggtgacgac actatgttca ccactgataa tgagaaggtt agcctcttca atttcagaaa   1500
gaatgctgac ccacagatgg ttagagaggc ctacgcagca ggtctcatca agacgatcta   1560
cccgagtaac aatctccagg agatcaaata ccttcccaag aaggttaaag atgcagtcaa   1620
aagattcagg actaattgca tcaagaacac agagaaagac atatttctca agatcagaag   1680
tactattcca gtatggacga ttcaaggctt gcttcataaa ccaaggcaag taatagagat   1740
tggagtctct aaaaaggtag ttcctactga atctaaggcc atgcatggag tctaagattc   1800
aaatcgagga tctaacagaa ctcgccgtga agactggcga acagttcata cagagtcttt   1860
tacgactcaa tgacaagaag aaaatcttcg tcaacatggt ggagcacgac actctggtct   1920
actccaaaaa tgtcaaagat acagtctcag aagaccaaag ggctattgag acttttcaac   1980
aaaggataat ttcgggaaac ctcctcggat tccattgccc agctatctgt cacttcatcg   2040
aaaggacagt agaaaaggaa ggtggctcct acaaatgcca tcattgcgat aaaggaaagg   2100
ctatcattca agatctctct gccgacagtg gtcccaaaga tggaccccca cccacgagga   2160
```

```
gcatcgtgga aaaagaagac gttccaacca cgtcttcaaa gcaagtggat tgatgtgaca   2220
tctccactga cgtaagggat gacgcacaat cccactatcc ttcgcaagac ccttcctcta   2280
tataaggaag ttcatttcat ttggagagga cacgctcgag gaattccatg gtgagcaagg   2340
gccacgagct gttcaccggg gtggtgccca tcctggtcga gctggacggc gacgtaaacg   2400
gccacaagtt cagcgtgtcc ggcgagggcg agggcgatgc cacctacggc catctgaccc   2460
tgaagttcat ctgcaccacc ggcaagctgc ccgtgccctg gcccaccctc gtgaccacct   2520
tcacctacgg cgtgcagtgc ttcagccgct accccgacca catgaagcag cacgacttct   2580
gcaagtccgc catgcccgaa ggctacgtcc aggagcgcac catcttcttc aaggacgacg   2640
gcaactacaa gacccgcgcc gaggtgaagt tcgagggcga caccctggtg aaccgcatcg   2700
agctgaaggg catcgacttc aaggaggacg gcaacatcct ggggcacaag ctggagtaca   2760
actacaacag ccacaacgtc tatatcatgg ccgacaagca gaagaacggc atcaaggtga   2820
acttcaagat ccgccacaac atcgaggacg gcagcgtgca gctcgccgac cactaccagc   2880
agaacacccc catcggcgac ggccccgtgc tgctgcccga caaccactac ctgagcaccc   2940
agtccgccct gagcaaagac cccaacgaga agcgcgatca catggtcctg ctggagttcg   3000
tgaccgccgc cgggatcact cacggcatgg acgagctgta caagtaagat cgatcctcta   3060
gagtcctgct ttaatgagat atgcgagacg cctatgatcg catgatattt gctttcaatt   3120
ctgttgtgca cgttgtaaaa aacctgagca tgtgtagctc agatccttac cgccggtttc   3180
ggttcattct aatgaatata tcacccgtta ctatcgtatt tttatgaata atattctccg   3240
ttcaatttac tgattgtacc ctactactta tatgtacaat attaaaatga aaacaatata   3300
ttgtgctgaa taggtttata gcgacatcta tgatagagcg ccacaataac aaacaattgc   3360
gttttattat tacaaatcca attttaaaaa aagcggcaga accggtcaaa cctaaaagac   3420
tgattacata aatcttattc aaatttcaaa aggccccagg ggctagtatc tacgacacac   3480
cgagcggcga actaataacg ttcactgaag ggaactccgg ttccccgccg gcgcgcatgg   3540
gtgagattcc ttgaagttga gtattggccg tccgctctac cgaaagttac gggcaccatt   3600
caacccggtc cagcacggcg gccgggtaac cgacttgctg ccccgagaat tatgcagcat   3660
tttttggtg tatgtgggcc ccaaatgaag tgcaggtcaa accttgacag tgacgacaaa   3720
tcgttgggcg ggtccagggc gaattttgcg acaacatgtc gaggctcagc aggacctgca   3780
ggcatgcaag ctagcttact agtgatgcat attctatagt gtcacctaaa tctgcggccg   3840
ctcgacgaat taattccaat cccacaaaaa tctgagctta acagcacagt tgctcctctc   3900
agagcagaat cgggtattca acaccctcat atcaactact acgttgtgta taacggtcca   3960
catgccggta tatacgatga ctggggttgt acaaaggcgg caacaaacgg cgttcccgga   4020
gttgcacaca agaaatttgc cactattaca gaggcaagag cagcagctga cgcgtacaca   4080
acaagtcagc aaacagacag gttgaacttc atccccaaag gagaagctca actcaagccc   4140
aagagctttg ctaaggccct aacaagccca ccaaagcaaa aagcccactg gctcacgcta   4200
ggaaccaaaa ggcccagcag tgatccagcc ccaaaagaga tctcctttgc cccggagatt   4260
acaatggacg atttcctcta tctttacgat ctaggaagga agttcgaagg tgaaggtgac   4320
gacactatgt tcaccactga taatgagaag gttagcctct tcaatttcag aaagaatgct   4380
gacccacaga tggttagaga ggcctacgca gcaggtctca tcaagacgat ctacccgagt   4440
aacaatctcc aggagatcaa ataccttccc aagaaggtta aagatgcagt caaaagattc   4500
aggactaatt gcatcaagaa cacagagaaa gacatatttc tcaagatcag aagtactatt   4560
```

```
ccagtatgga cgattcaagg cttgcttcat aaaccaaggc aagtaataga gattggagtc   4620
tctaaaaagg tagttcctac tgaatctaag gccatgcatg gagtctaaga ttcaaatcga   4680
ggatctaaca gaactcgccg tgaagactgg cgaacagttc atacagagtc ttttacgact   4740
caatgacaag aagaaaatct tcgtcaacat ggtggagcac gacactctgg tctactccaa   4800
aaatgtcaaa gatacagtct cagaagacca aagggctatt gagacttttc aacaaaggat   4860
aatttcggga aacctcctcg gattccattg cccagctatc tgtcacttca tcgaaaggac   4920
agtagaaaag gaaggtggct cctacaaatg ccatcattgc gataaaggaa aggctatcat   4980
tcaagatctc tctgccgaca gtggtcccaa agatggaccc ccacccacga ggagcatcgt   5040
ggaaaaagaa gacgttccaa ccacgtcttc aaagcaagtg gattgatgtg acatctccac   5100
tgacgtaagg gatgacgcac aatcccacta tccttcgcaa gacccttcct ctatataagg   5160
aagttcattt catttggaga ggacacgctc gaggaattcg gtaccccatc acaagtttgt   5220
acaaaaaagc aggctccgcg gccgccccct tcaccatggc gattttggat tctgctggcg   5280
ttactacggt gacggagaac ggtggcggag agttcgtcga tcttgatagg cttcgtcgac   5340
ggaaatcgag atcggattct tctaacggac ttcttctctc tggttccgat aataattctc   5400
cttcggatga tgttggagct cccgccgacg ttagggatcg gattgattcc gttgttaacg   5460
atgacgctca gggaacagcc aatttggccg gagataataa cggtggtggc gataataacg   5520
gtggtggaag aggcggcgga gaaggaagag gaaacgccga tgctacgttt acgtatcgac   5580
cgtcggttcc agctcatcgg agggcgagag agagtccact tagctccgac gcaatcttca   5640
aacagagcca tgccggatta ttcaacctct gtgtagtagt tcttattgct gtaaacagta   5700
gactcatcat cgaaaatctt atgaagtatg gttggttgat cagaacggat ttctggttta   5760
gttcaagatc gctgcgagat tggccgcttt tcatgtgttg tatatccctt tcgatctttc   5820
ctttggctgc ctttacggtt gagaaattgg tacttcagaa atacatatca gaacctgttg   5880
tcatctttct tcatattatt atcaccatga cagaggtttt gtatccagtt tacgtcaccc   5940
taaggtgtga ttctgctttt ttatcaggtg tcactttgat gctcctcact tgcattgtgt   6000
ggctaaagtt ggtttcttat gctcatacta gctatgacat aagatcccta gccaatgcag   6060
ctgataaggc caatcctgaa gtctcctact acgttagctt gaagagcttg gcatatttca   6120
tggtcgctcc cacattgtgt tatcagccaa gttatccacg ttctgcatgt atacggaagg   6180
gttgggtggc tcgtcaattt gcaaaactgg tcatattcac cggattcatg ggatttataa   6240
tagaacaata tataaatcct attgtcagga actcaaagca tcctttgaaa ggcgatcttc   6300
tatatgctat tgaaagagtg ttgaagcttt cagttccaaa tttatatgtg tggctctgca   6360
tgttctactg cttcttccac ctttggttaa acatattggc agagcttctc tgcttcgggg   6420
atcgtgaatt ctacaaagat tggtggaatg caaaaagtgt gggagattac tggagaatgt   6480
ggaatatgcc tgttcataaa tggatggttc gacatatata cttcccgtgc ttgcgcagca   6540
agataccaaa gacactcgcc attatcattg ctttcctagt ctctgcagtc tttcatgagc   6600
tatgcatcgc agttccttgt cgtctcttca agctatgggc ttttcttggg attatgtttc   6660
aggtgccttt ggtcttcatc acaaactatc tacaggaaag gtttggctca acggtgggga   6720
acatgatctt ctggttcatc ttctgcattt tcggacaacc gatgtgtgtg cttctttatt   6780
accacgacct gatgaaccga aaaggatcga tgtcatgaaa gggtgggcgc gccgacccag   6840
ctttcttgta caaagtggtg atgggttcga aatcgataag cttggatcct ctagagtcct   6900
gctttaatga gatatgcgag acgcctatga tcgcatgata tttgctttca attctgttgt   6960
```

```
gcacgttgta aaaaacctga gcatgtgtag ctcagatcct taccgccggt ttcggttcat   7020
tctaatgaat atatcacccg ttactatcgt atttttatga ataatattct ccgttcaatt   7080
tactgattgt accctactac ttatatgtac aatattaaaa tgaaaacaat atattgtgct   7140
gaataggttt atagcgacat ctatgataga gcgccacaat aacaaacaat tgcgttttat   7200
tattacaaat ccaattttaa aaaaagcggc agaaccggtc aaacctaaaa gactgattac   7260
ataaatctta ttcaaatttc aaaaggcccc aggggctagt atctacgaca caccgagcgg   7320
cgaactaata acgttcactg aagggaactc cggttccccg ccggcgcgca tgggtgagat   7380
tccttgaagt tgagtattgg ccgtccgctc taccgaaagt tacgggcacc attcaacccg   7440
gtccagcacg gcggccgggt aaccgacttg ctgccccgag aattatgcag catttttttg   7500
gtgtatgtgg gccccaaatg aagtgcaggt caaaccttga cagtgacgac aaatcgttgg   7560
gcgggtccag ggcgaatttt gcgacaacat gtcgaggctc agcaggacct gcaggcatgc   7620
aagctagctt actagtgatg catattctat agtgtcacct aaatctgcgg ccgctgacca   7680
agtcagcttg gcactggccg tcgttttaca acgtcgtgac tgggaaaacc ctggcgttac   7740
ccaacttaat cgccttgcag cacatccccc tttcgccagc tggcgtaata gcgaagaggc   7800
ccgcaccgat cgcccttccc aacagttgcg cagcctgaat ggcgaatggg aaattgtaaa   7860
cgttaatatt ttgttaatat tttgttaaaa ttcgcgttaa atttttgtta aatcagctca   7920
tttttaacc aataggccga aatcggcaaa atcccttata aatcaaaaga atagaccgag   7980
atagggttga gtgttgttcc agtttggaac aagagtccac tattaaagaa cgtggactcc   8040
aacgtcaaag ggcgaaaaac cgtctatcag ggcgatggcc cactacgtga accatcaccc   8100
taatcaagtt ttttggggtc gaggtgccgt aaagcactaa atcggaaccc taaagggatg   8160
ccccgattta gagcttgacg gggaaagccg gcgaacgtgg cgagaaagga agggaagaaa   8220
gcgaaaggag cgggcgctag ggcgctggca agtgtagcgg tcacgctgcg cgtaaccacc   8280
acacccgccg cgcttaatgc gccgctacag ggcgcgtcag gtggcacttt tcggggaaat   8340
gtgcgcggaa cccctatttg tttatttttc taaatacatt caaatatgta tccgctcatg   8400
agacaataac cctgataaat gcttcaataa tattgaaaaa ggaagagtat gagtattcaa   8460
catttccgtg tcgcccttat tccctttttt gcggcatttt gccttcctgt ttttgctcac   8520
ccagaaacgc tggtgaaagt aaaagatgct gaagatcagt tgggtgcacg agtgggttac   8580
atcgaactgg atctcaacag cggtaagatc cttgagagtt ttcgccccga agaacgtttt   8640
ccaatgatga gcacttttaa agttctgcta tgtggcgcgg tattatcccg tattgacgcc   8700
gggcaagagc aactcggtcg ccgcatacac tattctcaga atgacttggt tgagtactca   8760
ccagtcacag aaaagcatct tacggatggc atgacagtaa gagaattatg cagtgctgcc   8820
ataaccatga gtgataacac tgcggccaac ttacttctga caacgatcgg aggaccgaag   8880
gagctaaccg cttttttgca caacatgggg gatcatgtaa ctcgccttga tcgttgggaa   8940
ccggagctga atgaagccat accaaacgac gagcgtgaca ccacgatgcc tgtagcaatg   9000
gcaacaacgt tgcgcaaact attaactggc gaactactta ctctagcttc ccggcaacaa   9060
ttaatagact ggatggaggc ggataaagtt gcaggaccac ttctgcgctc ggcccttccg   9120
gctggctggt ttattgctga taaatctgga gccggtgagc gtgggtctcg cggtatcatt   9180
gcagcactgg ggccagatgg taagccctcc cgtatcgtag ttatctacac gacggggagt   9240
caggcaacta tggatgaacg aaatagacag atcgctgaga taggtgcctc actgattaag   9300
cattggtaac tgtcagacca agtttactca tatatacttt agattgattt aaaacttcat   9360
```

```
ttttaattta aaaggatcta ggtgaagatc ctttttgata atctcatgac caaaatccct   9420
taacgtgagt tttcgttcca ctgagcgtca gaccccgtag aaaagatcaa aggatcttct   9480
tgagatcctt tttttctgcg cgtaatctgc tgcttgcaaa caaaaaaacc accgctacca   9540
gcggtggttt gtttgccgga tcaagagcta ccaactcttt ttccgaaggt aactggcttc   9600
agcagagcgc agataccaaa tactgtcctt ctagtgtagc cgtagttagg ccaccacttc   9660
aagaactctg tagcaccgcc tacatacctc gctctgctaa tcctgttacc agtggctgct   9720
gccagtggcg ataagtcgtg tcttaccggg ttggactcaa gacgatagtt accggataag   9780
gcgcagcggt cgggctgaac ggggggttcg tgcacacagc ccagcttgga gcgaacgacc   9840
tacaccgaac tgagatacct acagcgtgag ctatgagaaa gcgccacgct tcccgaaggg   9900
agaaaggcgg acaggtatcc ggtaagcggc agggtcggaa caggagagcg cacgagggag   9960
cttccagggg gaaacgcctg gtatctttat agtcctgtcg ggtttcgcca cctctgactt  10020
gagcgtcgat ttttgtgatg ctcgtcaggg gggcggagcc tatggaaaaa cgccagcaac  10080
gcggcctttt tacggttcct ggccttttgc tggccttttg ctcacatgtt ctttcctgcg  10140
ttatcccctg attctgtgga taaccgtatt accgcctttg agtgagctga taccgctcgc  10200
cgcagccgaa cgaccgagcg cagcgagtca gtgagcgagg aagcggaaga gcgcccaata  10260
cgcaaaccgc ctctccccgc gcgttggccg attcattaat gcagctggca cgacaggttt  10320
cccgactgga aagcgggcag tgagcgcaac gcaattaatg tgagttagct cactcattag  10380
gcaccccagg ctttacactt tatgcttccg gctcgtatgt tgtgtggaat tgtgagcgga  10440
taacaatttc acacaggaaa cagctatgac catgattacg aatttggcca agtcggcctc  10500
taatacgact cactataggg agctcgtcga gcggccgcac tagtgatatc ccgcggccat  10560
ggcggccggg agcatgcgac gtcgggccca attcgcccta tagtgagtcg tattacaatt  10620
cactggccgt cgttttacaa cgtcgtgact gggaaaaccc tggcgttacc caacttaatc  10680
gccttgcagc acatccccct ttcgccagct ggcgtaatag cgaagaggcc cgcaccgatc  10740
gcccttccca acagttgcgc agcctgaatg gcgaatggaa attgtaaacg ttaatgggtt  10800
tctggagttt aatgagctaa gcacatacgt cagaaaccat tattgcgcgt tcaaaagtcg  10860
cctaaggtca ctatcagcta gcaaatattt cttgtcaaaa atgctccact gacgttccat  10920
aaattcccct cggtatccaa ttagagtctc atattcactc tcaatccaaa taatctgcaa  10980
tggcaattac cttatccgca acttctttac ctatttccgc ccggatccgg gcaggttctc  11040
cggccgcttg ggtggagagg ctattcggct atgactgggc acaacagaca atcggctgct  11100
ctgatgccgc cgtgttccgg ctgtcagcgc aggggcgccc ggttcttttt gtcaagaccg  11160
acctgtccgg tgccctgaat gaactgcagg acgaggcagc gcggctatcg tggctggcca  11220
cgacgggcgt tccttgcgca gctgtgctcg acgttgtcac tgaagcggga agggactggc  11280
tgctattggg cgaagtgccg gggcaggatc tcctgtcatc tcaccttgct cctgccgaga  11340
aagtatccat catggctgat gcaatgcggc ggctgcatac gcttgatccg gctacctgcc  11400
cattcgacca ccaagcgaaa catcgcatcg agcgagcacg tactcggatg gaagccggtc  11460
ttgtcgatca ggatgatctg gacgaagagc atcaggggct cgcgccagcc gaactgttcg  11520
ccaggctcaa ggcgcgcatg cccgacggcg aggatctcgt cgtgacccat ggcgatgcct  11580
gcttgccgaa tatcatggtg gaaaatggcc gcttttctgg attcatcgac tgtggccggc  11640
tgggtgtggc ggaccgctat caggacatag cgttggctac ccgtgatatt gctgaagagc  11700
ttggcggcga atgggctgac cgcttcctcg tgctttacgg tatcgccgct cccgattcgc  11760
```

```
agcgcatcgc cttctatcgc cttcttgacg agttcttctg agcgggactc tggggttcga  11820
aatgaccgac caagcgacgc ccaacctgcc atcacgagat ttcgattcca ccgccgcctt  11880
ctatgaaagg ttgggcttcg gaatcgtttt ccgggacgcc ggctggatga tcctccagcg  11940
cggggatctc atgctggagt tcttcgccca ccccgatcca acacttacgt ttgcaacgtc  12000
caagagcaaa tagaccacga acgccggaag gttgccgcag cgtgtggatt gcgtctcaat  12060
tctctcttgc aggaatgcaa tgatgaatat gatactgact atgaaacttt gagggaatac  12120
tgcctagcac cgtcacctca taacgtgcat catgcatgcc ctgacaacat ggaacatcgc  12180
tatttttctg aagaattatg ctcgttggag gatgtcgcgg caattgcagc tattgccaac  12240
atcgaactac ccctcacgca tgcattcatc aatattattc atgcggggaa aggcaagatt  12300
aatccaactg gcaaatcatc cagcgtgatt ggtaacttca gttccagcga cttgattcgt  12360
tttggtgcta cccacgtttt caataaggac gagatggtgg agtaaagaag gagtgcgtcg  12420
aagcagatcg ttcaaacatt tggcaataaa gtttcttaag attgaatcct gttgccggtc  12480
ttgcgatgat tatcatataa tttctgttga attacgttaa gcatgtaata attaacatgt  12540
aatgcatgac gttatttatg agatgggttt ttatgattag agtcccgcaa ttatacattt  12600
aatacgcgat agaaaacaaa atatagcgcg caaactagga taaattatcg cgcgcggtgt  12660
catctatgtt actagatcga attaattcag tacattaaaa acgtccgcaa tgtgttatta  12720
agttgtctaa gcgtcaattt gtttacacca caatatatcc tgccaccagc cagccaacag  12780
ctccccgacc ggcagctcgg cacaaaatca ccactcgata caggcagccc atcagtccgg  12840
gacggcgtca gcgggagagc cgttgtaagg cggcagactt tgctcatgtt accgatgcta  12900
ttcggaagaa cggcaactaa gctgccgggt ttgaaacacg gatgatctcg cggagggtag  12960
catgttgatt gtaacgatga cagagcgttg ctgcctgtga tcaaatatca tctccctcgc  13020
agagatccga attatcagcc ttcttattca tttctcgctt aaccgtgaca ggctgtcgat  13080
cttgagaact atgccgacat aataggaaat cgctggataa agccgctgag gaagctgagt  13140
ggcgctattt ctttagaagt gaacgttgac gatgtcgacg gatcttttcc gctgcataac  13200
cctgcttcgg ggtcattata gcgatttttt cggtatatcc atcctttttc gcacgatata  13260
caggattttg ccaaagggtt cgtgtagact ttccttggtg tatccaacgg cgtcagccgg  13320
gcaggatagg tgaagtaggc ccacccgcga gcgggtgttc cttcttcact gtcccttatt  13380
cgcacctggc ggtgctcaac gggaatcctg ctctgcgagg ctggccggct accgccggcg  13440
taacagatga gggcaagcgg atggctgatg aaaccaagcc aaccaggggt gatgctgcca  13500
acttactgat ttagtgtatg atggtgtttt tgaggtgctc cagtggcttc tgtttctatc  13560
agctgtccct cctgttcagc tactgacggg gtggtgcgta acggcaaaag caccgccgga  13620
catcagcgct atctctgctc tcactgccgt aaaacatggc aactgcagtt cacttacacc  13680
gcttctcaac ccggtacgca ccagaaaatc attgatatgg ccatgaatgg cgttggatgc  13740
cgggcaacag cccgcattat gggcgttggc ctcaacacga ttttacgtca cttaaaaaac  13800
tcaggccgca gtcggtaacc tcgcgcatac agccgggcag tgacgtcatc gtctgcgcgg  13860
aaatggacga acagtggggc tatgtcgggg ctaaatcgcg ccagcgctgg ctgttttacg  13920
cgtatgacag tctccggaag acggttgttg cgcacgtatt cggtgaacgc actatggcga  13980
cgctggggcg tcttatgagc ctgctgtcac cctttgacgt ggtgatatgg atgacggatg  14040
gctggccgct gtatgaatcc cgcctgaagg gaaagctgca cgtaatcagc aagcgatata  14100
cgcagcgaat tgagcggcat aacctgaatc tgaggcagca cctggcacgg ctgggacgga  14160
```

```
agtcgctgtc gttctcaaaa tcggtggagc tgcatgacaa agtcatcggg cattatctga  14220
acataaaaca ctatcaataa gttggagtca ttacccaacc aggaagggca gcccacctat  14280
caaggtgtac tgccttccag acgaacgaag agcgattgag gaaaaggcgg cggcggccgg  14340
catgagcctg tcggcctacc tgctggccgt cggccagggc tacaaaatca cgggcgtcgt  14400
ggactatgag cacgtccgcg agctggcccg catcaatggc gacctgggcc gcctgggcgg  14460
cctgctgaaa ctctggctca ccgacgaccc gcgcacggcg cggttcggtg atgccacgat  14520
cctcgccctg ctggcgaaga tcgaagagaa gcaggacgag cttggcaagg tcatgatggg  14580
cgtggtccgc ccgagggcag agccatgact tttttagccg ctaaaacggc cgggggggtgc  14640
gcgtgattgc caagcacgtc cccatgcgct ccatcaagaa gagcgacttc gcggagctgg  14700
tattcgtgca gggcaagatt cggaatacca agtacgagaa ggacggccag acggtctacg  14760
ggaccgactt cattgccgat aaggtggatt atctggacac caaggcacca ggcgggtcaa  14820
atcaggaata agggcacatt gccccggcgt gagtcggggc aatcccgcaa ggagggtgaa  14880
tgaatcggac gtttgaccgg aaggcataca ggcaagaact gatcgacgcg gggttttccg  14940
ccgaggatgc cgaaaccatc gcaagccgca ccgtcatgcg tgcgccccgc gaaaccttcc  15000
agtccgtcgg ctcgatggtc cagcaagcta cggccaagat cgagcgcgac agcgtgcaac  15060
tggctccccc tgccctgccc gcgccatcgg ccgccgtgga gcgttcgcgt cgtctcgaac  15120
aggaggcggc aggtttggcg aagtcgatga ccatcgacac gcgaggaact atgacgacca  15180
agaagcgaaa aaccgccggc gaggacctgg caaaacaggt cagcgaggcc aagcaggccg  15240
cgttgctgaa acacacgaag cagcagatca aggaaatgca gctttccttg ttcgatattg  15300
cgccgtggcc ggacacgatg cgagcgatgc caaacgacac ggcccgctct gccctgttca  15360
ccacgcgcaa caagaaaatc ccgcgcgagg cgctgcaaaa caaggtcatt ttccacgtca  15420
acaaggacgt gaagatcacc tacaccggcg tcgagctgcg ggccgacgat gacgaactgg  15480
tgtggcagca ggtgttggag tacgcgaagc gcacccctat cggcgagccg atcaccttca  15540
cgttctacga gctttgccag gacctgggct ggtcgatcaa tggccggtat tacacgaagg  15600
ccgaggaatg cctgtcgcgc ctacaggcga cggcgatggg cttcacgtcc gaccgcgttg  15660
ggcacctgga atcggtgtcg ctgctgcacc gcttccgcgt cctggaccgt ggcaagaaaa  15720
cgtcccgttg ccaggtcctg atcgacgagg aaatcgtcgt gctgtttgct ggcgaccact  15780
acacgaaatt catatgggag aagtaccgca agctgtcgcc gacggcccga cggatgttcg  15840
actatttcag ctcgcaccgg gagccgtacc cgctcaagct ggaaaccttc cgcctcatgt  15900
gcggatcgga ttccacccgc gtgaagaagt ggcgcgagca ggtcggcgaa gcctgcgaag  15960
agttgcgagg cagcggcctg gtggaacacg cctgggtcaa tgatgacctg gtgcattgca  16020
aacgctaggg ccttgtgggg tcagttccgg ctgggggttc agcagccagc gctttactgg  16080
catttcagga acaagcgggc actgctcgac gcacttgctt cgctcagtat cgctcgggac  16140
gcacggcgcg ctctacgaac tgccgataaa cagaggatta aaattgacaa ttgtgattaa  16200
ggctcagatt cgacggcttg gagcggccga cgtgcaggat ttccgcgaga tccgattgtc  16260
ggccctgaag aaagctccag agatgttcgg gtccgtttac gagcacgagg agaaaaagcc  16320
catggaggcg ttcgctgaac ggttgcgaga tgccgtggca ttcggcgcct acatcgacgg  16380
cgagatcatt gggctgtcgg tcttcaaaca ggaggacggc cccaaggacg ctcacaaggc  16440
gcatctgtcc ggcgttttcg tggagcccga acagcgaggc cgaggggtcg ccggtatgct  16500
gctgcgggcg ttgccggcgg gtttattgct cgtgatgatc gtccgacaga ttccaacggg  16560
```

```
aatctggtgg atgcgcatct tcatcctcgg cgcacttaat atttcgctat tctggagctt  16620
gttgtttatt tcggtctacc gcctgccggg cggggtcgcg gcgacggtag gcgctgtgca  16680
gccgctgatg gtcgtgttca tctctgccgc tctgctaggt agcccgatac gattgatggc  16740
ggtcctgggg gctatttgcg gaactgcggg cgtggcgctg ttggtgttga caccaaacgc  16800
agcgctagat cctgtcggcg tcgcagcggg cctggcgggg gcggtttcca tggcgttcgg  16860
aaccgtgctg acccgcaagt ggcaacctcc cgtgcctctg ctcaccttta ccgcctggca  16920
actggcggcc ggaggacttc tgctcgttcc agtagcttta gtgtttgatc cgccaatccc  16980
gatgcctaca ggaaccaatg ttctcggcct ggcgtggctc ggcctgatcg gagcgggttt  17040
aacctacttc ctttggttcc gggggatctc gcgactcgaa cctacagttg tttccttact  17100
gggctttctc agccgggatg gcgctaagaa gctattgccg ccgatcttca tatgcggtgt  17160
gaaataccgc acagatgcgt aaggagaaaa taccgcatca ggcgctcttc cgcttcctcg  17220
ctcactgact cgctgcgctc ggtcgttcgg ctgcggcgag cggtatcagc tcactcaaag  17280
gcggtaatac ggttatccac agaatcaggg gataacgcag gaaagaacat gtgagcaaaa  17340
ggccagcaaa aggccaggaa ccgtaaaaag gccgcgttgc tggcgttttt ccataggctc  17400
cgcccccctg acgagcatca caaaaatcga cgctcaagtc agaggtggcg aaacccgaca  17460
ggactataaa gataccaggc gtttccccct ggaagctccc tcgtgcgctc tcctgttccg  17520
accctgccgc ttaccggata cctgtccgcc tttctccctt cgggaagcgt ggcgctttct  17580
caatgctcac gctgtaggta tctcagttcg gtgtaggtcg ttcgctccaa gctgggctgt  17640
gtgcacgaac cccccgttca gcccgaccgc tgcgccttat ccggtaacta tcgtcttgag  17700
tccaacccgg taagacacga cttatcgcca ctggcagcag ccactggtaa caggattagc  17760
agagcgaggt atgtaggcgg tgctacagag ttcttgaagt ggtggcctaa ctacggctac  17820
actagaagga cagtatttgg tatctgcgct ctgctgaagc cagttacctt cggaaaaaga  17880
gttggtagct cttgatccgg caaacaaacc accgctggta gcggtggttt ttttgtttgc  17940
aagcagcaga ttacgcgcag aaaaaaagga tatcaagaag atcctttgat cttttctacg  18000
gggtctgacg ctcagtggaa cgaaaactca cgttaaggga ttttggtcat gagattatca  18060
aaaaggatct tcacctagat ccttttaaat taaaaatgaa gttttaaatc aatctaaagt  18120
atatatgagt aaacttggtc tgacagttac caatgcttaa tcagtgaggc acctatctca  18180
gcgatctgtc tatttcgttc atccatagtt gcctgactcc ccgtcgtgta gataactacg  18240
atacgggagg gcttaccatc tggccccagt gctgcaatga taccgcgaga cccacgctca  18300
ccggctccag atttatcagc aataaaccag ccagccggaa gggccgagcg cagaagtggt  18360
cctgcaactt tatccgcctc catccagtct attaaacaag tggcagcaac ggattcgcaa  18420
acctgtcacg ccttttgtgc caaaagccgc gccaggtttg cgatccgctg tgccaggcgt  18480
taggcgtcat atgaagattt cggtgatccc tgagcaggtg gcggaaacat tggatgctga  18540
gaaccatttc attgttcgtg aagtgttcga tgtgcaccta tccgaccaag gctttgaact  18600
atctaccaga agtgtgagcc cctaccggaa ggattacatc tcggatgatg actctgatga  18660
agactctgct tgctatggcg cattcatcga ccaagagctt gtcgggaaga ttgaactcaa  18720
ctcaacatgg aacgatctag cctctatcga acacattgtt gtgtcgcaca cgcaccgagg  18780
caaaggagtc gcgcacagtc tcatcgaatt tgcgaaaaag tgggcactaa gcagacagct  18840
ccttggcata cgattagaga cacaaacgaa caatgtacct gcctgcaatt tgtacgcaaa  18900
atgtggcttt actctcggcg gcattgacct gttcacgtat aaaactagac ctcaagtctc  18960
```

```
gaacgaaaca gcgatgtact ggtactggtt ctcgggagca caggatgacg cctaacaatt  19020
cattcaagcc gacaccgctt cgcggcgcgg cttaattcag gagttaaaca tcatgaggga  19080
agcggtgatc gccgaagtat cgactcaact atcagaggta gttggcgtca tcgagcgcca  19140
tctcgaaccg acgttgctgg ccgtacattt gtacggctcc gcagtggatg gcggcctgaa  19200
gccacacagt gatattgatt tgctggttac ggtgaccgta aggcttgatg aaacaacgcg  19260
gcgagctttg atcaacgacc ttttggaaac ttcggcttcc cctggagaga gcgagattct  19320
ccgcgctgta gaagtcacca ttgttgtgca cgacgacatc attccgtggc gttatccagc  19380
taagcgcgaa ctgcaatttg gagaatggca gcgcaatgac attcttgcag gtatcttcga  19440
gccagccacg atcgacattg atctggctat cttgctgaca aaagcaagag aacatagcgt  19500
tgccttggta ggtccagcgg cggaggaact ctttgatccg gttcctgaac aggatctatt  19560
tgaggcgcta aatgaaacct taacgctatg gaactcgccg cccgactggg ctggcgatga  19620
gcgaaatgta gtgcttacgt tgtcccgcat ttggtacagc gcagtaaccg gcaaaatcgc  19680
gccgaaggat gtcgctgccg actgggcaat ggagcgcctg ccggcccagt atcagcccgt  19740
catacttgaa gctaggcagg cttatcttgg acaagaagat cgcttggcct cgcgcgcaga  19800
tcagttggaa gaatttgttc actacgtgaa aggcgagatc accaaggtag tcggcaaata  19860
atgtctaaca attcgttcaa gccgacgccg cttcgcggcg cggcttaact caagcgttag  19920
agagctgggg aagactatgc gcgatctgtt gaaggtggtt ctaagcctcg tacttgcgat  19980
ggcatcgggg caggcacttg ctgacctgcc aattgtttta gtggatgaag ctcgtcttcc  20040
ctatgactac tccccatcca actacgacat ttctccaagc aactacgaca actccataag  20100
caattacgac aatagtccat caaattacga caactctgag agcaactacg ataatagttc  20160
atccaattac gacaatagtc gcaacggaaa tcgtaggctt atatatagcg caaatgggtc  20220
tcgcactttc gccggctact acgtcattgc caacaatggg acaacgaact tcttttccac  20280
atctggcaaa aggatgttct acaccccaaa aggggggcgc ggcgtctatg gcggcaaaga  20340
tgggagcttc tgcggggcat tggtcgtcat aaatggccaa ttttcgcttg ccctgacaga  20400
taacggcctg aagatcatgt atctaagcaa ctagcctgct ctctaataaa atgttaggag  20460
cttggctgcc atttttgggg tgaggccgtt cgcggccgag ggcgcagcc cctgggggga   20520
tgggaggccc gcgttagcgg gccgggaggg ttcgagaagg gggggcaccc cccttcggcg  20580
tgcgcggtca cgcgccaggg cgcagccctg gttaaaaaca aggtttataa atattggttt  20640
aaaagcaggt taaaagacag gttagcggtg gccgaaaaac gggcggaaac ccttgcaaat  20700
gctggatttt ctgcctgtgg acagcccctc aaatgtcaat aggtgcgccc ctcatctgtc  20760
agcactctgc ccctcaagtg tcaaggatcg cgcccctcat ctgtcagtag tcgcgcccct  20820
caagtgtcaa taccgcaggg cacttatccc caggcttgtc cacatcatct gtgggaaact  20880
cgcgtaaaat caggcgtttt cgccgatttg cgaggctggc cagctccacg tcgccggccg  20940
aaatcgagcc tgcccctcat ctgtcaacgc cgcgccgggt gagtcggccc ctcaagtgtc  21000
aacgtccgcc cctcatctgt cagtgagggc caagttttcc gcgaggtatc cacaacgccg  21060
gcggccggcc gcggtgtctc gcacacggct tcgacggcgt ttctggcgcg tttgcagggc  21120
catagacggc cgccagccca gcggcgaggg caaccagccc ggtgagcgtc ggaaaggg    21178
```

<210> SEQ ID NO 44
<211> LENGTH: 22635
<212> TYPE: DNA
<213> ORGANISM: Arabidopsis thaliana

<400> SEQUENCE: 44

```
tcgacatctt gctgcgttcg gatattttcg tggagttccc gccacagacc cggattgaag     60
gcgagatcca gcaactcgcg ccagatcatc ctgtgacgga actttggcgc gtgatgactg    120
gccaggacgt cggccgaaag agcgacaagc agatcacgat tttcgacagc gtcggatttg    180
cgatcgagga tttttcggcg ctgcgctacg tccgcgaccg cgttgaggga tcaagccaca    240
gcagcccact cgaccttcta gccgacccag acgagccaag ggatcttttt ggaatgctgc    300
tccgtcgtca ggctttccga cgtttgggtg gttgaacaga agtcattatc gtacggaatg    360
ccagcactcc cgaggggaac cctgtggttg gcatgcacat acaaatggac gaacggataa    420
accttttcac gccctttaa atatccgtta ttctaataaa cgctcttttc tcttaggttt     480
acccgccaat atatcctgtc aaacactgat agtttaaact gaaggcggga aacgacaatc    540
tgatcatgag cggagaatta agggagtcac gttatgaccc ccgccgatga cgcgggacaa    600
gccgttttac gtttggaact gacagaaccg caacgattga aggagccact cagccccaat    660
acgcaaaccg cctctccccg cgcgttggcc gattcattaa tgcagctggc acgacaggtt    720
tcccgactgg aaagcgggca gtgagcgcaa cgcaattaat gtgagttagc tcactcatta    780
ggcaccccag gctttacact ttatgcttcc ggctcgtatg ttgtgtggaa ttgtgagcgg    840
ataacaattt cacacaggaa acagctatga ccatgattac gccaagctat ttaggtgaca    900
ctatagaata ctcaagctat gcatccaacg cgttgggagc tctcccatat cgacctgcag    960
gcggccgctc gacgaattaa ttccaatccc acaaaaatct gagcttaaca gcacagttgc   1020
tcctctcaga gcagaatcgg gtattcaaca ccctcatatc aactactacg ttgtgtataa   1080
cggtccacat gccggtatat acgatgactg ggttgtaca aaggcggcaa caaacggcgt    1140
tcccggagtt gcacacaaga aatttgccac tattacagag gcaagagcag cagctgacgc   1200
gtacacaaca agtcagcaaa cagacaggtt gaacttcatc cccaaaggag aagctcaact   1260
caagcccaag agctttgcta aggccctaac aagcccacca aagcaaaaag cccactggct   1320
cacgctagga accaaaaggc ccagcagtga tccagcccca aaagagatct cctttgcccc   1380
ggagattaca atggacgatt tcctctatct ttacgatcta ggaaggaagt tcgaaggtga   1440
aggtgacgac actatgttca ccactgataa tgagaaggtt agcctcttca atttcagaaa   1500
gaatgctgac ccacagatgg ttagagaggc ctacgcagca ggtctcatca agacgatcta   1560
cccgagtaac aatctccagg agatcaaata ccttcccaag aaggttaaag atgcagtcaa   1620
aagattcagg actaattgca tcaagaacac agagaaagac atatttctca agatcagaag   1680
tactattcca gtatggacga ttcaaggctt gcttcataaa ccaaggcaag taatagagat   1740
tggagtctct aaaaaggtag ttcctactga atctaaggcc atgcatggag tctaagattc   1800
aaatcgagga tctaacagaa ctcgccgtga agactggcga acagttcata cagagtcttt   1860
tacgactcaa tgacaagaag aaaatcttcg tcaacatggt ggagcacgac actctggtct   1920
actccaaaaa tgtcaaagat acagtctcag aagaccaaag ggctattgag acttttcaac   1980
aaaggataat ttcgggaaac ctcctcggat tccattgccc agctatctgt cacttcatcg   2040
aaaggacagt agaaaaggaa ggtggctcct acaaatgcca tcattgcgat aaaggaaagg   2100
ctatcattca agatctctct gccgacagtg gtcccaaaga tggaccccca cccacgagga   2160
gcatcgtgga aaaagaagac gttccaacca cgtcttcaaa gcaagtggat tgatgtgaca   2220
tctccactga cgtaagggat gacgcacaat cccactatcc ttcgcaagac ccttcctcta   2280
tataaggaag ttcatttcat ttggagagga cacgctcgag gaattccatg gtgagcaagg   2340
```

```
gccacgagct gttcaccggg gtggtgccca tcctggtcga gctggacggc gacgtaaacg   2400
gccacaagtt cagcgtgtcc ggcgagggcg agggcgatgc cacctacggc catctgaccc   2460
tgaagttcat ctgcaccacc ggcaagctgc ccgtgccctg gcccaccctc gtgaccacct   2520
tcacctacgg cgtgcagtgc ttcagccgct accccgacca catgaagcag cacgacttct   2580
gcaagtccgc catgcccgaa ggctacgtcc aggagcgcac catcttcttc aaggacgacg   2640
gcaactacaa gacccgcgcc gaggtgaagt tcgagggcga caccctggtg aaccgcatcg   2700
agctgaaggg catcgacttc aaggaggacg gcaacatcct ggggcacaag ctggagtaca   2760
actacaacag ccacaacgtc tatatcatgg ccgacaagca gaagaacggc atcaaggtga   2820
acttcaagat ccgccacaac atcgaggacg gcagcgtgca gctcgccgac cactaccagc   2880
agaacacccc catcggcgac ggccccgtgc tgctgcccga caaccactac ctgagcaccc   2940
agtccgccct gagcaaagac cccaacgaga agcgcgatca catggtcctg ctggagttcg   3000
tgaccgccgc cgggatcact cacggcatgg acgagctgta caagtaagat cgatcctcta   3060
gagtcctgct ttaatgagat atgcgagacg cctatgatcg catgatattt gctttcaatt   3120
ctgttgtgca cgttgtaaaa aacctgagca tgtgtagctc agatccttac cgccggtttc   3180
ggttcattct aatgaatata tcacccgtta ctatcgtatt tttatgaata atattctccg   3240
ttcaatttac tgattgtacc ctactactta tatgtacaat attaaaatga aaacaatata   3300
ttgtgctgaa taggtttata gcgacatcta tgatagagcg ccacaataac aaacaattgc   3360
gttttattat tacaaatcca attttaaaaa aagcggcaga accggtcaaa cctaaaagac   3420
tgattacata aatcttattc aaatttcaaa aggccccagg ggctagtatc tacgacacac   3480
cgagcggcga actaataacg ttcactgaag ggaactccgg ttccccgccg gcgcgcatgg   3540
gtgagattcc ttgaagttga gtattggccg tccgctctac cgaaagttac gggcaccatt   3600
caacccggtc cagcacggcg gccgggtaac cgacttgctg ccccgagaat tatgcagcat   3660
tttttggtg tatgtgggcc ccaaatgaag tgcaggtcaa accttgacag tgacgacaaa   3720
tcgttgggcg ggtccagggc gaattttgcg acaacatgtc gaggctcagc aggacctgca   3780
ggcatgcaag ctagcttact agtgatgcat attctatagt gtcacctaaa tctgcggccg   3840
ctcgacgaat taattccaat cccacaaaaa tctgagctta acagcacagt tgctcctctc   3900
agagcagaat cgggtattca acaccctcat atcaactact acgttgtgta taacggtcca   3960
catgccggta tatacgatga ctggggttgt acaaaggcgg caacaaacgg cgttcccgga   4020
gttgcacaca agaaatttgc cactattaca gaggcaagag cagcagctga cgcgtacaca   4080
acaagtcagc aaacagacag gttgaacttc atccccaaag gagaagctca actcaagccc   4140
aagagctttg ctaaggccct aacaagccca ccaaagcaaa aagcccactg gctcacgcta   4200
ggaaccaaaa ggcccagcag tgatccagcc ccaaaagaga tctcctttgc cccggagatt   4260
acaatggacg atttcctcta tctttacgat ctaggaagga agttcgaagg tgaaggtgac   4320
gacactatgt tcaccactga taatgagaag gttagcctct tcaatttcag aaagaatgct   4380
gacccacaga tggttagaga ggcctacgca gcaggtctca tcaagacgat ctacccgagt   4440
aacaatctcc aggagatcaa ataccttccc aagaaggtta aagatgcagt caaaagattc   4500
aggactaatt gcatcaagaa cacagagaaa gacatatttc tcaagatcag aagtactatt   4560
ccagtatgga cgattcaagg cttgcttcat aaaccaaggc aagtaataga gattggagtc   4620
tctaaaaagg tagttcctac tgaatctaag gccatgcatg gagtctaaga ttcaaatcga   4680
ggatctaaca gaactcgccg tgaagactgg cgaacagttc atacagagtc ttttacgact   4740
```

-continued

```
caatgacaag aagaaaatct tcgtcaacat ggtggagcac gacactctgg tctactccaa   4800
aaatgtcaaa gatacagtct cagaagacca aagggctatt gagacttttc aacaaaggat   4860
aatttcggga aacctcctcg gattccattg cccagctatc tgtcacttca tcgaaaggac   4920
agtagaaaag gaaggtggct cctacaaatg ccatcattgc gataaaggaa aggctatcat   4980
tcaagatctc tctgccgaca gtggtcccaa agatggaccc ccacccacga ggagcatcgt   5040
ggaaaaagaa gacgttccaa ccacgtcttc aaagcaagtg gattgatgtg acatctccac   5100
tgacgtaagg gatgacgcac aatcccacta tccttcgcaa gacccttcct ctatataagg   5160
aagttcattt catttggaga ggacacgctc gaggaattcg gtaccccatc acaagtttgt   5220
acaaaaaagc aggctccgcg gccgcccct tcaccatggc gattttggat tctgctggcg   5280
ttactacggt gacggagaac ggtggcggag agttcgtcga tcttgatagg cttcgtcgac   5340
ggaaatcgag atcggattct tctaacggac ttcttctctc tggttccgat aataattctc   5400
cttcggatga tgttggagct cccgccgacg ttagggatcg gattgattcc gttgttaacg   5460
atgacgctca gggaacagcc aatttggccg gagataataa cggtggtggc gataataacg   5520
gtggtggaag aggcggcgga gaaggaagag gaaacgccga tgctacgttt acgtatcgac   5580
cgtcggttcc agctcatcgg agggcgagag agagtccact tagctccgac gcaatcttca   5640
aacaggttta aaatctcaga aatcttcgaa tttggtgttt gcttgttgtt ttatatggaa   5700
ttgagtttgg tgattgtttt gcattgcaga gccatgccgg attattcaac ctctgtgtag   5760
tagttcttat tgctgtaaac agtagactca tcatcgaaaa tcttatgaag gtttgctgtt   5820
acttgtttct ccttttagga attgaattgc ttgaaaattt atcagagacg aataactttg   5880
ttgttgctat cattcatgta gtatggttgg ttgatcagaa cggatttctg gtttagttca   5940
agatcgctgc gagattggcc gcttttcatg tgttggtaaa agaagatgtt ttttatttcc   6000
agcaatgtta cattgttata cgtataatga tgagtttagt gatcaagttc ctctttgatt   6060
cttctttctt gttgcagtat atccctttcg atctttcctt tggctgcctt tacggttgag   6120
aaattggtac ttcagaaata catatcagaa cctgtgagta attactattc tccagccatt   6180
actgtaattt ttattgaaga caagtttgta tcatgaagaa cttacaagtt ctgttttgaa   6240
aatgctcaag gttgtcatct ttcttcatat tattatcacc atgacagagg ttttgtatcc   6300
agtttacgtc accctaaggt gatactgttt ttctggtctc agtttgtgat actgtttta    6360
agtttagttg tctgacccgg tgatcttgaa aatggacagg tgtgattctg ctttttttatc   6420
aggtgtcact ttgatgctcc tcacttgcat tgtgtggcta aagttggttt cttatgctca   6480
tactagctat gacataagat ccctagccaa tgcagctgat aaggtaaaat acgaaaaaga   6540
agcgtatgta ttagtcactt gcactgtgtt actgttttaa ccaaacactg ttatgaactt   6600
taggccaatc ctgaagtctc ctactacgtt agcttgaaga gcttggcata tttcatggtc   6660
gctcccacat tgtgttatca ggtaactgca aagtgcatca accattctta tacttgcaag   6720
agtttcttgt ctaaacctcg gatctttgct tttccccagc caagttatcc acgttctgca   6780
tgtatacgga agggttgggt ggctcgtcaa tttgcaaaac tggtcatatt caccggattc   6840
atgggattta taatagaaca agtacgtttt cacatcttgc tttattagtt ttccttggtg   6900
aaaatcatca tccctgcgtt gtcaccactt gacttcatgt tcttttgtta cattttggca   6960
gtatataaat cctattgtca ggaactcaaa gcatcctttg aaaggcgatc ttctatatgc   7020
tattgaaaga gtgttgaagc tttcagttcc aaatttatat gtgtggctct gcatgttcta   7080
ctgcttcttc cacctttggt atgctgtgat cccatctctt tcaaaataat ttgcaaattc   7140
```

gaaaaaccga aaaaggctaa atctcatacg aatttgatat ttttagtttc ttagagtcgg 7200
tgatgtaatt tcagttactg aacgcaaatc tcttgtccaa aggttaaaca tattggcaga 7260
gcttctctgc ttcggggatc gtgaattcta caaagattgg tggaatgcaa aaagtgtggg 7320
agatgtgagc tattttactc aaaagaaaac ttatgatttt taatgttgtc gttgtttttg 7380
ggtcatctaa ctaaccaaat tcatgtattc actgtcttcc tttatcagta ctggagaatg 7440
tggaatatgg tatggttctc ttcctaaaca tcaccttctt ttgtacacaa aatagaagaa 7500
gagagctaat taagatcttg ttttccttga cagcctgttc ataaatggat ggttcgacat 7560
atatacttcc cgtgcttgcg cagcaagata ccaaaggtga gtgagatata taccgatatg 7620
caattgtcga gatttgtttc tgtgatataa atttaaccct ccacacactt gtttttcaga 7680
cactcgccat tatcattgct ttcctagtct ctgcagtctt tcatgaggta tacatacttt 7740
ctacattgcc ctgtctctag acgcatgaac acacgctagt gaaagaaatg ctaatattca 7800
aagcattgtt tttacttaac gatcttgtgt tacaaatttc cttttgacag ctatgcatcg 7860
cagttccttg tcgtctcttc aagctatggg cttttcttgg gattatgttt caggttaaaa 7920
aattactaaa ctgctgcagt cgatttttac taaactctaa tctcatattc tgaccaacca 7980
atttgtttga gtaggtgcct ttggtcttca tcacaaacta tctacaggaa aggtttggct 8040
caacggtatg ctctcaaaac ccgagaaaat agaacgaata actctttctt tcatagccta 8100
gccatttaaa tcgcaatgct gaaacttaat aataaaggtg atctgttttg gaatgggatc 8160
atattattag gtggggaaca tgatcttctg gttcatcttc tgcattttcg gacaaccgat 8220
gtgtgtgctt ctttattacc acgacctgat gaaccgaaaa ggatcgatgt catgaaaggg 8280
tgggcgcgcc gacccagctt tcttgtacaa agtggtgatg ggttcgaaat cgataagctt 8340
ggatcctcta gagtcctgct ttaatgagat atgcgagacg cctatgatcg catgatattt 8400
gctttcaatt ctgttgtgca cgttgtaaaa aacctgagca tgtgtagctc agatccttac 8460
cgccggtttc ggttcattct aatgaatata tcacccgtta ctatcgtatt tttatgaata 8520
atattctccg ttcaatttac tgattgtacc ctactactta tatgtacaat attaaaatga 8580
aaacaatata ttgtgctgaa taggtttata gcgacatcta tgatagagcg ccacaataac 8640
aaacaattgc gttttattat tacaaatcca attttaaaaa aagcggcaga accggtcaaa 8700
cctaaaagac tgattacata aatcttattc aaatttcaaa aggccccagg ggctagtatc 8760
tacgacacac cgagcggcga actaataacg ttcactgaag ggaactccgg ttccccgccg 8820
gcgcgcatgg gtgagattcc ttgaagttga gtattggccg tccgctctac cgaaagttac 8880
gggcaccatt caacccggtc cagcacggcg gccgggtaac cgacttgctg ccccgagaat 8940
tatgcagcat ttttttggtg tatgtgggcc ccaaatgaag tgcaggtcaa accttgacag 9000
tgacgacaaa tcgttgggcg ggtccagggc gaattttgcg acaacatgtc gaggctcagc 9060
aggacctgca ggcatgcaag ctagcttact agtgatgcat attctatagt gtcacctaaa 9120
tctgcggccg ctgaccaagt cagcttggca ctggccgtcg ttttacaacg tcgtgactgg 9180
gaaaaccctg gcgttaccca acttaatcgc cttgcagcac atcccccttt cgccagctgg 9240
cgtaatagcg aagaggcccg caccgatcgc ccttcccaac agttgcgcag cctgaatggc 9300
gaatgggaaa ttgtaaacgt taatattttg ttaatatttt gttaaaattc gcgttaaatt 9360
tttgttaaat cagctcattt tttaaccaat aggccgaaat cggcaaaatc ccttataaat 9420
caaaagaata gaccgagata gggttgagtg ttgttccagt ttggaacaag agtccactat 9480
taaagaacgt ggactccaac gtcaaagggc gaaaaaccgt ctatcagggc gatggcccac 9540

```
tacgtgaacc atcaccctaa tcaagttttt tggggtcgag gtgccgtaaa gcactaaatc   9600
ggaaccctaa agggatgccc cgatttagag cttgacgggg aaagccggcg aacgtggcga   9660
gaaaggaagg gaagaaagcg aaaggagcgg gcgctagggc gctggcaagt gtagcggtca   9720
cgctgcgcgt aaccaccaca cccgccgcgc ttaatgcgcc gctacagggc gcgtcaggtg   9780
gcacttttcg gggaaatgtg cgcggaaccc ctatttgttt atttttctaa atacattcaa   9840
atatgtatcc gctcatgaga caataaccct gataaatgct tcaataatat tgaaaaagga   9900
agagtatgag tattcaacat ttccgtgtcg cccttattcc cttttttgcg gcattttgcc   9960
ttcctgtttt tgctcaccca gaaacgctgg tgaaagtaaa agatgctgaa gatcagttgg  10020
gtgcacgagt gggttacatc gaactggatc tcaacagcgg taagatcctt gagagttttc  10080
gccccgaaga acgttttcca atgatgagca cttttaaagt tctgctatgt ggcgcggtat  10140
tatcccgtat tgacgccggg caagagcaac tcggtcgccg catacactat tctcagaatg  10200
acttggttga gtactcacca gtcacagaaa agcatcttac ggatggcatg acagtaagag  10260
aattatgcag tgctgccata accatgagtg ataacactgc ggccaactta cttctgacaa  10320
cgatcggagg accgaaggag ctaaccgctt ttttgcacaa catgggggat catgtaactc  10380
gccttgatcg ttgggaaccg gagctgaatg aagccatacc aaacgacgag cgtgacacca  10440
cgatgcctgt agcaatggca acaacgttgc gcaaactatt aactggcgaa ctacttactc  10500
tagcttcccg gcaacaatta atagactgga tggaggcgga taaagttgca ggaccacttc  10560
tgcgctcggc ccttccggct ggctggttta ttgctgataa atctggagcc ggtgagcgtg  10620
ggtctcgcgg tatcattgca gcactggggc cagatggtaa gccctcccgt atcgtagtta  10680
tctacacgac ggggagtcag gcaactatgg atgaacgaaa tagacagatc gctgagatag  10740
gtgcctcact gattaagcat tggtaactgt cagaccaagt ttactcatat atactttaga  10800
ttgatttaaa acttcatttt taatttaaaa ggatctaggt gaagatcctt tttgataatc  10860
tcatgaccaa aatcccttaa cgtgagtttt cgttccactg agcgtcagac cccgtagaaa  10920
agatcaaagg atcttcttga gatccttttt ttctgcgcgt aatctgctgc ttgcaaacaa  10980
aaaaaccacc gctaccagcg gtggtttgtt tgccggatca agagctacca actctttttc  11040
cgaaggtaac tggcttcagc agagcgcaga taccaaatac tgtccttcta gtgtagccgt  11100
agttaggcca ccacttcaag aactctgtag caccgcctac atacctcgct ctgctaatcc  11160
tgttaccagt ggctgctgcc agtggcgata agtcgtgtct taccgggttg gactcaagac  11220
gatagttacc ggataaggcg cagcggtcgg gctgaacggg gggttcgtgc acacagccca  11280
gcttggagcg aacgacctac accgaactga gatacctaca gcgtgagcta tgagaaagcg  11340
ccacgcttcc cgaagggaga aaggcggaca ggtatccggt aagcggcagg gtcggaacag  11400
gagagcgcac gagggagctt ccagggggaa acgcctggta tctttatagt cctgtcgggt  11460
ttcgccacct ctgacttgag cgtcgatttt tgtgatgctc gtcagggggg cggagcctat  11520
ggaaaaacgc cagcaacgcg gcctttttac ggttcctggc cttttgctgg ccttttgctc  11580
acatgttctt tcctgcgtta tcccctgatt ctgtggataa ccgtattacc gcctttgagt  11640
gagctgatac cgctcgccgc agccgaacga ccgagcgcag cgagtcagtg agcgaggaag  11700
cggaagagcg cccaatacgc aaaccgcctc tccccgcgcg ttggccgatt cattaatgca  11760
gctggcacga caggtttccc gactggaaag cgggcagtga gcgcaacgca attaatgtga  11820
gttagctcac tcattaggca ccccaggctt tacactttat gcttccggct cgtatgttgt  11880
gtggaattgt gagcggataa caatttcaca caggaaacag ctatgaccat gattacgaat  11940
```

```
ttggccaagt cggcctctaa tacgactcac tatagggagc tcgtcgagcg gccgcactag  12000
tgatatcccg cggccatggc ggccgggagc atgcgacgtc gggcccaatt cgccctatag  12060
tgagtcgtat tacaattcac tggccgtcgt tttacaacgt cgtgactggg aaaaccctgg  12120
cgttacccaa cttaatcgcc ttgcagcaca tccccctttc gccagctggc gtaatagcga  12180
agaggcccgc accgatcgcc cttcccaaca gttgcgcagc ctgaatggcg aatggaaatt  12240
gtaaacgtta atgggtttct ggagtttaat gagctaagca catacgtcag aaaccattat  12300
tgcgcgttca aaagtcgcct aaggtcacta tcagctagca aatatttctt gtcaaaaatg  12360
ctccactgac gttccataaa ttcccctcgg tatccaatta gagtctcata ttcactctca  12420
atccaaataa tctgcaatgg caattacctt atccgcaact tctttaccta tttccgcccg  12480
gatccgggca ggttctccgg ccgcttgggt ggagaggcta ttcggctatg actgggcaca  12540
acagacaatc ggctgctctg atgccgccgt gttccggctg tcagcgcagg ggcgcccggt  12600
tctttttgtc aagaccgacc tgtccggtgc cctgaatgaa ctgcaggacg aggcagcgcg  12660
gctatcgtgg ctggccacga cgggcgttcc ttgcgcagct gtgctcgacg ttgtcactga  12720
agcgggaagg gactggctgc tattgggcga agtgccgggg caggatctcc tgtcatctca  12780
ccttgctcct gccgagaaag tatccatcat ggctgatgca atgcggcggc tgcatacgct  12840
tgatccggct acctgcccat tcgaccacca agcgaaacat cgcatcgagc gagcacgtac  12900
tcggatggaa gccggtcttg tcgatcagga tgatctggac gaagagcatc aggggctcgc  12960
gccagccgaa ctgttcgcca ggctcaaggc gcgcatgccc gacggcgagg atctcgtcgt  13020
gacccatggc gatgcctgct tgccgaatat catggtggaa aatggccgct tttctggatt  13080
catcgactgt ggccggctgg gtgtggcgga ccgctatcag gacatagcgt tggctacccg  13140
tgatattgct gaagagcttg gcggcgaatg ggctgaccgc ttcctcgtgc tttacggtat  13200
cgccgctccc gattcgcagc gcatcgcctt ctatcgcctt cttgacgagt tcttctgagc  13260
gggactctgg ggttcgaaat gaccgaccaa gcgacgccca acctgccatc acgagatttc  13320
gattccaccg ccgccttcta tgaaaggttg ggcttcggaa tcgttttccg ggacgccggc  13380
tggatgatcc tccagcgcgg ggatctcatg ctggagttct tcgcccaccc cgatccaaca  13440
cttacgtttg caacgtccaa gagcaaatag accacgaacg ccggaaggtt gccgcagcgt  13500
gtggattgcg tctcaattct ctcttgcagg aatgcaatga tgaatatgat actgactatg  13560
aaactttgag ggaatactgc ctagcaccgt cacctcataa cgtgcatcat gcatgccctg  13620
acaacatgga acatcgctat ttttctgaag aattatgctc gttggaggat gtcgcggcaa  13680
ttgcagctat tgccaacatc gaactacccc tcacgcatgc attcatcaat attattcatg  13740
cggggaaagg caagattaat ccaactggca aatcatccag cgtgattggt aacttcagtt  13800
ccagcgactt gattcgtttt ggtgctaccc acgttttcaa taaggacgag atggtggagt  13860
aaagaaggag tgcgtcgaag cagatcgttc aaacatttgg caataaagtt tcttaagatt  13920
gaatcctgtt gccggtcttg cgatgattat catataattt ctgttgaatt acgttaagca  13980
tgtaataatt aacatgtaat gcatgacgtt atttatgaga tgggttttta tgattagagt  14040
cccgcaatta tacatttaat acgcgataga aaacaaaata tagcgcgcaa actaggataa  14100
attatcgcgc gcggtgtcat ctatgttact agatcgaatt aattcagtac attaaaaacg  14160
tccgcaatgt gttattaagt tgtctaagcg tcaatttgtt tacaccacaa tatatcctgc  14220
caccagccag ccaacagctc cccgaccggc agctcggcac aaaatcacca ctcgatacag  14280
gcagcccatc agtccgggac ggcgtcagcg ggagagccgt tgtaaggcgg cagactttgc  14340
```

```
tcatgttacc gatgctattc ggaagaacgg caactaagct gccgggtttg aaacacggat  14400
gatctcgcgg agggtagcat gttgattgta acgatgacag agcgttgctg cctgtgatca  14460
aatatcatct ccctcgcaga gatccgaatt atcagccttc ttattcattt ctcgcttaac  14520
cgtgacaggc tgtcgatctt gagaactatg ccgacataat aggaaatcgc tggataaagc  14580
cgctgaggaa gctgagtggc gctatttctt tagaagtgaa cgttgacgat gtcgacggat  14640
cttttccgct gcataaccct gcttcggggt cattatagcg atttttttcgg tatatccatc  14700
ctttttcgca cgatatacag gattttgcca aagggttcgt gtagactttc cttggtgtat  14760
ccaacggcgt cagccgggca ggataggtga agtaggccca cccgcgagcg ggtgttcctt  14820
cttcactgtc ccttattcgc acctggcggt gctcaacggg aatcctgctc tgcgaggctg  14880
gccggctacc gccggcgtaa cagatgaggg caagcggatg gctgatgaaa ccaagccaac  14940
caggggtgat gctgccaact tactgattta gtgtatgatg gtgtttttga ggtgctccag  15000
tggcttctgt ttctatcagc tgtccctcct gttcagctac tgacggggtg gtgcgtaacg  15060
gcaaaagcac cgccggacat cagcgctatc tctgctctca ctgccgtaaa acatggcaac  15120
tgcagttcac ttacaccgct tctcaacccg gtacgcacca gaaaatcatt gatatggcca  15180
tgaatggcgt tggatgccgg gcaacagccc gcattatggg cgttggcctc aacacgattt  15240
tacgtcactt aaaaaactca ggccgcagtc ggtaacctcg cgcatacagc cgggcagtga  15300
cgtcatcgtc tgcgcggaaa tggacgaaca gtggggctat gtcggggcta aatcgcgcca  15360
gcgctggctg ttttacgcgt atgacagtct ccggaagacg gttgttgcgc acgtattcgg  15420
tgaacgcact atggcgacgc tggggcgtct tatgagcctg ctgtcaccct ttgacgtggt  15480
gatatggatg acggatggct ggccgctgta tgaatcccgc ctgaagggaa agctgcacgt  15540
aatcagcaag cgatatacgc agcgaattga gcggcataac ctgaatctga ggcagcacct  15600
ggcacggctg ggacggaagt cgctgtcgtt ctcaaaatcg gtggagctgc atgacaaagt  15660
catcgggcat tatctgaaca taaaacacta tcaataagtt ggagtcatta cccaaccagg  15720
aagggcagcc cacctatcaa ggtgtactgc cttccagacg aacgaagagc gattgaggaa  15780
aaggcggcgg cggccggcat gagcctgtcg gcctacctgc tggccgtcgg ccagggctac  15840
aaaatcacgg gcgtcgtgga ctatgagcac gtccgcgagc tggcccgcat caatggcgac  15900
ctgggccgcc tgggcggcct gctgaaactc tggctcaccg acgacccgcg cacggcgcgg  15960
ttcggtgatg ccacgatcct cgccctgctg gcgaagatcg aagagaagca ggacgagctt  16020
ggcaaggtca tgatgggcgt ggtccgcccg agggcagagc catgactttt ttagccgcta  16080
aaacggccgg ggggtgcgcg tgattgccaa gcacgtcccc atgcgctcca tcaagaagag  16140
cgacttcgcg gagctggtat tcgtgcaggg caagattcgg aataccaagt acgagaagga  16200
cggccagacg gtctacggga ccgacttcat tgccgataag gtggattatc tggacaccaa  16260
ggcaccaggc gggtcaaatc aggaataagg gcacattgcc ccggcgtgag tcggggcaat  16320
cccgcaagga gggtgaatga atcggacgtt tgaccggaag gcatacaggc aagaactgat  16380
cgacgcgggg ttttccgccg aggatgccga aaccatcgca agccgcaccg tcatgcgtgc  16440
gccccgcgaa accttccagt ccgtcggctc gatggtccag caagctacgg ccaagatcga  16500
gcgcgacagc gtgcaactgg ctccccctgc cctgcccgcg ccatcggccg ccgtggagcg  16560
ttcgcgtcgt ctcgaacagg aggcggcagg tttggcgaag tcgatgacca tcgacacgcg  16620
aggaactatg acgaccaaga agcgaaaaac cgccggcgag gacctggcaa aacaggtcag  16680
cgaggccaag caggccgcgt tgctgaaaca cacgaagcag cagatcaagg aaatgcagct  16740
```

```
ttccttgttc gatattgcgc cgtggccgga cacgatgcga gcgatgccaa acgacacggc  16800
ccgctctgcc ctgttcacca cgcgcaacaa gaaaatcccg cgcgaggcgc tgcaaaacaa  16860
ggtcattttc cacgtcaaca aggacgtgaa gatcacctac accggcgtcg agctgcgggc  16920
cgacgatgac gaactggtgt ggcagcaggt gttggagtac gcgaagcgca cccctatcgg  16980
cgagccgatc accttcacgt tctacgagct ttgccaggac ctgggctggt cgatcaatgg  17040
ccggtattac acgaaggccg aggaatgcct gtcgcgccta caggcgacgg cgatgggctt  17100
cacgtccgac cgcgttgggc acctggaatc ggtgtcgctg ctgcaccgct tccgcgtcct  17160
ggaccgtggc aagaaaacgt cccgttgcca ggtcctgatc gacgaggaaa tcgtcgtgct  17220
gtttgctggc gaccactaca cgaaattcat atgggagaag taccgcaagc tgtcgccgac  17280
ggcccgacgg atgttcgact atttcagctc gcaccgggag ccgtacccgc tcaagctgga  17340
aaccttccgc ctcatgtgcg gatcggattc cacccgcgtg aagaagtggc gcgagcaggt  17400
cggcgaagcc tgcgaagagt tgcgaggcag cggcctggtg gaacacgcct gggtcaatga  17460
tgacctggtg cattgcaaac gctagggcct tgtggggtca gttccggctg ggggttcagc  17520
agccagcgct ttactggcat ttcaggaaca agcgggcact gctcgacgca cttgcttcgc  17580
tcagtatcgc tcgggacgca cggcgcgctc tacgaactgc cgataaacag aggattaaaa  17640
ttgacaattg tgattaaggc tcagattcga cggcttggag cggccgacgt gcaggatttc  17700
cgcgagatcc gattgtcggc cctgaagaaa gctccagaga tgttcgggtc cgtttacgag  17760
cacgaggaga aaaagcccat ggaggcgttc gctgaacggt tgcgagatgc cgtggcattc  17820
ggcgcctaca tcgacggcga gatcattggg ctgtcggtct tcaaacagga ggacggcccc  17880
aaggacgctc acaaggcgca tctgtccggc gttttcgtgg agcccgaaca gcgaggccga  17940
ggggtcgccg gtatgctgct gcgggcgttg ccggcgggtt tattgctcgt gatgatcgtc  18000
cgacagattc caacgggaat ctggtggatg cgcatcttca tcctcggcgc acttaatatt  18060
tcgctattct ggagcttgtt gtttatttcg gtctaccgcc tgccgggcgg ggtcgcggcg  18120
acggtaggcg ctgtgcagcc gctgatggtc gtgttcatct ctgccgctct gctaggtagc  18180
ccgatacgat tgatggcggt cctgggggct atttgcggaa ctgcgggcgt ggcgctgttg  18240
gtgttgacac caaacgcagc gctagatcct gtcggcgtcg cagcgggcct ggcgggggcg  18300
gtttccatgg cgttcggaac cgtgctgacc cgcaagtggc aacctcccgt gcctctgctc  18360
acctttaccg cctggcaact ggcggccgga ggacttctgc tcgttccagt agctttagtg  18420
tttgatccgc caatcccgat gcctacagga accaatgttc tcggcctggc gtggctcggc  18480
ctgatcggag cgggtttaac ctacttcctt tggttccggg ggatctcgcg actcgaacct  18540
acagttgttt ccttactggg ctttctcagc cgggatggcg ctaagaagct attgccgccg  18600
atcttcatat gcggtgtgaa ataccgcaca gatgcgtaag gagaaaatac cgcatcaggc  18660
gctcttccgc ttcctcgctc actgactcgc tgcgctcggt cgttcggctg cggcgagcgg  18720
tatcagctca ctcaaaggcg gtaatacggt tatccacaga atcaggggat aacgcaggaa  18780
agaacatgtg agcaaaaggc cagcaaaagg ccaggaaccg taaaaaggcc gcgttgctgg  18840
cgtttttcca taggctccgc ccccctgacg agcatcacaa aaatcgacgc tcaagtcaga  18900
ggtggcgaaa cccgacagga ctataaagat accaggcgtt tccccctgga agctccctcg  18960
tgcgctctcc tgttccgacc ctgccgctta ccggatacct gtccgccttt ctcccttcgg  19020
gaagcgtggc gctttctcaa tgctcacgct gtaggtatct cagttcggtg taggtcgttc  19080
gctccaagct gggctgtgtg cacgaacccc ccgttcagcc cgaccgctgc gccttatccg  19140
```

```
gtaactatcg tcttgagtcc aacccggtaa gacacgactt atcgccactg gcagcagcca  19200
ctggtaacag gattagcaga gcgaggtatg taggcggtgc tacagagttc ttgaagtggt  19260
ggcctaacta cggctacact agaaggacag tatttggtat ctgcgctctg ctgaagccag  19320
ttaccttcgg aaaaagagtt ggtagctctt gatccggcaa acaaaccacc gctggtagcg  19380
gtggtttttt tgtttgcaag cagcagatta cgcgcagaaa aaaaggatat caagaagatc  19440
ctttgatctt ttctacgggg tctgacgctc agtggaacga aaactcacgt taagggattt  19500
tggtcatgag attatcaaaa aggatcttca cctagatcct tttaaattaa aaatgaagtt  19560
ttaaatcaat ctaaagtata tatgagtaaa cttggtctga cagttaccaa tgcttaatca  19620
gtgaggcacc tatctcagcg atctgtctat ttcgttcatc catagttgcc tgactccccg  19680
tcgtgtagat aactacgata cgggagggct taccatctgg ccccagtgct gcaatgatac  19740
cgcgagaccc acgctcaccg gctccagatt tatcagcaat aaaccagcca gccggaaggg  19800
ccgagcgcag aagtggtcct gcaactttat ccgcctccat ccagtctatt aaacaagtgg  19860
cagcaacgga ttcgcaaacc tgtcacgcct tttgtgccaa aagccgcgcc aggtttgcga  19920
tccgctgtgc caggcgttag gcgtcatatg aagatttcgg tgatccctga gcaggtggcg  19980
gaaacattgg atgctgagaa ccatttcatt gttcgtgaag tgttcgatgt gcacctatcc  20040
gaccaaggct ttgaactatc taccagaagt gtgagcccct accggaagga ttacatctcg  20100
gatgatgact ctgatgaaga ctctgcttgc tatggcgcat tcatcgacca agagcttgtc  20160
gggaagattg aactcaactc aacatggaac gatctagcct ctatcgaaca cattgttgtg  20220
tcgcacacgc accgaggcaa aggagtcgcg cacagtctca tcgaatttgc gaaaaagtgg  20280
gcactaagca gacagctcct tggcatacga ttagagacac aaacgaacaa tgtacctgcc  20340
tgcaatttgt acgcaaaatg tggctttact ctcggcggca ttgacctgtt cacgtataaa  20400
actagacctc aagtctcgaa cgaaacagcg atgtactggt actggttctc gggagcacag  20460
gatgacgcct aacaattcat tcaagccgac accgcttcgc ggcgcggctt aattcaggag  20520
ttaaacatca tgagggaagc ggtgatcgcc gaagtatcga ctcaactatc agaggtagtt  20580
ggcgtcatcg agcgccatct cgaaccgacg ttgctggccg tacatttgta cggctccgca  20640
gtggatggcg gcctgaagcc acacagtgat attgatttgc tggttacggt gaccgtaagg  20700
cttgatgaaa caacgcggcg agctttgatc aacgaccttt tggaaacttc ggcttcccct  20760
ggagagagcg agattctccg cgctgtagaa gtcaccattg ttgtgcacga cgacatcatt  20820
ccgtggcgtt atccagctaa gcgcgaactg caatttggag aatggcagcg caatgacatt  20880
cttgcaggta tcttcgagcc agccacgatc gacattgatc tggctatctt gctgacaaaa  20940
gcaagagaac atagcgttgc cttggtaggt ccagcggcgg aggaactctt tgatccggtt  21000
cctgaacagg atctatttga ggcgctaaat gaaaccttaa cgctatggaa ctcgccgccc  21060
gactgggctg gcgatgagcg aaatgtagtg cttacgttgt cccgcatttg gtacagcgca  21120
gtaaccggca aaatcgcgcc gaaggatgtc gctgccgact gggcaatgga gcgcctgccg  21180
gcccagtatc agcccgtcat acttgaagct aggcaggctt atcttggaca agaagatcgc  21240
ttggcctcgc gcgcagatca gttggaagaa tttgttcact acgtgaaagg cgagatcacc  21300
aaggtagtcg gcaaataatg tctaacaatt cgttcaagcc gacgccgctt cgcggcgcgg  21360
cttaactcaa gcgttagaga gctggggaag actatgcgcg atctgttgaa ggtggttcta  21420
agcctcgtac ttgcgatggc atcggggcag gcacttgctg acctgccaat tgttttagtg  21480
gatgaagctc gtcttcccta tgactactcc ccatccaact acgacatttc tccaagcaac  21540
```

-continued

```
tacgacaact ccataagcaa ttacgacaat agtccatcaa attacgacaa ctctgagagc  21600

aactacgata atagttcatc caattacgac aatagtcgca acggaaatcg taggcttata  21660

tatagcgcaa atgggtctcg cactttcgcc ggctactacg tcattgccaa caatgggaca  21720

acgaacttct tttccacatc tggcaaaagg atgttctaca ccccaaaagg ggggcgcggc  21780

gtctatggcg gcaaagatgg gagcttctgc ggggcattgg tcgtcataaa tggccaattt  21840

tcgcttgccc tgacagataa cggcctgaag atcatgtatc taagcaacta gcctgctctc  21900

taataaaatg ttaggagctt ggctgccatt tttggggtga ggccgttcgc ggccgagggg  21960

cgcagcccct gggggatgg gaggcccgcg ttagcgggcc gggagggttc gagaaggggg  22020

ggcaccccc ttcggcgtgc gcggtcacgc gccagggcgc agccctggtt aaaaacaagg  22080

tttataaata ttggtttaaa agcaggttaa aagacaggtt agcggtggcc gaaaaacggg  22140

cggaaaccct tgcaaatgct ggattttctg cctgtggaca gcccctcaaa tgtcaatagg  22200

tgcgcccctc atctgtcagc actctgcccc tcaagtgtca aggatcgcgc ccctcatctg  22260

tcagtagtcg cgcccctcaa gtgtcaatac cgcagggcac ttatccccag gcttgtccac  22320

atcatctgtg ggaaactcgc gtaaaatcag gcgttttcgc cgatttgcga ggctggccag  22380

ctccacgtcg ccggccgaaa tcgagcctgc ccctcatctg tcaacgccgc gccgggtgag  22440

tcggcccctc aagtgtcaac gtccgcccct catctgtcag tgagggccaa gttttccgcg  22500

aggtatccac aacgccggcg gccggccgcg gtgtctcgca cacggcttcg acggcgtttc  22560

tggcgcgttt gcagggccat agacggccgc cagcccagcg gcgagggcaa ccagcccggt  22620

gagcgtcgga aaggg                                                   22635
```